(12) United States Patent
Negrete et al.

(10) Patent No.: US 11,433,121 B1
(45) Date of Patent: *Sep. 6, 2022

(54) LIPID COMPOSITION FOR THE DELIVERY OF THERAPEUTIC CARGOS

(71) Applicant: National Technology & Engineering Solutions of Sandia, LLC, Albuquerque, NM (US)

(72) Inventors: Oscar Negrete, Livermore, CA (US); Annette Estelle LaBauve, Hayward, CA (US); Joseph S. Schoeniger, Oakland, CA (US); Edwin A. Saada, Dublin, CA (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 134 days.

This patent is subject to a terminal disclaimer.

(21) Appl. No.: 16/839,194

(22) Filed: Apr. 3, 2020

(51) Int. Cl.
*A61K 38/46* (2006.01)
*A61K 47/28* (2006.01)
*A61K 47/14* (2017.01)
*A61K 9/16* (2006.01)

(52) U.S. Cl.
CPC .......... *A61K 38/465* (2013.01); *A61K 9/1676* (2013.01); *A61K 47/14* (2013.01); *A61K 47/28* (2013.01)

(58) Field of Classification Search
CPC .... A61K 38/465; A61K 9/1676; A61K 47/14; A61K 47/28
See application file for complete search history.

(56) References Cited

U.S. PATENT DOCUMENTS

| | | | |
|---|---|---|---|
| 8,734,816 B2 | 5/2014 | Liu et al. |
| 8,992,984 B1 | 3/2015 | Brinker et al. |
| 9,480,653 B2 | 11/2016 | Brinker et al. |
| 9,579,283 B2 | 2/2017 | Brinker et al. |
| 9,855,217 B2 | 1/2018 | Brinker et al. |
| 10,022,327 B2 | 7/2018 | Brinker et al. |

(Continued)

FOREIGN PATENT DOCUMENTS

| | | |
|---|---|---|
| WO | 2008140573 A2 | 11/2008 |
| WO | 2014093635 A1 | 6/2014 |

(Continued)

OTHER PUBLICATIONS

U.S. Appl. No. 15/788,634, filed Oct. 19, 2017, Brinker, et al.

(Continued)

*Primary Examiner* — Jianfeng Song
(74) *Attorney, Agent, or Firm* — Medley, Behrens & Lewis, LLC; Madelynne J. Farber; Samantha Updegraff

(57) ABSTRACT

A construct includes a core comprising an external surface and a plurality of pores, a cargo disposed in a pore of the plurality of pores, the cargo comprising a CRISPR Cas9 component or a nucleic acid sequence encoding a CRISPR Cas9 component; and a coating coupled to the core, wherein the coating comprises a cationic lipid, a pegylated lipid, a zwitterionic lipid, and a sterol. The coating may comprise a molar ratio of about 1 cationic lipid to 1 zwitterionic lipid to 0.9 sterol to 0.15 PEGylated lipid, wherein each molar ratio optionally varies by about plus or minus 10%. A method of treatment is also provided.

11 Claims, 25 Drawing Sheets

Specification includes a Sequence Listing.

(56) References Cited

U.S. PATENT DOCUMENTS

| | | | |
|---|---|---|---|
| 2014/0079774 | A1 | 3/2014 | Brinker et al. |
| 2014/0301951 | A1 | 10/2014 | Liu et al. |
| 2015/0010475 | A1 | 1/2015 | Brinker et al. |
| 2015/0164798 | A1 | 6/2015 | Brinker et al. |
| 2015/0272885 | A1* | 10/2015 | Ashley ................ A61K 9/5078 424/450 |
| 2015/0320681 | A1 | 11/2015 | Brinker et al. |
| 2016/0090603 | A1 | 3/2016 | Carnes et al. |
| 2016/0106671 | A1 | 4/2016 | Brinker et al. |
| 2016/0151482 | A1 | 6/2016 | Carnes et al. |
| 2016/0287717 | A1 | 10/2016 | Brinker et al. |
| 2016/0338954 | A1 | 11/2016 | Brinker et al. |
| 2017/0165375 | A1 | 6/2017 | Ashley et al. |
| 2017/0172923 | A1 | 6/2017 | Won |
| 2017/0232115 | A1 | 8/2017 | Ashley et al. |
| 2018/0028686 | A1 | 2/2018 | Brinker et al. |
| 2018/0049984 | A1 | 2/2018 | Brinker et al. |
| 2018/0105430 | A1 | 4/2018 | Carnes et al. |
| 2018/0110831 | A1 | 4/2018 | Brinker et al. |
| 2018/0169009 | A1 | 6/2018 | Johnson et al. |
| 2018/0344641 | A1 | 12/2018 | Brinker et al. |
| 2019/0091150 | A1 | 3/2019 | Brinker et al. |
| 2020/0405650 | A1* | 12/2020 | Noureddine ............ A61K 9/127 |

FOREIGN PATENT DOCUMENTS

| | | | | |
|---|---|---|---|---|
| WO | 2015042268 | A1 | 3/2015 | |
| WO | 2015042279 | A1 | 3/2015 | |
| WO | 2015089427 | A1 | 6/2015 | |
| WO | WO-2015089427 | A1 * | 6/2015 | ............. C12N 15/79 |
| WO | 2016013751 | A1 | 1/2016 | |
| WO | 2016145031 | A1 | 9/2016 | |
| WO | 2017023407 | A2 | 2/2017 | |
| WO | 2017041032 | A1 | 3/2017 | |
| WO | 2017041033 | A1 | 3/2017 | |
| WO | 2017120504 | A1 | 7/2017 | |

OTHER PUBLICATIONS

U.S. Appl. No. 15/858,923, filed Dec. 29, 2017, Brinker, et al.
U.S. Appl. No. 15/887,619, filed Feb. 2, 2018, Ashley, et al.
Ahmed F et al., "Shrinkage of a rapidly growing tumor by drug-loaded polymersomes: pH-triggered release through copolymer degradation," Molec. Pharmaceutics 2006;3(3):340-350.
Barbu EM et al., "beta-neurexin is a ligand for the Straphlococcus aureus MSCRAMM SdrC," PLos Pathog. 2010,6(1):e1000726 (11 pp.).
Barhenholz Y, "Doxil®—the first FDA-approved nano-drug: lessons learned," J. Controlled Release 2012;160:117-134.
Blenke EO et al., "CRISPR-Cas9 gene editing: delivery aspects and therapeutic potential," J. Controlled Release 2016;244:139-148.
Butler KS et al., "Protocells: modular mesoporous silica nanoparticle-supported lipid bilayers for drug delivery," Small 2016;12(16):2173-2185.
Carroll NJ et al., "Microparticles with bimodal nanoporosity derived by microemulsion templating," Langmuir 2009;25(23):13540-13544.
Cello J et al., "Chemical synthesis of poliovirus cDNA: generation of infectious virus in the absence of natural template," Science 2002;297(5583):1016-1018.
Chiu HY et al., "Intracellular chromobody delivery by mesoporous silica nanoparticles for antigen targeting and visualization in real time," Sci. Rep. 2016;6:25019 (12 pp.).
Citorik RJ et al., "Sequence-specific antimicrobials using efficiently delivered RNA-guided nucleases," Nat. Biotechnol. Nov. 2014;32(11):1141-5.
Cokol M et al., "Finding nuclear localization signals," EMBO Rep. 2000;1(5):411-415.
Cong Y et al., "Site-specific PEGylation at histidine tags," Bioconjug. Chern. 2012;23(2):248-263.

Cross R, "CRISPR's breakthrough problem," C&E News Feb. 13, 2017;95(7):28-33.
Durfee PN et al., "Mesoporous silica nanoparticle-supported lipid bilayers (protocells) for active targeting and delivery to individual leukemia cells," ACS Nano 2016;10:8325-8345.
Durfee PN et al., "Supporting Information for Mesoporous silica nanoparticle-supported lipid bilayers (protocells) for active targeting and delivery to individual leukemia cells," ACS Nano 2016;10:8325-8345 (30 pp.).
Epler K et al., "Delivery of ricin toxin A-chain by peptide-targeted mesoporous silica nanoparticle-supported lipid bilayers," Adv. Healthcare Mater. 2012;1:348-353.
Epler K et al., Supporting Information for "Delivery of ricin toxin A-chain by peptide-targeted mesoporous silica nanoparticle-supported lipid bilayers," Adv. Healthcare Mater. 2012;1:348-353 (17 pp.).
French CT et al., "Dissection of the Burkholderia intracellular life cycle using a photothermal nanoblade," Proc. Nat'l Acad. Sci. USA 2011;108(29):12095-12100.
Fu J et al., "Intracellular delivery of functional proteins and native drugs by cell-penetrating poly(disulfide)s," J. Am. Chern. Soc. 2015;137:12153-12160.
Fu J et al., Supporting Information for "Intracellular delivery of functional proteins and native drugs by cell-penetrating poly(disulfide)s," J. Am. Chern. Soc. 2015;137:12153-12160 (29 pp.).
Gao F et al., "Monodispersed mesoporous silica nanoparticles with very large pores for enhanced adsorption and release of DNA," J. Phys. Chem. B 2009;113(6):1796-1804.
Gibson DG et al., "Creation of a bacterial cell controlled by a chemically synthesized genome," Science 2010;329(5987):52-56.
Giordano RJ et al., "Structural basis for the interaction of a vascular endothelial growth factor mimic peptide motif and its corresponding receptors," Chern. Biol. 2005;12(10):1075-1083.
Giordano RJ et al., "Biopanning and rapid analysis of selective interactive ligands," Nat. Med. 2001;7(11 ):1249-1253.
Giordano RJ et al., "From combinatorial peptide selection to drug prototype (I): targeting the vascular endothelial growth factor receptor pathway," Proc. Nat'l Acad. Sci. USA 2010;107(11 ):5112-5117.
Gonzalez Porras MA et al., "A novel approach for targeted delivery to motoneurons using cholera toxin-B modified protocells," J. Neurosci. Methods 2016;273:160-174.
Gonzalez Porras MA et al., "Uptake and intracellular fate of cholera toxin subunit b-modified mesoporous silica nanoparticle-supported lipid bilayers (aka protocells) in motoneurons," Nanomedicine: Nanotechnology, Biology, and Medicine 2018;14(3):661-672.
Han DH et al., "Direct cellular delivery of human proteasomes to delay tau aggregation," Nature Commun. 2014;5(5):5633 (8 pp.).
Han DH et al., Supplementary Figures and Supplementary Note 1 for "Direct cellular delivery of human proteasomes to delay tau aggregation," Nature Commun. 2014;5(5):5633 (8 pp.) (28 pp.).
Jackson RJ et al., "Expression of mouse interleukin-4 by a recombinant ectromelia virus suppresses cytolytic lymphocyte responses and overcomes genetic resistance to mousepox," J. Viral. 2001;75(3):1205-1210.
Kennedy EM et al., "Inactivation of the human papillomavirus E6 or E7 gene in cervical carcinoma cells by using a bacterial CRISPR/Cas RNA-guided endonuclease," J. Virol. Oct. 2014;88(20):11965-72.
Kim MH et al., "Facile synthesis of monodispersed mesoporous silica nanoparticles with ultralarge pores and their application in gene delivery," ACS Nano 2011;5(5):3568-3576.
Kolonin MG et al., "Ligand-directed surface profiling of human cancer cells with combinatorial peptide libraries," Cancer Res. 2006;66(1):34-40.
Konermann S et al., "Genome-scale transcriptional activation by an engineered CRISPR-Cas9 complex," Nature 2015;517(7536):583-588.
LaCasse EC et al., "Nuclear localization signals overlap DNA- or RNA-binding domains in nucleic acid-binding proteins," Nucl. Acids Res. 1995;23(10):1647-1656.
Lambris JD et al., "Complement evasion by human pathogens," Nat. Rev. Microbial. 2008;6(2):132-142.

(56) References Cited

OTHER PUBLICATIONS

Li L et al., "Artificial virus delivers CRISPR-Cas9 system for genome editing of cells in mice," ACS Nano 2017;11:95-111.
Li Z et al., "Identification and characterization of a novel peptide ligand of epidermal growth factor receptor for targeted delivery of therapeutics," FASEB J. 2005;19(14):1978-1985.
Liberatore FA et al., "Site-directed chemical modification and cross-linking of a monoclonal antibody using equilibrium transfer alkylating cross-link reagents," Bioconjug. Chem. 1990;1(1):36-50.
Lin YS et al., "Synthesis and characterization of biocompatible and size-tunable multifunctional porous silica nanoparticles," Chem. Mater. 2009;21(17):3979-3986.
Lionakis MS et al., "Development of a ligand-directed approach to study the pathogenesis of invasive aspergillosis," Infect. Immun. 2005;73(11):7747-7758.
Liu J et al., "Delivery methods for site-specific nucleases: achieving the full potential of therapeutic engineering," J. Controlled Release 2016;244:83-97.
Lo A et al., "Hepatocellular carcinoma cell-specific peptide ligand for targeted drug delivery," Mol. Cancer Therap. 2008;7(3):579-589.
Lu Y et al., "Aerosol-assisted self-assembly of mesostructured spherical nanoparticles," Nature 1999;398:223-226.
Makarova KS et al., "Evolution and classification of the CRISPR-Cas systems," Nat. Rev. Microbiol. 2011;9(6):467-477.
Miller JB et al., "Non-viral CRISPR/Cas gene editing in vitro and invivo enabled by synthetic nanoparticle co-delivery of Cas9 mRNA and sgRNA," Angew. Chem. Int. Ed. Engl. 2017;56(4):1059-1063.
Mizutani M et al., "Anomalous pore expansion of highly monodispersed mesoporous silica spheres and its application to the synthesis of porous ferromagnetic composite," Chem. Mater. 2008;20:4777-4782.
Moore NM et al., "The effect of endosomal escape peptides on in vitro gene delivery of polyethylene glycol-based vehicles," J. Gene. Med. 2008;10(10):1134-1149.
Na HK et al., "Efficient functional delivery of siRNA using mesoporous silica nanoparticles with ultralarge pores," Small 2012;8(11):1752-1761.
Na HK et al., Supporting Information for "Efficient functional delivery of siRNA using mesoporous silica nanoparticles with ultralarge pores," Small 2012;8(11):1752-1761(11 pp.).
Ogunyankin MO et al., "Nanoscale patterning of membrane-bound proteins formed through curvature-induced partitioning of phase-specific receptor lipids," Langmuir 2013;29:6109-6115.
Ortega-Munoz M et al., "Vinyl sulfone functionalized silica: a "ready to use" pre-activated material for immobilization of biomolecules," J. Mater. Chem. 2010;20:7189-7196.
Paxton WF et al., "Monitoring and modulating ion traffic in hybrid lipid/polymer vesicles," Colloids Surf. 8 Biointerfaces 2017;159:268-276.
Poon IK et al., "Molecular mechanisms of late apoptotic/necrotic cell clearance," Cell Death Differ. 2010;17(3):381-397.
Ramakrishna S et al., "Surrogate reporter-based enrichment of cells containing RNA-guided Cas9 nuclease-induced mutations," Nature Commun. 2014;5:3378 (10 pp.).
Russell CA et al., "The potential of respiratory droplet-transmissible A/H5N1 influenza virus to evolve in a mammalian host," Science 2012;336(6088):1541-1547.
Sava Gallis DF et al., "Multifunctional, tunable metal-organic framework materials platform for bioimaging applications," ACS Appl. Mater. Interfaces 2017;9(27):22268-22277.
Seo SJ et al., "Gene delivery techniques for adult stem cell-based regenerative therapy," Nanomedicine 2013;8(11):1875-91.

Shen D et al., "Biphase stratification approach to three-dimensional dendritic biodegradable mesoporous silica nanospheres," Nano Lett. 2014;14(2):923-932.
Shen D et al., Supporting Information for "Biphase stratification approach to three-dimensional dendritic biodegradable mesoporous silica nanospheres," Nano Lett. 2014;14(2):923-932.
Sun W et al., "Self-assembled DNA nanoclews for the efficient delivery of CRISPR-Cas9 for genome editing," Angew. Chem. Int. Ed. 2015;54:12029-12033.
Takeuchi S et al., "An axisymmetric flow-focusing microfluidic device," Adv. Mater. 2005;17(8):1067-1072.
Tarn D et al., "Mesoporous silica nanoparticle nanocarriers: biofunctionality and biocompatibility," Ace. Chem. Res. Mar. 19, 2013;46(3):792-801.
Ting CL et al., "Membrane stress profiles from self-consistent field theory," J. Chem. Phys. 2017;146(10):104901 (9 pp.).
Ting CL et al., "Metastable prepares in tension-free lipid bilayers," Phys. Rev. Lett. 2018;120:128103 (6 pp.).
Tonelli RR et al., "Role of the gp85/trans-sialidases in Trypanosoma cruzi tissue tropism: preferential binding of a conserved peptide motif to the vasculature in vivo," PLoS Negl. Dis. 2010;4:e864 (8 pp.).
Townson JL et al., "Re-examining the size/charge paradigm: differing in vivo characteristics of size- and charge-matched mesoporous silica nanoparticles," J. Am. Chem. Soc. 2013;135(43):16030-16033.
Tu J et al., "Mesoporous silica nanoparticles with large pores for the encapsulation and release of proteins," ACS Appl. Mater. Interfaces 2016;8:32211-32219.
Tu J et al., Supporting Information for "Mesoporous silica nanoparticles with large pores for the encapsulation and release of proteins," ACS Appl. Mater. Interfaces 2016;8:32211-32219 (4 pp.).
Tumpey TM et al., "Characterization of the reconstructed 1918 Spanish influenza pandemic virus," Science 2005;310(5745):77-80.
Vouillot L et al., "Comparison of T7E1 and surveyor mismatch cleavage assays to detect mutations triggered by engineered nucleases," G3 (Bethesda) 2015;5(3):407-415.
Weber ND et al., "DNA cleavage enzymes for treatment of persistent viral infections: recent advances and the pathway forward," Virology 2014;0:353-361.
Weis K, "Importins and exportins: how to get in and out of the nucleus," [published erratum appears in Trends Biochem. Sci. Jul. 1998;23(7):235] Trends Biochem. Sci. 1998;23(5):185-189.
Yao VJ et al., "Ligand-targeted theranostic nanomedicines against cancer," J. Controlled Release 2016;240:267-286.
Yin H et al., "Therapeutic genome editing by combined viral and non-viral delivery of CRISPR system components in vivo," Nat. Biotechnol. Mar. 2016;34(3):328-333.
Zhang K et al., "Facile large-scale synthesis of monodisperse mesoporous silica nanospheres with tunable pore structure," J. Am. Chem. Soc. 2013;135(7):2427-2430.
Zuris JA et al., "Cationic lipid-mediated delivery of proteins enables efficient protein-based genome editing in vitro and in vivo," Nature Biotechnol. 2015;33(1):73-80.
F Torney, BG Trewyn, VSY Lin, K Wang. "Mesoporous silica nanoparticles deliver DNA and chemicals into plants." Nature Nanotechnology, vol. 2, May 2007, pp. 295-300. (Year: 2007).
LaBauve, AE et al, "Lipid-Coated Mesoporous Silica Nanoparticles for the Delivery of the ML336 Antiviral to Inhibit Encephalitic Alphavirus Infection," Sci Rep. 2018; 8: 13990, Sep. 18, 2018. doi: 10.1038/s41598-018-32033-w, 13 pages.
U.S. Appl. No. 16/141,725, filed Sep. 25, 2018, 115 pages.

* cited by examiner

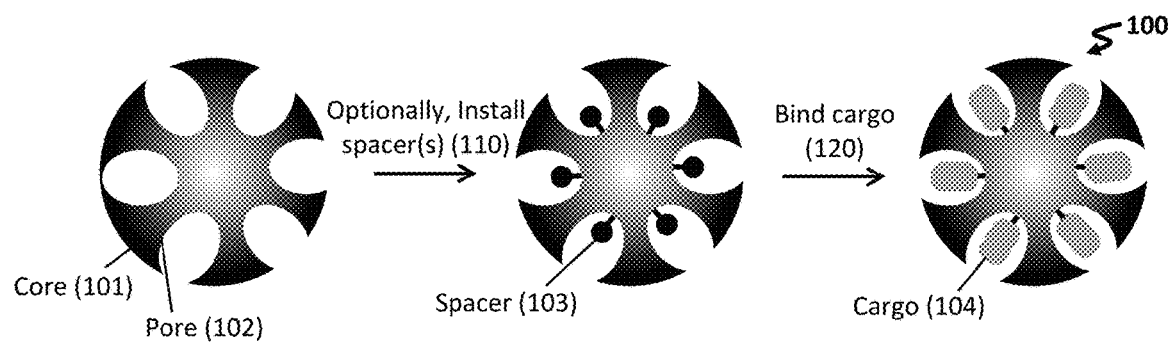
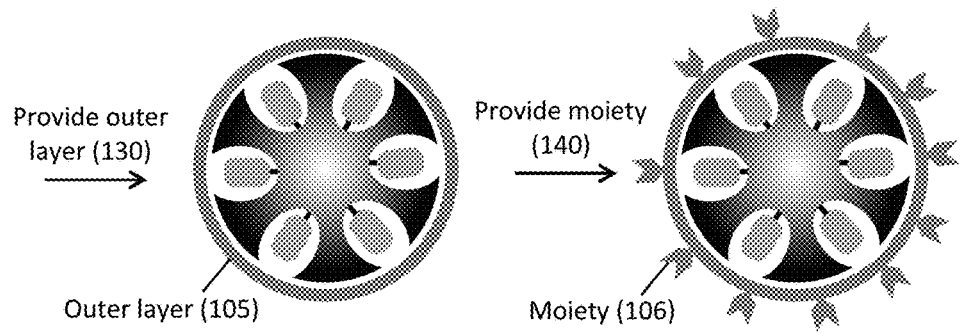
FIG. 1A
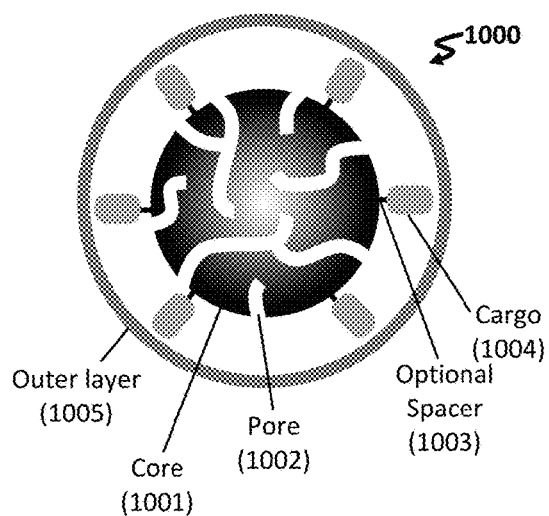
FIG. 1B
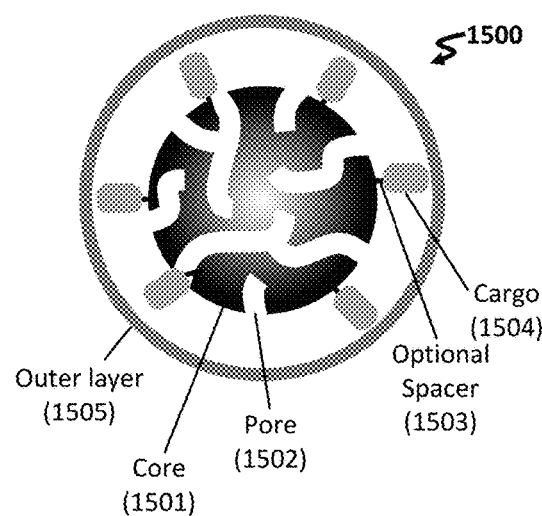
FIG. 1C

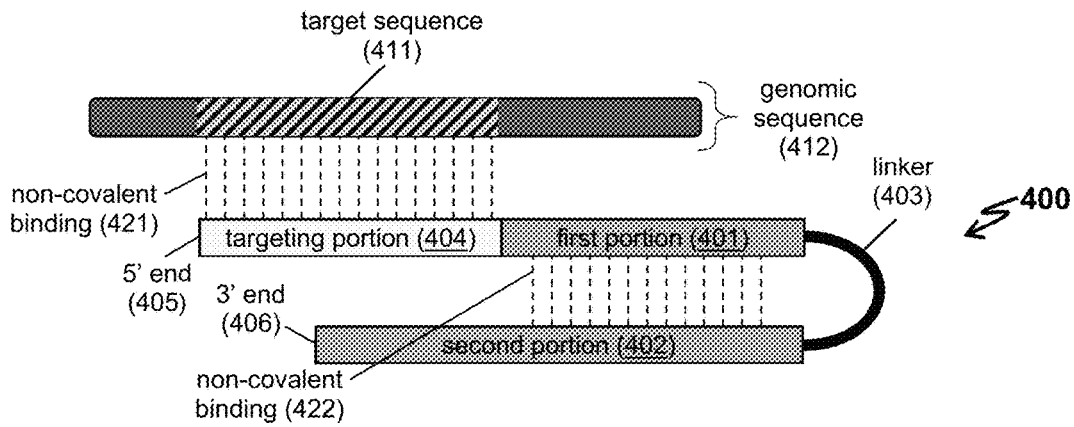

FIG. 7C

```
SEQ ID NO:110
UniProtKB/Swiss-Prot: Q99ZW2.1
RecName: Full=CRISPR-associated endonuclease Cas9/Csn1; AltName: Full=SpyCas9
[Streptococcus pyogenes serotype M1]
    1 MDKKYSIGLD IGTNSVGWAV ITDEYKVPSK KFKVLGNTDR HSIKKNLIGA LLFDSGETAE
   61 ATRLKRTARR RYTRRKNRIC YLQEIFSNEM AKVDDSFFHR LEESFLVEED KKHERHPIFG
  121 NIVDEVAYHE KYPTIYHLRK KLVDSTDKAD LRLIYLALAH MIKFRGHFLI EGDLNPDNSD
  181 VDKLFIQLVQ TYNQLFEENP INASGVDAKA ILSARLSKSR RLENLIAQLP GEKKNGLFGN
  241 LIALSLGLTP NFKSNFDLAE DAKLQLSKDT YDDDLDNLLA QIGDQYADLF LAAKNLSDAI
  301 LLSDILRVNT EITKAPLSAS MIKRYDEHHQ DLTLLKALVR QQLPEKYKEI FFDQSKNGYA
  361 GYIDGGASQE EFYKFIKPIL EKMDGTEELL VKLNREDLLR KQRTFDNGSI PHQIHLGELH
  421 AILRRQEDFY PFLKDNREKI EKILTFRIPY YVGPLARGNS RFAWMTRKSE ETITPWNFEE
  481 VVDKGASAQS FIERMTNFDK NLPNEKVLPK HSLLYEYFTV YNELTKVKYV TEGMRKPAFL
  541 SGEQKKAIVD LLFKTNRKVT VKQLKEDYFK KIECFDSVEI SGVEDRFNAS LGTYHDLLKI
  601 IKDKDFLDNE ENEDILEDIV LTLTLFEDRE MIEERLKTYA HLFDDKVMKQ LKRRRYTGWG
  661 RLSRKLINGI RDKQSGKTIL DFLKSDGFAN RNFMQLIHDD SLTFKEDIQK AQVSGQGDSL
  721 HEHIANLAGS PAIKKGILQT VKVVDELVKV MGRHKPENIV IEMARENQTT QKGQKNSRER
  781 MKRIEEGIKE LGSQILKEHP VENTQLQNEK LYLYYLQNGR DMYVDQELDI NRLSDYDVDH
  841 IVPQSFLKDD SIDNKVLTRS DKNRGKSDNV PSEEVVKKMK NYWRQLLNAK LITQRKFDNL
  901 TKAERGGLSE LDKAGFIKRQ LVETRQITKH VAQILDSRMN TKYDENDKLI REVKVITLKS
  961 KLVSDFRKDF QFYKVREINN YHHAHDAYLN AVVGTALIKK YPKLESEFVY GDYKVYDVRK
 1021 MIAKSEQEIG KATAKYFFYS NIMNFFKTEI TLANGEIRKR PLIETNGETG EIVWDKGRDF
 1081 ATVRKVLSMP QVNIVKKTEV QTGGFSKESI LPKRNSDKLI ARKKDWDPKK YGGFDSPTVA
 1141 YSVLVVAKVE KGKSKKLKSV KELLGITIME RSSFEKNPID FLEAKGYKEV KKDLIIKLPK
 1201 YSLFELENGR KRMLASAGEL QKGNELALPS KYVNFLYLAS HYEKLKGSPE DNEQKQLFVE
 1261 QHKHYLDEII EQISEFSKRV ILADANLDKV LSAYNKHRDK PIREQAENII HLFTLTNLGA
 1321 PAAFKYFDTT IDRKRYTSTK EVLDATLIHQ SITGLYETRI DLSQLGGD
```

FIG. 8A

SEQ ID NO:111
dCas9 (D10A,H840A)
```
   1 MDKKYSIGLA IGTNSVGWAV ITDEYKVPSK KFKVLGNTDR HSIKKNLIGA LLFDSGETAE
  61 ATRLKRTARR RYTRRKNRIC YLQEIFSNEM AKVDDSFFHR LEESFLVEED KKHERHPIFG
 121 NIVDEVAYHE KYPTIYHLRK KLVDSTDKAD LRLIYLALAH MIKFRGHFLI EGDLNPDNSD
 181 VDKLFIQLVQ TYNQLFEENP INASGVDAKA ILSARLSKSR RLENLIAQLP GEKKNGLFGN
 241 LIALSLGLTP NFKSNFDLAE DAKLQLSKDT YDDDLDNLLA QIGDQYADLF LAAKNLSDAI
 301 LLSDILRVNT EITKAPLSAS MIKRYDEHHQ DLTLLKALVR QQLPEKYKEI FFDQSKNGYA
 361 GYIDGGASQE EFYKFIKPIL EKMDGTEELL VKLNREDLLR KQRTFDNGSI PHQIHLGELH
 421 AILRRQEDFY PFLKDNREKI EKILTFRIPY YVGPLARGNS RFAWMTRKSE ETITPWNFEE
 481 VVDKGASAQS FIERMTNFDK NLPNEKVLPK HSLLYEYFTV YNELTKVKYV TEGMRKPAFL
 541 SGEQKKAIVD LLFKTNRKVT VKQLKEDYFK KIECFDSVEI SGVEDRFNAS LGTYHDLLKI
 601 IKDKDFLDNE ENEDILEDIV LTLTLFEDRE MIEERLKTYA HLFDDKVMKQ LKRRRYTGWG
 661 RLSRKLINGI RDKQSGKTIL DFLKSDGFAN RNFMQLIHDD SLTFKEDIQK AQVSGQGDSL
 721 HEHIANLAGS PAIKKGILQT VKVVDELVKV MGRHKPENIV IEMARENQTT QKGQKNSRER
 781 MKRIEEGIKE LGSQILKEHP VENTQLQNEK LYLYYLQNGR DMYVDQELDI NRLSDYDVDA
 841 IVPQSFLKDD SIDNKVLTRS DKNRGKSDNV PSEEVVKKMK NYWRQLLNAK LITQRKFDNL
 901 TKAERGGLSE LDKAGFIKRQ LVETRQITKH VAQILDSRMN TKYDENDKLI REVKVITLKS
 961 KLVSDFRKDF QFYKVREINN YHHAHDAYLN AVVGTALIKK YPKLESEFVY GDYKVYDVRK
1021 MIAKSEQEIG KATAKYFFYS NIMNFFKTEI TLANGEIRKR PLIETNGETG EIVWDKGRDF
1081 ATVRKVLSMP QVNIVKKTEV QTGGFSKESI LPKRNSDKLI ARKKDWDPKK YGGFDSPTVA
1141 YSVLVVAKVE KGKSKKLKSV KELLGITIME RSSFEKNPID FLEAKGYKEV KKDLIIKLPK
1201 YSLFELENGR KRMLASAGEL QKGNELALPS KYVNFLYLAS HYEKLKGSPE DNEQKQLFVE
1261 QHKHYLDEII EQISEFSKRV ILADANLDKV LSAYNKHRDK PIREQAENII HLFTLTNLGA
1321 PAAFKYFDTT IDRKRYTSTK EVLDATLIHQ SITGLYETRI DLSQLGGD
```
FIG. 8B

SEQ ID NO:112
NCBI Reference Sequence: WP_011054416.1
CRISPR-associated protein Csn1
[Streptococcus pyogenes]
```
   1 MDKKYSIGLD IGTNSVGWAV ITDDYKVPSK KLKGLGNTDR HGIKKNLIGA LLFDSGETAE
  61 ATRLKRTARR RYTRRKNRIC YLQEIFSNEM AKVDDSFFHR LEESFLVEED KKHERHPIFG
 121 NIVDEVAYHE KYPTIYHLRK KLADSTDKVD LRLIYLALAH MIKFRGHFLI EGDLNPDNSD
 181 VDKLFIQLVQ TYNQLFEENP INASRVDAKA ILSARLSKSR RLENLIAQLP GEKKNGLFGN
 241 LIALSLGLTP NFKSNFDLAE DAKLQLSKDT YDDDLDNLLA QIGDQYADLF LAAKNLSDAT
 301 LLSDILRVNS EITKAPLSAS MIKRYDEHHQ DLTLLKALVR QQLPEKYKEI FFDQSKNGYA
 361 GYIDGGASQE EFYKFIKPIL EKMDGTEELL AKLNREDLLR KQRTFDNGSI PYQIHLGELH
 421 AILRRQEDFY PFLKDNREKI EKILTFRIPY YVGPLARGNS RFAWMTRKSE ETITPWNFEE
 481 VVDKGASAQS FIERMTNFDK NLPNEKVLPK HSLLYEYFTV YNELTKVKYV TEGMRKPAFL
 541 SGEQKKAIVD LLFKTNRKVT VKQLKEDYFK KIECFDSVEI SGVEDRFNAS LGTYHDLLKI
 601 IKDKDFLDNE ENEDILEDIV LTLTLFEDRE MIEERLKTYA HLFDDKVMKQ LKRRRYTGWG
 661 RLSRKLINGI RDKQSGKTIL DFLKSDGFAN RNFMQLIHDD SLTFKEDIQK AQVSGQGDSL
 721 HEHIANLAGS PAIKKGILQT VKVVDELVKV MGRHKPENIV IEMARENQTT QKGQKNSRER
 781 MKRIEEGIKE LGSDILKEYP VENTQLQNEK LYLYYLQNGR DMYVDQELDI NRLSDYDVDH
 841 IVPQSFLKDD SIDNKVLTRS DKNRGKSDNV PSEEVVKKMK NYWRQLLNAK LITQRKFDNL
 901 TKAERGGLSE LDKVGFIKRQ LVETRQITKH VAQILDSRMN TKYDENDKLI REVKVITLKS
 961 KLVSDFRKDF QFYKVREINN YHHAHDAYLN AVVGTALIKK YPKLESEFVY GDYKVYDVRK
1021 MIAKSEQEIG KATAKYFFYS NIMNFFKTEI TLANGEIRKR PLIETNGETG EIVWDKGRDF
1081 ATVRKVLSMP QVNIVKKTEV QTGGFSKESI LPKRNSDKLI ARKKDWDPKK YGGFDSPTVA
1141 YSVLVVAKVE KGKSKKLKSV KELLGITIME RSSFEKDPID FLEAKGYKEV RKDLIIKLPK
1201 YSLFELENGR KRMLASAGEL QKGNELALPS KYVNFLYLAS HYEKLKGSPE DNEQKQLFVE
1261 QHKHYLDEII EQISEFSKRV ILADANLDKV LSAYNKHRDK PIREQAENII HLFTLTNLGA
1321 PAAFKYFDTT IDRKRYTSTK EVLDATLIHQ SITGLYETRI DLSQLGGD
```
FIG. 8C

SEQ ID NO:113
UniProtKB/Swiss-Prot: A0Q5Y3.1
RecName: Full=CRISPR-associated endonuclease Cas9
[Francisella tularensis subsp. novicida U112]

```
   1 MNFKILPIAI DLGVKNTGVF SAFYQKGTSL ERLDNKNGKV YELSKDSYTL LMNNRTARRH
  61 QRRGIDRKQL VKRLFKLIWT EQLNLEWDKD TQQAISFLFN RRGFSFITDG YSPEYLNIVP
 121 EQVKAILMDI FDDYNGEDDL DSYLKLATEQ ESKISEIYNK LMQKILEFKL MKLCTDIKDD
 181 KVSTKTLKEI TSYEFELLAD YLANYSESLK TQKFSYTDKQ GNLKELSYYH HDKYNIQEFL
 241 KRHATINDRI LDTLLTDDLD IWNFNFEKFD FDKNEEKLQN QEDKDHIQAH LHHFVFAVNK
 301 IKSEMASGGR HRSQYFQEIT NVLDENNHQE GYLKNFCENL HNKKYSNLSV KNLVNLIGNL
 361 SNLELKPLRK YFNDKIHAKA DHWDEQKFTE TYCHWILGEW RVGVKDQDKK DGAKYSYKDL
 421 CNELKQKVTK AGLVDFLLEL DPCRTIPPYL DNNNRKPPKC QSLILNPKFL DNQYPNWQQY
 481 LQELKKLQSI QNYLDSFETD LKVLKSSKDQ PYFVEYKSSN QQIASGQRDY KDLDARILQF
 541 IFDRVKASDE LLLNEIYFQA KKLKQKASSE LEKLESSKKL DEVIANSQLS QILKSQHTNG
 601 IFEQGTFLHL VCKYYKQRQR ARDSRLYIMP EYRYDKKLHK YNNTGRFDDD NQLLTYCNHK
 661 PRQKRYQLLN DLAGVLQVSP NFLKDKIGSD DDLFISKWLV EHIRGFKKAC EDSLKIQKDN
 721 RGLLNHKINI ARNTKGKCEK EIFNLICKIE GSEDKKGNYK HGLAYELGVL LFGEPNEASK
 781 PEFDRKIKKF NSIYSFAQIQ QIAFAERKGN ANTCAVCSAD NAHRMQQIKI TEPVEDNKDK
 841 IILSAKAQRL PAIPTRIVDG AVKKMATILA KNIVDDNWQN IKQVLSAKHQ LHIPIITESN
 901 AFEFEPALAD VKGKSLKDRR KKALERISPE NIFKDKNNRI KEFAKGISAY SGANLTDGDF
 961 DGAKEELDHI IPRSHKKYGT LNDEANLICV TRGDNKNKGN RIFCLRDLAD NYKLKQFETT
1021 DDLEIEKKIA DTIWDANKKD FKFGNYRSFI NLTPQEQKAF RHALFLADEN PIKQAVIRAI
1081 NNRNRTFVNG TQRYFAEVLA NNIYLRAKKE NLNTDKISFD YFGIPTIGNG RGIAEIRQLY
1141 EKVDSDIQAY AKGDKPQASY SHLIDAMLAF CIAADEHRND GSIGLEIDKN YSLYPLDKNT
1201 GEVFTKDIFS QIKITDNEFS DKKLVRKKAI EGFNTHRQMT RDGIYAENYL PILIHKELNE
1261 VRKGYTWKNS EEIKIFKGKK YDIQQLNNLV YCLKFVDKPI SIDIQISTLE ELRNILTTNN
1321 IAATAEYYYI NLKTQKLHEY YIENYNTALG YKKYSKEMEF LRSLAYRSER VKIKSIDDVK
1381 QVLDKDSNFI IGKITLPFKK EWQRLYREWQ NTTIKDDYEF LKSFFNVKSI TKLHKKVRKD
1441 FSLPISTNEG KFLVKRKTWD NNFIYQILND SDSRADGTKP FIPAFDISKN EIVEAIIDSF
1501 TSKNIFWLPK NIELQKVDNK NIFAIDTSKW FEVETPSDLR DIGIATIQYK IDNNSRPKVR
1561 VKLDYVIDDD SKINYFMNHS LLKSRYPDKV LEILKQSTII EFESSGFNKT IKEMLGMKLA
1621 GIYNETSNN
```

FIG. 8D

SEQ ID NO:114
UniProtKB/Swiss-Prot: G3ECR1.2
RecName: Full=CRISPR-associated endonuclease Cas9
[Streptococcus thermophilus]

```
   1 MLFNKCIIIS INLDFSNKEK CMTKPYSIGL DIGTNSVGWA VITDNYKVPS KKMKVLGNTS
  61 KKYIKKNLLG VLLFDSGITA EGRRLKRTAR RRYTRRRNRI LYLQEIFSTE MATLDDAFFQ
 121 RLDDSFLVPD DKRDSKYPIF GNLVEEKVYH DEFPTIYHLR KYLADSTKKA DLRLVYLALA
 181 HMIKYRGHFL IEGEFNSKNN DIQKNFQDFL DTYNAIFESD LSLENSKQLE EIVKDKISKL
 241 EKKDRILKLF PGEKNSGIFS EFLKLIVGNQ ADFRKCFNLD EKASLHFSKE SYDEDLETLL
 301 GYIGDDYSDV FLKAKKLYDA ILLSGFLTVT DNETEAPLSS AMIKRYNEHK EDLALLKEYI
 361 RNISLKTYNE VFKDDTKNGY AGYIDGKTNQ EDFYVYLKNL LAEFEGADYF LEKIDREDFL
 421 RKQRTFDNGS IPYQIHLQEM RAILDKQAKF YPFLAKNKER IEKILTFRIP YYVGPLARGN
 481 SDFAWSIRKR NEKITPWNFE DVIDKESSAE AFINRMTSFD LYLPEEKVLP KHSLLYETFN
 541 VYNELTKVRF IAESMRDYQF LDSKQKKDIV RLYFKDKRKV TDKDIIEYLH AIYGYDGIEL
 601 KGIEKQFNSS LSTYHDLLNI INDKEFLDDS SNEAIIEEII HTLTIFEDRE MIKQRLSKFE
 661 NIFDKSVLKK LSRRHYTGWG KLSAKLINGI RDEKSGNTIL DYLIDDGISN RNFMQLIHDD
 721 ALSFKKKIQK AQIIGDEDKG NIKEVVKSLP GSPAIKKGIL QSIKIVDELV KVMGGRKPES
 781 IVVEMARENQ YTNQGKSNSQ QRLKRLEKSL KELGSKILKE NIPAKLSKID NNALQNDRLY
 841 LYYLQNGKDM YTGDDLDIDR LSNYDIDHII PQAFLKDNSI DNKVLVSSAS NRGKSDDFPS
 901 LEVVKKRKTF WYQLLKSKLI SQRKFDNLTK AERGGLLPED KAGFIQRQLV ETRQITKHVA
 961 RLLDEKFNNK KDENNRAVRT VKIITLKSTL VSQFRKDFEL YKVREINDFH HAHDAYLNAV
1021 IASALLKKYP KLEPEFVYGD YPKYNSFRER KSATEKVYFY SNIMNIFKKS ISLADGRVIE
1081 RPLIEVNEET GESVWNKESD LATVRRVLSY PQVNVVKKVE EQNHGLDRGK PKGLFNANLS
1141 SKPKPNSNEN LVGAKEYLDP KKYGGYAGIS NSFAVLVKGT IEKGAKKKIT NVLEFQGISI
1201 LDRINYRKDK LNFLLEKGYK DIELIIELPK YSLFELSDGS RRMLASILST NNKRGEIHKG
1261 NQIFLSQKFV KLLYHAKRIS NTINENHRKY VENHKKEFEE LFYYILEFNE NYVGAKKNGK
1321 LLNSAFQSWQ NHSIDELCSS FIGPTGSERK GLFELTSRGS AADFEFLGVK IPRYRDYTPS
1381 SLLKDATLIH QSVTGLYETR IDLAKLGEG
```

FIG. 8E

SEQ ID NO:115
NCBI Reference Sequence: WP_011681470.1
CRISPR-associated endonuclease Cas9 2
[Streptococcus thermophilus]

```
   1 MTKPYSIGLD IGTNSVGWAV TTDNYKVPSK KMKVLGNTSK KYIKKNLLGV LLFDSGITAE
  61 GRRLKRTARR RYTRRRNRIL YLQEIFSTEM ATLDDAFFQR LDDSFLVPDD KRDSKYPIFG
 121 NLVEEKAYHD EFPTIYHLRK YLADSTKKAD LRLVYLALAH MIKYRGHFLI EGEFNSKNND
 181 IQKNFQDFLD TYNAIFESDL SLENSKQLEE IVKDKISKLE KKDRILKLFP GEKNSGIFSE
 241 FLKLIVGNQA DFRKCFNLDE KASLHFSKES YDEDLETLLG YIGDDYSDVF LKAKKLYDAI
 301 LLSGFLTVTD NETEAPLSSA MIKRYNEHKE DLALLKEYIR NISLKTYNEV FKDDTKNGYA
 361 GYIDGKTNQE DFYVYLKKLL AEFEGADYFL EKIDREDFLR KQRTFDNGSI PYQIHLQEMR
 421 AILDKQAKFY PFLAKNKERI EKILTFRIPY YVGPLARGNS DFAWSIRKRN EKITPWNFED
 481 VIDKESSAEA FINRMTSFDL YLPEEKVLPK HSLLYETFNV YNELTKVRFI AESMRDYQFL
 541 DSKQKKDIVR LYFKDKRKVT DKDIIEYLHA IYGYDGIELK GIEKQFNSSL STYHDLLNII
 601 NDKEFLDDSS NEAIIEEIIH TLTIFEDREM IKQRLSKFEN IFDKSVLKKL SRRHYTGWGK
 661 LSAKLINGIR DEKSGNTILD YLIDDGISNR NFMQLIHDDA LSFKKKIQKA QIIGDEDKGN
 721 IKEVVKSLPG SPAIKKGILQ SIKIVDELVK VMGGRKPESI VVEMARENQY TNQGKSNSQQ
 781 RLKRLEKSLK ELGSKILKEN IPAKLSKIDN NALQNDRLYL YYLQNGKDMY TGDDLDIDRL
 841 SNYDIDHIIP QAFLKDNSID NKVLVSSASN RGKSDDVPSL EVVKKRKTFW YQLLKSKLIS
 901 QRKFDNLTKA ERGGLSPEDK AGFIQRQLVE TRQITKHVAR LLDEKFNNKK DENNRAVRTV
 961 KIITLKSTLV SQFRKDFELY KVREINDFHH AHDAYLNAVV ASALLKKYPK LEPEFVYGDY
1021 PKYNSFRERK SATEKVYFYS NIMNIFKKSI SLADGRVIER PLIEVNEETG ESVWNKESDL
1081 ATVRRVLSYP QVNVVKKVEE QNHGLDRGKP KGLFNANLSS KPKPNSNENL VGAKEYLDPK
1141 KYGGYAGISN SFTVLVKGTI EKGAKKKITN VLEFQGISIL DRINYRKDKL NFLLEKGYKD
1201 IELIIELPKY SLFELSDGSR RMLASILSTN NKRGEIHKGN QIFLSQKFVK LLYHAKRISN
1261 TINENHRKYV ENHKKEFEEL FYYILEFNEN YVGAKKNGKL LNSAFQSWQN HSIDELCSSF
1321 IGPTGSERKG LFELTSRGSA ADFEFLGVKI PRYRDYTPSS LLKDATLIHQ SVTGLYETRI
1381 DLAKLGEG
```

FIG. 8F

SEQ ID NO:116
UniProtKB/Swiss-Prot: Q927P4.1
RecName: Full=CRISPR-associated endonuclease Cas9
Listeria innocua Clip11262
```
   1 MKKPYTIGLD IGTNSVGWAV LTDQYDLVKR KMKIAGDSEK KQIKKNFWGV RLFDEGQTAA
  61 DRRMARTARR RIERRRNRIS YLQGIFAEEM SKTDANFFCR LSDSFYVDNE KRNSRHPFFA
 121 TIEEEVEYHK NYPTIYHLRE ELVNSSEKAD LRLVYLALAH IIKYRGNFLI EGALDTQNTS
 181 VDGIYKQFIQ TYNQVFASGI EDGSLKKLED NKDVAKILVE KVTRKEKLER ILKLYPGEKS
 241 AGMFAQFISL IVGSKGNFQK PFDLIEKSDI ECAKDSYEED LESLLALIGD EYAELFVAAK
 301 NAYSAVVLSS IITVAETETN AKLSASMIER FDTHEEDLGE LKAFIKLHLP KHYEEIFSNT
 361 EKHGYAGYID GKTKQADFYK YMKMTLENIE GADYFIAKIE KENFLRKQRT FDNGAIPHQL
 421 HLEELEAILH QQAKYYPFLK ENYDKIKSLV TFRIPYFVGP LANGQSEFAW LTRKADGEIR
 481 PWNIEEKVDF GKSAVDFIEK MTNKDTYLPK ENVLPKHSLC YQKYLVYNEL TKVRYINDQG
 541 KTSYFSGQEK EQIFNDLFKQ KRKVKKKDLE LFLRNMSHVE SPTIEGLEDS FNSSYSTYHD
 601 LLKVGIKQEI LDNPVNTEML ENIVKILTVF EDKRMIKEQL QQFSDVLDGV VLKKLERRHY
 661 TGWGRLSAKL LMGIRDKQSH LTILDYLMND DGLNRNLMQL INDSNLSFKS IIEKEQVTTA
 721 DKDIQSIVAD LAGSPAIKKG ILQSLKIVDE LVSVMGYPPQ TIVVEMAREN QTTGKGKNNS
 781 RPRYKSLEKA IKEFGSQILK EHPTDNQELR NNRLYLYYLQ NGKDMYTGQD LDIHNLSNYD
 841 IDHIVPQSFI TDNSIDNLVL TSSAGNREKG DDVPPLEIVR KRKVFWEKLY QGNLMSKRKF
 901 DYLTKAERGG LTEADKARFI HRQLVETRQI TKNVANILHQ RFNYEKDDHG NTMKQVRIVT
 961 LKSALVSQFR KQFQLYKVRD VNDYHHAHDA YLNGVVANTL LKVYPQLEPE FVYGDYHQFD
1021 WFKANKATAK KQFYTNIMLF FAQKDRIIDE NGEILWDKKY LDTVKKVMSY RQMNIVKKTE
1081 IQKGEFSKAT IKPKGNSSKL IPRKTNWDPM KYGGLDSPNM AYAVVIEYAK GKNKLVFEKK
1141 IIRVTIMERK AFEKDEKAFL EEQGYRQPKV LAKLPKYTLY ECEEGRRRML ASANEAQKGN
1201 QQVLPNHLVT LLHHAANCEV SDGKSLDYIE SNREMFAELL AHVSEFAKRY TLAEANLNKI
1261 NQLFEQNKEG DIKAIAQSFV DLMAFNAMGA PASFKFFETT IERKRYNNLK ELLNSTIIYQ
1321 SITGLYESRK RLDD
```

FIG. 8G

SEQ ID NO:117
UniProtKB/Swiss-Prot: Q7MRD3
CRISPR-associated endonuclease Cas9
Wolinella succinogenes
```
   1 MIERILGVDL GISSLGWAIV EYDKDDEAAN RIIDCGVRLF TAAETPKKKE SPNKARREAR
  61 GIRRVLNRRR VRMNMIKKLF LRAGLIQDVD LDGEGGMFYS KANRADVWEL RHDGLYRLLK
 121 GDELARVLIH IAKHRGYKFI GDDEADEESG KVKKAGVVLR QNFEAAGCRT VGEWLWRERG
 181 ANGKKRNKHG DYEISIHRDL LVEEVEAIFV AQQEMRSTIA TDALKAAYRE IAFFVRPMQR
 241 IEKMVGHCTY FPEERRAPKS APTAEKFIAI SKFFSTVIID NEGWEQKIIE RKTLEELLDF
 301 AVSREKVEFR HLRKFLDLSD NEIFKGLHYK GKPKTAKKRE ATLFDPNEPT ELEFDKVEAE
 361 KKAWISLRGA AKLREALGNE FYGRFVALGK HADEATKILT YYKDEGQKRR ELTKLPLEAE
 421 MVERLVKIGF SDFLKLSLKA IRDILPAMES GARYDEAVLM LGVPHKEKSA ILPPLNKTDI
 481 DILNPTVIRA FAQFRKVANA LVRKYGAFDR VHFELAREIN TKGEIEDIKE SQRKNEKERK
 541 EAADWIAETS FQVPLTRKNI LKKRLYIQQD GRCAYTGDVI ELERLFDEGY CEIDHILPRS
 601 RSADDSFANK VLCLARANQQ KTDRTPYEWF GHDAARWNAF ETRTSAPSNR VRTGKGKIDR
 661 LLKKNFDENS EMAFKDRNLN DTRYMARAIK TYCEQYWVFK NSHTKAPVQV RSGKLTSVLR
 721 YQWGLESKDR ESHTHHAVDA IIIAFSTQGM VQKLSEYYRF KETHREKERP KLAVPLANFR
 781 DAVEEATRIE NTETVKEGVE VKRLLISRPP RARVTGQAHE QTAKPYPRIK QVKNKKKWRL
 841 APIDEEKFES FKADRVASAN QKNFYETSTI PRVDVYHKKG KFHLVPIYLH EMVLNELPNL
 901 SLGTNPEAMD ENFFKFSIFK DDLISIQTQG TPKKPAKIIM GYFKNMHGAN MVLSSINNSP
 961 CEGFTCTPVS MDKKHKDKCK LCPEENRIAG RCLQGFLDYW SQEGLRPPRK EFECDQGVKF
1021 ALDVKKYQID PLGYYYEVKQ EKRLGTIPQM RSAKKLVKK
```

FIG. 8H crRNA (first portion)

| | | |
|---|---|---|
| S. pyogenes | GUUUUAGAGCUAUG-CUGUUUUGAAU-GGUCCCAAAAC | (SEQ ID NO:20) |
| L. innocua | GUUUUAGAGCUAUG-UUAUUUUGAAU-GCUAACAAAAC | (SEQ ID NO:21) |
| S. thermophilus 1 | GUUUUAGAGCUGUG-UUGUUUCGAAU-GGUUCCAAAAC | (SEQ ID NO:22) |
| S. thermophilus 2 | GUUUUUGUACUCUC-AAGAUUUAAGU-AACUGUACAAC | (SEQ ID NO:23) |
| F. novicida | CUAACAGUAGUUA-CCAAAUAAUUCAGCAACUGAAAC | (SEQ ID NO:24) |
| W. succinogenes | GCAACACUU-UAUAGCAAAUCCGCUUAGCCUGUGAAAC | (SEQ ID NO:25) |
| Consen. 1st seq. A | XXXXXXXXXXUXUXXXXXXXXXXXXXXXXXXXXXAAC | (SEQ ID NO:26) |
| Consen. 1st seq. B | XXXXXXXXXXUX | (SEQ ID NO:27) |
| Consen. 1st seq. C | XXXXXXXXXXUXUXXX | (SEQ ID NO:28) |

| | | |
|---|---|---|
| S. pyogenes | GUUUUAGAGCUAUGCUGUUUUGAAUGGUCCCAAAAC | (SEQ ID NO:20) |
| L. innocua | GUUUUAGAGCUAUGUUAUUUUGAAUGCUAACAAAAC | (SEQ ID NO:21) |
| S. thermophilus 1 | GUUUUAGAGCUGUGUUGUUUCGAAUGGUUCCAAAAC | (SEQ ID NO:22) |
| S. thermophilus 2 | GUUUUUGUACUCUCAAGAUUUAAGUAACUGUACAAC | (SEQ ID NO:23) |
| Consens. 1st seq. D | GUUUUXGXXCUXUXXXXXUUXXAXUXXXXXXAXAAC | (SEQ ID NO:29) |
| Consens. 1st seq. E | GUUUUXGXXCUX | (SEQ ID NO:30) |

| | | |
|---|---|---|
| F. novicida | CUAACAGUAGUUUACCAAAU-AAUUCAGCAACUGAAAC | (SEQ ID NO:24) |
| W. succinogenes | GCAACACUU-UAUAGCAAAUCCGCUUAGCCUGUGAAAC | (SEQ ID NO:25) |
| Consens. 1st seq. F | XXAACAXUXXUXUAXCAAAUXXXXUXAXCXXXUGAAAC | (SEQ ID NO:31) |
| Consens. 1st seq. G | XXAACAXUXXUXUAXC | (SEQ ID NO:32) |

FIG. 9 tracrRNA (second portion)

```
S. pyogenes      UUGUUGGAAC-CAUUCAA--AAC---AGCAUAGCAAGUUAAA    (SEQ ID NO:40)
L. innocua       AUAUUGUUAG-UAUUCAA--AAU---AACAUAGCAAGUUAAA    (SEQ ID NO:41)
S. thermophilus 1 GGUUUGAAAC-CAUUCGA--AAC---AACACAGCGAGUUAAA   (SEQ ID NO:42)
S. thermophilus 2 CUU-ACACAGUUACUUA---AAUCUUGCAGAAGCUA-CAAA    (SEQ ID NO:43)
F. novicida 1    GUU-UCAGU--UGUUAGA-UUAUUUGGUAUGUACUUGUGUU     (SEQ ID NO:44)
F. novicida 2    AUU-ACAGAG-CAUU-AA-UUAUUUGGUACAUUUAUAAUUU     (SEQ ID NO:45)
W. succinogenes 1 UUU--CAAGG-CAUCGAACGGAUUUGCUAUAAAGUG-UUGC    (SEQ ID NO:46)
W. succinogenes 2 UUUGUUAAAG-C-UGGAUGGGAUU-AUUAUAGAGUG-UUGC    (SEQ ID NO:47)
Consen. 2nd seq. A ZZZZZZZZZZZZZZZZZZZZZZZAZZZZZAZZZZZZZZZZZ   (SEQ ID NO:48)
Consen. 2nd seq. B                            ZAZZZZZZZZZZZZ   (SEQ ID NO:49)
Consen. 2nd seq. C                              ZZZZZZZZZZZZ   (SEQ ID NO:50)
```

FIG. 10A

```
S. pyogenes      UUGUUGGAACCAUCAAAACAGCAUAGCAAGU-UAAA    (SEQ ID NO:40)
L. innocua       AUAUUGUUAGUAUCAAAAUAACAUAGCAAGU-UAAA    (SEQ ID NO:41)
S. thermophilus 1 GGUUUGAAACCAUCGAAACAACACAGCGAGU-UAAA   (SEQ ID NO:42)
S. thermophilus 2 CUUACACAGUUACUUAAAUC-UUGCAGAAGCUACAAA   (SEQ ID NO:43)
Consen. 2nd seq. D ZZZZZZZZZZAZUZZAAZZZZZZAGZZZZUZZAAA   (SEQ ID NO:51)
Consen. 2nd seq. E                       ZAGZZZZUZZAAA   (SEQ ID NO:52)
```

FIG. 10B

```
F. novicida 1    GUUCAGUUGUUAG-AU-UAUUUGGUAUGUACUUGUGUU    (SEQ ID NO:44)
F. novicida 2    AUUACAGAGCAUUA-AU-UAUUUGGUACAUUUAUAAUUU   (SEQ ID NO:45)
W. succinogenes 1 U-UUCAAGGCAUCGAACGGAUUUGCUAUAAAG-UUGC    (SEQ ID NO:46)
W. succinogenes 2 UUUGUUAAAGCUGG-AUGGGAUUAUUAUAGAG-UUGC    (SEQ ID NO:47)
Consen. 2nd seq. F ZZUZZZZZZZUZZAZZZZUUZZUAZZZZZUZZZZZ      (SEQ ID NO:53)
Consen. 2nd seq. G                    ZZUAZZZZZUZZZZZ      (SEQ ID NO:54)
```

FIG. 10C

```
Long tracrRNA (second portion)

S. pyogenes              ------GU----UGGAA------CCAUUCAAAACAGCAU------AGC--
L. innocua               AU---AU----UGUUA------GUAUUCAAAAUAACAU------AGC--
S. thermophilus 1        UU---GUGGUUUGAAA------CCAUUCGAAACAACAC------AGC--
S. thermophilus 2        UAAUAAUAG--UGUAAGGGACGCCUUACACAGUUACUUAAAUCUUGCAG
Consen. tracRNA seq. A   ZZZZZZUZZZZUGZZAZZZZZZZZZUZCZZAZZZZCZZZZZZZZGCZZ
Consen. tracRNA seq. B                                             ZZZZZZZZGCZZ S. pyogenes              AAGUUA---AAAUAAGGCU-AGU-CCGUUAUCAAC---UUGAAA--AAG
L. innocua               AAGUUA---AAAUAAGGCUUUGU-CCGUUAUCAAC---UUUUAAUUAAG
S. thermophilus 1        GAGUUA---AAAUAAGGCUUAGU-CCGUACUCAAC---UUGAAA--AGG
S. thermophilus 2        AAGCUACAAAGAUAAGGCUUCAUGCCGAAAUCAACACCCUGUCAUUUUA
Consen. tracRNA seq. A   ZAGZUAZZZAZAUAAGGCUZZZUZCCGZZZUCAACZZZZUZZZAZZZZZ
Consen. tracRNA seq. B   ZAGZUAZZZAZAUAAGGCUZZZUZCCG S. pyogenes              UGGCACCGAGUCGGUGCUUUUUU    (SEQ ID NO:60)
L. innocua               UAGCGCUGUUUCGGCGCUUUUUU    (SEQ ID NO:61)
S. thermophilus 1        UGGCACCGAUUCGGUGUUUUUUU    (SEQ ID NO:62)
S. thermophilus 2        UGGCAGGGUGUUUUCG-UUAUUU    (SEQ ID NO:63)
Consen. tracRNA seq. A   UZGCZZZGZZUZZZZGZUUZUUU    (SEQ ID NO:64)
Consen. tracRNA seq. B                              (SEQ ID NO:65)
```

FIG. 11

| Genus | | A | -L- | B | | |
|---|---|---|---|---|---|---|
| Sp var. 1 | | GUUUUAGAGCUA | -L- | UAGCAAGUUAAAAUAAGGCUAGUCCG | SEQ ID NO:80 |
| Cons. var. 1 | | XXXXXXXXXXXUXUXXXXXXXXXXXXAAC | -L- | ZZZZZZZZZZZZZZZZZZAZZZZZZZZAZZZZZZZZAZZZZZZZZZZZ | SEQ ID NO:81 |
| Cons. var. 2A | | XXXXXXXXXUX | -L- | ZAZZZZZZZZZZZZZ | SEQ ID NO:82 |
| Cons. var. 2B | | XXXXXXXXXUXUXXX | -L- | ZAZZZZZZZZZZZZZ | SEQ ID NO:83 |
| Cons. var. 3A | | XXXXXXXXXXUX | -L- | ZZZZZZZZGCZZZZAGZUAZZZAZZAZAUAAGGCUZZZZUXCCG | SEQ ID NO:84 |
| Cons. var. 3A | | XXXXXXXXXUXUXXX | -L- | ZZZZZZZZGCZZZZAGZUAZZZAZZAZAUAAGGCUZZZZUXCCG | SEQ ID NO:85 |
| Sp var. 2 | | GUUUUXGXXCUXUXXXXUXXAXUXXXXAXAAC | -L- | ZZZZZZZZZZZAZUZZAAZZZZZZZAGZZZZUZZAAA | SEQ ID NO:86 |
| Sp var. 3 | | GUUUXGXXCUX | -L- | ZZZZZZZZZZZAZUZZAAUZZZZZZZAGZZZZUZZAAA | SEQ ID NO:87 |
| Sp var. 4 | | GUUUXGXXCUX | -L- | ZAGZZZUZZAAA | SEQ ID NO:88 |
| Sp var. 5 | | GUUUXGXXCUX | -L- | ZZZZZZZZGCZZZAGZUAZZZAZAUAAGGCUZZZUZZAAA | SEQ ID NO:89 |
| Fn var. 1 | | XXAACAXUXXUXUAXCAAAUXXUXAXCXXXUGAAAC | -L- | ZZZZZZZZZAZUZZAZZZZZAGZZZZUZZAAA | SEQ

SEQ ID NO:100
nnnnnnnnnn nnnnnnnnnn nnnnnnnnnn nnnnnnnnnn nnnnnnnnnn nnnnnnnnnn    60
nnnnnnnnnn nnnnnnnnnn guuuuagagc uannnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnuagcaagu uaaaauaagg cuaguccg                           218 where n at each of positions 1-80 can be present or absent such that this
region can contain anywhere from 12 to 80 nucleotides and n is a, c, t, g, u,
or modified forms thereof; and where n at each of positions 93-192 can be
present or absent such that this region can contain anywhere from 3 to 100
nucleotides and n is a, c, t, g, u, or modified forms thereof

SEQ ID NO:101
nnnnnnnnnn nnnnnnnnnn nnnnnnnnnn nnnnnnnnnn nnnnnnnnnn nnnnnnnnnn    60
nnnnnnnnnn nnnnnnnnnn guuuuagagc uannnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnuagcaagu uaaaauaagg cuuuguccg                          219 where n at each of positions 1-80 can be present or absent such that this
region can contain anywhere from 12 to 80 nucleotides and n is a, c, t, g, u,
or modified forms thereof; and where n at each of positions 93-192 can be
present or absent such that this region can contain anywhere from 3 to 100
nucleotides and n is a, c, t, g, u, or modified forms thereof

SEQ ID NO:102
nnnnnnnnnn nnnnnnnnnn nnnnnnnnnn nnnnnnnnnn nnnnnnnnnn nnnnnnnnnn    60
nnnnnnnnnn nnnnnnnnnn guuuuagagc uagaaauagc aaguuaaaau aaggcuaguc   120
cguuaucaac uugaaaaagu ggcaccgagu cggugcuuuu uuu                     163 where n at each of positions 1-80 can be present or absent such that this
region can contain anywhere from 12 to 80 nucleotides and n is a, c, t, g, u,
or modified forms thereof

SEQ ID NO:103
nnnnnnnnnn nnnnnnnnnn nnnnnnnnnn nnnnnnnnnn nnnnnnnnnn nnnnnnnnnn    60
nnnnnnnnnn nnnnnnnnnn guuuuagagc uagaaauagc aaguuaaaau aaggcuaguc   120
cguuaucaac uugaaaaagu ggcaccgagu cggugcuuuu uuu                     163
where n at each of positions 1-80 can be present or absent such that this
region can contain anywhere from 12 to 80 nucleotides and n is a, c, t, g, u,
or modified forms thereof

FIG. 13

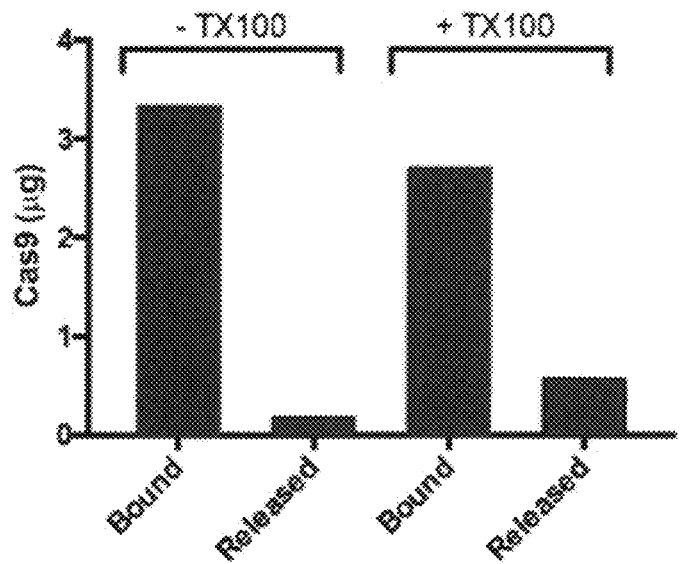
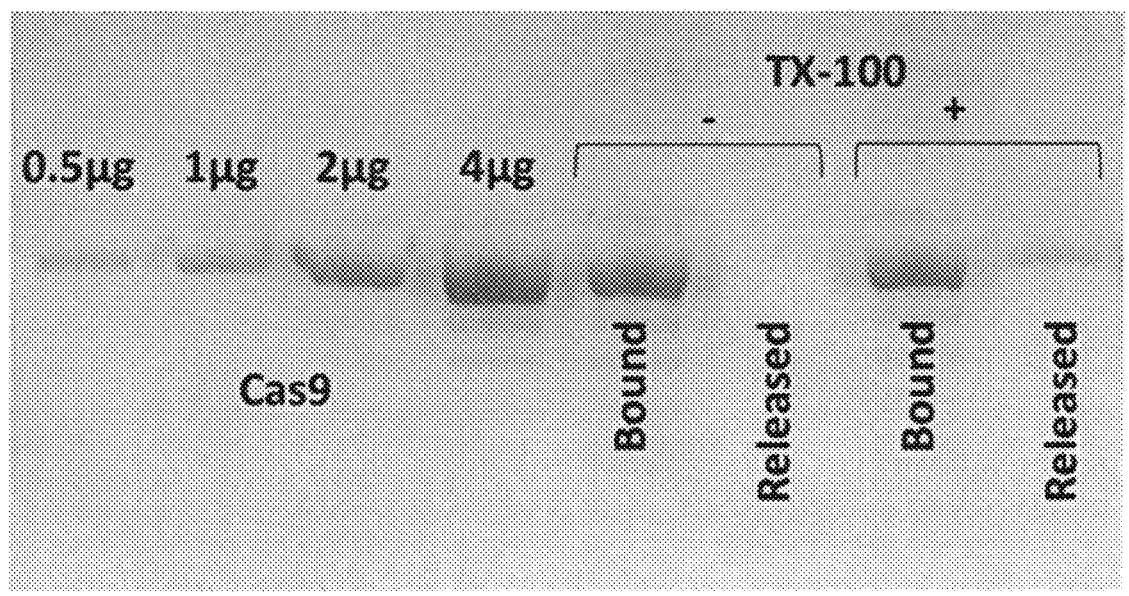
FIG. 16

LIPID COMPOSITION FOR THE DELIVERY OF THERAPEUTIC CARGOS

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD15013_ST25.txt," created on Apr. 1, 2020 (size of 164 kilobytes), which is hereby incorporated by reference in its entirety.

FIELD

This disclosure relates to a blend of coating materials for a nanoparticle with a gene-editing agent payload.

BACKGROUND

CRISPR (clustered, regularly interspaced, short 37 palindromic repeats)/Cas9 is a bacterial derived gene editing system that has been repurposed to edit specifically targeted sequences opening a new avenue with enormous unrealized implications in health, disease prevention, diagnosis, and treatment. Efficient intracellular delivery of CRISPR-Cas9 remains a hurdle in the advancement of this technology. Porous nanoparticles are an attractive delivery vehicle for a variety of cargos including small molecule drugs and proteins due to the low toxicity, high biocompatibility, facile synthesis and amenability to chemical functionalization.

However, efficacious delivery of therapeutic agents such as CRISPR-Cas9 still remains a challenge for certain classes of agents. For instance, due to delivery efficiency, certain coatings and gene-editing agents display effectiveness in cellular assays but show reduced efficacy in vivo. In addition, different coatings will interact differently with different types of particles and gene-editing agent payloads. Thus, there is a need for additional delivery constructs that can be configured to accommodate such agents.

SUMMARY

The present disclosure relates, in part, to a biocompatible, non-toxic construct including a core, a cargo, and a coating. The present disclosure demonstrates a tailored coating layer resulting in an improved and efficient delivery of CRISPR/Cas9 using a lipid coated mesoporous silica nanoparticle resulting in editing in over 30% of target cells in vitro.

In some embodiments, the core is a mesoporous nanoparticle (e.g., a mesoporous silica nanoparticle). In particular embodiments, the core has a dimension (e.g., a diameter, a width, or a length, or an effective average particle size) greater than about 50 nm (e.g., from about 50 nm to 300 nm, 50 nm to 100 nm, 50 nm to 150 nm, 50 nm to 200 nm, 50 nm to 250 nm, 75 nm to 100 nm, 75 nm to 150 nm, 75 nm to 200 nm, 75 nm to 250 nm, 75 nm to 300 nm, 100 nm to 150 nm, 100 nm to 200 nm, 100 nm to 250 nm, 100 nm to 300 nm, 125 nm to 150 nm, 125 nm to 200 nm, 125 nm to 250 nm, 125 nm to 300 nm, 150 nm to 200 nm, 150 nm to 250 nm, 150 nm to 300 nm, 175 nm to 200 nm, 175 nm to 250 nm, 175 nm to 300 nm, 200 nm to 250 nm, 200 nm to 300 nm, 225 nm to 250 nm, 225 nm to 300 nm, 250 nm to 300 nm, or 275 nm to 300 nm).

In particular embodiments, the core includes a plurality of pores, in which an average dimension of the pores is sufficiently large enough to accommodate a large cargo. In some embodiments, the average dimension is greater than about 2 nm, (e.g., of from about 5 nm to 35 nm, including from 5 nm to 10 nm, 5 nm to 15 nm, 5 nm to 20 nm, 5 nm to 25 nm, 5 nm to 30 nm, 8 nm to 10 nm, 8 nm to 15 nm, 8 nm to 20 nm, 8 nm to 25 nm, 8 nm to 30 nm, 8 nm to 35 nm, 10 nm to 15 nm, 10 nm to 20 nm, 10 nm to 25 nm, 10 nm to 30 nm, 10 nm to 35 nm, 12 nm to 15 nm, 12 nm to 20 nm, 12 nm to 25 nm, 12 nm to 30 nm, 12 nm to 35 nm, 15 nm to 20 nm, 15 nm to 25 nm, 15 nm to 30 nm, 15 nm to 35 nm, 18 nm to 20 nm, 18 nm to 25 nm, 18 nm to 30 nm, 18 nm to 35 nm, 20 nm to 25 nm, 20 nm to 30 nm, 20 nm to 35 nm, 25 nm to 30 nm, 25 nm to 35 nm, or 30 nm to 35 nm).

The cargo is, for example, an mRNA or a CRISPR component, such as any described herein. Exemplary CRISPR components include a Cas protein, a guide nucleic acid, a plasmid, as well as combinations thereof (e.g., a ribonucleoprotein complex). In some embodiments, an average dimension of the pores is greater than a dimension of the cargo. In other embodiments, an average dimension of the pores is smaller than a dimension of the cargo.

The construct further includes an outer layer or coating. An exemplary coating includes a cationic lipid, a zwitterionic lipid, a PEGylated lipid, and a sterol.

In a second aspect, a formulation including a plurality of constructs (e.g., any described herein) is disclosed along with a pharmaceutically acceptable excipient.

In a third aspect, a construct includes: a core comprising an external surface and a plurality of pores, wherein an average dimension of the plurality of pores is greater than about 2 nm. It also includes a cargo disposed in a pore of the plurality of pores, the cargo comprising one or more selected from the group consisting of: peptides, proteins, nucleic acids, mRNA, aptamers, antibodies, pharmaceuticals, carbohydrates, dyes, and markers. It also includes a coating coupled to the core, wherein the coating comprises a cationic lipid, a pegylated lipid, a zwitterionic lipid, and a sterol. The coating comprises a molar ratio of about 1 cationic lipid to 1 zwitterionic lipid to 0.9 sterol to 0.15 PEGylated lipid, wherein each molar ratio optionally varies by about plus or minus 10%. The cationic lipid is 1,2-dioleoyl-3-trimethyl-ammonium-propane, the zwitterionic lipid is 1,2-dioleoyl-sn-glycero-3-phosphoethanolamine, the sterol is cholesterol, and the PEGylated lipid is 1,2-distearoyl-sn-glycero-3-phosphoethanolamine-N-[methoxy-(polyethylene glycol)-2000].

In a fourth aspect, the present disclosure features a method of treating a subject, the method including: administering to a subject in need thereof, an effective amount of a construct, the construct including: a core comprising an external surface and a plurality of pores, wherein an average dimension of the plurality of pores is greater than about 2 nm; a cargo disposed in a pore of the plurality of pores, the cargo comprising a CRISPR Cas9 component or a nucleic acid sequence encoding a CRISPR Cas9 component; and a coating coupled to the core. The coating comprises a cationic lipid, a pegylated lipid, a zwitterionic lipid, and a sterol.

In a fifth aspect, the disclosure features a method of forming the construct.

Definitions

As used herein, the term "about" means +/−10% of any recited value. As used herein, this term modifies any recited value, range of values, or endpoints of one or more ranges.

By "micro" is meant having at least one dimension that is less than 1 mm but equal to or larger than 1 μm. For instance, a microstructure (e.g., any structure described herein, such as a microparticle) can have a length, width, height, cross-sectional dimension, circumference, radius (e.g., external or internal radius), or diameter that is less than 1 mm but equal to or larger than 1 μm. In another instance, the microstructure has a dimension that is of from about 1 μm to 1 mm.

By "nano" is meant having at least one dimension that is less than 1 m but equal to or larger than 1 nm. For instance, a nanostructure (e.g., any structure described herein, such as a nanoparticle) can have a length, width, height, cross-sectional dimension, circumference, radius (e.g., external or internal radius), or diameter that is less than 1 m but equal to or larger than 1 nm. In another instance, the nanostructure has a dimension that is of from about 1 nm to about 1 μm.

The term "cargo" is used herein to describe a molecule or compound, whether a small molecule or macromolecule having an activity relevant to its use in particles (e.g., a construct, a nanoparticle, or a mesoporous silica nanoparticle), especially including biological activity, that can be included in or with particles according to the present disclosure. In principal embodiments of the present disclosure, the cargo is a nucleic acid sequence, such as double stranded (ds) plasmid DNA. The cargo may be included within the pores, associated with the pore (e.g., by way of a spacer), and/or on the surface of the core (e.g., by way of a spacer) according to the present disclosure. Additional representative cargo may include, for example, a small molecule bioactive agent, a nucleic acid (e.g., RNA or DNA), a polypeptide, including a protein or a carbohydrate. Particular examples of such cargo include RNA, such as mRNA, siRNA, shRNA micro RNA, a polypeptide or protein, including a protein toxin (e.g., ricin toxin A-chain or diphtheria toxin A-chain), and/or DNA (including double stranded or linear DNA, complementary DNA (cDNA), minicircle DNA, naked DNA and plasmid DNA, which optionally may be supercoiled and/or packaged (e.g., with histones) and which may be optionally modified with a nuclear localization sequence). Cargo may also include a reporter as described herein.

The phrase "effective average particle size" as used herein to describe a multiparticulate (e.g., a porous nanoparticulate) means that at least 50% of the particles therein are of a specified size. Accordingly, "effective average particle size of less than about 2,000 nm in diameter" means that at least 50% of the particles therein are less than about 2,000 nm in diameter. In certain embodiments, nanoparticulates have an effective average particle size of less than about 2,000 nm (i.e., 2 microns), less than about 1,900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods. In certain aspects of the present disclosure, the particles are monodisperse and generally no greater than about 50 nm in average diameter, often less than about 30 nm in average diameter, as otherwise described herein. The term "$D_{50}$" refers to the particle size below which 50% of the particles in a multiparticulate fall. Similarly, the term "$D_{90}$" refers to the particle size below which 90% of the particles in a multiparticulate fall.

The term "monodisperse" is used as a standard definition established by the National Institute of Standards and Technology (NIST) (*Particle Size Characterization*, Special Publication 960-1, January 2001) to describe a distribution of particle size (diameter) within a population of particles, in this case nanoparticles, which particle distribution may be considered monodisperse if at least 90% of the distribution lies within 5% of the median size, measured by dynamic light scattering (DLS) that calculates particles hydrodynamic diameter and polydispersity index (PDI) using a Malvern Zetasizer. See, e.g., LaBauve, et al, *Lipid-Coated Mesoporous Silica Nanoparticles for the Delivery of the ML336 Antiviral to Inhibit Encephalitic Alphavirus Infection*, Sci Rep. 2018; 8: 13990, 2018 Sep. 18. doi: 10.1038/s41598-018-32033-w, incorporated herein by reference for more information on measurement technique.

The term "lipid" is used to describe the components which are used to form lipid mono-, bi-, or multilayers on the surface of the particles (e.g., a core of the particle), that are used in the present disclosure (e.g., as constructs) and may include a PEGylated lipid. Various embodiments provide nanostructures, that are constructed from nanoparticles, which support one or more lipid layers (e.g., bilayer(s) or multilayer(s)).

The terms "targeting ligand" and "targeting active species" are used to describe a compound or moiety (e.g., an antigen), which is complexed or covalently bonded to the surface of a particle (e.g., either directly on an outer surface of a delivery platform or on an outer layer). The targeting ligand, in turn, binds to a moiety on the surface of a cell to be targeted so that the constructs may bind to the surface of the targeted cell, enter the cell or an organelle thereof, and/or deposit their contents into the cell. The targeting active species for use in the present disclosure may be a targeting peptide (e.g., a receptor ligand, a cell penetration peptide, a fusogenic peptide, or an endosomolytic peptide, as otherwise described herein), a polypeptide including an antibody or antibody fragment, an aptamer, or a carbohydrate, among other species that bind (e.g., selectively bind) to a targeted cell.

The term "reporter" is used to describe an imaging agent or moiety that is incorporated into the outer layer or cargo of particles according to an embodiment of the present disclosure and provides a signal that can be measured. The moiety may provide a fluorescent signal or may be a radioisotope which allows radiation detection, among others. Exemplary fluorescent labels for use in particles (e.g., via conjugation or adsorption to the outer layer or the core, via integration into the matrix of the core, and/or via incorporation into cargo elements such as DNA, RNA-sn-glycero-3-phosphoethanolamine (Texas Red® DHPE, 583/608), Alexa Fluor® 647 hydrazide (649/666), Alexa Fluor® 647 carboxylic acid, succinimidyl ester (650/668), Ulysis™ Alexa Fluor® 647 Nucleic Acid Labeling Kit (650/670), Alexa Fluor® 647 conjugate of annexin V (650/665), other fluorescent labels, colorimetric labels, quantum dots, nanoparticles, microparticles, barcodes, radio labels (e.g., RF labels or barcodes), avidin, biotin, tags, dyes, an enzyme that can optionally include one or more linking agents and/or one or more dyes, as well as combinations thereof, etc.). Additional reporters can include a detection agent (e.g., a dye, such as an electroactive detection agent, a fluorescent dye, a luminescent dye, a chemiluminescent dye, a colorimetric dye, a radioactive agent, a contrast agent, etc.), a particle (e.g., such as a microparticle, a nanoparticle, a latex bead, a colloidal particle, a magnetic particle, a fluorescent particle, etc.), and/or a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes). Moieties that enhance the fluorescent signal or slow the fluorescent fading may also be incorporated and include SlowFade® Gold antifade reagent (with and without DAPI) and Image-iT® FX signal enhancer. All of these are well known in the art.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs. In any nucleic acid described herein, U may be replaced with T and vice versa.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

A sugar modification may include, but is not limited to, a locked nucleic acid (LNA, in which the 2'-hydroxyl is connected by a $C_1$-6 alkylene or $C_1$-6 heteroalkylene bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides), the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary, according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with this disclosure. In certain embodiments, a polypeptide to be utilized in accordance with the disclosed technology includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the disclosed technology.

The term "conservative amino acid substitution" refers to the interchangeability in proteins of amino acid residues having similar side chains (e.g., of similar size, charge, and/or polarity). For example, a group of amino acids having aliphatic side chains consisting of glycine, alanine, valine, leucine, and isoleucine; a group of amino acids having aliphatic-hydroxyl side chains consisting of serine and threonine; a group of amino acids having amide containing side chains consisting of asparagine and glutamine; a group of amino acids having aromatic side chains consisting of phenylalanine, tyrosine, and tryptophan; a group of amino acids having basic side chains consisting of lysine, arginine, and histidine; a group of amino acids having acidic side chains consisting of glutamic acid and aspartic acid; and a group of amino acids having sulfur containing side chains consisting of cysteine and methionine. Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, such as, for example, 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

The term "chimeric" as used herein as applied to a nucleic acid or polypeptide refers to two components that are defined by structures derived from different sources. For example, where "chimeric" is used in the context of a chimeric polypeptide (e.g., a chimeric Cas9/Csn1 protein), the chimeric polypeptide includes amino acid sequences that are derived from different polypeptides. A chimeric polypeptide may comprise either modified or naturally occurring polypeptide sequences (e.g., a first amino acid sequence from a modified or unmodified Cas9/Csn1 protein; and a second amino acid sequence other than the Cas9/Csn1 protein). Similarly, "chimeric" in the context of a polynucleotide encoding a chimeric polypeptide includes nucleotide sequences derived from different coding regions (e.g., a first nucleotide sequence encoding a modified or unmodified Cas9/Csn1 protein; and a second nucleotide sequence encoding a polypeptide other than a Cas9/Csn1 protein).

The term "chimeric polypeptide" refers to a polypeptide that is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

"Heterologous," as used herein, means a nucleotide or polypeptide sequence that is not found in the native nucleic acid or protein, respectively. For example, in a chimeric Cas9/Csn1 protein, the RNA-binding domain of a naturally-occurring bacterial Cas9/Csn1 polypeptide (or a variant thereof) may be fused to a heterologous polypeptide sequence (i.e., a polypeptide sequence from a protein other than Cas9/Csn1 or a polypeptide sequence from another organism). The heterologous polypeptide sequence may exhibit an activity (e.g., enzymatic activity) that will also be exhibited by the chimeric Cas9/Csn1 protein (e.g., methyltransferase activity, acetyltransferase activity, kinase activity, ubiquitinating activity, etc.). A heterologous nucleic acid sequence may be linked to a naturally occurring nucleic acid sequence (or a variant thereof) (e.g., by genetic engineering) to generate a chimeric nucleotide sequence encoding a chimeric polypeptide. As another example, in a fusion variant Cas9 site-directed polypeptide, a variant Cas9 site-directed polypeptide may be fused to a heterologous polypeptide (i.e., a polypeptide other than Cas9), which exhibits an activity that will also be exhibited by the fusion variant Cas9 site-directed polypeptide. A heterologous nucleic acid sequence may be linked to a variant Cas9 site-directed polypeptide (e.g., by genetic engineering) to generate a nucleotide sequence encoding a fusion variant Cas9 site-directed polypeptide.

"Recombinant," as used herein, means that a particular nucleic acid, as defined herein, is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions and may indeed act to modulate production of a desired product by various mechanisms. Alternatively, DNA sequences encoding RNA (e.g., DNA-targeting RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention but may be a naturally occurring amino acid sequence.

A "target sequence" as used herein is a polynucleotide (e.g., as defined herein, including a DNA, RNA, or DNA/RNA hybrid, as well as modified forms thereof) that includes a "target site." The terms "target site" or "target protospacer DNA" are used interchangeably herein to refer to a nucleic acid sequence present in a target genomic sequence (e.g., DNA or RNA in a host cell) to which a targeting portion of the guiding component will bind provided sufficient conditions (e.g., sufficient complementarity) for binding exist. Suitable DNA/RNA binding conditions include physiological conditions normally present in a cell. Other suitable DNA/RNA binding conditions (e.g., conditions in a cell-free system) are known in the art; see, e.g., Sambrook, supra.

By "cleavage" it is meant the breakage of the covalent backbone of a target sequence (e.g., a nucleic acid molecule). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guiding component and a nuclease is used for targeted double-stranded DNA cleavage. In other embodiments, a complex comprising a guiding component and a nuclease is used for targeted single-stranded RNA cleavage.

"Nuclease" and "endonuclease" are used interchangeably herein to mean an enzyme which possesses catalytic activity for DNA cleavage and/or RNA cleavage.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

A "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

By "linker" or "spacer", unless otherwise indicated, is meant any useful multivalent (e.g., bivalent) component useful for joining to different portions or segments. Exemplary linkers and spacers include a nucleic acid sequence, a chemical linker, etc. In one instance, the linker of the guiding component (e.g., linker L in the interacting portion of the guiding component) can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single molecule guiding component is 4 nt.

The term "histone-packaged supercoiled plasmid DNA" is used to describe a component of particles according to the present disclosure that employ a plasmid DNA that has been "supercoiled" (i.e., folded in on itself using a supersaturated salt solution or other ionic solution which causes the plasmid to fold in on itself and "supercoil" in order to become more dense for efficient packaging into the particles). The plasmid may be virtually any plasmid that expresses any number of polypeptides or encode RNA, including small hairpin RNA/shRNA or small interfering RNA/siRNA, as otherwise described herein. Once supercoiled (using the concentrated salt or other anionic solution), the supercoiled plasmid DNA is then complexed with histone proteins to produce a histone-packaged "complexed" supercoiled plasmid DNA.

"Packaged" DNA herein refers to DNA that is loaded into particles (e.g., adsorbed into the pores, confined directly within the core itself, or confined partially within a pore). To minimize the DNA spatially, it is often packaged, which can be accomplished in several different ways, from adjusting the charge of the surrounding medium to creation of small complexes of the DNA with, for example, lipids, proteins, or other nanoparticles (usually, although not exclusively cationic). Packaged DNA is often achieved via lipoplexes (i.e., complexing DNA with cationic lipid mixtures). In addition, DNA has also been packaged with cationic proteins (including proteins other than histones), as well as gold nanoparticles (e.g., NanoFlares—an engineered DNA and metal complex in which the core of the nanoparticle is gold).

One or more histone proteins, as well as other means to package the DNA into a smaller volume such as normally cationic nanoparticles, lipids, or proteins, may be used to package the supercoiled plasmid DNA "histone-packaged supercoiled plasmid DNA." In certain aspects of the disclosed technology, a combination of histone proteins H1, H2A, H2B, H3, and H4 in a preferred ratio of 1:2:2:2:2, although other histone proteins may be used in other, similar ratios, as is known in the art or may be readily practiced pursuant to the teachings of the present disclosure. The DNA may also be double stranded linear DNA, instead of plasmid DNA, which also may be optionally supercoiled and/or packaged with histones or other packaging components.

Other histone proteins which may be used in this aspect of the disclosed technology include, for example, H1F, H1A, H1B, H2A, H2B, H1F0, H1FNT, H1FOO, H1FX, H1H1, HIST1H1A, HIST1H1B, HIST1H1C, HIST1H1D, HIST1H1E, HIST1H1T, H2AF, H2AFB1, H2AFB2, H2AFB3, H2AFJ, H2AFV, H2AFX, H2AFY, H2AFY2, H2AFZ, H2A1, HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, H2A2, HIST2H2AA3, HIST2H2AC, H2BF, H2BFM, HSBFS, HSBFWT, H2B1, HIST1H2BA, HIST1HSBB, HIST1HSBC, HIST1HSBD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, H2B2, HIST2H2BE, H3A1, HIST1H3A, HIST1H3B, HIST1H3C, HIST1H3D, HIST1H3E, HIST1H3F, HIST1H3G, HIST1H3H, HIST1H3I, HIST1H3J, H3A2, HIST2H3C, H3A3, HIST3H3, H41, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, H44, and HIST4H4.

The term "nuclear localization sequence" refers to a peptide sequence incorporated or otherwise crosslinked into histone proteins, which comprise the histone-packaged supercoiled plasmid DNA. In certain embodiments, particles according to the present disclosure may further comprise a plasmid (often a histone-packaged supercoiled plasmid DNA) which is modified (crosslinked) with a nuclear localization sequence (note that the histone proteins may be crosslinked with the nuclear localization sequence or the plasmid itself can be modified to express a nuclear localization sequence), which enhances the ability of the histone-packaged plasmid to penetrate the nucleus of a cell and deposit its contents there (to facilitate expression and ultimately cell death). These peptide sequences assist in carrying the histone-packaged plasmid DNA and the associated histones into the nucleus of a targeted cell, whereupon the plasmid will express peptides and/or nucleotides as desired to deliver therapeutic and/or diagnostic molecules (polypeptide and/or nucleotide) into the nucleus of the targeted cell. One or more crosslinking agents, known in the art, may be used to covalently link a nuclear localization sequence to a histone protein (often at a lysine group or other group which has a nucleophilic or electrophilic group in the side chain of the amino acid exposed pendant to the polypeptide), which can be used to introduce the histone packaged plasmid into the nucleus of a cell. Alternatively, a nucleotide sequence that expresses the nuclear localization sequence can be positioned in a plasmid in proximity to that which expresses histone protein, such that the expression of the histone protein conjugated to the nuclear localization sequence will occur thus facilitating transfer of a plasmid into the nucleus of a targeted cell.

The terms "nucleic acid regulatory sequences," "control elements," and "regulatory elements," used interchangeably herein, refer to transcriptional and translational control sequences, such as promoters, enhancers, polyadenylation signals, internal ribosomal entry sites (IRES), terminators, and protein degradation signals, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

A "promoter sequence" is a DNA regulatory region capable of binding RNA polymerase in a cell and initiating transcription of a downstream (3' direction) coding sequence. For purposes of defining the present disclosed technology, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, and terminators, that provide for the expression of a coding sequence in a host cell.

A "vector" or "expression vector" is a replicon, such as a plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

In accordance with the present disclosure there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

By an "effective amount" or a "sufficient amount" of an agent (e.g., a cargo), as used herein, is that amount sufficient to effect beneficial or desired results, such as clinical results, and, as such, an "effective amount" depends upon the context in which it is being applied. For example, in the context of administering an agent that employs a CRISPR component to genetically modify a gene, an effective amount of an agent is, for example, an amount sufficient to achieve increased or decreased expression of that gene, as compared to the response obtained without administration of the agent.

By "subject" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

By "salt" is meant an ionic form of a compound or structure (e.g., any formulas, compounds, or compositions described herein), which includes a cation or anion compound to form an electrically neutral compound or structure. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the disclosed technology or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, and valerate salts. Representative cationic salts include metal salts, such as alkali or alkaline earth salts, e.g., barium, calcium (e.g., calcium edetate), lithium, magnesium, potassium, and sodium; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and pyridinium. Other cationic salts include organic salts, such as chloroprocaine, choline, dibenzylethylenediamine, diethanolamine, ethylenediamine, methylglucamine, and procaine. Exemplary salts include pharmaceutically acceptable salts.

By "pharmaceutically acceptable salt" is meant a salt that is, within the scope of sound medical judgment, suitable for use in contact with the tissues of humans and animals without for example, undue toxicity, irritation, or allergic response, and are commensurate with a reasonable benefit/risk ratio.

By "pharmaceutically acceptable excipient" is meant any ingredient other than a compound or structure (e.g., any formulas, compounds, or compositions described herein) and having the properties of being nontoxic and non-inflammatory in a subject. Exemplary, non-limiting excipients include adjuvants, antiadherents, antioxidants, binders, carriers, coatings, compression aids, diluents, disintegrants, dispersing agents, dyes (colors), emollients, emulsifiers, fillers (diluents), film formers or coatings, flavors, fragrances, glidants (flow enhancers), isotonic carriers, lubricants, preservatives, printing inks, solvents, sorbents, stabilizers, suspending or dispersing agents, surfactants, sweeteners, waters of hydration, or wetting agents. Any of the excipients can be selected from those approved, for example, by the United States Food and Drug Administration or other governmental agency as being acceptable for use in humans or domestic animals. Exemplary excipients include, but are not limited to alcohol, butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, glycerol, hydroxypropyl cellulose, hydroxypropyl methylcellulose, lactated Ringer's solution, lactose, magnesium stearate, maltitol, maltose, mannitol, methionine, methylcellulose, methyl paraben, microcrystalline cellulose, polyethylene glycol, polyol, polyvinyl pyrrolidone, povidone, pregelatinized starch, propyl paraben, retinyl palmitate, Ringer's solution, shellac, silicon dioxide, sodium carboxymethyl cellulose, sodium chloride injection, sodium citrate, sodium starch glycolate, sorbitol, starch (corn), stearic acid, stearic acid, sucrose, talc, titanium dioxide, vegetable oil, vitamin A, vitamin E, vitamin C, water, and xylitol.

As used herein, the terms "top," "bottom," "upper," "lower," "above," and "below" are used to provide a relative relationship between structures. The use of these terms does not indicate or require that a particular structure must be located at a particular location in the apparatus.

By "alkenyl" is meant an optionally substituted $C_2$-24 alkyl group having one or more double bonds. The alkenyl group can be cyclic (e.g., $C_3$-24 cycloalkenyl) or acyclic. The alkenyl group can also be substituted or unsubstituted. For example, the alkenyl group can be substituted with one or more substitution groups, as described herein for alkyl.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, and tetracosyl. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., -OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O)Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$R$^D$, where R$^D$ is selected from the group consisting of (a) $C_{1-6}$ alkyl, (b) $C_{4-18}$ aryl, and (c) $C_{1-6}$ alk-$C_{4-18}$ aryl; (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "alkynyl" is meant an optionally substituted $C_{2-24}$ alkyl group having one or more triple bonds. The alkynyl group can be cyclic or acyclic such as ethynyl or 1-propynyl. The alkynyl group can also be substituted or unsubstituted. For example, the alkynyl group can be substituted with one or more substitution groups, as described herein for alkyl.

By "amido" is meant —C(O)NR$^{N1}$R$^{N2}$, where each of R$^{N1}$ and R$^{N2}$ is, independently, H, optionally substituted alkyl, or optionally substituted aryl; or where a combination of R$^{N1}$ and R$^{N2}$, taken together with the nitrogen atom to which each are attached, form a heterocyclyl group, as defined herein.

By "amino" is meant —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group, as defined herein.

By "aryl" is meant a group that contains any carbon-based aromatic group including, but not limited to, benzyl, naphthalene, phenyl, biphenyl, and phenoxybenzene. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)Ak, in which Ak is an alkyl group, as defined herein); (2) $C_{1-6}$ alkyl; (3) $C_{1-6}$ alkoxy (e.g., —OAk, in which Ak is an alkyl group, as defined herein); (4) $C_{1-6}$ alkoxy-$C_{1-6}$ alkyl (e.g., an alkyl group, which is substituted with an alkoxy group —OAk, in which Ak is an alkyl group, as defined herein); (5) $C_{1-6}$ alkylsulfinyl (e.g., —S(O)Ak, in which Ak is an alkyl group, as defined herein); (6) $C_{1-6}$ alkylsulfinyl-$C_{1-6}$ alkyl (e.g., an alkyl group, which is substituted by an alkylsulfinyl group —S(O)Ak, in which Ak is an alkyl group, as defined herein); (7) $C_{1-6}$ alkylsulfonyl (e.g., —$SO_2$Ak, in which Ak is an alkyl group, as defined herein); (8) $C_{1-6}$ alkylsulfonyl-$C_{1-6}$ alkyl (e.g., an alkyl group, which is substituted by an alkylsulfonyl group —$SO_2$Ak, in which Ak is an alkyl group, as defined herein); (9) aryl; (10) amino (e.g., —$R^{N1}R^{N2}$, where each of $R^{N1}$ and $R^{N2}$ is, independently, H or optionally substituted alkyl, or $R^{N1}$ and $R^{N2}$, taken together with the nitrogen atom to which each are attached, form a heterocyclyl group); (11) $C_{1-6}$ aminoalkyl (e.g., meant an alkyl group, as defined herein, substituted by an amino group); (12) heteroaryl; (13) $C_{1-6}$ alk-$C_{4-18}$ aryl (e.g., -$A^L$Ar, in which $A^L$ is an alkylene group and Ar is an aryl group, as defined herein); (14) aryloyl (e.g., —C(O)Ar, in which Ar is an aryl group, as defined herein); (15) azido (e.g., an —$N_3$ group); (16) cyano (e.g., a —CN group); (17) $C_{1-6}$ azidoalkyl (e.g., a —$N_3$ azido group attached to the parent molecular group through an alkyl group, as defined herein); (18) carboxyaldehyde (e.g., a —C(O)H group); (19) carboxyaldehyde-$C_{1-6}$ alkyl (e.g., -$A^L$C(O)H, in which $A^L$ is an alkylene group, as defined herein); (20) $C_{3-8}$ cycloalkyl; (21) $C_{1-6}$ alk-$C_{3-8}$ cycloalkyl (e.g., -$A^L$Cy, in which $A^L$ is an alkylene group and Cy is a cycloalkyl group, as defined herein); (22) halo (e.g., F, Cl, Br, or I); (23) $C_{1-6}$ haloalkyl (e.g., an alkyl group, as defined herein, substituted with one or more halo); (24) heterocyclyl; (25) heterocyclyloxy (e.g., —OHet, in which Het is a heterocyclyl group); (26) heterocyclyloyl (e.g., —C(O)Het, in which Het is a heterocyclyl group); (27) hydroxyl (e.g., a —OH group); (28) $C_{1-6}$ hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —$NO_2$ group); (30) $C_{1-6}$ nitroalkyl (e.g., an alkyl group, as defined herein, substituted by one to three nitro groups); (31) N-protected amino; (32) N-protected amino-$C_{1-6}$ alkyl; (33) oxo (e.g., an =O group); (34) $C_{1-6}$ thioalkoxy (e.g., —SAk, in which Ak is an alkyl group, as defined herein); (35) thio-$C_{1-6}$ alkoxy-$C_{1-6}$ alkyl (e.g., an alkyl group, which is substituted by an thioalkoxy group —SAk, in which Ak is an alkyl group, as defined herein); (36) —$(CH_2)_rCO_2R^A$, where r is an integer of from zero to four, and $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —$(CH_2)_rCONR^BR^C$, where r is an integer of from zero to four and where each $R^B$ and $R^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —$(CH_2)_rSO_2R^D$, where r is an integer of from zero to four and where $R^D$ is selected from the group consisting of (a) $C_{1-6}$ alkyl, (b) $C_{4-18}$ aryl, and (c) $C_{1-6}$ alk-$C_{4-18}$ aryl; (39) —$(CH_2)_rSO_2NR^ER^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —$(CH_2)_rNR^GR^H$, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45) cycloalkoxy (e.g., —OCy, in which Cy is a cycloalkyl group, as defined herein); (46) cycloalkylalkoxy (e.g., —$OA^L$Cy, in which $A^L$ is an alkylene group and Cy is a cycloalkyl group, as defined herein); and (47) arylalkoxy (e.g., —$OA^L$Ar, in which $A^L$ is an alkylene group and Ar is an aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a multivalent (e.g., bivalent, trivalent, tetravalent, etc.) form of an aryl group, as described herein. Exemplary arylene groups include phenylene, naphthylene, biphenylene, triphenylene, diphenyl ether, acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group. The arylene group can be branched or unbranched. The arylene group can also be substituted or unsubstituted. For example, the arylene group can be substituted with one or more substitution groups, as described herein for aryl.

By "azido" is meant an —$N_3$ group.

By "carbamido" is meant —$NR^{N1}C(O)NR^{N2}R^{N3}$, where each of $R^{N1}$ and $R^{N2}$ and $R^{N3}$ is, independently, H, optionally substituted alkyl, or optionally substituted aryl; or where a combination of $R^{N2}$ and $R^{N3}$, taken together with the nitrogen atom to which each are attached, form a heterocyclyl group, as defined herein.

By "carbonyl" is meant a —C(O)— group, which can also be represented as >C=O.

By "carboxyl" is meant a —$CO_2$H group.

By "halo" is meant F, Cl, Br, or I.

By "heteroalkyl" is meant an alkyl group, as defined herein, containing one, two, three, or four non-carbon heteroatoms (e.g., independently selected from the group consisting of nitrogen, oxygen, phosphorous, sulfur, or halo).

By "heteroalkylene" is meant a divalent form of an alkylene group, as defined herein, containing one, two, three, or four non-carbon heteroatoms (e.g., independently selected from the group consisting of nitrogen, oxygen, phosphorous, sulfur, or halo).

By "heteroaryl" is meant a subset of heterocyclyl groups, as defined herein, which are aromatic, i.e., they contain 4n+2 pi electrons within the mono- or multicyclic ring system.

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, and benzothieny. Heterocyclics include, for example, thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazolyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, and benzothienyl.

By "hydroxyl" is meant —OH.

By "imido" is meant —C(O)NR$^{N1}$C(O)—, where R$^{N1}$ is, independently, H, optionally substituted alkyl, or optionally substituted aryl.

By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P. G. M. Wuts and T. W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkylsulfonate with reactive group O), such as —SO$_2$—R$^{S1}$, where R$^{S1}$ is optionally substituted C$_{1-12}$ alkyl, such as mesyl or benzylsulfonyl; an optionally substituted arylsulfonyl group (e.g., forming an arylsulfonate with reactive group O), such as —SO$_2$—R$^{S4}$, where R$^{S4}$ is optionally substituted C$_{4-18}$ aryl, such as tosyl or phenylsulfonyl; an optionally substituted alkoxycarbonyl or aryloxycarbonyl group (e.g., forming a carbonate with reactive group O), such as —C(O)—OR$^{T1}$, where R$^{T1}$ is optionally substituted C$_{1-12}$ alkyl or optionally substituted C$_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—(R$^{T2}$)$_3$, where each R$^{T2}$ is, independently, optionally substituted C$_{1-12}$ alkyl or optionally substituted C$_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenylsulfonyl, benzyl, Boc, and Cbz. Such protecting groups can employ any useful agent to cleave the protecting group, thereby restoring the reactivity of the unprotected reactive group.

By "thio" is meant an —S— group.

By "thiol" is meant an —SH group.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, η bond interactions, hydrophobic interactions, inclusion complexes, clathration, van der Waals interactions, and combinations thereof.

Other features and advantages of the disclosed technology will be apparent from the following description and the claims.

BRIEF DESCRIPTION OF THE DRAWINGS

FIGS. 1A-1C is a schematic showing exemplary constructs. Provided are (A) an exemplary method 100 for providing a non-limiting construct having a core 101, a spacer 103, a cargo 104, and an outer layer 105; (B) another exemplary construct 1000; and (C) yet another exemplary construct 1500.

FIGS. 7A-7C are schematics showing exemplary CRISPR components.

FIGS. 8A-8H shows non-limiting amino acid sequences for various nucleases. Provided are sequences for (A) a Cas9 endonuclease for S. pyogenes serotype M1 (SEQ ID NO:110), (B) a deactivated Cas9 having D10A and H840A mutations (SEQ ID NO:111), (C) a Cas protein Csn1 for S. pyogenes (SEQ ID NO:112), (D) a Cas9 endonuclease for F. novicida U112 (SEQ ID NO:113), (E) a Cas9 endonuclease for S. thermophilus 1 (SEQ ID NO:114), (F) a Cas9 endonuclease for S. thermophilus 2 (SEQ ID NO:115), (G) a Cas9 endonuclease for L. innocua (SEQ ID NO:116), and (H) a Cas9 endonuclease for W. succinogenes (SEQ ID NO:117).

FIG. 9 shows non-limiting nucleic acid sequences of crRNA that can be employed as a first portion in any guiding component described herein. Provided are sequences for *S. pyogenes* (SEQ ID NO:20), *L. innocua* (SEQ ID NO:21), *S. thermophilus* 1 (SEQ ID NO:22), *S. thermophilus* 2 (SEQ ID NO:23), *F. novicida* (SEQ ID NO:24), and *W. succinogenes* (SEQ ID NO:25). Also provided are various consensus sequences (SEQ ID NOs:26-32), in which each X, independently, can be absent, A, C, T, G, or U, as well as modified forms thereof (e.g., as described herein). In another embodiment, for each consensus sequence (SEQ ID NOs:26-32), each X at each position is a nucleic acid (or a modified form thereof) that is provided in an aligned reference sequence. For instance, for consensus SEQ ID NO:26, the first position includes an X, and this X can be absent or any nucleic acid (e.g., A, C, T, G, or U, as well as modified forms thereof). Alternatively, this X can be any nucleic acid provided in an aligned reference sequence (e.g., aligned reference sequences SEQ ID NO:20-25 for the consensus sequence in SEQ ID NO:26). Thus, X at position 1 in SEQ ID NO:26 can also be G (as in SEQ ID NOs:20-23 and 25) or C (as in SEQ ID NO:24), in which this subset of substitutions is defined as a conservative subset. Similarly, for each X at each position for the consensus sequences (SEQ ID NOs:26-32), conservative subsets can be determined based on FIG. 9, and these consensus sequences include nucleic acid sequences encompassed by such conservative subsets. Gray highlight indicates a conserved nucleic acid, and the dash indicates an absent nucleic acid.

FIGS. 10A-10C shows non-limiting nucleic acid sequences of tracrRNA that can be employed as a second portion and/or linker in any guiding component described herein. Provided are sequences for *S. pyogenes* (SEQ ID NO:40), *L. innocua* (SEQ ID NO:41), *S. thermophilus* 1 (SEQ ID NO:42), *S. thermophilus* 2 (SEQ ID NO:43), *F. novicida* 1 (SEQ ID NO:44), *F. novicida* 2 (SEQ ID NO:45), *W. succinogenes* 1 (SEQ ID NO:46), and *W. succinogenes* 2 (SEQ ID NO:47). Also provided are various consensus sequences (SEQ ID NOs:48-54), in which each Z, independently, can be absent, A, C, T, G, or U, as well as modified forms thereof (e.g., as described herein). Consensus sequences are shown for (A) an alignment of all SEQ ID NOs:40-47, providing consensus sequences SEQ ID NOs: 48-50; (B) an alignment of SEQ ID NOs:40-43, providing consensus sequences SEQ ID NOs:51-52; and (C) an alignment of SEQ ID NOs:44-47, providing consensus sequences SEQ ID NOs:53-54. In another embodiment, for each consensus sequence (SEQ ID NOs:48-54), each Z at each position is a nucleic acid (or a modified form thereof) that is provided in an aligned reference sequence. For instance, for consensus SEQ ID NO:48, the first position includes a Z, and this Z can be absent or any nucleic acid (e.g., A, C, T, G, or U, as well as modified forms thereof). Alternatively, this Z can be any nucleic acid provided in an aligned reference sequence (e.g., aligned reference sequences SEQ ID NO:40-47 for the consensus sequence in SEQ ID NO:48). Thus, Z at position 2 in SEQ ID NO:48 can also be U (as in SEQ ID NOs:40, 41, and 43-47) or G (as in SEQ ID NO:42), in which this subset of substitutions is defined as a conservative subset. Similarly, for each Z at each position for the consensus sequences (SEQ ID NOs:48-54), conservative subsets can be determined based on FIGS. 10A-10C, and these consensus sequences include nucleic acid sequences encompassed by such conservative subsets. Gray highlight indicates a conserved nucleic acid, and the dash indicates an absent nucleic acid.

FIG. 11 shows non-limiting nucleic acid sequences of extended tracrRNA that can be employed as a second portion and/or linker in any guiding component described herein. Provided are sequences for *S. pyogenes* (SEQ ID NO:60), *L. innocua* (SEQ ID NO:61), *S. thermophilus* 1 (SEQ ID NO:62), and *S. thermophilus* 2 (SEQ ID NO:63). Also provided are various consensus sequences (SEQ ID NOs:64-65), in which each Z, independently, can be absent, A, C, T, G, or U, as well as modified forms thereof (e.g., as described herein). In another embodiment, for each consensus sequence (SEQ ID NOs:64-65), each Z at each position is a nucleic acid (or a modified form thereof) that is provided in an aligned reference sequence. For instance, for consensus SEQ ID NO:64, the first position includes a Z, and this Z can be absent or any nucleic acid (e.g., A, C, T, G, or U, as well as modified forms thereof). Alternatively, this Z can be any nucleic acid provided in an aligned reference sequence (e.g., aligned reference sequences SEQ ID NO:60-63 for the consensus sequence in SEQ ID NO:64). Thus, Z at position 1 in SEQ ID NO:64 can also be absent (as in SEQ ID NO:60), A (as in SEQ ID NO:61), or U (as in SEQ ID NOs:63-64), in which this subset of substitutions is defined as a conservative subset. Similarly, for each Z at each position for the consensus sequences (SEQ ID NOs:64-65), conservative subsets can be determined based on FIG. 11, and these consensus sequences include nucleic acid sequences encompassed by such conservative subsets. Gray highlight indicates a conserved nucleic acid, and the dash indicates an absent nucleic acid.

FIG. 12 shows non-limiting nucleic acid sequences of a guiding component (e.g., a synthetic, non-naturally occurring guiding component) having a generic structure of A-L-B, in which A includes a first portion (e.g., any one of SEQ ID NOs:20-32, or a fragment thereof), L is a linker (e.g., a covalent bond, a nucleic acid sequence, a fragment of any one of SEQ ID NOs:40-54 and 60-65, or any other useful linker), and B is a second portion (e.g., any one of SEQ ID NOs:40-54 and 60-65, or a fragment thereof). Also provided are various embodiments of single-stranded guiding components (SEQ ID NOs:80-93). Exemplary non-limiting guiding components include SEQ ID NO:81, or a fragment thereof, where X at each position is defined as in SEQ ID NO:26 and Z at each position is as defined in SEQ ID NO:48; SEQ ID NO:82, or a fragment thereof, where X at each position is defined as in SEQ ID NO:27 and Z at each position is as defined in SEQ ID NO:49; SEQ ID NO:83, where X at each position is defined as in SEQ ID NO:28 and Z at each position is as defined in SEQ ID NO:49; SEQ ID NO:84, or a fragment thereof, where X at each position is defined as in SEQ ID NO:27 and Z at each position is as defined in SEQ ID NO:65; SEQ ID NO:85, or a fragment thereof, where X at each position is defined as in SEQ ID NO:28 and Z at each position is as defined in SEQ ID NO:65; SEQ ID NO:86, or a fragment thereof, where X at each position is defined as in SEQ ID NO:29 and Z at each position is defined as in SEQ ID NO:51; SEQ ID NO:87, or a fragment thereof, where X at each position is defined as in SEQ ID NO:30 and Z at each position is defined as in SEQ ID NO:51; SEQ ID NO:88, or a fragment thereof, where X at each position is defined as in SEQ ID NO:30 and Z at each position is defined as in SEQ ID NO:52; SEQ ID NO:89, or a fragment thereof, where X at each position is defined as in SEQ ID NO:30 and Z at each position is defined as in SEQ ID NO:65; SEQ ID NO:90, or a fragment thereof, where X at each position is defined as in SEQ ID NO:31 and Z at each position is defined as in SEQ ID NO:51; SEQ ID NO:91, or a fragment thereof, where X at each position is defined as in SEQ ID NO:32 and Z at each position is as defined in SEQ ID NO:53; SEQ ID NO:92, or a fragment thereof, where X at each position is defined as in SEQ ID NO:32 and Z at each position is as defined in SEQ ID NO:54; and SEQ ID NO:93, or a fragment thereof, where X at each position is defined as in SEQ ID NO:32 and Z at each position is defined as in SEQ ID NO:65. The fragment can include any useful number of nucleotides (e.g., one or more contiguous nucleotides, such as a fragment including about 4, 5, 6, 7, 8, 9, 10, 11, 12, 15, 18, 20, or more contiguous nucleotides of any sequences described herein, such as a sequence for the first portion, e.g., any one of SEQ ID NOs:20-32; and also such as a fragment including about 4, 5, 6, 7, 8, 9, 10, 11, 12, 15, 18, 20, 24, 26, 28, 30, 32, 34, 38, 36, 40, or more contiguous nucleotides of any sequences described herein, such as a sequence for the first portion, e.g., any one of SEQ ID NOs:40-54 and 60-65).

FIG. 13 shows additional non-limiting nucleic acid sequences of a guiding component (e.g., a synthetic, non-naturally occurring guiding component). Provided are various embodiments of single-stranded guiding components (SEQ ID NOs:100-103). Exemplary non-limiting guiding components include SEQ ID NO:100, or a fragment thereof, where n at each of positions 1-80 can be present or absent such that this region can contain anywhere from 12 to 80 nucleotides and n is A, C, T, G, U, or modified forms thereof, and where n at each of positions 93-192 can be present or absent such that this region can contain anywhere from 3 to 100 nucleotides and n is A, C, T, G, U, or modified forms thereof, SEQ ID NO:101, or a fragment thereof, where n at each of positions 1-80 can be present or absent such that this region can contain anywhere from 12 to 80 nucleotides and n is A, C, T, G, U, or modified forms thereof, and where n at each of positions 93-192 can be present or absent such that this region can contain anywhere from 3 to 100 nucleotides and n is A, C, T, G, U, or modified forms thereof, SEQ ID NO:102, or a fragment thereof, where n at each of positions 1-80 can be present or absent such that this region can contain anywhere from 12 to 80 nucleotides and n is A, C, T, G, U, or modified forms thereof, and SEQ ID NO:103, or a fragment thereof, where n at each of positions 1-80 can be present or absent such that this region can contain anywhere from 12 to 80 nucleotides and n is A, C, T, G, U, or modified forms thereof.

FIG. 16 is a graph showing Cas9 loading and release in exemplary LC-MSNs by densitometry.

DETAILED DESCRIPTION

Figure 2:
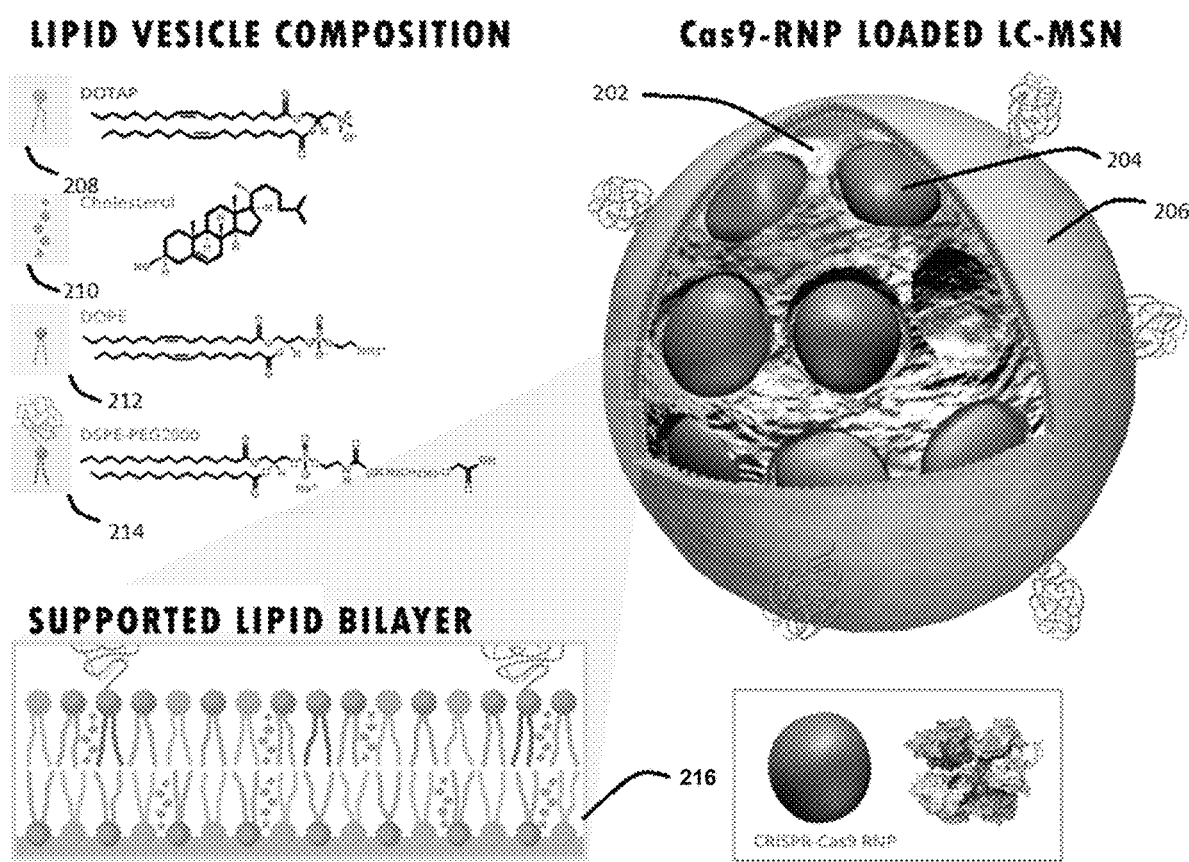
FIG. 2 is a schematic showing an exemplary lipid coated mesoporous silica nanoparticles (LC-MSN) in accordance with present disclosure.

The present disclosure relates to particle-based constructs configured to transport a CRISPR-based cargo in vivo and in vitro as an attempt to overcome a major hurdle in clinical translation of CRISPR-based countermeasures. The construct is directed to attacking viral infections by targeting critical host factor or viral genomes directly. In particular embodiments, the construct includes a porous nanoparticle core, in which the pores are employed to completely or partially confine the cargo. Nanoparticles of various pore sizes were screened to determine those most effective in vitro editing efficiency, stability, and monodispersity. The construct and cargo are encapsulated partially or completely by a coating comprising a cationic lipid, a pegylated lipid, a zwitterionic lipid, and a sterol.

The construct can include any useful component and can be assembled in any useful process. FIG. 1A provides an exemplary method 100 for assembling a construct. As can be seen, the method can include providing a core 101 including a plurality of pores 102. The pores are inside or part of the external surface. Furthermore, a first pore can optionally be connected to or coupled to a second pore. The pores can be characterized in any useful manner, such as, e.g., by an average dimension of the plurality of pores.

Optionally, the method can include expanding the pores present in the core. In this instance, the pores of the initial core can be characterized by a first dimension. After expansion, the initial core can include a plurality of expanded pores, where an average dimension of the plurality of expanded pores is characterized by a second dimension of the same type (e.g. length, width, or height) that is greater than the first dimension. Pore expansion can be accomplished in any useful manner, e.g., by use of a swelling agent to expand an initial pore size to a larger pore size.

Spacers can optionally be used to attach a cargo to the core. As seen in FIG. 1A, the method can optionally include installing 110 a spacer 103 to be disposed within at least one pore and/or upon the external surface of the core. The spacer can be installed by use of a linking agent (e.g., $L^1$-$R^L$-$L^2$, in which $R^L$ is a linking group such as any described herein; each of $L^1$ and $L^2$ is, independently, a reactive group such as any functional group described herein; and each of $L^1$ and $L^2$ can be the same or different). The linking agent can include a first reactive group to form a bond with the core, as well as a second reactive group to form a bond with the cargo. The linking agent may be divalent (having two reactive groups) or multivalent (having more than two reactive groups). If a linker is not used, certain cargo can be loaded through electrostatic interactions.

The cargo can be introduced to the core to provide a loaded core. As seen in FIG. 1A, the method can include binding 120 a cargo 104 to a spacer. In one non-limiting instance, the installed spacer 103 can include a reactive group that interacts with a reactive group present on the cargo, thereby forming a bond (e.g., a covalent or non-covalent bond). In other embodiments, the cargo itself has a reactive group that interacts directly with the core surface (particle).

Then, an outer layer 105 is provided on the external surface of the core 130. The outer layer includes a blend of lipids and a sterol. In one instance, the method includes providing an outer layer 130, thereby forming an exemplary construct. The outer layer 105 can be formed, e.g., by exposing the loaded core to a lipid and sterol formulation to form the outer layer 105.

The outer layer can include one or more moieties (e.g., targeting ligands). These moieties can be introduced before or after providing the outer layer. The cargo should be loaded before the outer layer. In yet other embodiments, the moieties can be introduced simultaneously with providing the outer layer. In forming the outer layer 105, a lipid formulation including cationic and anionic lipids, the sterol components (e.g., cholesterol), and the targeting ligand moieties can be prepared; and the resulting formulation can be used to form the outer layer. As seen in FIG. 1A, the method can include providing 140 one or more moieties 106, thereby forming an exemplary construct.

As seen in FIG. 1A, one exemplary construct includes a core 101 having a plurality of pores 102, a spacer 103 disposed within a pore, a cargo 104 attached to the spacer, and an outer layer 105 optionally including a moiety 106. FIG. 1B provides another exemplary construct 1000 having interconnected pores 1002 within the core 1001, spacers 1003 disposed on an external surface of the core, a cargo 1004 attached to the spacer, and an outer layer 1005. In another instance, FIG. 1C provides yet another exemplary construct 1500 having interconnected pores 1502 within the core 1501, spacers 1503 disposed on an external surface of the core or within a pore, a cargo 1504 attached to the spacer, and an outer layer 1505.

A particular embodiment with a highly effective outer layer is shown in FIG. 2. The mesoporous nanoparticle 202 has a CRISPR-Cas9 cargo 204 disposed in its pores, and the core is at least partially encapsulated by an outer coating 206 comprising four components, a cationic lipid, DOTAP 208, a sterol, cholesterol 210, a zwitterionic lipid DOPE 212, and a Pegylated lipid, DSPE-PEG2000 214. A PEG portion 216 of the DSPE-PEG2000 component 214 extends outward from the encapsulating outer coating 206. The Examples below shows the efficient delivery of CRISPR-56 Cas9 RNP components using lipid coated mesoporous silica nanoparticles (LC-MSN) modified from previous studies.

Core

In an embodiment, the core is a particle, providing a surface upon which an outer layer and a cargo can be supported. In other non-limiting embodiments, the core provides a charged surface that allows for electrostatic interactions with the cargo and/or the outer layer, or a portion thereof.

In one instance, the core can be characterized by a first dimension (e.g., core circumference, pore size of the core, core diameter, core length, or core width). Exemplary values for a core dimension (e.g., core circumference, core diameter, core length, or core width, as well as an average or mean value for any of these) include, without limitation, greater than about 1 nm (e.g., greater than about 5 nm, 10 nm, 20 nm, 30 nm, 40 nm, 50 nm, 60 nm, 70 nm, 80 nm, 90 nm, 100 nm, 125 nm, 150 nm, 200 nm, 300 nm, 500 nm, 750 nm, 1 m, 2 m, 5 m, m, or 20 m), including from about 5 nm to about 300 nm (e.g., from 5 nm to 20 nm, 5 nm to 30 nm, 5 nm to 40 nm, 5 nm to 50 nm, 5 nm to 75 nm, 5 nm to 100 nm, 5 nm to 150 nm, 5 nm to 200 nm, 5 nm to 250 nm, 10 nm to 20 nm, 10 nm to 30 nm, 10 nm to 40 nm, 10 nm to 50 nm, 10 nm to 75 nm, 10 nm to 100 nm, 10 nm to 150 nm, 10 nm to 200 nm, 10 nm to 250 nm, 10 nm to 300 nm, 25 nm to 30 nm, 25 nm to 40 nm, 25 nm to 50 nm, 25 nm to 75 nm, 25 nm to 100 nm, 25 nm to 150 nm, 25 nm to 200 nm, 25 nm to 250 nm, 25 nm to 300 nm, 50 nm to 75 nm, 50 nm to 100 nm, 50 nm to 150 nm, 50 nm to 200 nm, 50 nm to 250 nm, 50 nm to 300 nm, 75 nm to 100 nm, 75 nm to 150 nm, 75 nm to 200 nm, 75 nm to 250 nm, 75 nm to 300 nm, 100 nm to 150 nm, 100 nm to 200 nm, 100 nm to 250 nm, 100 nm to 300 nm, 150 nm to 200 nm, 150 nm to 250 nm, 150 nm to 300 nm, 200 nm to 250 nm, 200 nm to 300 nm, 250 nm to 300 nm, or 275 nm to 300 nm).

In one instance, the particle includes a porous core (e.g., a silica core that is spherical and ranges in diameter from about 10 nm to about 250 nm (e.g., having a mean diameter of about 150 nm)). In particular embodiments, the silica core is monodisperse in size distribution.

The core can be further characterized by an electrostatic property. In some embodiments, the core has a negative charge (e.g., a net negative charge), such as a zeta potential of from about −10 mV to about −200 mV (e.g., from −10 mV to −100 mV, −10 mV to −75 mV, −10 mV to −50 mV, −10 mV to −30 mV, −15 mV to −100 mV, −15 mV to −75 mV, −15 mV to −50 mV, −15 mV to −30 mV, −20 mV to −100 mV, −20 mV to −75 mV, −20 mV to −50 mV, −20 mV to −30 mV, −30 mV to −100 mV, −30 mV to −75 mV, −30 mV to −50 mV, −40 mV to −100 mV, −40 mV to −75 mV, −40 mV to −50 mV, −50 mV to −100 mV, −50 mV to −75 mV, −60 mV to −100 mV, or −60 mV to −75 mV). Zeta potential measurements are obtained using a Malvern Zetasizer.

The core can be porous. In particular embodiments, the pore has a dimension (e.g., average pore size, pore diameter, pore radius, pore circumference, pore length, pore width, or pore depth) that is greater than about 0.5 nm (e.g., of from about 0.5 nm to about 30 nm, including from 0.5 nm to 10 nm, 0.5 nm to 20 nm, 0.5 nm to 25 nm, 1 nm to 10 nm, 1 nm to 15 nm, 1 nm to 20 nm, 1 nm to 25 nm, 1 nm to 30 nm, 2 nm to 5 nm, 2 nm to 10 nm, 2 nm to 20 nm, 2 nm to 25 nm, or 2 nm to 30 nm).

A particle or a portion thereof (e.g., a core) may have a variety of shapes and cross-sectional geometries that may depend, in part, upon the process used to produce the particles. The core or particle can be a nanoparticle (e.g., having a diameter less than about 1 m) or a microparticle (e.g., having a diameter greater than or equal to about 1 m). In one embodiment, a core or particle may have a shape that is a sphere, a donut (toroidal), a rod, a tube, a flake, a fiber, a plate, a wire, a cube, or a whisker. A collection of cores may have two or more of the aforementioned shapes. In one embodiment, a cross-sectional geometry of the core may be one or more of circular, ellipsoidal, triangular, rectangular, or polygonal. In one embodiment, a core may consist essentially of non-spherical cores. For example, such cores may have the form of ellipsoids, which may have all three principal axes of differing lengths or may be oblate or prelate ellipsoids of revolution. Non-spherical cores alternatively may be laminar in form, wherein laminar refers to particles in which the maximum dimension along one axis is substantially less than the maximum dimension along each of the other two axes. Non-spherical cores may also have the shape of frusta of pyramids or cones, or of elongated rods. In one embodiment, the cores may be irregular in shape. In one embodiment, a plurality of cores may consist essentially of spherical cores. Particles and cores for use in the present disclosure may be PEGylated and/or aminated as otherwise described in Int. Pub. Nos. WO 2015/042268 and WO 2015/042279, which is incorporated herein by reference in their entirety.

The particle size distribution (e.g., size of the core for the protocell or a size of the silica carrier), according to the present disclosure, depends on the application, but is principally monodisperse (e.g., a uniform sized population varying no more than about 5-20% in diameter, as otherwise described herein). In certain embodiments, particles or cores can range, e.g., from around 1 nm to around 500 nm in size, including all integers and ranges there between. The size is measured as the longest axis of the core. In various embodiments, the cores are from around 5 nm to around 500 nm and from around 10 nm to around 100 nm in size. In certain alternative embodiments, the cores or particles are monodisperse and range in size from about 25 nm to about 300 nm. The sizes used include 50 nm (+/−10 nm) and 150 nm (+/−15 nm), within a narrow monodisperse range, but may be more narrow in range.

When the core is porous, the pores can be from around 0.5 nm to about 25 nm in diameter, often about 1 to around 20 nm in diameter, including all integers and ranges there between. In one embodiment, the pores are from around 1 to around 10 nm in diameter. In one embodiment, around 90% of the pores are from around 1 to around 20 nm in diameter. In another embodiment, around 95% of the pores are around 1 to around 20 nm in diameter.

In certain embodiments, cores or particles according to the disclosed technology: are monodisperse and range in size from about 25 nm to about 300 nm; are anionic, neutral or cationic for specific targeting (e.g., cationic); are optionally modified with agents such as PEI (polyethylene imine), NMe$^{3+}$, dye, crosslinker, ligands (ligands provide neutral charge); and optionally, are used in combination with a cargo to be delivered to the target.

In some embodiments, these cores or particles are often monodisperse and provide colloidally stable compositions. These compositions can be used to target host cells because of enhanced biodistribution/bioavailability of these compositions, and optionally, specific cells, with a wide variety of therapeutic and/or diagnostic agents that exhibit varying release rates at the site of activity.

The cores can be produced, for example, by templating with a surfactant, a cross-linked micelle, or a detergent (see, e.g., Gao F et al., *J. Phys. Chem. B.* 2009; 113:1796-804; Lin Y S et al., *Chem. Mater.* 2009; 21(17):3979-86; Carroll N J et al., *Langmuir* 2009; 25(23):13540-4; and Zhang K et al., *J. Am. Chem. Soc.* 2013 Feb. 20; 135(7):2427-30). In yet another instance, cores are formed by dendritic growth (see, e.g., Shen D et al., *Nano Lett.* 2014; 14(2):923-32). In some instances, the cores are formed by expanding a pore, e.g., by use of a swelling agent, such as an alkylbenzene (e.g., 1,3,5-trimethylbenzene or triisopropylbenzene), an alkane (e.g., heptane, decane, or dodecane), a glycol (e.g., poly (propylene glycol)), or a tertiary amine (see, e.g., Kim M H et al., *ACS Nano* 2011; 5(5):3568-76; and Na H K et al., *Small* 2012; 8(11):1752-61). In other instances, cores are formed by an aerosol process, such as EISA (see, e.g., Lu Y et al., *Nature* 1999; 398:223-6; and Durfee P N et al., *ACS Nano* 2016; 10:8325-45).

Each batch of cores or particles can be characterized by, for example, assessment of size and polydispersity using dynamic light scattering (DLS) (NIST-NCL PCC-1), and surface charge or zeta potential measurements (e.g., with a Zetasizer instrument (Malvern Instruments, Ltd) (NIST-NCL PCC-2 (charge and zeta potential), and verification of low endotoxin contamination per health industry product standards (NCL STE-1.1). Resultant cores can be further processed, such as by modifying core condensation (e.g., by using acidified ethanol for silica) or modifying core surface charge (e.g., by use of amine-containing silanes, such as APTES).

The core can be formed of, for example, a metal oxide, alum, or silica, including mesoporous forms thereof). In particular embodiments, the core is composed of a mesoporous silica nanoparticle (MSN). Exemplary, non-limiting MSNs for use in the disclosed technology are described in Int. Pub. Nos. WO 2015/042268 and WO 2015/042279, each of which is incorporated herein in its entirety.

Figure 18A:
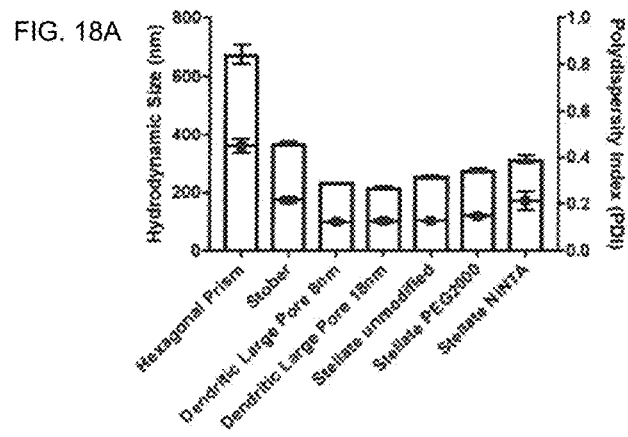
FIGS. 18A-18D are graphs showing size, charge, polydispersity, and colloidal stability information of exemplary particles and comparative examples.
Figure 18B:
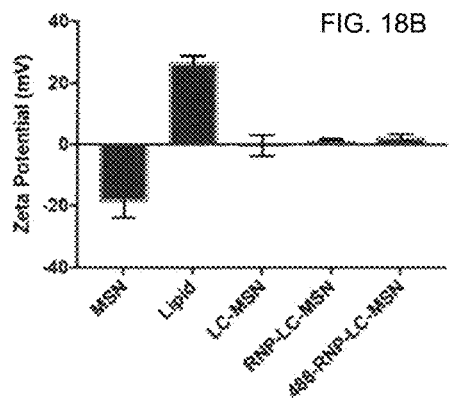
Figure 18C:
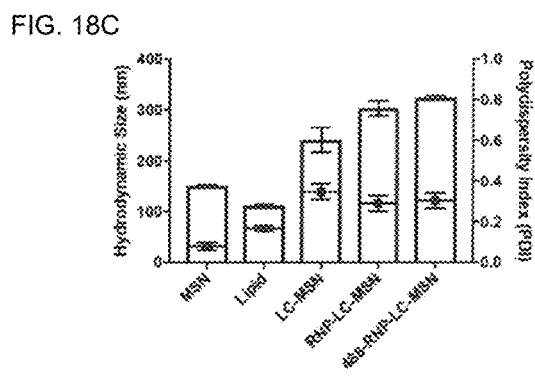
Figure 18D:
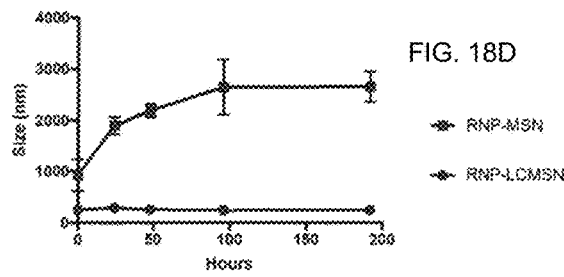

In an embodiment, a stellate particle is used as the core. A stellate particle has a radial pore morphology with a small particle diameter. It also has more uniform polydispersity (FIGS. 18A and 18C) and colloidal stability (FIG. 18D) compared to other particle types such as small-pore hexagonal prism, dendritic MSN with 8 or 18 nm pores, and non-porous Stöber M S N. FIG. 18D shows comparison of the RNP-loaded MSN with and without lipids. FIG. 18C shows size measurements during LC-MSN assembly. The FIG. 18B illustrates the overall charge of the particle. Neutrally charged particles are more stable in vivo than charged particles. The combination of the negatively charged nanoparticle cores (MSN) with the positively charged lipid (cationic lipid), has a neutral charge if particles are unloaded (LC-MSN) or even when loaded with RNP (RNP-LC-MSN and 488-RNP-LC-MSN). The negatively charged core and positively charged (cationic) lipid promotes in vivo stability and delivery efficacy.

The synthesis of stellate MSN involves a base-catalyzed condensation reaction of tetraorthosilicate with a surfactant that acts as a substrate. A single synthesis reaction can yield between 500-800 milligrams of MSN that are stable when stored in ethanol for over a year.

Figure 14A:
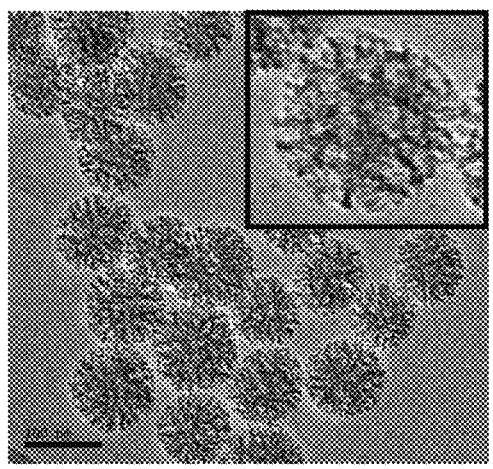
FIGS. 14A-14C are TEM micrographs showing exemplary stellate nanoparticles in various levels of magnification.
Figure 14B:
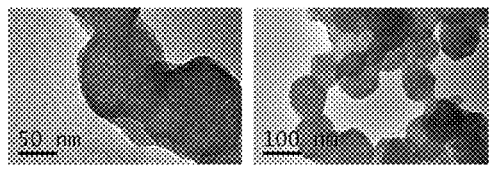
Figure 14C:
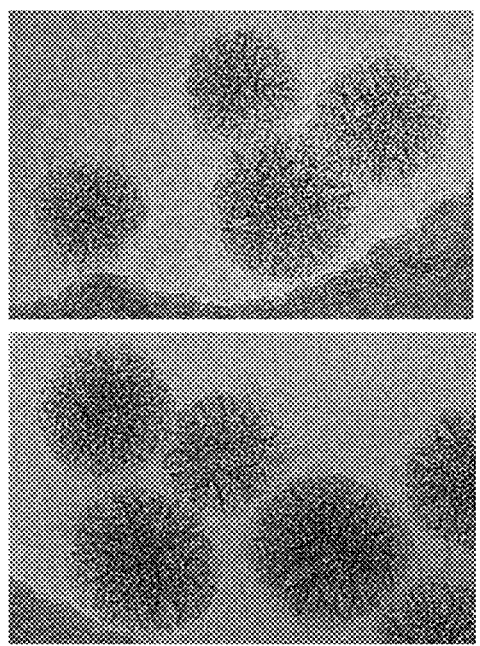
Figure 15:
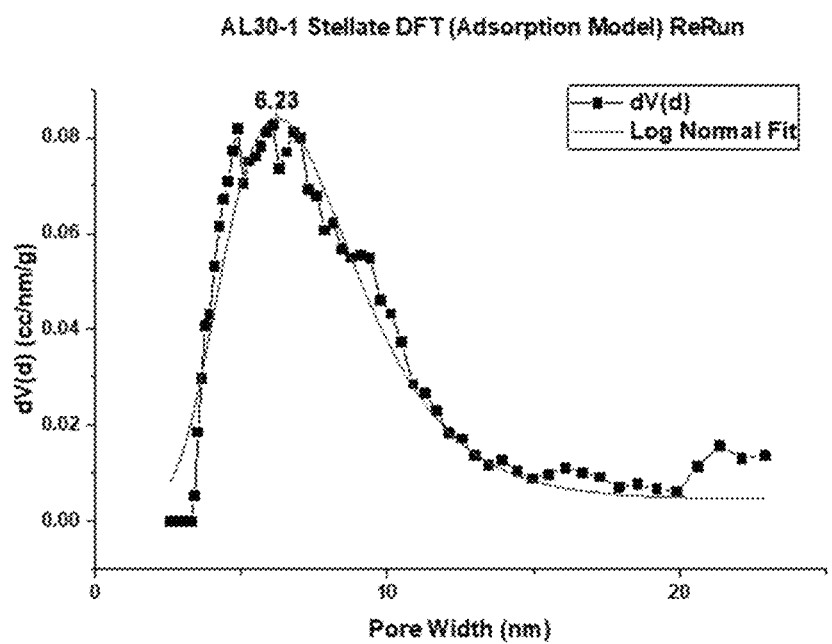
FIG. 15 is a graph showing porosimetry data.

DLS and TEM were used to assess the size and morphology of stellate MSN (FIGS. 14A-14C). The unique radiating arm morphology of the stellate particles can be seen in FIGS. 14A-14C. The average size (diameter) of stellate particles may be, for example, about 75 to 400 nm, such as about 100 to 200 nm, or about 110 to 160 nm. Arm length for the stellate particle may range from about 30 to 200 nm, such as about 50 to 100 nm, or about 55 to 80 nm. The average diameter may be assessed by a Zetasizer instrument (Malvern Instruments, Ltd). Porosimetry was performed with nitrogen adsorption-desorption analysis to determine the pore size range, which may be, for example, 3 to 20 nm, such as 5 to 15 nm or 6.5 to 10 nm (FIG. 15).

While MSNs are promising therapeutic carriers, MSNs can have low colloidal stability and are subject to aggregation in physiological solutions, reducing circulation time and preventing desirable cell uptake. Similarly, permanently charged cationic liposomes are successfully used as nucleic acid transfection reagents in cell culture, however, they have limited in vivo stability. The net neutral charge (FIG. 18B) of the RNP loaded LC-MSNs overcomes challenges presented by these individual components to enable improvements in colloidal stability and subsequent circulation time, with biocompatibility and lower cytoxicity.

In an embodiment, a spacer can be employed to attach a core (e.g., an external surface and/or a pore of the core) to one or more cargos. A spacer can include, for example, a bond (e.g., a covalent bond or a coordination bond), an atom, a molecule, a nucleic acid, or a protein. A spacer can be provided as a linking agent, which in turn reacts with a reactive group (e.g., a functional group present on the core or the cargo) to form a bond. Thus, a reacted linking agent can result in a spacer present between the core and the cargo.

A spacer can include a coordination bond. In some instances, the coordination bond includes one or more functional groups that form a bond to a metal (e.g., a divalent metal). Exemplary functional groups include an amino, an amido, a carboxyl, a thiol, a heterocyclyl (e.g., a heteroaryl, imidazolyl, etc.), or an amino acid (e.g., histidine, cysteine, lysine, etc.), as well as chelate forms thereof (e.g., as in iminodiacetic acid or nitriloacetic acid). Exemplary metals include nickel, cobalt, copper, iron, or zinc, as well as cationic forms thereof.

A non-zero length spacer can include a linking group. In some instances, a linking agent (e.g., to form the non-zero length spacer) includes at least two reactive groups and a linking group disposed between the reactive groups. In some instances, a first reactive group forms a bond with the core, and a second reactive group forms a bond with the cargo. The linking group can be, for example, an optionally substituted alkylene, heteroalkylene, arylene, nucleic acid, or peptide, and can have a functionality, such as, for example, a cleavable moiety, thereby detaching the cargo from the core. The spacer can optionally include a cleavable moiety.

Exemplary cleavable moieties include a labile group, or a scissile group, including but not limited to a disulfide bond.

The spacer can be provided as a linking agent, which in turn reacts with a reactive group (e.g., a functional group present on the core or the cargo) to form a bond. In some instances, the linking agent is $L^1$-$R^L$-$L^2$, in which $R^L$ is a linking group (e.g., any useful chemical group, such as a covalent bond, a nucleic acid sequence, a monomer, etc.) and each of $L^1$ and $L^2$ is, independently, a reactive group (e.g., a functional group that is one of a cross-linker group, a binding group, or a click-chemistry group, such as any described herein), and in which each of $L^1$ and $L^2$ can be the same or different.

Figure 4A:
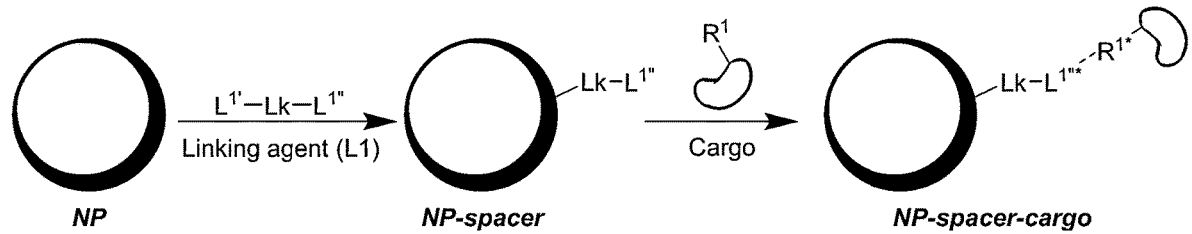
FIGS. 4A-4E is a schematic view showing (A) exemplary linking agents and methods employing linking agent L1 to provide a construct having a nanoparticle (NP) core, a spacer, and an attached cargo, (B) another exemplary spacer having a reactive group L" that interacts with a reactive group R$^1$ present on a cargo, and yet other exemplary spacers present between the NP and the cargo. Also provided are (D) another exemplary spacer and (B) another exemplary method employing linking agent L2 to provide a construct having a NP core, a spacer, and an attached cargo.

FIG. 4A provides an exemplary linking agent $L^{1'}$-Lk-$L^{1''}$ (compound L1), where Lk is a linking group and where each of $L^{1'}$ and $L^{1''}$ is, independently, a reactive group (e.g., a functional group that is one of a cross-linker group, a binding group, or a click-chemistry group, such as any described herein). In some instances, a reactive group can include a protecting group (e.g., any described herein), which provides a reactive group upon exposure to particular chemical or biological conditions (e.g., an acidic condition, a basic condition, the presence of a protease, etc.).

As seen in FIG. 4A, a first group of the linking agent can be used to react with a core (NP), thereby providing a NP-spacer. A second group of the linking agent can then react with a functional group $R^1$ of the cargo, thereby providing a NP-spacer-cargo construct. Any useful linking agent and spacer can be employed.

Figure 4B:
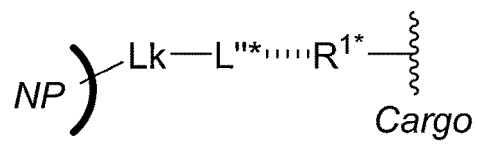

FIG. 4B provides an exemplary spacer present between a core (NP) and the cargo.

The spacer Lk-$L''^*$-$R^*$, in which Lk is a linking group (e.g., any described herein), $L''^*$ is a reactive group of the linking agent (that underwent a reaction), and $R^1$ is a second reactive group present on the cargo (that underwent a reaction). The dashed line indicates that the bond can be covalent or non-covalent.

Figure 4C:
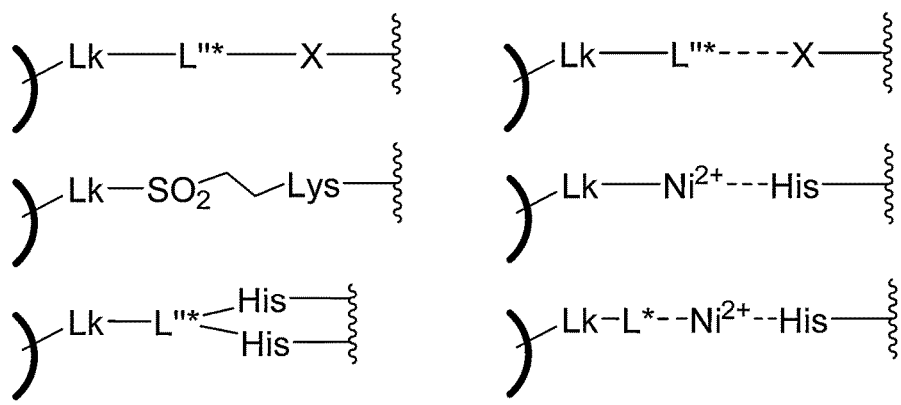

Further spacers are provided in FIG. 4C. In some embodiments, the spacer can include a covalent bond between reacted $L''^*$ and reacted X. In one instance, $L''^*$-X can be represented by a reacted sulfone group of the linking agent, a reacted Lys of the cargo, and an alkylene group between the sulfone and Lys. In another instance, two groups on the cargo react with the linking agent, thereby providing a multivalent spacer $L''^* <(His)_2$ between the NP and the cargo. In other embodiments, the spacer can include a non-covalent bond between reacted $L''^*$ and reacted X. In one instance, $L''^*$-X can be represented by a chelated $Ni^{2+}$ of the linking agent, a chelated His of the cargo, and a coordination bond between the nickel and His. In another instance, the linking agent provides a reactive group $L^*$, the cargo includes a reactive His, and an intermediate $Ni^{2+}$ is provided to provide a chelating bridge between the linking agent and the cargo.

Figure 4D:
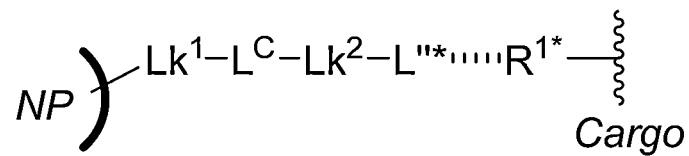

FIG. 4D provides another exemplary spacer present between a core (NP) and the cargo. The spacer -$Lk^1$-$L^C$-$Lk^2$-$L''^*$-$R^{1*}$, in which $Lk^1$ is a first linking group (e.g., any described herein), $L^C$ is a cleavable moiety (e.g., any described herein), $Lk^2$ is a second linking group (e.g., any described herein), $L''^*$ is a reactive group of the linking agent (that underwent a reaction), and $R^{1*}$ is a second reactive group present on the cargo (that underwent a reaction). The dashed line indicates that the bond can be covalent or non-covalent. Exemplary linking groups (e.g., for $Lk^1$ and/or $Lk^2$) includes an optionally substituted alkylene group, an optionally substituted heteroalkylene group, or a poly(ethylene glycol) group.

A cleavable moiety ($L^C$) can include any useful moiety capable of releasing a bound cargo upon exposure to a particular cleaving condition or cleaving agent. In one non-limiting embodiment, the cleavable moiety includes a disulfide group (e.g., —S—S—), in which the cleaving condition includes a reducing condition and the cleaving agent is a reducing agent (e.g., dithiothreitol (DTT), tris(2-carboxyethyl)phosphine (TCEP), or (2S)-2-amino-1,4-dimercaptobutane (DTBA)). In another non-limiting embodiment, the cleavable moiety includes a hydrazone group (e.g., >C=N—NH—), in which the cleaving condition includes an acidic condition and the cleaving agent is an acidic agent (e.g., an acid having a pH less than about 4.5).

A reactive linking group of the linking agent (L" or L"*) can include any useful moiety, such as one or more anionic moieties (e.g., a chelating anionic moiety, such as a polycarboxylic acid, a carboxylic acid, a carbonate, etc.) and one or more cationic moieties (e.g., a chelated cationic metal, such as a cationic transition metal, including $Co^{2+}$, $Ni^{2+}$, $Fe^{2+}$, $Cu^{2+}$, or $Zn^{2+}$). Further exemplary anionic moieties can include those having one or more carboxylic or carbonate moieties, such as iminodiacetic acid (IDA), nitrilotriacetic acid (NTA), ethylenediamine tetraacetic acid (EDTA), diethylenetriaminepentaacetic acid (DTPA), (ethylene glycol-bis(R-aminoethyl ether)-N,N,N'N'-tetraacetic acid) (EGTA), (1,2-bis(o-aminophenoxy)ethane-N,N,N',N'-tetraacetic acid) (BAPTA), carboxylmethylaspartate (CMA), as well as acidic and basic forms thereof.

A second reactive group present on the cargo ($R^1$ or $R^{1*}$) can include any useful moiety capable of forming a bond with the reactive linking group of the linking agent. In one non-limiting embodiment, the reactive linking group includes a cationic moiety, and the second reactive group present on the cargo is a moiety capable of forming a bond with the cationic moiety. Exemplary second reactive groups include one or more histidine residues located at any useful position of the cargo (e.g., at the N-terminus or the C-terminus for a protein cargo).

Figure 4E:
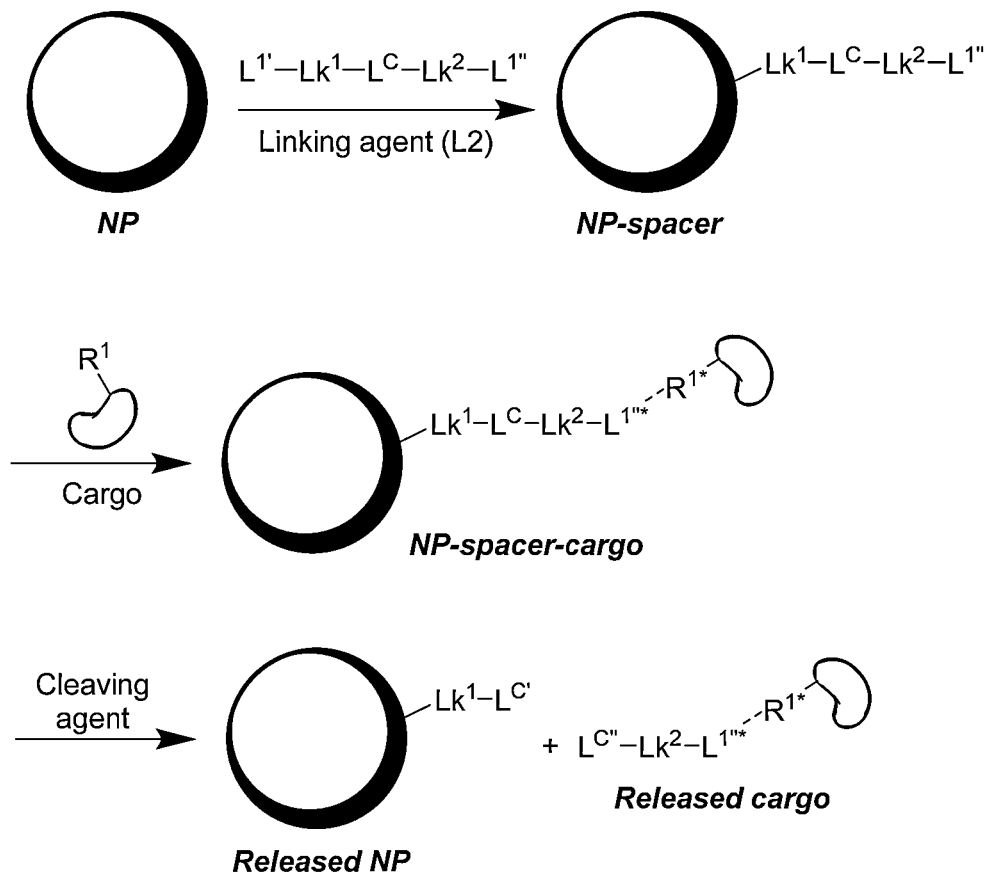

FIG. 4E provides an exemplary linking agent $L^{1'}$-$Lk^1$-$L^C$-$Lk^2$-$L^{1''}$ (compound L2), where $Lk^1$ and $Lk^2$ are linking groups, where $L^C$ is a cleavable moiety, and where each of $L^{1'}$ and $L^{1''}$ is, independently, a reactive group (e.g., a functional group that is one of a cross-linker group, a binding group, or a click-chemistry group, such as any described herein). A first group of the linking agent L2 can be used to react with a core (NP), thereby providing a NP-spacer. A second group of the linking agent can then react with a functional group $R^1$ of the cargo, thereby providing a NP-spacer-cargo construct. Any useful linking agent and spacer can be employed. Next, as the linker as a cleavable moiety $L^C$, the construct can be exposed to a cleaving agent that reacts with $L^C$ to provide a released particle (released NP) and a released cargo.

Figure 5A:
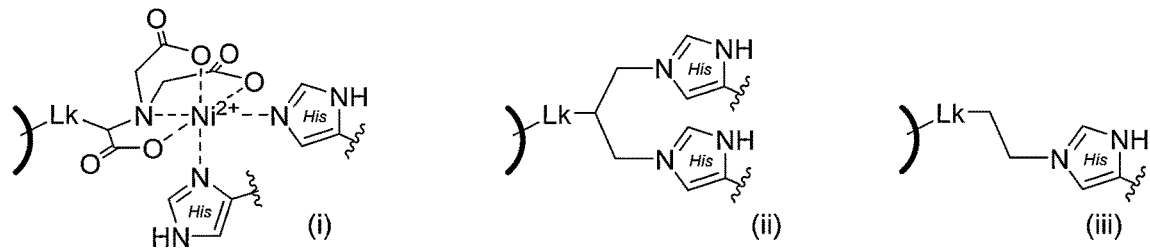
FIGS. 5A-5C is a schematic view showing further exemplary linking agents and spacers. Provided are schematics of (A) exemplary spacers (i)-(iii) present between a core and a cargo, (B) an exemplary reaction scheme between a linking agent and a reactive group present on a cargo, thereby forming a spacer between the core and the cargo, and (C) yet another reaction scheme between another linking agent and a reactive group present on a cargo.
Figure 5B:
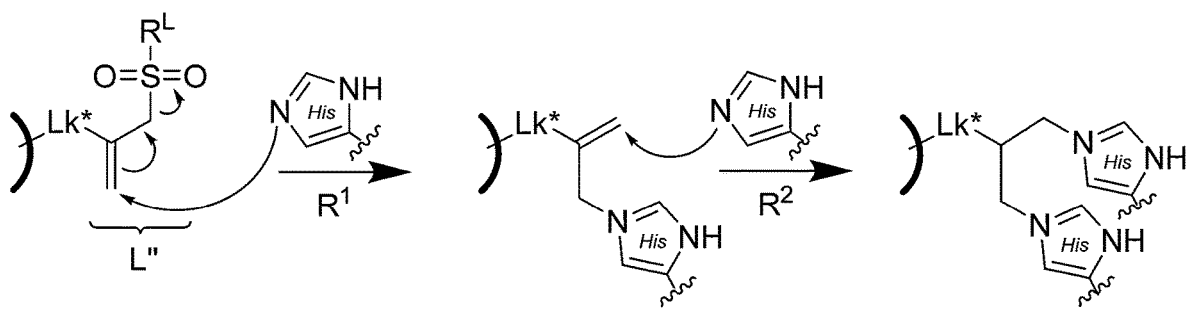
Figure 5C:
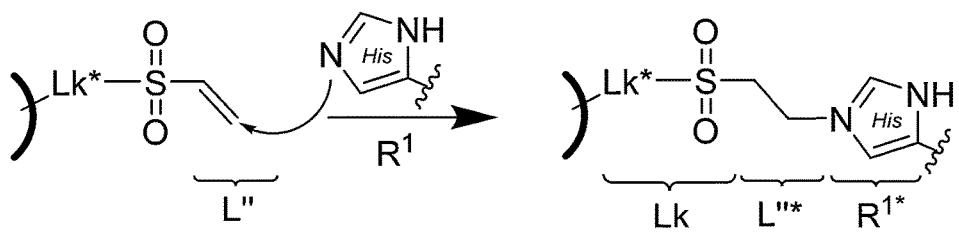

FIGS. 5A-5B provides schematics of exemplary reaction schemes for linking agents and spacers. As seen in FIG. 5A, the spacer can include multiple coordination bonds (i), multiple covalent bonds (ii), or a single covalent bond (iii) between the core and the cargo. Such spacers can employ any useful linking agent and reaction schemes. FIG. 5B provides an exemplary reaction scheme in which the linking agent includes a reactive group L" having an alkene and a sulfone leaving group. The reactive group $R^1$ of the cargo participates in an addition reaction with L", thereby providing a single covalent bond present in the spacer. Then, a second reactive group $R^2$ of the cargo participated in another addition reaction with the linking agent, thereby providing a second covalent bond present in the spacer. FIG. 5C provides an exemplary reaction scheme in which the linking agent includes a reactive group L" having an alkene and a sulfone leaving group, and the reactive group $R^1$ of the cargo participates in an addition reaction to provide a single covalent bond. Other exemplary spacers and linking agents are described in Cong Y et al., *Bioconjug. Chem.* 2012; 23(2):248-63; Liberatore F A et al., *Bioconjug. Chem.* 1990; 1(1):36-50; Han D H et al., *Nature Commun.* 2014; 5(5): 5633; and Shen D et al., *Nano Lett.* 2014; 14(2):923-32, each of which is incorporated herein by reference in its entirety.

Reactive groups can be present on any useful bonding components, such as spacers, linking agents, a surface of the core, and/or a cargo. Pairs of reactive groups can be chosen to facilitate any useful reaction between any bonding components. In one instance, the first bonding component includes a nucleophilic reactive group (e.g., an amino group, a thio group, a hydroxyl group, an anion, etc.), and the second bonding component includes an electrophilic reactive group (e.g., an alkenyl group, an alkynyl group, a carbonyl group, an ester group, an imido group, an epoxide group, an amido group, a carbamido group, a cation, etc.).

Exemplary reactive groups include any chemical group configured to form a bond. In general, a first chemical group reacts with a second chemical group to form a bond (e.g., a covalent bond), in which the first and second chemical groups form a reactive pair.

In one instance, the reactive group is a cross-linker group. In another non-limiting instance, the reactive pair is a cross-linker reaction pair, which includes a first cross-linker group and a second cross-linker group that reacts with that first cross-linker group. Exemplary cross-linker groups and cross-linker reaction pairs include those for forming a covalent bond between a carboxyl group (e.g., $-CO_2H$) and an amino group (e.g., $-NH_2$); or between an imido group (e.g., maleimido or succinimido) and a thiol group (e.g., $-SH$); or between an epoxide group and a thiol group (e.g., $-SH$); or between an epoxide group and an amino group (e.g., $-NH_2$); or between an ester group (e.g., $-CO_2R$, in which R is an organic moiety, such as optionally substituted alkyl, aryl, etc.) and an amino group (e.g., $-NH_2$); or between an carbamido group (e.g., $-NHC(O)Het$, where Het is a N-containing heterocyclyl) and an amino group (e.g., $-NH_2$); or between a phospho group (e.g., $-P(O)(OH)_2$) and an amino group (e.g., $-NH_2$), such as 1-ethyl-3-(3-dimethylaminopropyl)carbodiimide (EDC) and dicyclohexylcarbodiimide (DCC), optionally used with N-hydroxysuccinimide (NHS) and/or N-hydroxysulfosuccinimide (sulfo-NHS). Other cross-linkers include those for forming a covalent bond between an amino group (e.g., $-NH_2$) and a thymine moiety, such as succinimidyl-[4-(psoralen-8-yloxy)]-butyrate (SPB); a hydroxyl group (e.g., $-OH$) and a sulfur-containing group (e.g., free thiol, $-SH$, sulfhydryl, cysteine moiety, or mercapto group), such as p-maleimidophenyl isocyanate (PMPI); between an amino group (e.g., $-NH_2$) and a sulfur-containing group (e.g., free thiol, $-SH$, sulfhydryl, cysteine moiety, or mercapto group), such as succinimidyl 4-(p-maleimidophenyl)butyrate (SMPB) and/or succinimidyl 4-(N-maleimidomethyl)cyclohexane-1-carboxylate (SMCC); between a sulfur-containing group (e.g., free thiol, $-SH$, sulfhydryl, cysteine moiety, or mercapto group) and a carbonyl group (e.g., an aldehyde group, such as for an oxidized glycoprotein carbohydrate), such as N-beta-maleimidopropionic acid hydrazide-trifluoroacetic acid salt (BMPH), 3-(2-pyridyldithio)propionyl hydrazide (PDPH), and/or a 3-(2-pyridyldithio)propionyl group (PDP); and between a maleimide-containing group and a sulfur-containing group (e.g., free thiol, $-SH$, sulfhydryl, cysteine moiety, or mercapto group). Yet other cross-linkers include those for forming a covalent bond between two or more unsaturated hydrocarbon bonds, e.g., such as a reaction of forming a covalent bond between a first alkene group and a second alkene group.

In another instance, the reactive group is a binding group. In another non-limiting instance, the reactive pair is a binding reaction pair, which includes a first binding group and a second binding group that reacts with that first binding group. Exemplary binding groups and binding reaction pairs include those for forming a bond between biotin and avidin, biotin and streptavidin, biotin and neutravidin, desthiobiotin and avidin (or a derivative thereof, such as streptavidin or neutravidin), hapten and an antibody, an antigen and an antibody, a primary antibody and a secondary antibody, and lectin and a glycoprotein.

In yet another instance, the reactive group is a click-chemistry group. In another non-limiting instance, the reactive pair is a click-chemistry reaction pair, which includes a first click-chemistry group and a second click-chemistry group that reacts with that first click-chemistry group. Exemplary click-chemistry groups include, e.g., a click-chemistry group, e.g., one of a click-chemistry reaction pair selected from the group consisting of a Huisgen 1,3-dipolar cycloaddition reaction between an alkynyl group and an azido group to form a triazole-containing spacer; a Diels-Alder reaction between a diene having a $4\pi$ electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a $2\pi$ electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group.

Exemplary reactive groups include an amino (e.g., $-NH_2$), a thio (e.g., a thioalkoxy group or a thiol group), a hydroxyl, an ester (e.g., an acrylate), an imido (e.g., maleimido or a succinimido), an epoxide, an isocyanate, an isothiocyanate, an anhydride, an amido, a carbamido (e.g., a urea derivative), an azide, an optionally substituted alkynyl, or an optionally substituted alkenyl.

Exemplary linking groups include any moiety, including any useful subunit, which can be optionally repeated, that provides a spacer having any useful property. Exemplary linking groups include a bond (e.g., a covalent bond), optionally substituted alkylene, optionally substituted heteroalkylene (e.g., poly(ethylene glycol)), optionally substituted arylene, and optionally substituted heteroarylene. Yet other exemplary linking groups are those including an ethylene glycol group, e.g., $-OCH_2CH_2-$, including a poly(ethylene glycol) (PEG) group $-(OCH_2CH_2)_n$, a four-arm PEG group (such as $C(CH_2O(CH_2CH_2O)_n-)_4$ or $C(CH_2O(CH_2CH_2O)_nCH_2-)_4$ or $C(CH_2O(CH_2CH_2O)_n CH_2CH_2-)_4$ or $C(CH_2O(CH_2CH_2O)_nCH_2CH_2NHC(O) CH_2CH_2-)_4$ $C(CH_2O(CH_2CH_2O)_nCH_2C(O)O-)_4)$, an eight-arm PEG group (such as $-(OCH_2CH_2)_nO [CH_2CHO ((CH_2CH_2O)_n-)CH_2O]_6(CH_2CH_2O)_n-$ or $-CH_2 (OCH_2CH_2)_nO[CH_2CHO((CH_2CH_2O)_nCH_2)CH_2O]_6 (CH_2CH_2O)_nCH_2-$ or $-CH_2CH_2(OCH_2CH_2)_nO [CH_2CHO((CH_2CH_2O)_nCH_2CH_2)CH_2O]_6(CH_2CH_2O)_n CH_2CH_2-$ or $R(O(CH_2CH_2O)_n-)_8$ or $R(O(CH_2 CH_2O)_nCH_2-)_8$ or $R(O(CH_2CH_2O)_nCH_2CH_2-)_8$, in which R includes a tripentaerythritol core), or a derivatized PEG group (e.g., methyl ether PEG (mPEG), a propylene glycol group, etc.); including dendrimers thereof, copolymers thereof (e.g., having at least two monomers that are different), branched forms thereof, start forms thereof, comb forms thereof, etc., in which n is any useful number in any of these (e.g., any useful n to provide any useful number average molar mass $M_n$). Yet other linking groups can include a nucleic acid, a peptide, as well as modified forms thereof.

Exemplary linking agents can include a poly(ethylene glycol) group (e.g., a multivalent poly(ethylene glycol) precursor having a reactive functional group, such as an amino group, an ester group, an acrylate group, a hydroxyl group, a carboxylic acid group, etc.), such as eight arm-PEG amine (8-arm PEG-NH$_2$, e.g., catalog nos. PSB-811, PSB-812, or PSB-814 available from Creative PEGWorks, Chapel Hill, N.C.) or an eight-arm PEG succinimidyl ester (such as 8-arm PEG succinimidyl NHS ester or 8-arm PEG-SCM (succinimidyl carboxyl methyl ester), e.g., catalog nos. PSB-841, PSB-842, or PSB-844 available from Creative PEGWorks) or an eight-arm PEG vinylsulfone or an eight-arm PEG hydroxyl or a linear PEG thiol or a linear PEG hydroxyl or poly(ethylene glycol) diacrylate) (PEG-DA) or triethylene glycol acrylate (TEGA) or 2-carboxyethyl acrylate (CEA) or 2-hydroxyethylacrylate (HEA), as well as copolymers thereof and/or combinations thereof; an amino acid (e.g., a poly(amino acid) precursor or a protein, such as a poly(lysine) precursor, a poly(arginine) precursor, lysozyme, avidin, or albumin); a glycerol group (e.g., a poly(glycerol) precursor); a vinyl group (e.g., a poly(vinyl) precursor or a poly(vinyl alcohol) precursor); a hydroxyacid group (e.g., a poly(lactic acid) precursor, a poly(glycolic acid) precursor, or a poly(lactic-co-glycolic acid) precursor); an acrylate group (e.g., a poly(acrylic acid) precursor or a poly(methacrylic acid) precursor); a silyl ether group (e.g., a poly(silyl ether) precursor); an olefin group (e.g., a poly(acetylene) precursor); and/or an aromatic group (e.g., a poly(pyrrole) precursor, a poly(aniline) precursor, or a poly(thiophene) precursor).

Other exemplary, non-limiting linking agents include 3-aminopropyltrimethoxysilane (3-APTMS); (R,S)-1-(3,4-(methylenedioxy)-6-nitrophenyl)ethyl chloroformate (Men-POC); 1-(6-nitrobenzo[d][1,3]dioxol-5-yl)ethyl (3-(trimethoxysilyl)propyl)carbamate; phenyltrichlorosilane (PTCS); an epoxysilane; sulfo-NHS-acetate; 1-(3-(trimethoxysilyl)propyl)-1H-pyrrole-2,5-dione; 3-glycidoxypropyltrimethoxysilane (3-GPTMS); N-(3-(trimethoxysilyl)propyl)-1H-imidazole-1-carboxamide; N-(6-aminohexyl)-1H-imidazole-1-carboxamide; anhydrides; isocyanotopropyltrimethoxysilane (IPTMS); isocyanates; isothiocyanates; and maleimides.

Yet other non-limiting linking agents include a covalent spacer or a non-covalent spacer. In some embodiments: the spacer may comprise a flexible arm, e.g., 2, 3, 4, 5, 6, 7, 8, 9, 10, 11, 12, 13, 14, or 15 carbon atoms. Exemplary spacers include BS3 ([bis(sulfosuccinimidyl) suberate]; BS3 is a homobifunctional N-hydroxysuccinimide ester that targets accessible primary amines), NHS/EDC (N-hydroxysuccinimide and N-ethyl-'(dimethylaminopropyl)carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups). Examples of other suitable spacers are succinic acid, Lys, Glu, Asp, a dipeptide such as Gly-Lys, an α-helical spacer (e.g., A(EAAAK)$_n$A, where n is 1, 2, 3, 4, or 5), an alkyl chain (e.g., an optionally substituted C$_{1-12}$ alkylene or alkynyl chain), or a polyethylene glycol (e.g., (CH$_2$CH$_2$O)$_m$, where m is from 1 to 50).

Protecting groups can be employed to protect a reactive group and/or to provide reduced reactivity (e.g., binding) of an agent (e.g., a capture probe). Exemplary protecting groups include any described herein, including optionally substituted aryl groups, a poly(ethylene glycol) group, UV-labile groups, etc.).

Functional groups can be present on a spacer, a core, or a cargo. In addition, a functional group can include any useful chemical group, such as a reactive group or a protecting group. In some instances, the linking agent reacts with a functional group (e.g., present on the cargo or the core), thereby forming an attached spacer that can be further reacted with another functional group.

Cargos

The construct can include CRISPR components, as well as other cargos (e.g., associated with the nanoparticle core, with a pore (e.g., by way of a spacer), and/or within the outer layer). Cargos can include a variety of molecules, including peptides, proteins (e.g., including protein complexes, such as a ribonucleoprotein (RNP) complex including a nucleic acid and a protein), nucleic acids (e.g., a plasmid, mRNA), aptamers, including antisense oligonucleotides, antibodies, small molecule drugs, such as antimicrobials and/or antivirals, alpha/flavi inhibitors, coronavirus (CoV) inhibitors, carbohydrates, dyes, markers, or any other agent described herein.

The cargo can be characterized by a dimension (e.g., a cargo dimension). Exemplary dimensions for the cargo include cargo circumference, cargo diameter, cargo length, and cargo width. Exemplary dimensions (e.g., cargo circumference, diameter, length, or width) are about 2 nm to about 5000 nm (e.g., from 2 nm to 500 nm, 2 nm to 1000 nm, 2 nm to 2500 nm, 5 nm to 500 nm, 5 nm to 1000 nm, 5 nm to 2500 nm, 5 nm to 5000 nm, 25 nm to 500 nm, 25 nm to 1000 nm, 25 nm to 2500 nm, 25 nm to 5000 nm, 50 nm to 500 nm, 50 nm to 1000 nm, 50 nm tvary byo 2500 nm, 50 nm to 5000 nm, 75 nm to 500 nm, 75 nm to 1000 nm, 75 nm to 2500 nm, 75 nm to 5000 nm, 100 nm to 500 nm, 100 nm to 1000 nm, 100 nm to 2500 nm, 100 nm to 5000 nm, 500 nm to 1000 nm, 500 nm to 2500 nm, 500 nm to 5000 nm, 750 nm to 1000 nm, 750 nm to 2500 nm, 750 nm to 5000 nm, 1000 nm to 2500 nm, 1000 nm to 5000 nm, 2500 nm to 5000 nm, or 4000 nm to 5000 nm). Cargo size can be determined by dynamic light scattering (DLS) by methods disclosed above.

Exemplary cargos include an acidic, basic, and hydrophobic drug (e.g., antiviral agents, antibiotic agents, etc.); a protein (e.g., antibodies, carbohydrates, etc.); a nucleic acid (e.g., DNA, RNA, small interfering RNA (siRNA), minicircle DNA (mcDNA), small hairpin RNA (shRNA), complementary DNA (cDNA), naked DNA, and plasmid, as well as chimeras, single-stranded forms, duplex forms, and multiplex forms thereof and including nucleic acid sequences encoding any of these and including one or more modified nucleic acids); a CRISPR component (e.g., any described herein, including a guiding component (e.g., any described herein), a nuclease, a plasmid, a plasmid that encodes a CRISPR component, a ribonucleoprotein complex, a Cas enzyme or an ortholog or homolog thereof, a guide RNA, as well as a nucleic acid sequence encoding any of these or a complement thereof); a diagnostic/contrast agent, like quantum dots, iron oxide nanoparticles, gadolinium, and indium-111; a small molecule; a carbohydrate; a drug, a pro-drug, a vitamin, an antibody, a protein, a hormone, a growth factor, a cytokine, a steroid, an anticancer agent, a fungicide, an antimicrobial, an antibiotic, an antiviral agent, etc.; a morphogen; a toxin, e.g., a bacterial protein toxin; a peptide, e.g., an antimicrobial peptide; an antigen; an antibody; a detection agent (e.g., a particle, such as a conductive particle, a microparticle, a nanoparticle, a quantum dot, a latex bead, a colloidal particle, a magnetic particle, a fluorescent particle, etc.; or a dye, such as a fluorescent dye, a luminescent dye, a chemiluminescent dye, a colorimetric dye, a radioactive agent, an electroactive detection agent, etc.); a label (e.g., a quantum dot, a nanoparticle, a microparticle, a barcode, a fluorescent label, a colorimetric label, a radio label (e.g., an RF label or barcode), avidin, biotin, a tag, a dye, a marker, an electroactive label, an electrocatalytic label, and/or an enzyme that can optionally include one or more linking agents and/or one or more dyes); a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), and/or an enzyme (e.g., that reacts with one or more markers, such as any described herein)); as well as combinations thereof.

The nucleic acid can be provided in any useful form, such as RNA, DNA, DNA/RNA hybrids, phage, plasmid, linear forms thereof, concatenated forms thereof, circularized forms thereof, modified forms thereof, single stranded forms thereof, double stranded forms thereof, complements thereof, and encoded forms thereof.

In some instances, the cargo includes a plasmid. The plasmid can encode any useful CRISPR component (e.g., a guiding component or a nuclease). In addition, the plasmid can express any useful polypeptide and/or nucleic acid sequence, including a nuclear localization sequence, a cell penetrating peptide, a targeting peptide, a polypeptide toxin, a small hairpin RNA (shRNA), a small interfering RNA (siRNA), a reporter (e.g., a reporter protein), etc. Additional reporters include polypeptide reporters which may be expressed by plasmids (such as histone-packaged supercoiled DNA plasmids) and include polypeptide reporters such as fluorescent green protein and fluorescent red protein. Reporters pursuant to the disclosed technology are utilized principally in diagnostic applications including diagnosing the existence or progression of a disease state (e.g., diseased tissue) in a subject or patient and/or the progress of therapy in a patient or subject. The plasmid can be of any useful form (e.g., supercoiled and/or packaged plasmid). For instance, the plasmid can be a histone-packaged supercoiled plasmid including a mixture of histone proteins. Additional CRISPR components are described herein.

Exemplary anticancer agents include chemotherapeutic agents, such as an agent selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes, as well as functionalized or modified forms thereof (e.g., including polyethylene glycol (PEG)). These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY 317615, neuradiab, vitespan, Rta 744, Sdx 102, talampanel, atrasentan, XR 311, romidepsin, ADS-100380, sunitinib, 5-fluorouracil, vorinostat, etoposide, etoposide phosphate, gemcitabine, doxorubicin, liposomal doxorubicin, 5'-deoxy-5-fluorouridine, vincristine, temozolomide, ZK-304709, seliciclib, PD0325901, AZD-6244, capecitabine, L-glutamic acid, N-[4-[2-(2-amino-4,7-dihydro-4-oxo-1 H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-[5-(methylsulfonylpiperadinemethyl)-indolyl]-quinolone, vatalanib, AG-013736, AVE-0005, the acetate salt of [D-Ser(But)6, Azgly 10] (pyro-Glu-His-Trp-Ser-Tyr-D-Ser(But)-Leu-Arg-Pro-Azgly-NH$_2$ acetate [C$_{59}$H$_{84}$N$_{18}$O$_{14}$ —(C$_2$H$_4$O$_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714, TAK-165, HKI-272, erlotinib, lapatanib, canertinib, ABX-EGF antibody, erbitux, EKB-569, PKI-166, GW-572016, lonafarnib, BMS-214662, tipifarnib, amifostine, NVP-LAQ824, suberoyl analide hydroxamic acid, valproic acid, trichostatin A, FK-228, SU11248, sorafenib, KRN951, adriamycin, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib (e.g., including imatinib mesylate), leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-1, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, and darbepoetin alfa, among others. In some embodiments, the anticancer agent is selected from the group of doxorubicin, melphalan, bevacizumab, dactinomycin, cyclophosphamide, doxorubicin liposomal, amifostine, etoposide, gemcitabine, altretamine, topotecan, cyclophosphamide, paclitaxel, carboplatin, cisplatin, and taxol.

Exemplary antiviral agents (e.g., anti-HIV agents) include, for example, nucleoside reverse transcriptase inhibitors (NRTI), non-nucleoside reverse transcriptase inhibitors (NNRTI), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EH T899, zadaxin (thymosin alpha-1) and rnixtures thereof. Anti-HCV agents include, for example, interferon, pegylated intergeron, ribavirir NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

Other exemplary antiviral agents include broad spectrum antiviral agents, antibodies, small molecule antiviral agents, antiretroviral agents, etc. Further non-limiting antiviral agents include abacavir, ACH-3102, acyclovir (acyclovir), acyclovir, adefovir, amantadine, amprenavir, ampligen, arbidol, asunaprevir, atazanavir, atripla, balavir, BCX4430, boceprevir, brincidofovir, brivudine, cidofovir, clevudine, combivir, cytarabine, daclatasvir, dasabuvir, deleobuvir, dolutegravir, darunavir, delavirdine, didanosine, docosanol, edoxudine, efavirenz, elbasvir, emtricitabine, enfuvirtide, entecavir, ecoliever, faldaprevir, famciclovir, favipiravir, fomivirsen, fosamprenavir, foscarnet, fosfonet, ganciclovir, grazoprevir, ibacitabine, imunovir, idoxuridine, imiquimod, indinavir, interferon type III, interferon type II, interferon type I, interferon, interferon alfa 2b, lamivudine, laninamivir, ledipasvir (with or without sofosbuvir), lopinavir, loviride, maraviroc, moroxydine, methisazone, MK-3682, MK-8408, nelfinavir, nevirapine, nexavir, novir, ombitasvir (with or without paritaprevir and/or ritonavir), oseltamivir (Tamiflu), paritaprevir, peginterferon alfa-2a, penciclovir, peramivir, pleconaril, podophyllotoxin, raltegravir, resiquimod, ribavirin, rifampicin, rimantadine, ritonavir, pyramidine, samatasvir, saquinavir, simeprevir, sofosbuvir, stavudine, taribavirin, tecovirimat (ST-246), telaprevir, telbivudine, tenofovir, tenofovir disoproxil, tipiracil, tipranavir, trifluridine (with or without tipiracil), trizivir, tromantadine, truvada, umifenovir, valaciclovir (Valtrex), valganciclovir, vicriviroc, vidarabine, viramidine, zalcitabine, zanamivir (Relenza), zidovudine, including prodrugs, salts, and/or combinations thereof.

Exemplary antibiotics or antibacterial agents include gentamicin, kanamycin, neomycin, netilmicin, tobramycin, paromomycin, spectinomycin, geldanamycin, herbimycin, rifaximin, streptomycin, ertapenem, doripenem, imipenem/cilastatin, meropenem, cefadroxil, cefazolin, cephalothin, cephalexin, cefaclor, cefamandole, cefoxitin, cefprozil, cefuroxime, cefixime, cefdinir, cefditoren, cefoperazone cefotaxime, cefpodoxime, ceftazadime, ceftibuten, ceftizoxime ceftriaxone, cefepime, ceftaroline fosamil, ceftobiprole, teicoplanin, vancomycin, telavancin, daptomycin, oritavancin, WAP-8294A, azithromycin, clarithromycin, dirithromycin, erythromycin, roxithromycin, telithromycin, spiramycin, clindamycin, lincomycin, aztreonam, furazolidone, nitrofurantoin, oxazolidonones, linezolid, posizolid, radezolid, torezolid, amoxicillin, ampicillin, azlocillin, carbenicillin, cloxacillin dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, piperacillin/tazobactam, ticarcillin/clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, mafenide, sulfacetamide, sulfadiazine, sulfadimethoxine, sulfamethizole, sulfamethoxazole, sulfasalazine, sulfisoxazole, trimethoprim-sulfamethoxazole, sulfonamidochrysoidine, demeclocycline, doxycycline, vibramycin minocycline, tigecycline, oxytetracycline, tetracycline, clofazimine, capreomycin, cycloserine, ethambutol, rifampicin, rifabutin, rifapentine, arsphenamine, chloramphenicol, fosfomycin, fusidic acid, metronidazole, mupirocin, platensimycin, quinupristin/dalfopristin, thiamphenicol, tigecycline, and tinidazole and combinations thereof.

CRISPR Components

In an embodiment, the cargo includes a CRISPR component. CRISPR component includes any employing a nucleic acid sequence capable of recruiting a CRISPR-associated (Cas) protein to achieve genetic modification. An exemplary CRISPR component includes those having a trans-acting CRISPR RNA (tracrRNA) and CRISPR RNA (crRNA) fused into a single, synthetic 'guide RNA' that directs a Cas nuclease (e.g., Cas9) to virtually any desired DNA sequence (see, e.g., FIG. 6). The synthetic guide RNA (gRNA) can include at least three different portions: a first portion including the tracrRNA sequence, a second portion including the crRNA sequence, and a third portion including a targeting portion or a genomic specific sequence (gsRNA) that binds to a desired genomic target sequence (e.g., genomic target DNA sequence, including a portion or a strand thereof). The chimeric tracrRNA-crRNA sequence facilitates binding and recruitment of the endonuclease (e.g., Cas9), and the gsRNA sequence provides site-specificity to the target nucleic acid, thereby allowing Cas9 to selectively introduce site-specific breaks in the target.

In any embodiment herein, the cargo can include a CRISPR component. Exemplary CRISPR components can include a guide RNA, a Cas enzyme, and a nucleic acid sequence (e.g., a plasmid) encoding any of these. Yet other exemplary CRISPR components are shown in FIGS. 12, 13, 14A-14C, 15, 16, 17A-17C, 18A-18D, and 19, including, as applicable, a nucleic acid sequence encoding any of these (e.g., a nucleic acid sequence encoding any polypeptide sequence therein, such as SEQ ID Nos: 110-117 or a fragment thereof), a polypeptide generated by any nucleic acid sequence therein, as well as a complement of any nucleic acid sequence therein (e.g., a nucleic acid sequence that is a complement of any one of SEQ ID Nos: 20-32, 40-54, 60-65, 80-93, 100-103, or a fragment thereof).

In particular embodiments, the particle can include one or more CRISPR components (e.g., associated with or within a pore of the core (e.g., by way of a spacer), associated with a surface of the core, and/or within the outer layer).

Figure 6:
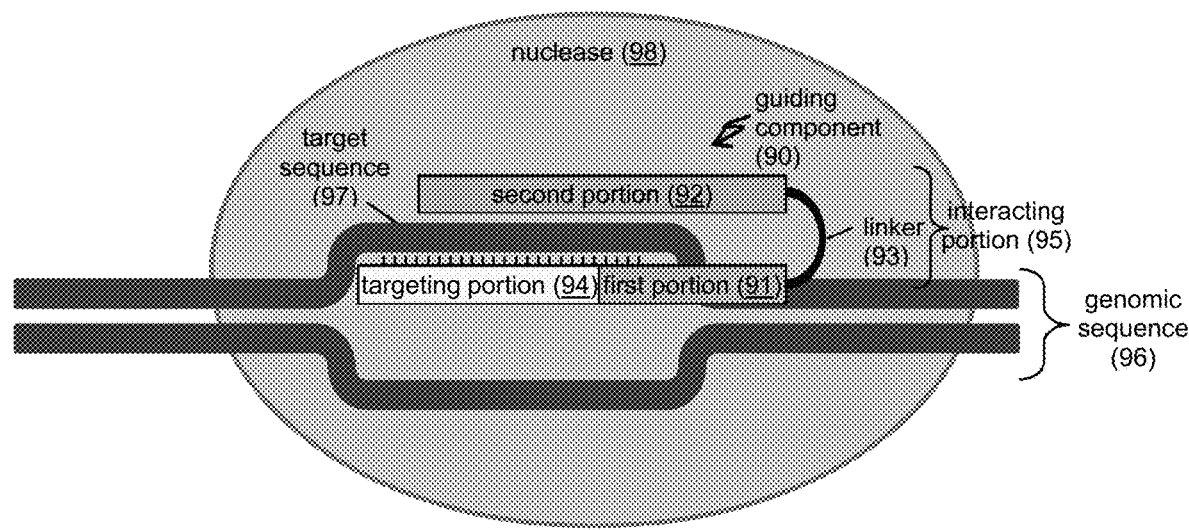
FIG. 6 is a schematic view of an exemplary CRISPR component that includes a guiding component 90 to bind to the target sequence 97, as well as a nuclease 98.

FIG. 6 and FIGS. 7A-7C show exemplary CRISPR components. FIG. 6 shows an exemplary CRISPR component that includes a guiding component 90 to bind to the target sequence 97, as well as a nuclease 98 (e.g., a Cas nuclease or an endonuclease, such as a Cas endonuclease) that interacts with the guiding component and the target sequence.

Figure 7A:
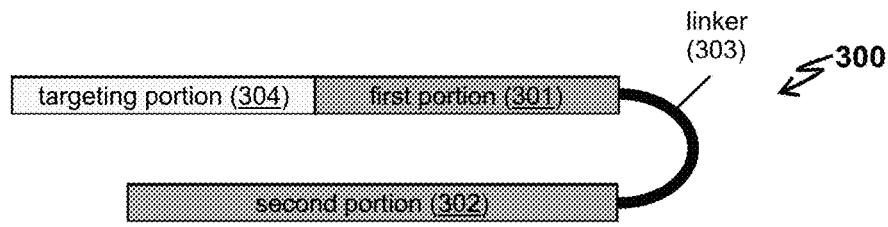
Figure 7B:
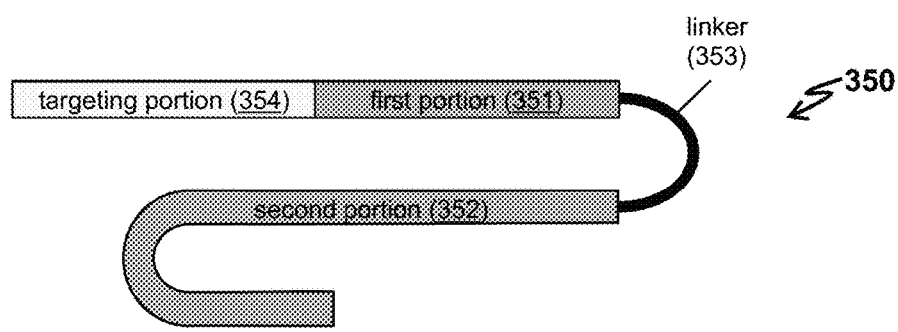

FIG. 7A shows a non-limiting guiding component 300 having a targeting portion 304, a first portion 301, a second portion 302, and a linker 303 disposed between the first and second portions. FIG. 7B shows another non-limiting guiding component 350 having a targeting portion 354, a first portion 351, a second portion 352 having a hairpin, and a linker 353 disposed between the first and second portions. FIG. 7C shows non-limiting interactions between the guiding component 400, the genomic sequence 412, and the first and second portion 401,402. As can be seen, the target sequence 411 of the genomic sequence 412 is targeted by way of non-covalent binding 421 to the targeting portion 404, and secondary structure can be optionally implemented by way of non-covalent binding 422 between the first portion 401 and the second portion 402. The targeting portion 404, first portion 401, linker 403, and second portion 402 can be attached in any useful manner (e.g., to provide a 5' end 405 and a 3' end 406).

This CRISPR/Cas system can be adapted to control genetic expression in targeted manner, such as, e.g., by employing synthetic, non-naturally occurring constructs that use crRNA nucleic acid sequences, tracrRNA nucleic acid sequences, and/or Cas polypeptide sequences, as well as modified forms thereof.

In an embodiment, a CRISPR component includes a guiding component. In general, the guiding component includes a nucleic acid sequence (e.g., a single polynucleotide) that includes at least two portions: a targeting portion, which is a nucleic acid sequence that imparts specific targeting to the target genomic locus (e.g., a guide RNA or gRNA); and an interacting portion, which is another nucleic acid sequence that binds to a nuclease (e.g., a Cas endonuclease). In some instances, the interacting portion includes two particular sequences that bind the nuclease, e.g., a short crRNA sequence attached to the guide nucleic acid sequence; and a tracrRNA sequence attached to the crRNA sequence. Exemplary targeting CRISPR components include a minicircle DNA vector optimized for in vivo expression.

Another CRISPR component includes a nuclease (e.g., that binds the targeting nucleic acid sequence). The nuclease CRISPR component can either be an enzyme, or a nucleic acid sequence that encodes for that enzyme. Exogenous endonuclease (e.g., Cas9) can be encoded by a cargo stored within the construct. In an embodiment, a nuclease such as Cas9 (e.g., SEQ ID NO:110) is employed, as well as nickase forms and deactivated forms (e.g., SEQ ID NO:111) thereof (e.g., including one or more mutations, such as D10A, H840A, N854A, and N863A in SEQ ID NO:110 or in an amino acid sequence sufficiently aligned with SEQ ID NO:110), including nucleic acid sequences that encode for such nuclease. Pathogen-directed and host-directed CRISPR components (e.g., guiding components and/or nuclease), as well as minicircle DNA vectors that encode Cas and guiding components can be developed. The nuclease can be configured to bind the target sequence and/or cleave the target sequence.

Non-limiting examples of nucleases are described in FIGS. 8A-8H. In some embodiments, a vector comprises a regulatory element operably linked to an enzyme-coding sequence encoding a nuclease (e.g., a CRISPR enzyme, such as a Cas protein). Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments, the CRISPR enzyme is Cas9 and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence.

The nuclease may be a Cas9 homolog or ortholog. In some embodiments, the nuclease is codon-optimized for expression in a eukaryotic cell. In some embodiments, the nuclease directs cleavage of one or two strands at the location of the target sequence. In some embodiments, the nuclease lacks DNA strand cleavage activity. In some embodiments, the first regulatory element is a polymerase III promoter. In some embodiments, the second regulatory element is a polymerase II promoter.

Any useful Cas protein or complex can be employed. Exemplary Cas proteins or complexes include those involved in Type I, Type II, or Type III CRISPR/Cas systems, including but not limited to the CRISPR-associated complex for antiviral defense (Cascade, including a RAMP protein), Cas3 and/or Cas 7 (e.g., for Type I systems, such as Type I-E systems), Cas9 (formerly known as Csn1 or Csx12, e.g., such as in Type II systems), Csm (e.g., in Type III-A systems), Cmr (e.g., in Type III-B systems), Cas10 (e.g., in Type III systems), as well as subassemblies or sub-components thereof and assemblies including such Cas proteins or complexes. Additional Cas proteins and complexes are described in Makarova K S et al., "Evolution and classification of the CRISPR-Cas systems," Nat. Rev. Microbiol. 2011; 9:467-77, which is incorporated herein by reference in its entirety.

In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the disclosed technology, nickases may be used for genome editing via homologous recombination. In some instances, the Cas protein includes a modification of one of more of D10A, H840A, N854A, and N863A in SEQ ID NO:110 or in an amino acid sequence sufficiently aligned with SEQ ID NO:110.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, the guiding component comprises a modification or sequence that provides for an additional desirable feature (e.g., modified or regulated stability; subcellular targeting; tracking, e.g., a fluorescent label; a binding site for a protein or protein complex; etc.). Non-limiting examples include: a short motif (referred to as the protospacer adjacent motif (PAM)); a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, and chloroplasts); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, and histone deacetylases); and combinations thereof.

A guiding component and a nuclease can form a complex (i.e., bind via non-covalent interactions). The guiding component provides target specificity to the complex by comprising a nucleotide sequence that is complementary to a sequence of a target sequence. The nuclease of the complex provides the site-specific activity. In other words, the nuclease is guided to a target sequence (e.g., a target sequence in a chromosomal nucleic acid; a target sequence in an extra-chromosomal nucleic acid, e.g., an episomal nucleic acid, a minicircle, etc.; a target sequence in a mitochondrial nucleic acid; a target sequence in a chloroplast nucleic acid; a target sequence in a plasmid, etc.) by virtue of its association with the protein-binding segment (e.g., the interacting portion) of the guiding component.

In some embodiments, the guiding component comprises two separate nucleic acid molecules (e.g., a separate targeting portion and a separate interacting portion; a separate first portion and a separate second portion; or a separate targeting portion-first portion that is covalently bound and a separate second portion). In other embodiments, the guiding component is a single nucleic acid molecule including a covalent bond or a linker between each separate portion (e.g., a targeting portion covalently linked to an interacting portion).

FIG. 6 shows an exemplary CRISPR component that includes a guiding component 90 to bind to the target sequence 97, as well as a nuclease 98 (e.g., a Cas nuclease or an endonuclease, such as a Cas endonuclease) that interacts with the guiding component and the target sequence. As can be seen, the guiding component 90 includes a targeting portion 94 configured to bind to the target sequence 97 of a genomic sequence 96 (e.g., a target sequence having substantially complementarity with the genomic sequence or a portion thereof). In this manner, the targeting portion confers specificity to the guiding component, thereby allowing certain target sequences to be activated, inactivated, and/or modified.

The guiding component 90 also includes an interacting portion 95, which in turn is composed of a first portion 91, a second portion 92, and a linker 93 that covalently links the first and second portions. The interacting portion 95 is configured to recruit the nuclease (e.g., a Cas nuclease) in proximity to the site of the target sequence. Thus, the interacting portion includes nucleic acid sequences that provide preferential binding (e.g., specific binding) of the nuclease. Once in proximity, the nuclease 98 can bind and/or cleave the target sequence or a sequence in proximity to the target sequence in a site-specific manner.

The first portion, second portion, and linker can be derived in any useful manner. In one instance, the first portion can include a crRNA sequence, a consensus sequence derived from known crRNA sequences, a modified crRNA sequence, or an entirely synthetic sequence known to bind a Cas nuclease or determined to competitively bind a Cas nuclease when compared to a known crRNA sequence. Exemplary sequences for a first portion are described in FIG. 9 (SEQ ID NOs:20-32). Another exemplary sequence for a first portion is 5'-GUUUUAGAGCUA-3' (SEQ ID NO:70). In some embodiments, the first portion is a nucleic acid sequence having at least 80% sequence identity (e.g., at least 85%, 90%, 95%, or 99% sequence identity) to any one of SEQ ID NOs:20-32 and 70 or a complement of any of these, or a fragment thereof (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more nucleotides).

In some embodiments, the first portion is a crRNA sequence that exhibits at least 50%, 60%, 70%, 80%, 90%, 95%, or 99% of sequence complementarity to any one of SEQ ID NOs:20-32 and 70. In other embodiments, the first portion is a fragment (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more nucleotides) of a crRNA sequence that exhibits at least 50%, 60%, 70%, 80%, 90%, 95%, or 99% of sequence complementarity to any one of SEQ ID NOs:20-32 and 70.

In another instance, the second portion can include a tracrRNA sequence, a consensus sequence derived from known tracrRNA sequences, a modified tracrRNA sequence, or an entirely synthetic sequence known to bind a Cas nuclease or determined to competitively bind a Cas nuclease when compared to a known tracrRNA sequence. Exemplary sequences for a second portion are described in FIGS. 10A-10C (SEQ ID NOs:40-54) and in FIG. 11 (SEQ ID NOs:60-65). Another exemplary sequence for a second portion is 5'-UAGCAAGUUAAAA UAAGGCUAGUCCG-3' (SEQ ID NO:71).

In some embodiments, the second portion is a nucleic acid sequence having at least 80% sequence identity (e.g., at least 85%, 90%, 95%, or 99% sequence identity) to any one of SEQ ID NOs:40-54, 60-65, and 71 or a complement of any of these, or a fragment thereof (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more nucleotides).

In some embodiments, the second portion is a tracrRNA sequence that exhibits at least 50%, 60%, 70%, 80%, 90%, 95%, or 99% of sequence complementarity to any one of SEQ ID NOs:40-54, 60-65, and 71. In other embodiments, the second portion is a fragment (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more nucleotides) of a tracrRNA sequence that exhibits at least 50%, 60%, 70%, 80%, 90%, 95%, or 99% of sequence complementarity to any one of SEQ ID NOs:40-54, 60-65, and 71.

The linker can be, for example, one or more transcribable elements, such as a nucleotide or a nucleic acid, or including one or more chemical linkers. Further, the linker can be derived from a fragment of any useful tracrRNA sequence (e.g., any described herein). The first and second portions can interact in any useful manner. For example, the first portion can have a sequence portion that is sufficiently complementary to a sequence portion of the second portion, thereby facilitating duplex formation or non-covalent bonding between the first and second portion. In another example, the second portion can include a first sequence portion that is sufficiently complementary to a second sequence portion, thereby facilitating hairpin formation within the second portion. Further, CRISPR components are described in FIG. 7A-7C.

In another embodiment, the guiding component has a structure of A-L-B, in which A includes a first portion (e.g., any one of SEQ ID NOs:20-32 and 70, or a fragment thereof), L is a linker (e.g., a covalent bond, a nucleic acid sequence, a fragment of any one of SEQ ID NOs:40-54, 60-65, and 71, or any other useful linker or spacer described herein), and B is a second portion (e.g., any one of SEQ ID NOs:40-54, 60-65, and 71, or a fragment thereof) (FIG. 12). In another embodiment, the guiding component is a sequence having at least 80% sequence identity (e.g., at least 85%, 90%, 95%, or 99% sequence identity) to any one SEQ ID NOs:80-93, or a fragment thereof.

In yet another embodiment, the guiding component is a sequence that exhibits at least 50%, 60%, 70%, 80%, 90%, 95%, or 99% of sequence complementarity to any one SEQ ID NOs:100-103, or a fragment thereof (FIG. 13). In another embodiment, the guiding component is a sequence having at least 80% sequence identity (e.g., at least 85%, 90%, 95%, or 99% sequence identity) to any one SEQ ID NOs:100-103, or a fragment thereof.

In some embodiments, the CRISPR component includes ds plasmid DNA, which is modified to express RNA and/or a protein. In other embodiments, the CRISPR component is supercoiled and/or packaged (e.g., within a complex, such as those containing histones, lipids (e.g., lipoplexes), proteins (e.g., cationic proteins), cationic carrier, nanoparticles (e.g., gold or metal nanoparticles), etc.), which may be optionally modified with a nuclear localization sequence (e.g., a peptide sequence incorporated or otherwise crosslinked into histone proteins, which comprise the histone-packaged supercoiled plasmid DNA). Other exemplary histone proteins include H1, H2A, H2B, H3 and H4, e.g., in a ratio of 1:2:2:2:2 with optional nuclear localization sequences (e.g., any described herein, such as SEQ ID NOs:9-12).

The CRISPR component can include any useful promoter sequence(s), expression control sequence(s) that controls and regulates the transcription and translation of another DNA sequence, and signal sequence(s) that encodes a signal peptide. The promoter sequence can include a DNA regulatory region capable of binding RNA polymerase in a cell and initiating transcription of a downstream (3' direction) coding sequence. For purposes of the present disclosed technology, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

In addition, the CRISPR components can be formed from any useful combination of one or more nucleic acids (or a polymer of nucleic acids, such as a polynucleotide). Exemplary nucleic acids or polynucleotides of the disclosed technology include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids, chimeras, or modified forms thereof. Exemplary modifications include any useful modification, such as to the sugar, the nucleobase, or the internucleoside linkage (e.g., to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present disclosure may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

Toxicity of CRISPR components, to the host, can be minimized. For instance, toxicity can result from protocells or carriers due to expression of Cas9 products or immune responses. Specifically, the lifetime of CRISPR components in the cell can be controlled by adding features that are stabilized or destabilized with cellular proteases, by inducing expression only under a microbial or viral promoter, and by using guiding components with modified backbones (e.g., 2-OMe) to minimize immune recognition.

Resistance to CRISPR components can be minimized. Any single antibiotic or antiviral countermeasure is prone to the development of resistance, so pathogens will likely mutate around individual guiding component targets. However, the development of resistance can be prevented by targeting orthogonal mechanisms via multiplexed guiding components in combination with current antivirals/antimicrobials.

Off-target mutations or genetic modification can be minimized. For instance, bioinformatic guiding component design programs can be used to determine minimal effective CRISPR component doses. If needed, the nickase version of Cas9 can be employed.

The CRISPR component can be employed to target a nucleic acid sequence (e.g., present in the host's genomic sequence and/or the pathogen's genomic sequence). In one instance, the target sequence can include a sequence present in the host's genomic sequence in order, e.g., activate, inactive, or modify expression of factor or proteins within the host's cellular machinery. For instance, the target sequence can bind to one or more genomic sequences for an immunostimulatory protein that, upon expression, would enhance the immune response by the host to an infection. Pathogens are known to down-regulate proteins that would otherwise assist in recognizing non-self protein motifs. Thus, in another instance, the target sequence can bind to one or more regulator proteins and enhance their transcription and expression. In yet another instance, one or more polypeptides may be up-regulated, as compared to the normal basal rate, and such up-regulation may be modified by the presence of the pathogen. Accordingly, the target sequence can be employed to bind to one or more up-regulated polypeptides in order to inactivate or repress transcription/expression of those polypeptides.

An exemplary target sequence (e.g., in a host or subject) includes, without limitation, a nucleic acid sequence encoding an immunostimulatory protein, a cluster of differentiation protein, a cell surface protein, a pathogen receptor protein (e.g., a pathogen recognition receptor, such as TLR9), a glycoprotein (e.g., granulocyte-colony stimulating factor), a cytokine (e.g., interferon or transforming growth factor beta (TGF-beta)), a pattern recognition receptor protein, a hormone (e.g., a prostaglandin), or a helicase enzyme.

In yet another instance, the target sequence can be employed to activate, inhibit, and/or modify a target sequence (e.g., associated with the presence of a pathogen, a tumor, etc.). For instance, the target sequence can be configured to activate one or more target sequences encoding proteins that promote programmed cell death or apoptosis (e.g., of the pathogen or of particular tissue types, such as metastatic growths, tumors, lesions, etc.). For instance, the target sequence can be configured to inactivate or modify one or more target sequences encoding proteins that are suppressed by the pathogen. Exemplary target sequence (e.g., in a pathogen) includes, without limitation, a nucleic acid sequence encoding a virulence factor (e.g., a lipase, a protease, a nuclease (e.g., a DNAse or an RNase), a hemolysin, a hyaluronidase, an immunoglobulin protease, an endotoxin, or an exotoxin), a cell surface protein (e.g., an adhesion), an envelope protein (e.g., a phospholipid, a lipopolysaccharide, a lipoprotein, or a polysaccharide), a glycoprotein, a polysaccharide protein, a transmembrane protein (e.g., an invasin), or a regulatory protein.

The CRISPR component can be employed to activate the target sequence (e.g., the Cas polypeptide can include one or more transcriptional activation domains, which upon binding of the Cas polypeptide to the target sequence, results in enhanced transcription and/or expression of the target sequence), inactivate the target sequence (e.g., the Cas polypeptide can bind to the target sequence, thereby inhibiting expression of one or more proteins encoded by the target sequence; the Cas polypeptide can introduce double-stranded or single-stranded breaks in the target sequence, thereby inactivating the gene; or the Cas polypeptide can include one or more transcriptional repressor domains, which upon binding of the Cas polypeptide to the target sequence, results in reduced transcription and/or expression of the target sequence), and/or modify the target sequence (e.g., the Cas polypeptide can cleave the target sequence of the pathogen and optionally inserts a further nucleic acid sequence).

Any useful transcriptional activation domains can be employed (e.g., VP64, VP16, HIV TAT, or a p65 subunit of nuclear factor KB). In particular, such activation domains are useful when employed with a deactivated or modified form of the Cas polypeptide with minimized cleavage activity. In this way, specific recruitment of the Cas polypeptide to the target sequence is enabled by the interacting portion of the target component, and transcriptional activity is controlled by the activation domains.

Further, transcriptional repressor domains can be employed (e.g., a Kruppel-associated box domain, a SID domain, an Engrailed repression domain (EnR), or a SID4X domain). In particular, such repressor domains can be employed with a deactivated or modified form of the Cas polypeptide with minimized cleavage activity or with an active Cas polypeptide with retained endonuclease activity.

A guiding component may be selected to target any target sequence. In some embodiments, the target sequence is a sequence within a genome of a host (e.g., a host cell) or a pathogen (e.g., a pathogen cell). In some embodiments, the guiding component is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guiding component is less than about 75, 50, 45, 40, 35, 30, 25, 20, 15, 12, or fewer nucleotides in length. The ability of a guiding component to direct sequence-specific binding of a CRISPR complex to a target sequence may be assessed by any suitable assay. For example, the components of a CRISPR system sufficient to form a CRISPR complex, including the guiding component to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target sequence may be evaluated in a test tube by providing the target sequence, components of a CRISPR complex, including the guiding component to be tested and a control guiding component different from the test guiding component, and comparing binding or rate of cleavage at the target sequence between the test and control guiding component reactions.

Outer Layer

The constructs disclosed herein include an outer layer (also referred to as a coating herein) disposed around the core. In particular embodiments, the outer layer includes a combination of lipids supported by or bonded to the surface of the core. The outer layer or coating may also include one or more moieties (e.g., one or more targeting ligands, such as a pegylated lipid). In other embodiments, the outer layer can include a polymer layer (e.g., supported by the surface of the core) that can optionally include one or more moieties (e.g., one or more targeting ligands).

The outer layer or coating, (lipid bilayer) can be characterized by its thickness (e.g., about 5 nm to about 3 to about 40 nm, such as about 4 to about 25 nm, or about 5 to about 15 nm), the number of layers within the outer layers (e.g., two, three, four, five, six, seven, or more lipid and/or polymer layers within the outer layer), and/or the net charge of the outer layer (e.g., a net non-negative charge, such as a net positive charge; or as determined by the composition of the lipid layer, such as one formed by use of a liposome formulation having more than about 20 mol. % of a cationic lipid, such as any herein (e.g., DOTAP)).

In an embodiment, the outer layer includes a cationic lipid, a pegylated lipid, a zwitterionic lipid, and a sterol, as well as salts of any of these (e.g., pharmaceutically acceptable salts).

The lipid layer can include one or more lipids selected from the group of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-distearoyl-sn-glycero-3-phosphoethanolamine (DSPE), 1,2-dilauroyl-sn-glycero-3-phosphocholine (DLPC), 1,2-dimyristoyl-sn-glycero-3-phosphocholine (DMPC), 1-palmitoyl-2-oleoyl-sn-glycero-3-phosphocholine (POPC), 1-stearoyl-2-oleoyl-sn-glycero-3-phosphocholine (SOPC), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-oleoyl-2-[12-[(7-nitro-2-1,3-benzoxadiazol-4-yl)amino]lauroyl]-sn-glycero-3-phosphocholine (18:1-12:0 NBD PC), 1,2-distearoyl-sn-glycero-3-phosphoethanolamine-N-[methoxy-(polyethylene glycol)-2000] (DSPE-PEG$_{2000}$), 1-palmitoyl-2-{12-[(7-nitro-2-1,3-benzoxadiazol-4-yl)amino]lauroyl}-sn-glycero-3-phosphocholine (16:0-12:0 NBD PC), a sterol (e.g., cholesterol, desmosterol, diplopterol, cholestanol, cholic acid, 12-deoxycholic acid, 7-deoxycholic acid, or a derivative thereof, such as cholesterol sulfate), and mixtures thereof and conjugated forms thereof (e.g., conjugated to PEG moieties, peptides, polypeptides, including immunogenic peptides, proteins and antibodies, and nucleic acids (e.g., RNA and DNA) by way of a covalent bond or by way of a linker or spacer (e.g., any described herein).

In an embodiment, the outer layer also includes a polymer, including, for example, polyethylene glycol (PEG) or polyethylene oxide (PEO) (e.g., a PEG-polyester), or a copolymer (e.g., a diblock copolymer, such as an amphiphilic diblock copolymer). Non-limiting polymers include a PEG-lactic acid polymer (PEG-LA, e.g., poly(ethyleneglycol)-b-poly(lactic acid) copolymer or PEG-b-poly(D,L-lactic acid)); a polycarbonate-polyglutamic acid polymer (PC-PGA, e.g., poly(trimethylene carbonate)-b-poly(glutamic acid); a poly(lactic acid) (PLA, e.g., methoxy poly(ethylene glycol)-Gly-Phe-Leu-Gly-Phe-poly(D,L-lactide), PEG-PLA, or maleimide-PEG-PLA); a poly(butadiene) (PBD, e.g., PEO-b-PBD or PEG-PBD); a poly(caprolactone) (PCL, e.g., PEG-PCL, PEO-PCL, PEG-b-poly(ε-caprolactone), mPEG-poly(ε-caprolactone), α-carboxyl PEG-poly(3-caprolactone)/PEG-PLA, or PEO-b-poly(γ-methyl-3-caprolactone)); and a PEG- or PEO-polypeptide (e.g., PEG-b-poly(2-hydroxyethyl aspartamide) substituted with octadecyl chains, poly(carboxyl ethylene glycol-γ-glutamate)-co-poly(distearin-γ-glutamate), or poly(ethylene glycol)-γ-glutamate)-co-poly (distearin-γ-glutamate)).

The outer layer can be a hybrid layer (e.g., including one or more lipids and one or more polymers). Exemplary hybrid layers can include a lipid (e.g., any described herein), an optional sterol, and a polymer (e.g., any described herein, such as a polymer including PEG or PEO).

Cores, lipids, polymers, and cargos can be PEGylated with a variety of polyethylene glycol-containing compositions as described herein. PEG molecules can have a variety of lengths and molecular weights and include, but are not limited to, PEG 200, PEG 1000, PEG 1500, PEG 2000, PEG 4600, PEG 5000, PEG 10,000, PEG-peptide conjugates or combinations thereof.

In one instance, the outer layer includes a cationic lipid (e.g., DOTAP), a zwitterionic lipid (e.g., DOPE), a sterol (e.g., cholesterol), and a PEGylated lipid (e.g., 1,2-distearoyl-sn-157 glycero-3-phosphoethanolamine-N-[carboxy-(polyethylene glycol)-2000 (DSPE-PEG2000)). These four components may be in a molar ratio of about 1 cationic lipid (e.g., DOTAP) to 1 zwitterionic lipid (e.g., DOPE) to 0.9 sterol (e.g., cholesterol) to 0.15 PEGylated lipid (e.g., DSPE-PEG2000). In an instance, each of these ratios may optionally vary by plus or minus 10%, or plus or minus 5%, or plus or minus 3%. Accordingly, each number recited in the ratio above, may range from a multiple of about 0.9 to 1.1, 0.95 to 1.05, or 0.97 to 1.03.

In an instance, the outer layer includes about 10 to about 50 mol. % cationic lipid (e.g., DOTAP), about 10 to 50 mol. % zwitterionic lipid (e.g., DOPE), about 5 to about 45 mol. % sterol (e.g., cholesterol), and about 2 to 8 mol. % of a PEGylated lipid (e.g., DSPE-PEG2000). In another instance, the outer layer includes about 20 to about 40 mol. % cationic lipid (e.g., DOTAP), about 20 to 40 mol. % zwitterionic lipid (e.g., DOPE), about 10 to about 35 mol. % sterol (e.g., cholesterol), and about 2.5 to 6 mol. % of a PEGylated lipid (e.g., DSPE-PEG2000). In another instance, the outer layer includes about 30 to about 35 mol. % cationic lipid (e.g., DOTAP), about 30 to 35 mol. % zwitterionic lipid (e.g., DOPE), about 27 to about 33 mol. % sterol (e.g., cholesterol), and about 3 to 5 mol. % of a PEGylated lipid (e.g., DSPE-PEG2000).

In particular embodiments, the outer layer includes about 33 mol % of the cationic lipid, about 33 mol % of the zwitterionic lipid, about 30 mol % of the sterol, and about 4% of the PEGylated lipid.

Exemplary cationic lipids include 1,2-dioleoyl-3-trimethylammonium-propane (DOTAP), 1,2-stearoyl-3-trimethylammonium-propane (18:0 TAP), 1,2-dipalmitoyl-3-trimethylammonium-propane (16:0 TAP), 1,2-dimyristoyl-3-trimethylammonium-propane (14:0 TAP), 1,2-di-O-octadecenyl-3-trimethylammonium propane (DOTMA), N1-[2-((1S)-1-[(3-aminopropyl)amino]-4-[di(3-amino-propyl)amino]butylcarboxamido)ethyl]-3,4-di[oleyloxy]-benzamide (MVL5), ethylphosphocholine (ethyl PC) (e.g., 1,2-dimyristoleoyl-sn-glycero-3-ethylphosphocholine, 1-palmitoyl-2-oleoyl-sn-glycero-3-ethylphosphocholine, 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, 1,2-dimyristoyl-sn-glycero-3-ethylphosphocholine, or 1,2-dilauroyl-sn-glycero-3-ethylphosphocholine), dimethyldioctadecylammonium (DDAB), 1,2-dipalmitoyl-sn-glycero-O-ethyl-3-phosphocholine (EDPPC), or any described herein.

Exemplary zwitterionic lipids include DOPC, DPPC, DOPE, DPPE, POPC, DLPC, DSPC, DMPC, SOPC, or any described herein.

Exemplary, non-limiting sterols include cholesterol (e.g., from ovine wool or from plant sources), campestanol, campesterol, cholestanol, cholestenone, desmosterol, 7-dehydrodesmosterol, dehydroepiandrosterone (DHEA), desmosterol, diosgenin, FF-MAS (14-demethyl-14-dehydrolanosterol), lanosterol, lathosterol, pregnenolone, sitostanol, sitosterol, stigmasterol, zymosterol, zymostenol, zymosterone, as well as derivatives thereof, such as sulfates thereof, esters thereof, stereoisomers thereof, deuterated forms thereof, sulfonated forms thereof, phosphorylated forms thereof, unsaturated forms thereof, keto forms thereof, oxidized forms thereof, an oxysterol thereof, PEGylated forms thereof (e.g., cholesterol-(polyethylene glycol-600)), or substituted forms thereof (e.g., having one or more hydroxyl, epoxy, alkyl, phospho, and/or halo, such as fluoro).

Exemplary PEGylated lipids (e.g., a lipid having a poly (ethylene glycol moiety)) include PEGylated DSPE (e.g., 1,2-distearoyl-sn-glycero-3-phosphoethanolamine-N-[amino(polyethylene glycol)-X] (DSPE X) or N-[carbonyl-2',3'-bis(methoxypolyethyleneglycol X)]-1,2-distearoyl-sn-glycero-3-phosphoethanolamine (DSPE-2arm PEGX)), PEGylated phosphoethanolamine (PE) (e.g., 1,2-dioleoyl-sn-glycero-3-phosphoethanolamine-N-[methoxy(polyethylene glycol)-X] (18:1 PEGX PE), 1,2-distearoyl-sn-glycero-3-phosphoethanolamine-N-[methoxy(polyethylene glycol)-X] (18:0 PEGX PE), 1,2-dimyristoyl-sn-glycero-3-phosphoethanolamine-N-[methoxy(polyethylene glycol)-X] (14:0 PEGX PE), or 1,2-dipalmitoyl-sn-glycero-3-phosphoethanolamine-N-[methoxy(polyethylene glycol)-5000](16:0 PEGX PE)), PEGylated DPPE (e.g., N-(carbonyl-methoxypolyethyleneglycol X)-1,2-dipalmitoyl-sn-glycero-3-phosphoethanolamine), PEGylated DMPE (e.g., N-(carbonyl-methoxypolyethyleneglycol X)-1,2-dimyristoyl-sn-glycero-3-phosphoethanolamine), PEGylated DPG (e.g., 1,2-dipalmitoyl-sn-glycerol, methoxypolyethylene glycol), PEGylated DSG (e.g., 1,2-distearoyl-sn-glycerol, methoxypolyethylene glycol), PEGylated DOG (e.g., 1,2-dioleoyl-sn-glycerol, methoxypolyethylene glycol), or PEGylated DMG (e.g., 1,2-dimyristoyl-sn-glycerol, methoxypolyethylene glycol), where X indicates an approximate number average molecular weight (Mn) as measured by Gel Permeation Chromotography (GPC) with appropriate standards, and where X is 500, 3000, 2000, 1000, 750, 550, or 350.

The outer layer of the particle can be composed of lipids, polymers, and/or components in an amount similar to that provided by the lipid formulation. For instance, an exemplary lipid formulation comprising about 47 mol. % of a cationic lipid can provide a lipid layer (for a construct) that comprises 47 mol. % of that cationic lipid. Thus, any composition provided for a lipid formulation herein also provides a composition for the outer layer.

Targeting Ligands

Optionally the construct can include one or more cell targeting species, cell receptor ligands, cell penetrating peptides, fusogenic peptides, and/or targeting peptides. Such species can be included within the cargo, configured to be expressed by a plasmid of the cargo, located within the outer layer, and/or provided by an external surface of the outer layer (e.g., provided by the outer lipid layer). In an embodiment, the targeting ligand can be added to the construct via the pegylated lipid, PEG2000 and derivatives thereof. The composition of the outer layer can include one or more components that facilitate ligand orientation, maximize cellular interaction, provide lipid stability, and/or confer enhanced cellular entry.

In some instances, the targeting ligand can be a cell penetration peptide, a fusogenic peptide, or an endosomolytic peptide, which are peptides that aid a particle in translocating across a lipid bilayer, such as a cellular membrane or endosome lipid bilayer of the host cell. In one embodiment, the targeting ligand is optionally crosslinked onto a lipid layer surface of the outer layer.

Endosomolytic peptides are a sub-species of fusogenic peptides as described herein. Representative and preferred electrostatic cell penetration (fusogenic) peptides include an 8 mer polyarginine ($NH_2$—RRRRRRRR—COOH, SEQ ID NO:1), among others known in the art, which are included in or on particles in order to enhance the penetration of into cells. Representative endosomolytic fusogenic peptides ("endosomolytic peptides") include H5WYG peptide ($NH_2$-GLFHAIAHIHGGWHGLIHGWYGGC-COOH, SEQ ID NO:2), RALA peptide ($NH_2$-WEARLARALARALARHLARALARALRAGEA-COOH, SEQ ID NO:3), KALA peptide ($NH_2$-WEAKLAKALAKALAKHLAKALAKALKAGEA-COOH), SEQ ID NO:4), GALA ($NH_2$-WEAALAEALAEHLAEALAEALEALAA-COOH, SEQ ID NO:5) and INF7 ($NH_2$-GLFEAIEGFIENGWEGMIDGWYG-COOH, SEQ ID NO:6), or fragments thereof, among others. In one instance, the targeting ligand includes an amino acid sequence having at least 80% sequence identity (e.g., at least 85%, 90%, 95%, or 99% sequence identity) to any one of SEQ ID NOs:1-6, or a fragment thereof.

Proteins gain entry into the nucleus through the nuclear envelope. Yet other ligands can include a nuclear localization sequence (NLS), e.g., $NH_2$-GNQSSNFGPMKGGNFG-GRSSGPY GGGGQYFAKPRNQGGYGGC-COOH (SEQ ID NO:9), RRMKWKK (SEQ ID NO:10), PKKKRKV (SEQ ID NO:11), and KR[PAATKKAGQA]KKKK (SEQ ID NO:12), the NLS of nucleoplasmin, a prototypical bipartite signal comprising two clusters of basic amino acids, separated by a spacer of about 10 amino acids. Numerous other nuclear localization sequences are well known in the art. See, for example, LaCasse E C et al., "Nuclear localization signals overlap DNA- or RNA-binding domains in nucleic acid-binding proteins," *Nucl. Acids Res.* 1995; 23:1647-56; Weis, K, "Importins and exportins: how to get in and out of the nucleus," [published erratum appears in *Trends Biochem. Sci.* 1998 July; 23(7):235] *Trends Biochem. Sci.* 1998; 23:185-9; and Cokol M et al., *EMBO Rep.* 2000 Nov. 15; 1(5): 411-5, each of which is incorporated herein by reference in its entirety.

Preferred ligands which may be used to target cells include peptides, affibodies, and antibodies (including monoclonal and/or polyclonal antibodies). In certain embodiments, targeting ligands selected from the group consisting of Fcγ from human IgG (which binds to Fcγ receptors on macrophages and dendritic cells), human complement C3 (which binds to CR1 on macrophages and dendritic cells), ephrin B2 (which binds to EphB4 receptors on alveolar type II epithelial cells), SP94 peptide (which binds to unknown receptor(s) on hepatocyte-derived cells), and MET receptor binding peptide. Exemplary, non-limiting SP94 peptides include SP94 free peptide (H2N-SFSIILT-PILPL-COOH, SEQ ID NO:126), a SP94 peptide modified with C-terminal Cys for conjugation (H2N-SFSIILTPIL-PLGGC-COOH, SEQ ID NO:127), and a further modified SP94 peptide (H2N-SFSIILTPILPLEEEGGC-COOH, SEQ ID NO:128). Exemplary MET binding peptides include ASVHFPP (SEQ ID NO:121), TATFWFQ (SEQ ID NO:122), TSPVALL (SEQ ID NO:123), IPLKVHP (SEQ ID NO:124), and WPRLTNM (SEQ ID NO:125).

Other exemplary targeting ligands include poly-L-arginine, including $(R)_n$, where 6<n<12, such as an R12 peptide (e.g., RRRRRRRRRRRR (SEQ ID NO:210)) or an R9 peptide (e.g., RRRRRRRRR (SEQ ID NO:211)); a polyhistidine-lysine, such as a $(KH)_9$ (e.g., KHKHKHKHKHKHKHKHKH (SEQ ID NO:212)); a Tat protein or derivatives and fragments thereof, such as RKKRRQRRR (SEQ ID NO:213), GRKKRRQRRRPQ (SEQ ID NO:214), GRKKRRQRRR (SEQ ID NO:215), GRKKRRQRRRPPQ (SEQ ID NO:216), YGRKKRRQRRR (SEQ ID NO:217), and RKKRRQRRRRKKRRQRRR (SEQ ID NO:218); a Cady protein or derivatives and fragments thereof, such as Ac-GLWRALWRLLRSLWRLLWRA-cysteamide (SEQ ID NO:219); a penetratin protein or derivatives and fragments thereof, such as RQIKIWFQNRRMKWKKGG (SEQ ID NO:220), RQIRIWFQNRRMRWRR (SEQ ID NO:221), and RQIKIWFQNRRMKWKK (SEQ ID NO:222); an antitrypsin protein or derivatives and fragments thereof, such as CSIPPEVKFNKPFVYLI (SEQ ID NO:223); a temporin protein or derivatives and fragments thereof, such as FVQWFSKFLGRIL-NH2 (SEQ ID NO:224); a MAP protein or derivatives and fragments thereof, such as KLALKLALKALKAALKLA (SEQ ID NO:225); a RW protein or derivatives and fragments thereof, such as RRWWRRWRR (SEQ ID NO:226); a pVEC protein or derivatives and fragments thereof, such as LLIILRR-RIRKQAHAHSK (SEQ ID NO:227); a transportan protein or derivatives and fragments thereof, such as GWTLN-SAGYLLGKIN LKALAALAKKIL (SEQ IDNO:228); a MPG protein or derivatives and fragments thereof, such as GALFLGFLGAAGSTMGAWSQPKKKRKV (SEQ ID NO:229); a Pep protein or derivatives and fragments thereof, such as KETWWETWWTEWSQPKKKRKV (SEQ ID NO:230), Ac-KETWWETWWTEWSQPKKKRKV-cysteamine (SEQ ID NO:231), and WKLFKKILKVL-amide (SEQ ID NO:232); a Bp100 protein or derivatives and fragments thereof, such as KKLFKKILKYL (SEQ ID NO:233) and KKLFKKILKYL-amide (SEQ ID NO:234); a maurocalcine protein or derivatives and fragments thereof, such as GDC(acm)LPHLKLC (SEQ ID NO:235); a calcitonin protein or derivatives and fragments thereof, such as LGTYTQDFNKFHTFPQTAIGVGAP (SEQ ID NO:236); a neurturin protein or derivatives and fragments thereof, such as GAAEAAARVYDLGLRRLRQRRRLRRERVRA (SEQ ID NO:237); and a human P1 protein or derivatives and fragments thereof, such as MGLGLHLLV-LAAALQGAWSQPKKKRKV (SEQ ID NO:238).

In one instance, the targeting ligand includes an amino acid sequence having at least 80% sequence identity (e.g., at least 85%, 90%, 95%, or 99% sequence identity) to any one of SEQ ID NOs:10-12 and 210-238 or a fragment thereof (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more amino acids).

Exemplary ligands also include a peptide that binds to ephrin B2, to target Vero cells; Fcγ to target THP-1 cells and primary alveolar macrophages; the 'GE11' peptide (see, e.g., Li Z et al., FASEB J 2006; 19: 1978-85) to target A549 cells and primary alveolar epithelial cells; the 'SP94' peptide (see, e.g., Lo A et al., Molec. Cancer Therap. 2008; 7:579-89) to target HepG2 cells and primary hepatocytes; human complement C3, which binds to receptors on macrophages and dendritic cells; or the 'H5WYG' peptide, which ruptures the membranes of acidic intracellular vesicles via the 'proton sponge' mechanism (see, e.g., Moore N M et al., J. Gene. Med. 2008 10: 1134-49).

Other ligands include a peptide (e.g., a peptide zip code or a cell penetrating peptide), an endosomolytic peptide, an antibody (including fragments thereof), affibodies, a carbohydrate, an aptamer, a cluster of differentiation (CD) protein, or a self-associated molecular pattern (SAMP) (e.g., as described in Lambris J D et al., Nat. Rev. Microbiol. 2008; 6(2):132; and Poon IKH, Cell Death Differ. 2010; 17:381-97, each of which is incorporated herein by reference in its entirety). Exemplary CD proteins include CD47 (OMIM Entry No. 601028, a marker of self that allows RBC to avoid phagocytosis), CD59 (OMIM Entry No. 107271, a marker that prevents lysis by complement), $C_1$ inhibitor (C1INH, OMIM Entry No. 606860, a marker that suppresses activation of the host's complement system), CD200 (OMIM Entry No. 155970, an immunosuppressive factor), CD55 (OMIM Entry No. 125240, a marker that inhibits the complement cascade), CD46 (OMIM Entry No. 120920, a marker that inhibits the complement cascade), and CD31 (OMIM Entry No. 173445, an adhesion regulator and a negative regulator of platelet-collagen interactions). Each recited OMIM Entry is incorporated herein by reference in its entirety.

Other useful ligands can be employed, such as those identified by the 'BRASIL' (Biopanning and Rapid Analysis of Selective Interactive Ligands) method (see, e.g., Giordano R J et al., Nat. Med. 2001; 7:1249-53; Giordano R J et al., Proc. Natl Acad. Sci. USA 2010; 107(11):5112-7; and Kolonin M G et al., Cancer Res. 2006; 66:34-40) to identify novel targeting peptides and single-chain variable fragments (scFvs) via phage display (see, e.g., Giordano R J et al., Chem. Biol. 2005; 12:1075-83; Giordano R J et al., Proc. Natl Acad. Sci. USA 2010; 107(11):5112-7; Kolonin M G et al., Cancer Res. 2006; 66:34-40; Tonelli R R et al., PLoS Negl. Dis. 2010; 4:e864; Lionakis M S et al., Infect. Immun. 2005; 73:7747-58; and Barbu E M et al., PLoS Pathog. 2010; 6:e1000726).

Particle Characteristics and Surface Properties

The construct (or particle) can be characterized by, e.g., overall charge, dimension, or dispersity. In some embodiments, one or more optional targeting ligands can be present in or on an outer layer. The particle can have a diameter, circumference, length, width, height, etc. Exemplary values for dimensions include, without limitation, greater than about 10 nm (e.g., greater than about 20 nm, 30 nm, 40 nm, 50 nm, 60 nm, 70 nm, 80 nm, 90 nm, 100 nm, 125 nm, 150 nm, 200 nm, 300 nm, 500 nm, 750 nm, 1 m, 2 m, 5 m, 10 m, 20 m) or of about 2 nm to 500 nm (e.g., from 2 nm to 50 nm, 2 nm to 100 nm, 2 nm to 150 nm, 2 nm to 200 nm, 2 nm to 300 nm, 2 nm to 400 nm, 10 nm to 50 nm, 10 nm to 100 nm, 10 nm to 150 nm, 10 nm to 200 nm, 10 nm to 300 nm, 10 nm to 400 nm, 10 nm to 500 nm, 20 nm to 50 nm, 20 nm to 100 nm, 20 nm to 150 nm, 20 nm to 200 nm, 20 nm to 300 nm, 20 nm to 400 nm, 20 nm to 500 nm, 50 nm to 100 nm, 50 nm to 150 nm, 50 nm to 200 nm, 50 nm to 300 nm, 50 nm to 400 nm, 50 nm to 500 nm, 100 nm to 150 nm, 100 nm to 200 nm, 100 nm to 300 nm, 100 nm to 400 nm, 100 nm to 500 nm, 150 nm to 200 nm, 150 nm to 300 nm, 150 nm to 400 nm, 150 nm to 500 nm, 200 nm to 300 nm, 200 nm to 400 nm, or 200 nm to 500 nm). In each case, the dimension of particle or construct is larger than the core dimension of the same type.

In particular embodiments, a plurality of particles is monodisperse in diameter, such as by having a polydispersity index (PdI) that is less than about 0.2 or by having a PdI that is of about 0.05 to about 0.2 (e.g., from 0.05 to 0.1, 0.05 to 0.15, 0.1 to 0.15, 0.1 to 0.2, or 0.15 to 0.2). The calculations used for the determination of size and PDI parameters are defined in the ISO standard documents 13321:1996 E and ISO 22412:2008. In some embodiments, the monodisperse particles range in a size of from about 50 nm to about 475 nm (e.g., from 150 nm (+/−10 nm) to 350 nm (+/−15 nm)).

In embodiments, the particle (or a plurality of particles) has a charge (or a net charge) that is near neutral (e.g., a zeta potential of about +5 mV to −5 mV, or about +10 to about −10 mV). As mentioned above, the construct can include appropriate targeting ligands to promote their cell-specific binding and internalization and can include a useful ligand to promote endosomal escape or nuclear localization within host cells.

Compositions and Formulations

The present constructs can be formulated, for example, for subcutaneous (SC), intranasal (IN), aerosol, intravenous (IV), intramuscular (IM), intraperitoneal (IP), oral, topical, transdermal, or retro-orbital delivery. Exemplary dosages include, e.g., about 0.01 g (construct)/kg (body wt.) to about 0.2 g/kg, such as, 0.05 g/kg to about 0.15 g/kf, or about 0.07 to 0.1 g/kg. A dose of 0.1 g/kg was well tolerated in mice and could translate to humans. A dose of 0.1 g LC-MSNs/kg/day was tested up to four days in mice. Daily doses can be given from 2 to 10 days, such as 2 to 8, or 3 to 5 days. Certain cargos may vary the dosage, for example, RNP delivery may be applied only up to four days.

The formulation or composition can include a plurality of particles (e.g., an effective amount thereof) and an optional pharmaceutically acceptable excipient (e.g., any described herein). In some instances, the pharmaceutical composition includes a population of particles (e.g., any described herein) in an amount effective for modulating or modifying a target gene within a subject in combination with a pharmaceutically acceptable carrier, additive, or excipient. In other instances, the composition further includes a drug, a therapeutic agent, etc., which is not disposed as cargo within the particle.

The composition can be formulated in any useful manner with a plurality of particles. Such formulations can be included with a medium, excipient (e.g., lactose, saccharide, carbohydrate, mannitol, leucine, PEG, or trehalose), additive, propellant, solution (e.g., aqueous solution, such as a buffer), additive, preservative, carrier (e.g., aqueous saline, aqueous dextrose, glycerol, or ethanol), binder (e.g., saccharide, cellulose preparation, starch paste, or methyl cellulose), filler, or disintegrator.

Pharmaceutical compositions according to the present disclosure include an effective population of constructs herein formulated to effect an intended result (e.g., immunogenic result, therapeutic result and/or diagnostic analysis, including the monitoring of therapy) formulated in combination with a pharmaceutically acceptable carrier, additive, or excipient. The particles within the population of the composition may be the same or different depending upon the desired result to be obtained. Pharmaceutical compositions according to the present disclosure may also comprise an addition bioactive agent or drug, such as an antibiotic or antiviral agent.

Formulations and compositions containing the particles according to the present disclosure may take the form of liquid, solid, semi-solid or lyophilized powder forms, such as, for example, solutions, suspensions, emulsions, sustained-release formulations, tablets, capsules, powders, suppositories, creams, ointments, lotions, aerosols, or patches, in unit dosage forms suitable for simple administration of precise dosages.

Methods for preparing such dosage forms are known or apparent to those skilled in the art; for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject according to the disclosed technology.

Methods

The constructs herein can be adapted to recognize the target and, if needed, deliver the one or more cargos to treat that target. Exemplary targets include a cell, a pathogen, an organ (e.g., dermis, vasculature, lymphoid tissue, liver, lung, spleen, kidneys, heart, brain, bone, muscle, etc.), a cellular target (e.g., targets of the subject, such as a human subject, including host tissue, host cytoplasm, host nucleus, etc., in any useful cell, such as e.g., hepatocytes, alveolar epithelial cells, and innate immune cells, etc.); as well as targets for exogenous cells and organisms, such as extracellular and/or intracellular components of a pathogen, e.g., bacteria), a molecular target (e.g., within the subject or the exogenous cell/organism, such as pathogen DNA, host DNA, pathogen RNA, pathogen proteins, surface proteins or carbohydrates of any subject or exogenous cell).

In one instance, the particle is employed to target a host (e.g., a subject), a pathogen, or both (e.g., thereby treating the subject and/or the target). Exemplary pathogens include a bacterium, such as *Bacillus* (e.g., *B. anthracis*), Enterobacteriaceae (e.g., *Salmonella, Escherichia coli, Yersinia pestis, Klebsiella*, and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prowazekii*, or *R. typhi*), *Francisella tularensis, Chlamydia psittaci, Coxiella burnetii, Mycoplasma* (e.g., *M. mycoides*), etc.; mycotoxins, mold spores, or bacterial spores such as *Clostridium botulinum* and *C. perfringens*; a virus, including DNA or RNA viruses, such as Adenoviridae (e.g., adenovirus), Arenaviridae (e.g., Machupo virus), Bunyaviridae (e.g., Hantavirus or Rift Valley fever virus), Coronaviridae (e.g., SARS-Cov-2), Orthomyxoviridae (e.g., influenza viruses), Filoviridae (e.g., Ebola virus and Marburg virus), Flaviviridae (e.g., Japanese encephalitis virus, hepatitis C virus, and Yellow fever virus), Hepadnaviridae (e.g., hepatitis B virus), Herpesviridae (e.g., herpes simplex viruses, herpesvirus, cytomegalovirus, Epstein-Barr virus, or varicella zoster viruses), Papillomaviridae (e.g., papilloma viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses and hepatitis A virus), Polyomaviridae, Poxviridae (e.g., variola viruses or vaccinia virus), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishma-* nia, or *Trypanosoma* (e.g., *T. brucei* and *T Cruzi*); a helminth, such as cestodes (tapeworms), trematodes (flukes), or nematodes (roundworms, e.g., *Ascaris lumbricoides, Trichuris trichiura, Necator americanus*, or *Ancylostoma duodenale*); a parasite (e.g., any protozoa or helminths described herein); or a fungus, such as Aspergilli, Candidae, *Coccidioides immitis*, and Cryptococci. Other pathogens include a multi-drug resistant (MDR) pathogen, such as MDR forms of any pathogen described herein. Additional pathogens are described in Cello J et al., *Science* 2002; 297:1016-8; Gibson D G et al., *Science* 2010; 329: 52-6; Jackson R J et al., *J. Virol.* 2001; 75:1205-10; Russell C A et al., *Science* 2012; 336:1541-7; Tumpey T M et al., *Science* 2005; 310:77-80; and Weber N D et al., *Virology* 2014; 454-455c:353-61, each of which is incorporated herein by reference in its entirety.

The constructs of the disclosed technology can be employed to treat any useful disease that would benefit from genetic knock-out of a known protein. For instance, the particles can be employed to treat a subject from a disease correlated with the presence of that known protein (e.g., a known protein expressed within the subject or within a pathogen infecting that subject). Other diseases include a genetic disorder (e.g., Huntington's disease, hemophilia, sickle cell anemia, metabolic disorders, etc.), in which expression of a known protein is correlated with the disease or its symptoms.

The constructs can be employed to transform a subject (e.g., by genetically modifying a target gene within the subject by employing a CRISPR component configured to bind to that target gene). Thus, in one instance, the particle can be configured to bind to a target sequence in a genomic sequence of the subject in order to modulate that target sequence. Modulation can include activating, inactivating, deactivating, and/or modifying expression or activity of the target sequence. For example, the cargo can bind to the target sequence, e.g., thereby inhibiting expression of one or more proteins encoded by the target sequence. In another example, the cargo cleaves the target sequence and optionally inserts a further nucleic acid sequence into the genomic sequence of the subject. In yet another example, the cargo activates the target sequence. Any useful target sequence can be modulated.

Methods of treating patients or subjects in need for a particular disease state or infection can include administration an effective amount of a pharmaceutical composition having a plurality of constructs (e.g., any described herein). Additional methods include diagnostic methods, which can include administering an effective amount of a population of diagnostic particles to a subject in need thereof. In some embodiments, the population of particles, or a portion thereof, includes a ligand (e.g., to bind to target cells) and a reporter (e.g., to indicate binding to the target cell), whereupon the binding of one or more particles to cells as evidenced by the reporter component (moiety) will enable a diagnosis of the existence of a disease state in the subject.

In accordance with the present disclosure, there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

The present disclosure also relates to methods of fabricating a construct (e.g., or a population of particles). The method can include, e.g., providing a core (including a plurality of cores) having any useful characteristic (e.g., any described herein, such as having a dimension greater than about 50 nm, having a negative charge, having one or more pores, and/or including a silica); incubating the core with one or more cargo (e.g., any herein, including a plasmid, a CRISPR component, etc.), thereby providing a loaded core; and exposing the loaded core to a lipid formulation (e.g., any described herein).

In other embodiments, the method can include providing a core and then expanding the pores present on the core. In some instance, a method can include: providing a core including an external surface and a plurality of pores in fluidic communication with the external surface (e.g., where an average dimension of the plurality of pores is characterized by a first dimension); expanding the pores (e.g., thereby providing a core comprising a plurality of expanded pores, wherein an average dimension of the plurality of expanded pores is characterized by a second dimension that is greater than the first dimension); incubating the core with one or more cargo, thereby providing a loaded core; and exposing the loaded core to a polymer formulation or a lipid formulation to form an outer layer supported upon the external surface of the core (e.g., thereby providing the construct).

Figure 3A:
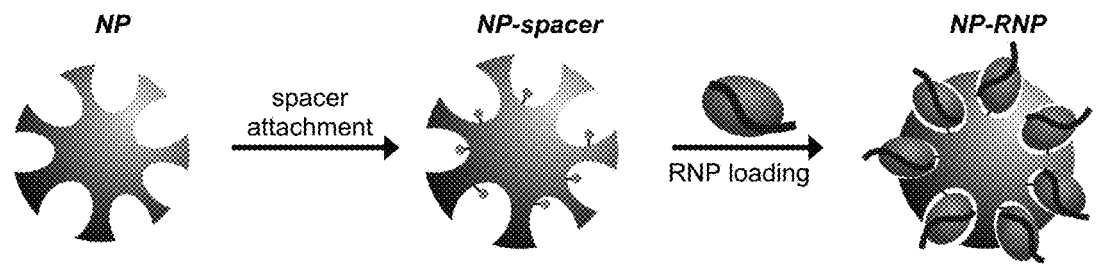
FIGS. 3A-3C is a schematic showing exemplary methods for providing a construct and its use for in vitro gene editing.
Figure 3B:
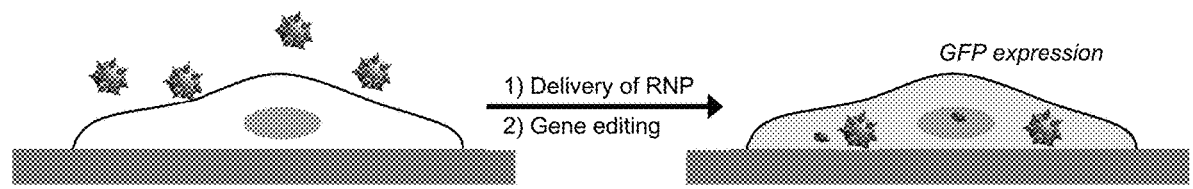
Figure 3C:
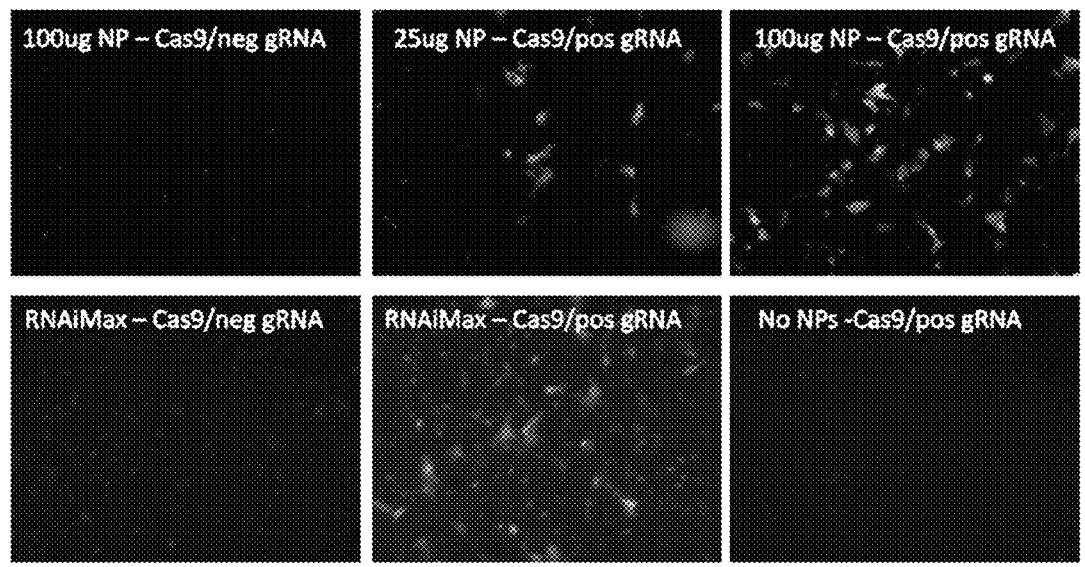

FIGS. 3A-3C shows exemplary methods for providing a construct and its use for in vitro gene editing. Provided are schematics of (A) an exemplary method for loading RNP within a construct and (B) an exemplary method for in vitro gene editing by use of an RNP-loaded construct. Also provided are (C) fluorescence photomicrographs showing delivery of an RNP-loaded construct to a reporter cell line with an AAVS1 target site, in which effective gene-editing by the RNP results in a frameshift mutation and GFP expression.

EXAMPLES

Numerous experiments were run with various LCMSN (lipid-coated mesoporous nanoparticle) constructs comprising lipid compositions and mesoporous nanoparticles (MSNs) until a surprisingly effective combination was found. In particular, a stellate MSN with a 33 mol %, DOTAP, 33 mol % DOPE, 30 mol % cholesterol and 4 mol % DSPE-PEG2000 synthesized in Example 3 below was chosen after trial and error experimentation to achieve surprisingly effective delivery of CRISPR-Cas9 RNP packaged in LC-MSN. To assess the LC-MSN with the selected coating, negative staining and cryo-EM was performed on CRISPR-Cas9 RNP-loaded LC-MSN. A complete lipid coat was visible on microscopic analysis. Further details are provided below.

Example 1: MSN Fabrication and Characterization

In Example 1A, Stellate MSN synthesis was carried out in a 50 mL round bottom flask, by combining triethanolamine (70 mg), CTATos (0.300 g, cas #138-32-9) with 20 mL water (Sigma). The solution was stirred at 75-80° C. for 30 min to ensure complete dissolution. Condensation was achieved by adding TEOS (2.9 mL) dropwise to the solution over 5 minutes stirring at 850 rpm. The reaction was then carried out for 2 hours at 75-80° C. with a condenser. MSN solution was removed from heat and cooled for 15 minutes then spun down for 15 minutes at 50,000×g. The collected MSN were washed twice by pure then 190 proof ethanol. Surfactant removal was carried out by suspending the MSN in 5% v (volume) HCl (12 N, 37%) in ethanol in a 100 mL round bottom flask and refluxing for 2 hours (using a cooling column, refrigerant). This was repeated with HCl 1% instead of 5% and then 190 proof ethanol then pure ethanol. The resulting MSN were resuspended in pure ethanol and passed through a 1 μm filter to remove any aggregates.

Size and zeta potential were assessed using a Zetasizer instrument (Malvern Instruments, Ltd). Morphology was assessed by TEM (JEOL 2010).

In addition, hexagonal prism small pore particles were prepared as previously described (LaBauve, et al, *Lipid-Coated Mesoporous Silica Nanoparticles for the Delivery of the ML336Antiviral to Inhibit Encephalitic Alphavirus Infection*, Sci Rep. 2018; 8: 13990, 2018 Sep. 18. doi: 10.1038/s41598-018-32033-w) incorporated herein by reference. These were stored in pure ethanol and quantified. The average size (diameter) by DLS was 160 nm and the zeta potential was −37 mV.

Example 2: Preparation of Liposomes

A 7.27 mg/mL liposome solution in 50:50 PBS:water (4 mM $MgCl_2$) composed of 33 mol % 1,2-dioleoyl-3-trimethylammonium-propane (DOTAP) 33 mol % 1,2-dioleoyl-sn-glycero-3-phosphoethanolamine (DOPE) 30 mol % Cholesterol and 4 mol % 1,2-distearoyl-sn-glycero-3-phosphoethanolamine-N-[carboxy-(polyethyleneglycol)-2000] (DPSE-PEG2000) (Avanti Polar Lipids) was used. Stock lipids were diluted in chloroform (Sigma) and 7.27 mg total lipids were combined in a glass scintillation vial then dried down using a rotary evaporator (Buchi Corp.). The resulting lipid films were placed under vacuum overnight to ensure complete solvent removal then resuspended in 1 mL 0.5×PBS 4 mM $MgCl_2$ solution. The suspension was placed in a sonication bath (Branson) and sonicated for 30 minutes at 30° C., then immediately extruded with 21 passes through a 100 nm filter (Whatman). Liposome size was assessed by DLS. See FIG. 18B, column labeled "lipid".

Example 3: Cargo Loading and LC-MSN Fabrication

100 μg of MSN stored in ethanol was spun down in a 1.5 mL Eppendorf tube at 21,000×g for 10 minutes and washed with 1 mL of water under sonication. Washed MSN were collected by centrifugation and resuspended in 10 μL of water. CRISPR-Cas-9/gRNA complex from ribonucleoproteins (RNPs) was complexed in 53.3 μL 100 mM NaCl, 50 mM Tris, 10% glycerol, at pH 8.0 by adding 20 μg of SpyCas9 and 6.67 μg sgRNA (a 1:3 ratio gRNA:Cas9) for a final Cas-9 concentration of 0.375 μg/uL and incubated at 30° C. for 15 minutes to achieve a ratio of 1:5 Cas9:MSN. The RNP solution was mixed with the MSN with pipetting and sonication then incubated at room temperature for 30 minutes. Liposomes were fused to RNP loaded MSN by adding 100 μL of extruded liposomes in a mix of 50:50 PBS:water supplemented with 4 mM MgCl2 and pipetting with occasional sonication. The resulting LC-MSN were collected by centrifugation for 15 minutes at 15,000×g and washed with 1 mL PBS then resuspended in 100 μL PBS with pipetting and sonication.

FIG. 18D shows comparison of the RNP-loaded MSN with and without lipids. FIG. 18C shows size measurements during LC-MSN assembly.

Example 4: LC-MSN Loading

Immediately after LC-MSN formation, 25 μg of LC-MSN in PBS was collected in 1.5 mL Eppendorf tubes. Either a 1.8% solution of TX-100 in PBS, or PBS (12.5 μL) was added and the solution was incubated at 37° C. shaking at 400 rpm for 4 hours. The LC-MSN was then spun down at 21,000×g for 10 minutes to separate the supernatant from remaining MSN. The pellets were resuspended in 37.5 μL of PBS and 4× Laemmli buffer was added and all samples were boiled for 10 minutes. Samples were run on a 10% polyacrylamide gel (Biorad) with standard known amounts on Cas-9 protein.

Loading and release was assessed by densitometry. See FIG. 16. Western blot gel images were taken and analyzed by ImageJ software where the density of signal across protein bands were quantified and normalized to Cas9 protein standards.

Example 5: Reporter Cell Line

Figure 19:
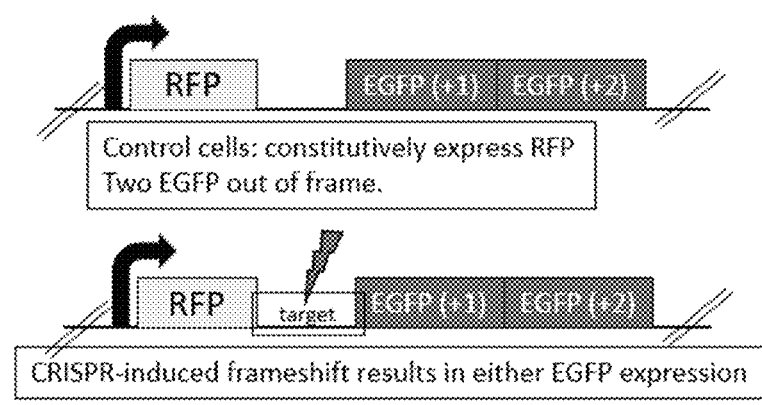
FIG. 19 is a schematic showing the mechanism of Example 5.

The reporter cell line was generating in A549 cells (ATCC) using a fluorescent reporter system from PNA Bio. The gene was cloned into a lentivirus vector, and particles derived from a single clone were used to transduce human A549 lung epithelial cells. The transduced cells constitutively express red fluorescent protein (RFP). The RFP signal is linked to a gene encoding green fluorescent protein (EGFP) gene. Expression of EGFP is dependent on double strand breaks that lead to a frame-shift mutation. See FIG. 19 illustrating this Example. Reporter and parental cell lines were maintained in F-K12 media (Gibco) supplemented with 10% FBS (Gibco) and penicillin/streptomycin.

Example 6: In Vitro Editing Experiments

Cells were seeded at 50,000 cells per well in 12-well plates (Costar) in 1 mL of F-K12 media supplemented with 5% FBS (Gibco) and pen/strep (Gibco) and were incubated overnight. The RNP loaded LC-MSNs were resuspended in PBS at 1 mg/mL. LC-MSNs were added directly to the 1 mL of media in each well at increasing concentrations of 20 μg/mL, 40 μg/mL, 60 μg/mL and 80 μg/mL. Media was replaced after 16 hours and editing efficiency was assessed at 72 hours by microscopy and flow cytometry.

Example 7: Flow Cytometry

Editing was assessed by flow cytometry. Cells in 12-well plates were lifted with 250 μL trypsin (Gibco) collected by centrifugation at 4000×g in 1.5 mL tubes, washed with 1 mL PBS (Gibco) and resuspended in 1 mL of PBS supplementing with 4% paraformaldehyde. Fixed cells were assessed with an Accuri C3 flow cytometer (BD). Untreated and RNP-CRISPR Max treated A549R cells were used as negative and positive controls respectively for gating.

Example 8: Cryo-EM Analysis

For cryo-EM analysis, freshly prepared RNP loaded and unloaded LC-MSNs were vitrified using an automatic plunge freezer EM (Leica). 4 μL of LC-MSN solution was added to a C-flat grid (Protochips, Inc.) with 2 μm holes and blotted with filter paper. The grid was plunged into liquid ethane for flash freezing. Frozen grids were stored in liquid nitrogen and transferred to a JEM 2200FS electron microscope (JEOL Ltd.). Grids were imaged at 200 keV using DE-20 (Direct Detector Inc.) direct electron detector camera. The energy selecting slit was set to 20 eV and the microscope had a field emission electron source and omega-type electron energy filter to remove inelastically scattered electrons from the image formation.

A DE-20 camera was used to collect images in movie mode with a frame rate of 25 frames/sec. After image collection, frame alignment was performed using the E_process_frames.py script provided by Direct Electron Inc. Images were collected at 40,000× magnification and the pixel size on the specimen scale corresponded to 1.5 Å/pixel. See FIG. 14C.

Example 9: Phosphotungstic Acid-Based Negative Staining of LC-MSN for TEM

RNP-loaded LC-MSNs were prepared as described above, diluted in PBS to 0.1 mg/mL then added (5 µL) to a TEM copper grid (Sigma Aldrich). After a 5 minute drying period, a phosphotungstinic acid solution (2% in water) was added (5 µL) to the grid and removed by dabbing with the corner of a Kimwipe (Kimtech) after 10-15 seconds. The grid was washed with 15 µL water and allowed to dry at room temperature prior to TEM imaging as described above. See FIG. 14B.

Example 10: In Vivo Delivery of CRISPR-Cas9 RNP LC-MSN

To assess the efficiency of the LC-MSN delivery vehicle in vivo a murine liver NPC was utilized.

Example 11: Comparison of Different Core Particles

Figure 17A:
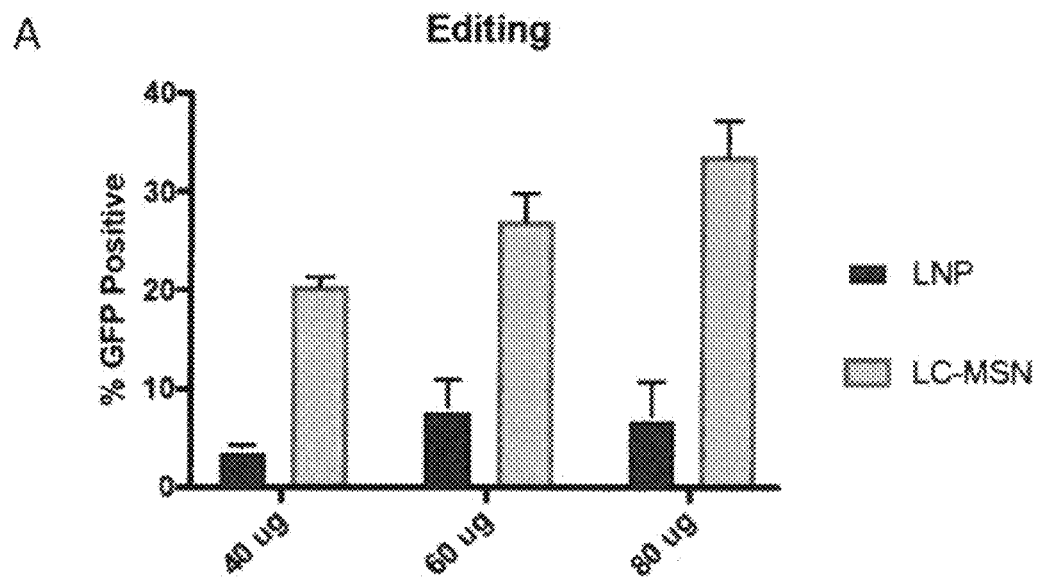
FIGS. 17A-17C are graphs showing editing efficiency of exemplary loaded LC-MSNs and comparative examples.
Figure 17B:
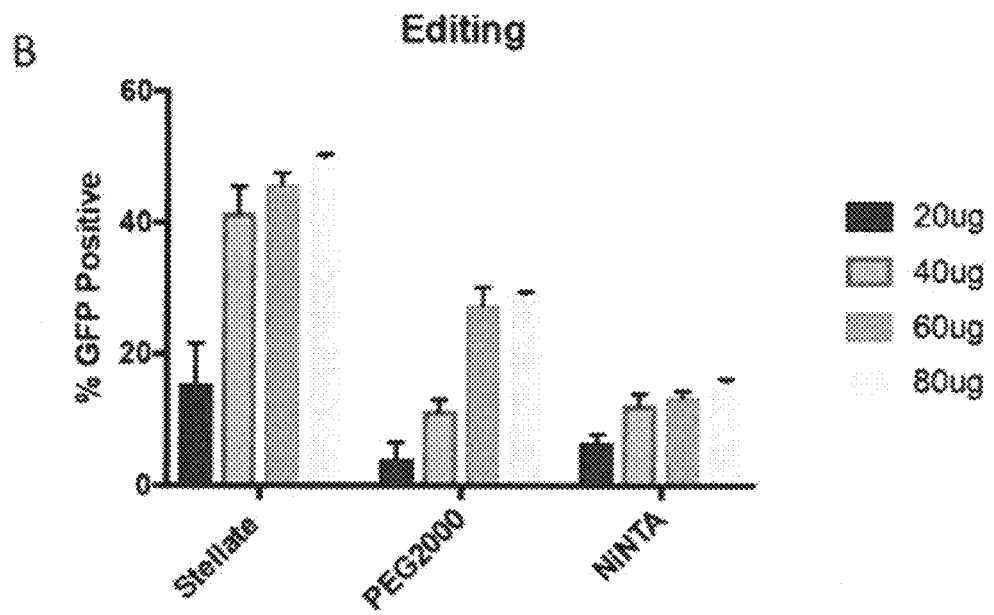
Figure 17C:
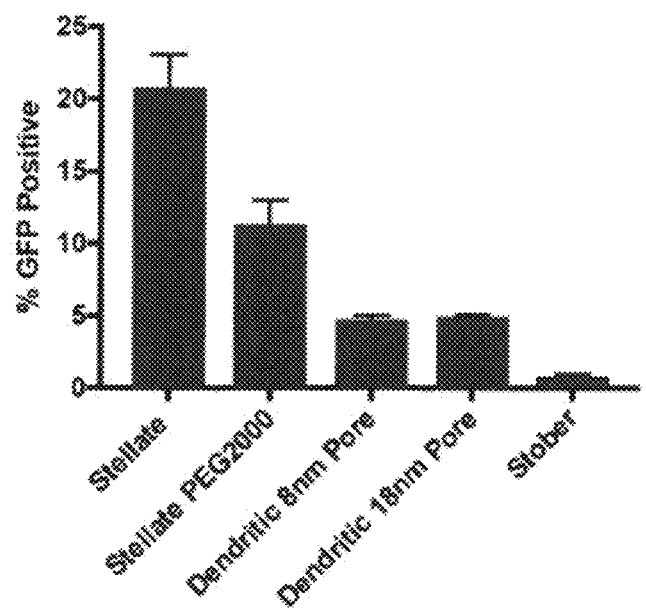

Delivery of the CRISPR-Cas-9 cargo was tested in vitro with varying types of particles (cores) that were able to form an LC-MSN of under 400 nm in average diameter (DLS by methods described herein) after loading of CRISPR-Cas9/gRNA cargo. See FIG. 18A. All particle types that were tested had an average diameter of 2 nm pores or greater. Hexagonal prisms had pore size of 2.5 nm, Stober particles are non-porous, Stellate particles were 12 nm and dendritic particles were either 8 nm or 18 nm in average pore size. These Examples were assayed by measuring % Green Fluorescent Protein (GFP) positive cells after 72-hour exposure of A549 reporter cells to 40, 60, and 80 µg/mL of the CRISPR-Cas9 loaded LC-MSN (FIG. 17A).

While several of the other particle types, including the dendritic 8 nm pore and 18 nm pore, resulted in a good sized stable LC-MSN, editing efficiency was surprisingly high (FIG. 17C) in the stellate core types. A stellate particle core with pore size range of 6-10.5 nm was selected to move forward with studies on CRISPR-RNP delivery.

Examples 12: Comparison of CRISPR-Cas9 Loaded LC-MSN (Example 3) to CRISPR-Cas-9 and Free Lipid Composition from Example 2 with No Core Particles While the liposome composition in Example 2 mixed with CRISPR-Cas9 RNP resulted in a low amount of editing in the absence of the MSN, editing increased substantially with the use of the stellate LC-MSNs of Example 3. See FIG. 17B. The figure also includes a comparison with NiNTA functionalized particles. The NiNTA particles were MSN cores functionalized to capture Cas9 that is 6×HIS tagged. This is another method used to load the particles with CRISPR RNPs.

All publications, patents, and patent applications mentioned in this specification are incorporated herein by reference to the same extent as if each independent publication or patent application was specifically and individually indicated to be incorporated by reference.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable NIST standards, or if an NIST standard does not exist for the property, then NCL, and then ASTM standards may be used, if none of the above standards are available, the most commonly used standard known by those of skill in the art may be used. The articles "a," "an," and "the," should be interpreted to mean "one or more" unless the context indicates the contrary.

The invention claimed is:

1. A construct comprising:
   a core comprising an external surface and a plurality of pores, wherein an average dimension of the plurality of pores is greater than about 2 nm;
   a cargo disposed in a pore of the plurality of pores, the cargo comprising a CRISPR Cas9 component, or a nucleic acid sequence encoding a CRISPR Cas9 component; and
   a coating coupled to the core, wherein the coating comprises a cationic lipid, a PEGylated lipid, a zwitterionic lipid, and a sterol.

2. The construct of claim 1, wherein the core is a stellate mesoporous silica nanoparticle.

3. The construct of claim 1, wherein the average diameter of the plurality of pores is of from about 3 nm to about 20 nm as determined by porosimetry with nitrogen adsorption-desorption analysis.

4. The construct of claim 1, wherein the core has an average diameter of about 75 to about 400 nm.

5. The construct of claim 2, wherein the mesoporous silica nanoparticle is monodisperse in particle diameter, wherein about 90% of the distribution lies within about 5% of the median diameter, as measured by dynamic light scattering.

6. The construct of claim 1, wherein the coating comprises about 10 to about 50 mol % of the cationic lipid and zwitterionic lipid, about 5 to about 45 mol. % of the sterol, and about 2 to 8 mol. % of the PEGylated lipid.

7. The construct of claim 1, wherein the coating comprises about 20 to about 40 mol % of the cationic lipid and zwitterionic lipid, about 10 to about 35 mol. % of the sterol, and about 2.5 to 6 mol. % of the PEGylated lipid.

8. The construct of claim 1, wherein the coating comprises a molar ratio of about 1 cationic lipid to 1 zwitterionic lipid to 0.9 sterol to 0.15 PEGylated lipid, wherein each molar ratio optionally varies by about plus or minus 10%.

9. The construct of claim 1, wherein the cationic lipid is 1,2-dioleoyl-3-trimethylammonium-propane, the zwitterionic lipid is 1,2-dioleoyl-sn-glycero-3-phosphoethanolamine, the sterol is cholesterol, and the PEGylated lipid is 1,2-distearoyl-sn-glycero-3-phosphoethanolamine-N-[methoxy-(polyethylene glycol)-2000].

10. The construct of claim 8, wherein the cationic lipid is 1,2-dioleoyl-3-trimethylammonium-propane, the zwitterionic lipid is 1,2-dioleoyl-sn-glycero-3-phosphoethanolamine, the sterol is cholesterol, and the PEGylated lipid is 1,2-distearoyl-sn-glycero-3-phosphoethanolamine-N-[methoxy-(polyethylene glycol)-2000].

11. The construct of claim 1, wherein the sterol is selected from the group consisting of: cholesterol, desmosterol, diplopterol, cholestanol, cholic acid, 12-deoxycholic acid, 7-deoxycholic acid, or a derivative thereof, and mixtures thereof and conjugated forms thereof.

* * * * *

SEQUENCE LISTING

```
<160> NUMBER OF SEQ ID NOS: 238

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Arg Arg Arg Arg Arg Arg Arg Arg
1               5
```

```
<210> SEQ ID NO 2
<211> LENGTH: 25
<212> TYPE: PRT
<213> ORGANISM: Artificial Sequence
<220> FEATURE:
<223> OTHER INFORMATION: Synthetic construct

<400> SEQUENCE: 2

Gly Leu Phe His Ala Ile Ala His Phe Ile His Gly Gly Trp His Gly
1               5                   10                  15

Leu Ile His Gly Trp Tyr Gly Gly Cys
            20                  25

<210> SEQ ID NO 3
<211> LENGTH: 30
<212> TYPE: PRT
<213> ORGANISM: Artificial Sequence
<220> FEATURE:
<223> OTHER INFORMATION: Synthetic construct

<400> SEQUENCE: 3

Trp Glu Ala Arg Leu Ala Arg Ala Leu Ala Arg Ala Leu Ala Arg His
1               5                   10                  15

Leu Ala Arg Ala Leu Ala Arg Ala Leu Arg Ala Gly Glu Ala
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic construct

<400> SEQUENCE: 4

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Gly Glu Ala
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic construct

<400> SEQUENCE: 5

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 6
<211> LENGTH: 23
<212> TYPE: PRT
<213> ORGANISM: Artificial Sequence
<220> FEATURE:
<223> OTHER INFORMATION: Synthetic construct

<400> SEQUENCE: 6

Gly Leu Phe Glu Ala Ile Glu Gly Phe Ile Glu Asn Gly Trp Glu Gly
1               5                   10                  15

Met Ile Asp Gly Trp Tyr Gly
            20
```

```
<210> SEQ ID NO 7

<400> SEQUENCE: 7

000

<210> SEQ ID NO 8

<400> SEQUENCE: 8

000

<210> SEQ ID NO 9
<211> LENGTH: 42
<212> TYPE: PRT
<213> ORGANISM: Artificial Sequence
<220> FEATURE:
<223> OTHER INFORMATION: Synthetic construct

<400> SEQUENCE: 9

Gly Asn Gln Ser Ser Asn Phe Gly Pro Met Lys Gly Asn Phe Gly
1               5                   10                  15

Gly Arg Ser Ser Gly Pro Tyr Gly Gly Gly Gln Tyr Phe Ala Lys
            20                  25                  30

Pro Arg Asn Gln Gly Gly Tyr Gly Gly Cys
        35                  40

<210> SEQ ID NO 10
<211> LENGTH: 7
<212> TYPE: PRT
<213> ORGANISM: Artificial Sequence
<220> FEATURE:
<223> OTHER INFORMATION: Synthetic construct

<400> SEQUENCE: 10

Arg Arg Met Lys Trp Lys Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic construct

<400> SEQUENCE: 11

Pro Lys Lys Lys Arg Lys Val
1               5

<210> SEQ ID NO 12
<211> LENGTH: 16
<212> TYPE: PRT
<213> ORGANISM: Artificial Sequence
<220> FEATURE:
<223> OTHER INFORMATION: Synthetic construct

<400> SEQUENCE: 12

Lys Arg Pro Ala Ala Thr Lys Lys Ala Gly Gln Ala Lys Lys Lys Lys
1               5                   10                  15

<210> SEQ ID NO 13

<400> SEQUENCE: 13

000
```

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 36
<212> TYPE: DNA
<213> ORGANISM: Artificial Sequence
<220> FEATURE:
<223> OTHER INFORMATION: Synthetic construct

<400> SEQUENCE: 20
guuuuagagc uaugcuguuu ugaauggucc caaaac        36

<210> SEQ ID NO 21
<211> LENGTH: 36
<212> TYPE: DNA
<213> ORGANISM: Artificial Sequence
<220> FEATURE:
<223> OTHER INFORMATION: Synthetic construct

<400> SEQUENCE: 21
guuuuagagc uauguuauuu ugaaugcuaa caaaac        36

<210> SEQ ID NO 22
<211> LENGTH: 36
<212> TYPE: DNA
<213> ORGANISM: Artificial Sequence
<220> FEATURE:
<223> OTHER INFORMATION: Synthetic construct

<400> SEQUENCE: 22
guuuuagagc uguuuguuu cgaaugguuc caaaac        36

```
<210> SEQ ID NO 23
<211> LENGTH: 36
<212> TYPE: DNA
<213> ORGANISM: Artificial Sequence
<220> FEATURE:
<223> OTHER INFORMATION: Synthetic construct

<400> SEQUENCE: 23
guuuuuguac ucucaagauu uaaguaacug uacaac                                36

<210> SEQ ID NO 24
<211> LENGTH: 37
<212> TYPE: DNA
<213> ORGANISM: Artificial Sequence
<220> FEATURE:
<223> OTHER INFORMATION: Synthetic construct

<400> SEQUENCE: 24
cuaacaguag uuuaccaaau aauucagcaa cugaaac                                37

<210> SEQ ID NO 25
<211> LENGTH: 37
<212> TYPE: DNA
<213> ORGANISM: Artificial Sequence
<220> FEATURE:
<223> OTHER INFORMATION: Synthetic construct

<400> SEQUENCE: 25
gcaacacuuu auagcaaauc cgcuuagccu gugaaac                                37

<210> SEQ ID NO 26
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(38)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., C or G)
<220> FEATURE:
<221> NAME/KEY: misc_feature
<222> LOCATION: (2)..(2)
<223> OTHER INFORMATION: n = A,T,C,G, or U (e.g., T,C, or U)
<220> FEATURE:
<221> NAME/KEY: misc_feature
<222> LOCATION: (3)..(3)
<223> OTHER INFORMATION: n = A,T,C,G, or U (e.g., A,T, or U)
<220> FEATURE:
<221> NAME/KEY: misc_feature
<222> LOCATION: (4)..(4)
<223> OTHER INFORMATION: n = A,T,C,G, or U (e.g., A,T, or U)
<220> FEATURE:
<221> NAME/KEY: misc_feature
<222> LOCATION: (5)..(5)
<223> OTHER INFORMATION: n = A,T,C,G, or U (e.g., T,C, or U)
<220> FEATURE:
<221> NAME/KEY: misc_feature
<222> LOCATION: (6)..(6)
<223> OTHER INFORMATION: n = A,T,C,G, or U (e.g., A,T, or U)
<220> FEATURE:
<221> NAME/KEY: misc_feature
<222> LOCATION: (7)..(7)
<223> OTHER INFORMATION: n = A,T,C,G, or U (e.g., C or G)
<220> FEATURE:
<221> NAME/KEY: misc_feature
<222> LOCATION: (8)..(8)
<223> OTHER INFORMATION: n = A,T,C,G, or U (e.g., A,T, or U)
```

```
<220> FEATURE:
<221> NAME/KEY: misc_feature
<222> LOCATION: (9)..(9)
<223> OTHER INFORMATION: n = A,T,C,G, or U (e.g., A,T,G, or U)
<220> FEATURE:
<221> NAME/KEY: misc_feature
<222> LOCATION: (10)..(10)
<223> OTHER INFORMATION: n = A,T,C,G, or U (e.g., C,G, or absent)
<220> FEATURE:
<221> NAME/KEY: misc_feature
<222> LOCATION: (11)..(11)
<223> OTHER INFORMATION: may be T
<220> FEATURE:
<221> NAME/KEY: misc_feature
<222> LOCATION: (12)..(12)
<223> OTHER INFORMATION: n = A,T,C,G, or U
<220> FEATURE:
<221> NAME/KEY: misc_feature
<222> LOCATION: (13)..(13)
<223> OTHER INFORMATION: may be T
<220> FEATURE:
<221> NAME/KEY: misc_feature
<222> LOCATION: (14)..(14)
<223> OTHER INFORMATION: n = A,T,C,G, or U (e.g., A,C, or G)
<220> FEATURE:
<221> NAME/KEY: misc_feature
<222> LOCATION: (15)..(15)
<223> OTHER INFORMATION: n = A,T,C,G, or U (e.g., G or absent)
<220> FEATURE:
<221> NAME/KEY: misc_feature
<222> LOCATION: (16)..(16)
<223> OTHER INFORMATION: n = A,T,C,G, or U (e.g., A,T,C, or U)
<220> FEATURE:
<221> NAME/KEY: misc_feature
<222> LOCATION: (17)..(17)
<223> OTHER INFORMATION: n = A,T,C,G, or U (e.g., A,T,C, or U)
<220> FEATURE:
<221> NAME/KEY: misc_feature
<222> LOCATION: (18)..(18)
<223> OTHER INFORMATION: n = A,T,C,G, or U (e.g., A or G)
<220> FEATURE:
<221> NAME/KEY: misc_feature
<222> LOCATION: (19)..(19)
<223> OTHER INFORMATION: n = A,T,C,G, or U (e.g., A,T, or U)
<220> FEATURE:
<221> NAME/KEY: misc_feature
<222> LOCATION: (20)..(20)
<223> OTHER INFORMATION: n = A,T,C,G, or U (e.g., A,T, or U)
<220> FEATURE:
<221> NAME/KEY: misc_feature
<222> LOCATION: (21)..(21)
<223> OTHER INFORMATION: n = A,T,C,G, or U (e.g., C,T, or U)
<220> FEATURE:
<221> NAME/KEY: misc_feature
<222> LOCATION: (22)..(22)
<223> OTHER INFORMATION: n = A,T,C,G, or U (e.g., A,T,C, or U)
<220> FEATURE:
<221> NAME/KEY: misc_feature
<222> LOCATION: (23)..(23)
<223> OTHER INFORMATION: n = A,T,C,G, or U (e.g., A or G)
<220> FEATURE:
<221> NAME/KEY: misc_feature
<222> LOCATION: (24)..(24)
<223> OTHER INFORMATION: n = A,T,C,G, or U (e.g., A,T,C, or U)
<220> FEATURE:
<221> NAME/KEY: misc_feature
<222> LOCATION: (25)..(25)
<223> OTHER INFORMATION: n = A,T,C,G, or U (e.g., A,T,G, or U)
<220> FEATURE:
<221> NAME/KEY: misc_feature
<222> LOCATION: (26)..(26)
<223> OTHER INFORMATION: n = A,T,C,G, or U (e.g., T,C, or U)
<220> FEATURE:
<221> NAME/KEY: misc_feature
<222> LOCATION: (27)..(27)
<223> OTHER INFORMATION: n = A,T,C,G, or U (e.g., A or absent)
<220> FEATURE:
<221> NAME/KEY: misc_feature
<222> LOCATION: (28)..(28)
```

```
<223> OTHER INFORMATION: n = A,T,C,G, or U (e.g., A or G)
<220> FEATURE:
<221> NAME/KEY: misc_feature
<222> LOCATION: (29)..(29)
<223> OTHER INFORMATION: n = A,T,C,G, or U (e.g., A,C, or G)
<220> FEATURE:
<221> NAME/KEY: misc_feature
<222> LOCATION: (30)..(30)
<223> OTHER INFORMATION: n = A,T,C,G, or U (e.g., A,T,C, or U)
<220> FEATURE:
<221> NAME/KEY: misc_feature
<222> LOCATION: (31)..(31)
<223> OTHER INFORMATION: n = A,T,C,G, or U (e.g., A,T,C, or U)
<220> FEATURE:
<221> NAME/KEY: misc_feature
<222> LOCATION: (32)..(32)
<223> OTHER INFORMATION: n = A,T,C,G, or U (e.g., A,C, or G)
<220> FEATURE:
<221> NAME/KEY: misc_feature
<222> LOCATION: (33)..(33)
<223> OTHER INFORMATION: n = A,T,C,G, or U (e.g., T,C, or U)
<220> FEATURE:
<221> NAME/KEY: misc_feature
<222> LOCATION: (34)..(34)
<223> OTHER INFORMATION: n = A,T,C,G, or U (e.g., A or G)
<220> FEATURE:
<221> NAME/KEY: misc_feature
<222> LOCATION: (35)..(35)
<223> OTHER INFORMATION: n = A,T,C,G, or U (e.g., A or C)

<400> SEQUENCE: 26
nnnnnnnnnn unnnnnnnnn nnnnnnnnnn nnnnnaac                            38

<210> SEQ ID NO 27
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., C or G)
<220> FEATURE:
<221> NAME/KEY: misc_feature
<222> LOCATION: (2)..(2)
<223> OTHER INFORMATION: n = A,T,C,G, or U (e.g., T,C, or U)
<220> FEATURE:
<221> NAME/KEY: misc_feature
<222> LOCATION: (3)..(3)
<223> OTHER INFORMATION: n = A,T,C,G, or U (e.g., A,T, or U)
<220> FEATURE:
<221> NAME/KEY: misc_feature
<222> LOCATION: (4)..(4)
<223> OTHER INFORMATION: n = A,T,C,G, or U (e.g., A,T, or U)
<220> FEATURE:
<221> NAME/KEY: misc_feature
<222> LOCATION: (5)..(5)
<223> OTHER INFORMATION: n = A,T,C,G, or U (e.g., T,C, or U)
<220> FEATURE:
<221> NAME/KEY: misc_feature
<222> LOCATION: (6)..(6)
<223> OTHER INFORMATION: n = A,T,C,G, or U (e.g., A,T, or U)
<220> FEATURE:
<221> NAME/KEY: misc_feature
<222> LOCATION: (7)..(7)
<223> OTHER INFORMATION: n = A,T,C,G, or U (e.g., C or G)
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
```

<222> LOCATION: (9)..(9)
<223> OTHER INFORMATION: n = A,T,C,G, or U (e.g., A,T,G, or U)
<220> FEATURE:
<221> NAME/KEY: misc_feature
<222> LOCATION: (10)..(10)
<223> OTHER INFORMATION: n = A,T,C,G, or U (e.g., C,G, or absent)
<220> FEATURE:
<221> NAME/KEY: misc_feature
<222> LOCATION: (11)..(11)
<223> OTHER INFORMATION: may be T
<220> FEATURE:
<221> NAME/KEY: misc_feature
<222> LOCATION: (12)..(12)
<223> OTHER INFORMATION: n = A,T,C,G, or U

<400> SEQUENCE: 27
nnnnnnnnnn un                                                         12

<210> SEQ ID NO 28
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., C or G)
<220> FEATURE:
<221> NAME/KEY: misc_feature
<222> LOCATION: (2)..(2)
<223> OTHER INFORMATION: n = A,T,C,G, or U (e.g., T,C, or U)
<220> FEATURE:
<221> NAME/KEY: misc_feature
<222> LOCATION: (3)..(3)
<223> OTHER INFORMATION: n = A,T,C,G, or U (e.g., A,T, or U)
<220> FEATURE:
<221> NAME/KEY: misc_feature
<222> LOCATION: (4)..(4)
<223> OTHER INFORMATION: n = A,T,C,G, or U (e.g., A,T, or U)
<220> FEATURE:
<221> NAME/KEY: misc_feature
<222> LOCATION: (5)..(5)
<223> OTHER INFORMATION: n = A,T,C,G, or U (e.g., T,C, or U)
<220> FEATURE:
<221> NAME/KEY: misc_feature
<222> LOCATION: (6)..(6)
<223> OTHER INFORMATION: n = A,T,C,G, or U (e.g., A,T, or U)
<220> FEATURE:
<221> NAME/KEY: misc_feature
<222> LOCATION: (7)..(7)
<223> OTHER INFORMATION: n = A,T,C,G, or U (e.g., C or G)
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
<222> LOCATION: (9)..(9)
<223> OTHER INFORMATION: n = A,T,C,G, or U (e.g., A,T,G, or U)
<220> FEATURE:
<221> NAME/KEY: misc_feature
<222> LOCATION: (10)..(10)
<223> OTHER INFORMATION: n = A,T,C,G, or U (e.g., C,G, or absent)
<220> FEATURE:
<221> NAME/KEY: misc_feature
<222> LOCATION: (11)..(11)
<223> OTHER INFORMATION: may be T
<220> FEATURE:
<221> NAME/KEY: misc_feature
<222> LOCATION: (12)..(12)
<223> OTHER INFORMATION: n = A,T,C,G, or U
<220> FEATURE:

<221> NAME/KEY: misc_feature
<222> LOCATION: (13)..(13)
<223> OTHER INFORMATION: may be T
<220> FEATURE:
<221> NAME/KEY: misc_feature
<222> LOCATION: (14)..(14)
<223> OTHER INFORMATION: n = A,T,C,G, or U (e.g., A,C, or G)
<220> FEATURE:
<221> NAME/KEY: misc_feature
<222> LOCATION: (15)..(15)
<223> OTHER INFORMATION: n = A,T,C,G, or U (e.g., G or absent)
<220> FEATURE:
<221> NAME/KEY: misc_feature
<222> LOCATION: (16)..(16)
<223> OTHER INFORMATION: n = A,T,C,G, or U (e.g., A,T,C, or U)

<400> SEQUENCE: 28
nnnnnnnnnn unannn                                                       16

<210> SEQ ID NO 29
<211> LENGTH: 36
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(36)
<223> OTHER INFORMATION: n = A,T,C,G, or U
<220> FEATURE:
<221> NAME/KEY: misc_feature
<222> LOCATION: (2)..(5)
<223> OTHER INFORMATION: may be T
<220> FEATURE:
<221> NAME/KEY: misc_feature
<222> LOCATION: (6)..(6)
<223> OTHER INFORMATION: n = A,T,C,G, or U (e.g., A,T, or U)
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
<222> LOCATION: (9)..(9)
<223> OTHER INFORMATION: n = A,T,C,G, or U (e.g., A or G)
<220> FEATURE:
<221> NAME/KEY: misc_feature
<222> LOCATION: (11)..(11)
<223> OTHER INFORMATION: may be T
<220> FEATURE:
<221> NAME/KEY: misc_feature
<222> LOCATION: (12)..(12)
<223> OTHER INFORMATION: n = A,T,C,G, or U (e.g., A,C, or G)
<220> FEATURE:
<221> NAME/KEY: misc_feature
<222> LOCATION: (13)..(13)
<223> OTHER INFORMATION: may be T
<220> FEATURE:
<221> NAME/KEY: misc_feature
<222> LOCATION: (14)..(14)
<223> OTHER INFORMATION: n = A,T,C,G, or U (e.g., C or G)
<220> FEATURE:
<221> NAME/KEY: misc_feature
<222> LOCATION: (15)..(15)
<223> OTHER INFORMATION: n = A,T,C,G, or U (e.g., A,T,C, or U)
<220> FEATURE:
<221> NAME/KEY: misc_feature
<222> LOCATION: (16)..(16)
<223> OTHER INFORMATION: n = A,T,C,G, or U (e.g., A,T, or U)
<220> FEATURE:
<221> NAME/KEY: misc_feature
<222> LOCATION: (17)..(17)
<223> OTHER INFORMATION: n = A,T,C,G, or U (e.g., A or G)
<220> FEATURE:
<221> NAME/KEY: misc_feature
<222> LOCATION: (18)..(18)
<223> OTHER INFORMATION: n = A,T,C,G, or U (e.g., A,T, or U)

```
<220> FEATURE:
<221> NAME/KEY: misc_feature
<222> LOCATION: (19)..(20)
<223> OTHER INFORMATION: may be T
<220> FEATURE:
<221> NAME/KEY: misc_feature
<222> LOCATION: (21)..(21)
<223> OTHER INFORMATION: n = A,T,C,G, or U (e.g., T,C, or U)
<220> FEATURE:
<221> NAME/KEY: misc_feature
<222> LOCATION: (22)..(22)
<223> OTHER INFORMATION: n = A,T,C,G, or U (e.g., A or G)
<220> FEATURE:
<221> NAME/KEY: misc_feature
<222> LOCATION: (24)..(24)
<223> OTHER INFORMATION: n = A,T,C,G, or U (e.g., A or G)
<220> FEATURE:
<221> NAME/KEY: misc_feature
<222> LOCATION: (25)..(25)
<223> OTHER INFORMATION: may be T
<220> FEATURE:
<221> NAME/KEY: misc_feature
<222> LOCATION: (26)..(26)
<223> OTHER INFORMATION: n = A,T,C,G, or U (e.g., A or G)
<220> FEATURE:
<221> NAME/KEY: misc_feature
<222> LOCATION: (27)..(27)
<223> OTHER INFORMATION: n = A,T,C,G, or U (e.g., A,C, or G)
<220> FEATURE:
<221> NAME/KEY: misc_feature
<222> LOCATION: (28)..(28)
<223> OTHER INFORMATION: n = A,T,C,G, or U (e.g., T,C, or U)
<220> FEATURE:
<221> NAME/KEY: misc_feature
<222> LOCATION: (29)..(29)
<223> OTHER INFORMATION: n = A,T,C,G, or U (e.g., A,T,C, or U)
<220> FEATURE:
<221> NAME/KEY: misc_feature
<222> LOCATION: (30)..(30)
<223> OTHER INFORMATION: n = A,T,C,G, or U (e.g., A,G, or C)
<220> FEATURE:
<221> NAME/KEY: misc_feature
<222> LOCATION: (31)..(31)
<223> OTHER INFORMATION: n = A,T,C,G, or U (e.g., T,C, or U)
<220> FEATURE:
<221> NAME/KEY: misc_feature
<222> LOCATION: (33)..(33)
<223> OTHER INFORMATION: n = A,T,C,G, or U (e.g., A or C)

<400> SEQUENCE: 29
guuuungnnc unannnnnuu nnanunnnnn nanaac                              36

<210> SEQ ID NO 30
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: n = A,T,C,G, or U
<220> FEATURE:
<221> NAME/KEY: misc_feature
<222> LOCATION: (2)..(5)
<223> OTHER INFORMATION: may be T
<220> FEATURE:
<221> NAME/KEY: misc_feature
<222> LOCATION: (6)..(6)
<223> OTHER INFORMATION: n = A,T,C,G, or U (e.g., A,T, or U)
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
<222> LOCATION: (9)..(9)
```

```
<223> OTHER INFORMATION: n = A,T,C,G, or U (e.g., A or G)
<220> FEATURE:
<221> NAME/KEY: misc_feature
<222> LOCATION: (11)..(11)
<223> OTHER INFORMATION: may be T
<220> FEATURE:
<221> NAME/KEY: misc_feature
<222> LOCATION: (12)..(12)
<223> OTHER INFORMATION: n = A,T,C,G, or U (e.g., A,C, or G)

<400> SEQUENCE: 30
guuuungnnc un                                                                  12

<210> SEQ ID NO 31
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(38)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., C or G)
<220> FEATURE:
<221> NAME/KEY: misc_feature
<222> LOCATION: (2)..(2)
<223> OTHER INFORMATION: n = A,T,C,G, or U (e.g., T,C, or U)
<220> FEATURE:
<221> NAME/KEY: misc_feature
<222> LOCATION: (7)..(7)
<223> OTHER INFORMATION: n = A,T,C,G, or U (e.g., C or G)
<220> FEATURE:
<221> NAME/KEY: misc_feature
<222> LOCATION: (8)..(8)
<223> OTHER INFORMATION: may be T
<220> FEATURE:
<221> NAME/KEY: misc_feature
<222> LOCATION: (9)..(9)
<223> OTHER INFORMATION: n = A,T,C,G, or U (e.g., A,T, or U)
<220> FEATURE:
<221> NAME/KEY: misc_feature
<222> LOCATION: (10)..(10)
<223> OTHER INFORMATION: n = A,T,C,G, or U (e.g., G or absent)
<220> FEATURE:
<221> NAME/KEY: misc_feature
<222> LOCATION: (11)..(11)
<223> OTHER INFORMATION: may be T
<220> FEATURE:
<221> NAME/KEY: misc_feature
<222> LOCATION: (12)..(12)
<223> OTHER INFORMATION: n = A,T,C,G, or U (e.g., A,T, or U)
<220> FEATURE:
<221> NAME/KEY: misc_feature
<222> LOCATION: (13)..(13)
<223> OTHER INFORMATION: may be T
<220> FEATURE:
<221> NAME/KEY: misc_feature
<222> LOCATION: (15)..(15)
<223> OTHER INFORMATION: n = A,T,C,G, or U (e.g., C or G)
<220> FEATURE:
<221> NAME/KEY: misc_feature
<222> LOCATION: (20)..(20)
<223> OTHER INFORMATION: may be T
<220> FEATURE:
<221> NAME/KEY: misc_feature
<222> LOCATION: (21)..(21)
<223> OTHER INFORMATION: n = A,T,C,G, or U (e.g., C or absent)
<220> FEATURE:
<221> NAME/KEY: misc_feature
<222> LOCATION: (22)..(22)
<223> OTHER INFORMATION: n = A,T,C,G, or U (e.g., A,C, or absent)
<220> FEATURE:
<221> NAME/KEY: misc_feature
```

```
<222> LOCATION: (23)..(23)
<223> OTHER INFORMATION: n = A,T,C,G, or U (e.g., A,G, or absent)
<220> FEATURE:
<221> NAME/KEY: misc_feature
<222> LOCATION: (24)..(24)
<223> OTHER INFORMATION: n = A,T,C,G, or U (e.g., T,C, or U)
<220> FEATURE:
<221> NAME/KEY: misc_feature
<222> LOCATION: (25)..(25)
<223> OTHER INFORMATION: may be T
<220> FEATURE:
<221> NAME/KEY: misc_feature
<222> LOCATION: (26)..(26)
<223> OTHER INFORMATION: n = A,T,C,G, or U (e.g., T,C, or U)
<220> FEATURE:
<221> NAME/KEY: misc_feature
<222> LOCATION: (28)..(28)
<223> OTHER INFORMATION: n = A,T,C,G, or U (e.g., G)
<220> FEATURE:
<221> NAME/KEY: misc_feature
<222> LOCATION: (30)..(30)
<223> OTHER INFORMATION: n = A,T,C,G, or U (e.g., A or C)
<220> FEATURE:
<221> NAME/KEY: misc_feature
<222> LOCATION: (31)..(31)
<223> OTHER INFORMATION: n = A,T,C,G, or U (e.g., A,T, or U)
<220> FEATURE:
<221> NAME/KEY: misc_feature
<222> LOCATION: (32)..(32)
<223> OTHER INFORMATION: n = A,T,C,G, or U (e.g., C or G)
<220> FEATURE:
<221> NAME/KEY: misc_feature
<222> LOCATION: (33)..(33)
<223> OTHER INFORMATION: may be T

<400> SEQUENCE: 31
nnaacanunn unuancaaau nnnnunancn nnugaaac                              38

<210> SEQ ID NO 32
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., C or G)
<220> FEATURE:
<221> NAME/KEY: misc_feature
<222> LOCATION: (2)..(2)
<223> OTHER INFORMATION: n = A,T,C,G, or U (e.g., T,C, or U)
<220> FEATURE:
<221> NAME/KEY: misc_feature
<222> LOCATION: (7)..(7)
<223> OTHER INFORMATION: n = A,T,C,G, or U (e.g., C or G)
<220> FEATURE:
<221> NAME/KEY: misc_feature
<222> LOCATION: (8)..(8)
<223> OTHER INFORMATION: may be T
<220> FEATURE:
<221> NAME/KEY: misc_feature
<222> LOCATION: (9)..(9)
<223> OTHER INFORMATION: n = A,T,C,G, or U (e.g., A,T, or U)
<220> FEATURE:
<221> NAME/KEY: misc_feature
<222> LOCATION: (10)..(10)
<223> OTHER INFORMATION: n = A,T,C,G, or U (e.g., G or absent)
<220> FEATURE:
<221> NAME/KEY: misc_feature
<222> LOCATION: (11)..(11)
<223> OTHER INFORMATION: may be T
<220> FEATURE:
```

```
<221> NAME/KEY: misc_feature
<222> LOCATION: (12)..(12)
<223> OTHER INFORMATION: n = A,T,C,G, or U (e.g., A,T, or U)
<220> FEATURE:
<221> NAME/KEY: misc_feature
<222> LOCATION: (13)..(13)
<223> OTHER INFORMATION: may be T
<220> FEATURE:
<221> NAME/KEY: misc_feature
<222> LOCATION: (15)..(15)
<223> OTHER INFORMATION: n = A,T,C,G, or U (e.g., C or G)

<400> SEQUENCE: 32
nnaacanunn unuanc                                                   16

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40
<211> LENGTH: 36
<212> TYPE: DNA
<213> ORGANISM: Artificial Sequence
<220> FEATURE:
<223> OTHER INFORMATION: Synthetic construct

<400> SEQUENCE: 40
uuguuggaac cauucaaaac agcauagcaa guuaaa                             36

<210> SEQ ID NO 41
```

```
<211> LENGTH: 36
<212> TYPE: DNA
<213> ORGANISM: Artificial Sequence
<220> FEATURE:
<223> OTHER INFORMATION: Synthetic construct

<400> SEQUENCE: 41
auauuguuag uauucaaaau aacauagcaa guuaaa                         36

<210> SEQ ID NO 42
<211> LENGTH: 36
<212> TYPE: DNA
<213> ORGANISM: Artificial Sequence
<220> FEATURE:
<223> OTHER INFORMATION: Synthetic construct

<400> SEQUENCE: 42
gguuugaaac cauucgaaac aacacagcga guuaaa                         36

<210> SEQ ID NO 43
<211> LENGTH: 36
<212> TYPE: DNA
<213> ORGANISM: Artificial Sequence
<220> FEATURE:
<223> OTHER INFORMATION: Synthetic construct

<400> SEQUENCE: 43
cuuacacagu uacuuaaauc uugcagaagc uacaaa                         36

<210> SEQ ID NO 44
<211> LENGTH: 37
<212> TYPE: DNA
<213> ORGANISM: Artificial Sequence
<220> FEATURE:
<223> OTHER INFORMATION: Synthetic construct

<400> SEQUENCE: 44
guuucaguug uuagauuauu ugguauguac uuguguu                        37

<210> SEQ ID NO 45
<211> LENGTH: 37
<212> TYPE: DNA
<213> ORGANISM: Artificial Sequence
<220> FEATURE:
<223> OTHER INFORMATION: Synthetic construct

<400> SEQUENCE: 45
auuacagagc auuaauuauu ugguacauuu auaauuu                        37

<210> SEQ ID NO 46
<211> LENGTH: 37
<212> TYPE: DNA
<213> ORGANISM: Artificial Sequence
<220> FEATURE:
<223> OTHER INFORMATION: Synthetic construct

<400> SEQUENCE: 46
uuucaaggca ucgaacggau uugcuauaaa guguugc                        37

<210> SEQ ID NO 47
<211> LENGTH: 37
<212> TYPE: DNA
<213> ORGANISM: Artificial Sequence
<220> FEATURE:
<223> OTHER INFORMATION: Synthetic construct

<400> SEQUENCE: 47
```
uuuguuaaag cuggauggga uuauuauaga guguugc                                37

```
<210> SEQ ID NO 48
<211> LENGTH: 41
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(41)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., A,T,G, or U)
<220> FEATURE:
<221> NAME/KEY: misc_feature
<222> LOCATION: (1)..(1)
<223> OTHER INFORMATION: n = A,T,C,G, or U
<220> FEATURE:
<221> NAME/KEY: misc_feature
<222> LOCATION: (2)..(2)
<223> OTHER INFORMATION: n = A,T,C,G, or U (e.g., T,G, or U)
<220> FEATURE:
<221> NAME/KEY: misc_feature
<222> LOCATION: (3)..(3)
<223> OTHER INFORMATION: n = A,T,C,G, or U (e.g., A,T,G, or U)
<220> FEATURE:
<221> NAME/KEY: misc_feature
<222> LOCATION: (4)..(4)
<223> OTHER INFORMATION: n = A,T,C,G, or U (e.g., T,G,U, or absent)
<220> FEATURE:
<221> NAME/KEY: misc_feature
<222> LOCATION: (5)..(5)
<223> OTHER INFORMATION: n = A,T,C,G, or U (e.g., A,T,U, or absent)
<220> FEATURE:
<221> NAME/KEY: misc_feature
<222> LOCATION: (6)..(6)
<223> OTHER INFORMATION: n = A,T,C,G, or U (e.g., T,G,C, or U)
<220> FEATURE:
<221> NAME/KEY: misc_feature
<222> LOCATION: (7)..(7)
<223> OTHER INFORMATION: n = A,T,C,G, or U (e.g., A,T,G, or U)
<220> FEATURE:
<221> NAME/KEY: misc_feature
<222> LOCATION: (8)..(8)
<223> OTHER INFORMATION: n = A,T,C,G, or U
<220> FEATURE:
<221> NAME/KEY: misc_feature
<222> LOCATION: (9)..(9)
<223> OTHER INFORMATION: n = A,T,C,G, or U (e.g., A,T,G, or U)
<220> FEATURE:
<221> NAME/KEY: misc_feature
<222> LOCATION: (10)..(10)
<223> OTHER INFORMATION: n = A,T,C,G, or U (e.g., C,G, or absent)
<220> FEATURE:
<221> NAME/KEY: misc_feature
<222> LOCATION: (11)..(11)
<223> OTHER INFORMATION: n = A,T,C,G, or U (e.g., T,U, or absent)
<220> FEATURE:
<221> NAME/KEY: misc_feature
<222> LOCATION: (12)..(12)
<223> OTHER INFORMATION: n = A,T,C,G, or U (e.g., T,C, or U)
<220> FEATURE:
<221> NAME/KEY: misc_feature
<222> LOCATION: (13)..(13)
<223> OTHER INFORMATION: n = A,T,C,G, or U (e.g., A,G, or absent)
<220> FEATURE:
<221> NAME/KEY: misc_feature
<222> LOCATION: (14)..(14)
<223> OTHER INFORMATION: n = A,T,C,G, or U (e.g., T,C, or U)
<220> FEATURE:
<221> NAME/KEY: misc_feature
<222> LOCATION: (15)..(15)
<223> OTHER INFORMATION: n = A,T,C,G, or U (e.g., T,C,G, or U)
<220> FEATURE:
```

```
<221> NAME/KEY: misc_feature
<222> LOCATION: (16)..(16)
<223> OTHER INFORMATION: n = A,T,C,G,U, or absent
<220> FEATURE:
<221> NAME/KEY: misc_feature
<222> LOCATION: (17)..(17)
<223> OTHER INFORMATION: n = A,T,C,G, or U (e.g., A or G)
<220> FEATURE:
<221> NAME/KEY: misc_feature
<222> LOCATION: (18)..(18)
<223> OTHER INFORMATION: n = A,T,C,G, or U (e.g., A,T,U, or absent)
<220> FEATURE:
<221> NAME/KEY: misc_feature
<222> LOCATION: (19)..(19)
<223> OTHER INFORMATION: n = A,T,C,G, or U (e.g., C,G, or absent)
<220> FEATURE:
<221> NAME/KEY: misc_feature
<222> LOCATION: (20)..(20)
<223> OTHER INFORMATION: n = A,T,C,G, or U (e.g., T,G,U, or absent)
<220> FEATURE:
<221> NAME/KEY: misc_feature
<222> LOCATION: (21)..(21)
<223> OTHER INFORMATION: n = A,T,C,G, or U (e.g., A,T,G, or U)
<220> FEATURE:
<221> NAME/KEY: misc_feature
<222> LOCATION: (23)..(23)
<223> OTHER INFORMATION: n = A,T,C,G, or U (e.g., T,C, or U)
<220> FEATURE:
<221> NAME/KEY: misc_feature
<222> LOCATION: (24)..(24)
<223> OTHER INFORMATION: n = A,T,C,G, or U (e.g., T,C,U, or absent)
<220> FEATURE:
<221> NAME/KEY: misc_feature
<222> LOCATION: (25)..(25)
<223> OTHER INFORMATION: n = A,T,C,G, or U (e.g., T,U, or absent)
<220> FEATURE:
<221> NAME/KEY: misc_feature
<222> LOCATION: (26)..(26)
<223> OTHER INFORMATION: n = A,T,C,G, or U (e.g., A,T,G, or U)
<220> FEATURE:
<221> NAME/KEY: misc_feature
<222> LOCATION: (27)..(27)
<223> OTHER INFORMATION: n = A,T,C,G, or U
<220> FEATURE:
<221> NAME/KEY: misc_feature
<222> LOCATION: (28)..(28)
<223> OTHER INFORMATION: n = A,T,C,G, or U (e.g., T,C, or U)
<220> FEATURE:
<221> NAME/KEY: misc_feature
<222> LOCATION: (30)..(30)
<223> OTHER INFORMATION: n = A,T,C,G, or U (e.g., T,C,G, or U)
<220> FEATURE:
<221> NAME/KEY: misc_feature
<222> LOCATION: (31)..(31)
<223> OTHER INFORMATION: n = A,T,C,G, or U (e.g., A or G)
<220> FEATURE:
<221> NAME/KEY: misc_feature
<222> LOCATION: (32)..(32)
<223> OTHER INFORMATION: n = A,T,C,G, or U (e.g., A,T,G, or U)
<220> FEATURE:
<221> NAME/KEY: misc_feature
<222> LOCATION: (33)..(34)
<223> OTHER INFORMATION: n = A,T,C,G, or U
<220> FEATURE:
<221> NAME/KEY: misc_feature
<222> LOCATION: (35)..(35)
<223> OTHER INFORMATION: n = A,T,C,G, or U (e.g., A,T, or U)
<220> FEATURE:
<221> NAME/KEY: misc_feature
<222> LOCATION: (36)..(36)
<223> OTHER INFORMATION: n = A,T,C,G, or U (e.g., A,T,G, or U)
<220> FEATURE:
<221> NAME/KEY: misc_feature
<222> LOCATION: (37)..(37)
<223> OTHER INFORMATION: n = A,T,C,G, or U (e.g., A,T,G,U, or absent)
<220> FEATURE:
<221> NAME/KEY: misc_feature
<222> LOCATION: (38)..(38)
<223> OTHER INFORMATION: n = A,T,C,G, or U (e.g., A,T,C, or U)
```

-continued

```
<220> FEATURE:
<221> NAME/KEY: misc_feature
<222> LOCATION: (39)..(40)
<223> OTHER INFORMATION: n = A,T,C,G, or U (e.g., A,T,G, or U)
<220> FEATURE:
<221> NAME/KEY: misc_feature
<222> LOCATION: (41)..(41)
<223> OTHER INFORMATION: n = A,T,C,G, or U (e.g., A,T,C, or U)

<400> SEQUENCE: 48 nnnnnnnnn nnnnnnnnn nannnnnan nnnnnnnnn n                    41

<210> SEQ ID NO 49
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(14)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., T,C, or U)
<220> FEATURE:
<221> NAME/KEY: misc_feature
<222> LOCATION: (3)..(3)
<223> OTHER INFORMATION: n = A,T,C,G, or U (e.g., T,C,G, or U)
<220> FEATURE:
<221> NAME/KEY: misc_feature
<222> LOCATION: (4)..(4)
<223> OTHER INFORMATION: n = A,T,C,G, or U (e.g., A or G)
<220> FEATURE:
<221> NAME/KEY: misc_feature
<222> LOCATION: (5)..(5)
<223> OTHER INFORMATION: n = A,T,C,G, or U (e.g., A,T,G, or U)
<220> FEATURE:
<221> NAME/KEY: misc_feature
<222> LOCATION: (6)..(7)
<223> OTHER INFORMATION: n = A,T,C,G, or U
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
<222> LOCATION: (9)..(9)
<223> OTHER INFORMATION: n = A,T,C,G, or U (e.g., A,T,G, or U)
<220> FEATURE:
<221> NAME/KEY: misc_feature
<222> LOCATION: (10)..(10)
<223> OTHER INFORMATION: n = A,T,C,G, or U (e.g., A,T,G,U, or absent)
<220> FEATURE:
<221> NAME/KEY: misc_feature
<222> LOCATION: (11)..(11)
<223> OTHER INFORMATION: n = A,T,C,G, or U (e.g., A,T,C, or U)
<220> FEATURE:
<221> NAME/KEY: misc_feature
<222> LOCATION: (12)..(12)
<223> OTHER INFORMATION: n = A,T,C,G, or U (e.g., A,T,G, or U)
<220> FEATURE:
<221> NAME/KEY: misc_feature
<222> LOCATION: (13)..(13)
<223> OTHER INFORMATION: n = A,T,C,G, or U (e.g., A,T,G, or U)
<220> FEATURE:
<221> NAME/KEY: misc_feature
<222> LOCATION: (14)..(14)
<223> OTHER INFORMATION: n = A,T,C,G, or U (e.g., A,T,C, or U)

<400> SEQUENCE: 49 nannnnnnn nnnn                                                14

<210> SEQ ID NO 50
```

```
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., T,C,G, or U)
<220> FEATURE:
<221> NAME/KEY: misc_feature
<222> LOCATION: (2)..(2)
<223> OTHER INFORMATION: n = A,T,C,G, or U (e.g., A or G)
<220> FEATURE:
<221> NAME/KEY: misc_feature
<222> LOCATION: (3)..(3)
<223> OTHER INFORMATION: n = A,T,C,G, or U (e.g., A,T,G, or U)
<220> FEATURE:
<221> NAME/KEY: misc_feature
<222> LOCATION: (4)..(5)
<223> OTHER INFORMATION: n = A,T,C,G, or U
<220> FEATURE:
<221> NAME/KEY: misc_feature
<222> LOCATION: (6)..(6)
<223> OTHER INFORMATION: n = A,T,C,G, or U (e.g., A,T, or U)
<220> FEATURE:
<221> NAME/KEY: misc_feature
<222> LOCATION: (7)..(7)
<223> OTHER INFORMATION: n = A,T,C,G, or U (e.g., A,T,G, or U)
<220> FEATURE:
<221> NAME/KEY: misc_feature
<222> LOCATION: (8)..(8)
<223> OTHER INFORMATION: n = A,T,C,G, or U (e.g., A,T,G,U, or absent)
<220> FEATURE:
<221> NAME/KEY: misc_feature
<222> LOCATION: (9)..(9)
<223> OTHER INFORMATION: n = A,T,C,G, or U (e.g., A,T,C, or U)
<220> FEATURE:
<221> NAME/KEY: misc_feature
<222> LOCATION: (10)..(11)
<223> OTHER INFORMATION: n = A,T,C,G, or U (e.g., A,T,G, or U)
<220> FEATURE:
<221> NAME/KEY: misc_feature
<222> LOCATION: (12)..(12)
<223> OTHER INFORMATION: n = A,T,C,G, or U (e.g., A,T,C, or U)

<400> SEQUENCE: 50
nnnnnnnnnn nn                                                         12

<210> SEQ ID NO 51
<211> LENGTH: 37
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(37)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U
<220> FEATURE:
<221> NAME/KEY: misc_feature
<222> LOCATION: (2)..(2)
<223> OTHER INFORMATION: n = A,T,C,G, or U (e.g., T,G, or U)
<220> FEATURE:
<221> NAME/KEY: misc_feature
<222> LOCATION: (3)..(3)
<223> OTHER INFORMATION: n = A,T,C,G, or U (e.g., A,T,G, or U)
<220> FEATURE:
<221> NAME/KEY: misc_feature
```

```
<222> LOCATION: (4)..(4)
<223> OTHER INFORMATION: n = A,T,C,G, or U (e.g., A,T, or U)
<220> FEATURE:
<221> NAME/KEY: misc_feature
<222> LOCATION: (5)..(5)
<223> OTHER INFORMATION: n = A,T,C,G, or U (e.g., T,C, or U)
<220> FEATURE:
<221> NAME/KEY: misc_feature
<222> LOCATION: (6)..(6)
<223> OTHER INFORMATION: n = A,T,C,G, or U (e.g., A or G)
<220> FEATURE:
<221> NAME/KEY: misc_feature
<222> LOCATION: (7)..(7)
<223> OTHER INFORMATION: n = A,T,C,G, or U
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
<222> LOCATION: (9)..(9)
<223> OTHER INFORMATION: n = A,T,C,G, or U (e.g., A or G)
<220> FEATURE:
<221> NAME/KEY: misc_feature
<222> LOCATION: (10)..(10)
<223> OTHER INFORMATION: n = A,T,C,G, or U (e.g., T,C,G, or U)
<220> FEATURE:
<221> NAME/KEY: misc_feature
<222> LOCATION: (11)..(11)
<223> OTHER INFORMATION: n = A,T,C,G, or U (e.g., T,C, or U)
<220> FEATURE:
<221> NAME/KEY: misc_feature
<222> LOCATION: (13)..(13)
<223> OTHER INFORMATION: n = A,T,C,G, or U (e.g., T,C, or U)
<220> FEATURE:
<221> NAME/KEY: misc_feature
<222> LOCATION: (14)..(14)
<223> OTHER INFORMATION: may be T
<220> FEATURE:
<221> NAME/KEY: misc_feature
<222> LOCATION: (15)..(15)
<223> OTHER INFORMATION: n = A,T,C,G, or U (e.g., T,C, or U)
<220> FEATURE:
<221> NAME/KEY: misc_feature
<222> LOCATION: (16)..(16)
<223> OTHER INFORMATION: n = A,T,C,G, or U (e.g., A or G)
<220> FEATURE:
<221> NAME/KEY: misc_feature
<222> LOCATION: (19)..(19)
<223> OTHER INFORMATION: n = A,T,C,G, or U (e.g., A,T, or U)
<220> FEATURE:
<221> NAME/KEY: misc_feature
<222> LOCATION: (20)..(20)
<223> OTHER INFORMATION: n = A,T,C,G, or U (e.g., T,C, or U)
<220> FEATURE:
<221> NAME/KEY: misc_feature
<222> LOCATION: (21)..(21)
<223> OTHER INFORMATION: n = A,T,C,G, or U (e.g., A or absent)
<220> FEATURE:
<221> NAME/KEY: misc_feature
<222> LOCATION: (22)..(22)
<223> OTHER INFORMATION: n = A,T,C,G, or U (e.g., A,T,G, or U)
<220> FEATURE:
<221> NAME/KEY: misc_feature
<222> LOCATION: (23)..(23)
<223> OTHER INFORMATION: n = A,T,C,G, or U (e.g., T,C, or U)
<220> FEATURE:
<221> NAME/KEY: misc_feature
<222> LOCATION: (24)..(24)
<223> OTHER INFORMATION: n = A,T,C,G, or U (e.g., A or G)
<220> FEATURE:
<221> NAME/KEY: misc_feature
<222> LOCATION: (25)..(25)
<223> OTHER INFORMATION: n = A,T,C,G, or U (e.g., T,C, or U)
<220> FEATURE:
<221> NAME/KEY: misc_feature
<222> LOCATION: (28)..(28)
<223> OTHER INFORMATION: n = A,T,C,G, or U (e.g., A or C)
<220> FEATURE:
```

```
<221> NAME/KEY: misc_feature
<222> LOCATION: (29)..(30)
<223> OTHER INFORMATION: n = A,T,C,G, or U (e.g., A or G)
<220> FEATURE:
<221> NAME/KEY: misc_feature
<222> LOCATION: (31)..(31)
<223> OTHER INFORMATION: n = A,T,C,G, or U (e.g., C or G)
<220> FEATURE:
<221> NAME/KEY: misc_feature
<222> LOCATION: (32)..(32)
<223> OTHER INFORMATION: may be T
<220> FEATURE:
<221> NAME/KEY: misc_feature
<222> LOCATION: (33)..(33)
<223> OTHER INFORMATION: n = A,T,C,G, or U (e.g., A or absent)
<220> FEATURE:
<221> NAME/KEY: misc_feature
<222> LOCATION: (34)..(34)
<223> OTHER INFORMATION: n = A,T,C,G, or U (e.g., T,C, or U)

<400> SEQUENCE: 51
nnnnnnnnnn nanunnaann nnnnnagnnn nunnaaa                        37

<210> SEQ ID NO 52
<211> LENGTH: 13
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(13)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., T,C, or U)
<220> FEATURE:
<221> NAME/KEY: misc_feature
<222> LOCATION: (4)..(4)
<223> OTHER INFORMATION: n = A,T,C,G, or U (e.g., A or C)
<220> FEATURE:
<221> NAME/KEY: misc_feature
<222> LOCATION: (5)..(6)
<223> OTHER INFORMATION: n = A,T,C,G, or U (e.g., A or G)
<220> FEATURE:
<221> NAME/KEY: misc_feature
<222> LOCATION: (7)..(7)
<223> OTHER INFORMATION: n = A,T,C,G, or U (e.g., C or G)
<220> FEATURE:
<221> NAME/KEY: misc_feature
<222> LOCATION: (8)..(8)
<223> OTHER INFORMATION: may be T
<220> FEATURE:
<221> NAME/KEY: misc_feature
<222> LOCATION: (9)..(9)
<223> OTHER INFORMATION: n = A,T,C,G, or U (e.g., A or absent)
<220> FEATURE:
<221> NAME/KEY: misc_feature
<222> LOCATION: (10)..(10)
<223> OTHER INFORMATION: n = A,T,C,G, or U (e.g.,T,C, or U)

<400> SEQUENCE: 52
nagnnnnunn aaa                                                  13

<210> SEQ ID NO 53
<211> LENGTH: 39
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(39)
<223> OTHER INFORMATION: n = A,T,C,G, or U
```

-continued

```
<220> FEATURE:
<221> NAME/KEY: misc_feature
<222> LOCATION: (1)..(1)
<223> OTHER INFORMATION: n = A,T,C,G, or U (e.g., A,T,G, or U)
<220> FEATURE:
<221> NAME/KEY: misc_feature
<222> LOCATION: (2)..(2)
<223> OTHER INFORMATION: n = A,T,C,G, or U (e.g., T,U, or absent)
<220> FEATURE:
<221> NAME/KEY: misc_feature
<222> LOCATION: (3)..(3)
<223> OTHER INFORMATION: may be T
<220> FEATURE:
<221> NAME/KEY: misc_feature
<222> LOCATION: (4)..(4)
<223> OTHER INFORMATION: n = A,T,C,G, or U (e.g., A,T,G, or U)
<220> FEATURE:
<221> NAME/KEY: misc_feature
<222> LOCATION: (5)..(5)
<223> OTHER INFORMATION: n = A,T,C,G, or U (e.g., T,C, or U)
<220> FEATURE:
<221> NAME/KEY: misc_feature
<222> LOCATION: (6)..(6)
<223> OTHER INFORMATION: n = A,T,C,G, or U (e.g., A,T, or U)
<220> FEATURE:
<221> NAME/KEY: misc_feature
<222> LOCATION: (7)..(8)
<223> OTHER INFORMATION: n = A,T,C,G, or U (e.g., A or G)
<220> FEATURE:
<221> NAME/KEY: misc_feature
<222> LOCATION: (9)..(9)
<223> OTHER INFORMATION: n = A,T,C,G, or U (e.g., A,T,G, or U)
<220> FEATURE:
<221> NAME/KEY: misc_feature
<222> LOCATION: (10)..(10)
<223> OTHER INFORMATION: n = A,T,C,G, or U (e.g., C or G)
<220> FEATURE:
<221> NAME/KEY: misc_feature
<222> LOCATION: (11)..(11)
<223> OTHER INFORMATION: n = A,T,C,G, or U (e.g., A,T,C, or U)
<220> FEATURE:
<221> NAME/KEY: misc_feature
<222> LOCATION: (12)..(12)
<223> OTHER INFORMATION: may be T
<220> FEATURE:
<221> NAME/KEY: misc_feature
<222> LOCATION: (13)..(13)
<223> OTHER INFORMATION: n = A,T,C,G, or U
<220> FEATURE:
<221> NAME/KEY: misc_feature
<222> LOCATION: (14)..(14)
<223> OTHER INFORMATION: n = A,T,C,G, or U (e.g., A or G)
<220> FEATURE:
<221> NAME/KEY: misc_feature
<222> LOCATION: (15)..(15)
<223> OTHER INFORMATION: n = A,T,C,G, or U (e.g., A or absent)
<220> FEATURE:
<221> NAME/KEY: misc_feature
<222> LOCATION: (17)..(17)
<223> OTHER INFORMATION: n = A,T,C,G, or U (e.g., T,C, or U)
<220> FEATURE:
<221> NAME/KEY: misc_feature
<222> LOCATION: (18)..(18)
<223> OTHER INFORMATION: n = A,T,C,G, or U (e.g., G or absent)
<220> FEATURE:
<221> NAME/KEY: misc_feature
<222> LOCATION: (19)..(19)
<223> OTHER INFORMATION: n = A,T,C,G, or U (e.g., T,G, or U)
<220> FEATURE:
<221> NAME/KEY: misc_feature
<222> LOCATION: (20)..(20)
<223> OTHER INFORMATION: n = A,T,C,G, or U (e.g., A or G)
<220> FEATURE:
<221> NAME/KEY: misc_feature
<222> LOCATION: (21)..(21)
<223> OTHER INFORMATION: n = A,T,C,G, or U (e.g., A,T, or U)
<220> FEATURE:
<221> NAME/KEY: misc_feature
<222> LOCATION: (22)..(23)
```

```
<223> OTHER INFORMATION: may be T
<220> FEATURE:
<221> NAME/KEY: misc_feature
<222> LOCATION: (24)..(24)
<223> OTHER INFORMATION: n = A,T,C,G, or U (e.g., A or G)
<220> FEATURE:
<221> NAME/KEY: misc_feature
<222> LOCATION: (25)..(25)
<223> OTHER INFORMATION: n = A,T,C,G, or U (e.g., T,C,G, or U)
<220> FEATURE:
<221> NAME/KEY: misc_feature
<222> LOCATION: (26)..(26)
<223> OTHER INFORMATION: may be T
<220> FEATURE:
<221> NAME/KEY: misc_feature
<222> LOCATION: (28)..(28)
<223> OTHER INFORMATION: n = A,T,C,G, or U (e.g., T,C, or U)
<220> FEATURE:
<221> NAME/KEY: misc_feature
<222> LOCATION: (29)..(29)
<223> OTHER INFORMATION: n = A,T,C,G, or U (e.g., A or G)
<220> FEATURE:
<221> NAME/KEY: misc_feature
<222> LOCATION: (30)..(30)
<223> OTHER INFORMATION: n = A,T,C,G, or U (e.g., A,T,G, or U)
<220> FEATURE:
<221> NAME/KEY: misc_feature
<222> LOCATION: (31)..(31)
<223> OTHER INFORMATION: n = A,T,C,G, or U (e.g., A,T, or U)
<220> FEATURE:
<221> NAME/KEY: misc_feature
<222> LOCATION: (32)..(32)
<223> OTHER INFORMATION: n = A,T,C,G, or U (e.g., T,C,G, or U)
<220> FEATURE:
<221> NAME/KEY: misc_feature
<222> LOCATION: (33)..(33)
<223> OTHER INFORMATION: n = A,T,C,G, or U (e.g., A,T,U, or absent)
<220> FEATURE:
<221> NAME/KEY: misc_feature
<222> LOCATION: (34)..(34)
<223> OTHER INFORMATION: may be T
<220> FEATURE:
<221> NAME/KEY: misc_feature
<222> LOCATION: (35)..(35)
<223> OTHER INFORMATION: n = A,T,C,G, or U (e.g., A or G)
<220> FEATURE:
<221> NAME/KEY: misc_feature
<222> LOCATION: (36)..(36)
<223> OTHER INFORMATION: n = A,T,C,G, or U (e.g., A,T, or U)
<220> FEATURE:
<221> NAME/KEY: misc_feature
<222> LOCATION: (37)..(38)
<223> OTHER INFORMATION: n = A,T,C,G, or U (e.g., T,G, or U)
<220> FEATURE:
<221> NAME/KEY: misc_feature
<222> LOCATION: (39)..(39)
<223> OTHER INFORMATION: n = A,T,C,G, or U (e.g., T,C, or U)

<400> SEQUENCE: 53
nnunnnnnnn nunnnannnn nuunnuannn nnnunnnnn                              39

<210> SEQ ID NO 54
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., A or G)
<220> FEATURE:
<221> NAME/KEY: misc_feature
```

```
<222> LOCATION: (2)..(2)
<223> OTHER INFORMATION: n = A,T,C,G, or U (e.g., T,C,G, or U)
<220> FEATURE:
<221> NAME/KEY: misc_feature
<222> LOCATION: (3)..(3)
<223> OTHER INFORMATION: may be T
<220> FEATURE:
<221> NAME/KEY: misc_feature
<222> LOCATION: (5)..(5)
<223> OTHER INFORMATION: n = A,T,C,G, or U (e.g., T,C, or U)
<220> FEATURE:
<221> NAME/KEY: misc_feature
<222> LOCATION: (6)..(6)
<223> OTHER INFORMATION: n = A,T,C,G, or U (e.g., A or G)
<220> FEATURE:
<221> NAME/KEY: misc_feature
<222> LOCATION: (7)..(7)
<223> OTHER INFORMATION: n = A,T,C,G, or U (e.g., A,T,G, or U)
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
<222> LOCATION: (9)..(9)
<223> OTHER INFORMATION: n = A,T,C,G, or U (e.g., T,C,G, or U)
<220> FEATURE:
<221> NAME/KEY: misc_feature
<222> LOCATION: (10)..(10)
<223> OTHER INFORMATION: n = A,T,C,G, or U (e.g., A,T,U, or absent)
<220> FEATURE:
<221> NAME/KEY: misc_feature
<222> LOCATION: (11)..(11)
<223> OTHER INFORMATION: may be T
<220> FEATURE:
<221> NAME/KEY: misc_feature
<222> LOCATION: (12)..(12)
<223> OTHER INFORMATION: n = A,T,C,G, or U (e.g., A or G)
<220> FEATURE:
<221> NAME/KEY: misc_feature
<222> LOCATION: (13)..(13)
<223> OTHER INFORMATION: n = A,T,C,G, or U (e.g., A,T, or U)
<220> FEATURE:
<221> NAME/KEY: misc_feature
<222> LOCATION: (14)..(15)
<223> OTHER INFORMATION: n = A,T,C,G, or U (e.g., T,G, or U)
<220> FEATURE:
<221> NAME/KEY: misc_feature
<222> LOCATION: (16)..(16)
<223> OTHER INFORMATION: n = A,T,C,G, or U (e.g., T,C, or U)

<400> SEQUENCE: 54
nnuannnnnn unnnnn                                                    16

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
```

```
<400> SEQUENCE: 58

000

<210> SEQ ID NO 59

<400> SEQUENCE: 59

000

<210> SEQ ID NO 60
<211> LENGTH: 88
<212> TYPE: DNA
<213> ORGANISM: Artificial Sequence
<220> FEATURE:
<223> OTHER INFORMATION: Synthetic construct

<400> SEQUENCE: 60
guuggaacca uucaaaacag cauagcaagu uaaaauaagg cuaguccguu aucaacuuga      60
aaaaguggca ccgagucggu gcuuuuuu                                         88

<210> SEQ ID NO 61
<211> LENGTH: 93
<212> TYPE: DNA
<213> ORGANISM: Artificial Sequence
<220> FEATURE:
<223> OTHER INFORMATION: Synthetic construct

<400> SEQUENCE: 61
auauuguuag uauucaaaau aacauagcaa guuaaaauaa ggcuuugucc guuaucaacu      60
uuuaauuaag uagcgcuguu ucggcgcuuu uuu                                   93

<210> SEQ ID NO 62
<211> LENGTH: 95
<212> TYPE: DNA
<213> ORGANISM: Artificial Sequence
<220> FEATURE:
<223> OTHER INFORMATION: Synthetic construct

<400> SEQUENCE: 62 uuugugguuug aaaccauucg aaacaacaca gcgaguuaaa auaaggcuua guccguacuc     60
aacuugaaaa gguggcaccg auucggguguu uuuuu                                95

<210> SEQ ID NO 63
<211> LENGTH: 118
<212> TYPE: DNA
<213> ORGANISM: Artificial Sequence
<220> FEATURE:
<223> OTHER INFORMATION: Synthetic construct

<400> SEQUENCE: 63
uaauaauagu guaagggacg ccuuacacag uuacuuaaau cuugcagaag cuacaaagau      60
aaggcuucau gccgaaauca acacccuguc auuuuauggc aggguguuuu cguuauuu       118

<210> SEQ ID NO 64
<211> LENGTH: 121
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(121)
<223> OTHER INFORMATION: n = A,T,C,G, or U
<220> FEATURE:
```

-continued

```
<221> NAME/KEY: misc_feature
<222> LOCATION: (1)..(2)
<223> OTHER INFORMATION: n = A,T,C,G, or U (e.g., A,T,U, or absent)
<220> FEATURE:
<221> NAME/KEY: misc_feature
<222> LOCATION: (3)..(3)
<223> OTHER INFORMATION: n = A,T,C,G, or U (e.g., A or absent)
<220> FEATURE:
<221> NAME/KEY: misc_feature
<222> LOCATION: (4)..(4)
<223> OTHER INFORMATION: n = A,T,C,G, or U (e.g., T,U, or absent)
<220> FEATURE:
<221> NAME/KEY: misc_feature
<222> LOCATION: (5)..(5)
<223> OTHER INFORMATION: n = A,T,C,G, or U (e.g., A or absent)
<220> FEATURE:
<221> NAME/KEY: misc_feature
<222> LOCATION: (6)..(6)
<223> OTHER INFORMATION: n = A,T,C,G, or U (e.g., A or G)
<220> FEATURE:
<221> NAME/KEY: misc_feature
<222> LOCATION: (7)..(7)
<223> OTHER INFORMATION: may be T
<220> FEATURE:
<221> NAME/KEY: misc_feature
<222> LOCATION: (8)..(8)
<223> OTHER INFORMATION: n = A,T,C,G, or U (e.g., A,G, or absent)
<220> FEATURE:
<221> NAME/KEY: misc_feature
<222> LOCATION: (9)..(9)
<223> OTHER INFORMATION: n = A,T,C,G, or U (e.g., G or absent)
<220> FEATURE:
<221> NAME/KEY: misc_feature
<222> LOCATION: (10)..(11)
<223> OTHER INFORMATION: n = A,T,C,G, or U (e.g., T,U, or absent)
<220> FEATURE:
<221> NAME/KEY: misc_feature
<222> LOCATION: (12)..(12)
<223> OTHER INFORMATION: may be T
<220> FEATURE:
<221> NAME/KEY: misc_feature
<222> LOCATION: (14)..(14)
<223> OTHER INFORMATION: n = A,T,C,G, or U (e.g., A,T,G, or U)
<220> FEATURE:
<221> NAME/KEY: misc_feature
<222> LOCATION: (15)..(15)
<223> OTHER INFORMATION: n = A,T,C,G, or U (e.g., A,T, or U)
<220> FEATURE:
<221> NAME/KEY: misc_feature
<222> LOCATION: (17)..(19)
<223> OTHER INFORMATION: n = A,T,C,G, or U (e.g., G or absent)
<220> FEATURE:
<221> NAME/KEY: misc_feature
<222> LOCATION: (20)..(20)
<223> OTHER INFORMATION: n = A,T,C,G, or U (e.g., A or absent)
<220> FEATURE:
<221> NAME/KEY: misc_feature
<222> LOCATION: (21)..(21)
<223> OTHER INFORMATION: n = A,T,C,G, or U (e.g., C or absent)
<220> FEATURE:
<221> NAME/KEY: misc_feature
<222> LOCATION: (22)..(22)
<223> OTHER INFORMATION: n = A,T,C,G, or U (e.g., G or absent)
<220> FEATURE:
<221> NAME/KEY: misc_feature
<222> LOCATION: (23)..(23)
<223> OTHER INFORMATION: n = A,T,C,G, or U (e.g., C or G)
<220> FEATURE:
<221> NAME/KEY: misc_feature
<222> LOCATION: (24)..(24)
<223> OTHER INFORMATION: n = A,T,C,G, or U (e.g., T,C, or U)
<220> FEATURE:
<221> NAME/KEY: misc_feature
<222> LOCATION: (25)..(25)
<223> OTHER INFORMATION: n = A,T,C,G, or U (e.g., A,T, or U)
<220> FEATURE:
<221> NAME/KEY: misc_feature
<222> LOCATION: (26)..(26)
<223> OTHER INFORMATION: may be T
```

```
-continued

<220> FEATURE:
<221> NAME/KEY: misc_feature
<222> LOCATION: (27)..(27)
<223> OTHER INFORMATION: n = A,T,C,G, or U (e.g., A,T, or U)
<220> FEATURE:
<221> NAME/KEY: misc_feature
<222> LOCATION: (29)..(29)
<223> OTHER INFORMATION: n = A,T,C,G, or U (e.g., A or G)
<220> FEATURE:
<221> NAME/KEY: misc_feature
<222> LOCATION: (30)..(30)
<223> OTHER INFORMATION: n = A,T,C,G, or U (e.g., A or C)
<220> FEATURE:
<221> NAME/KEY: misc_feature
<222> LOCATION: (32)..(32)
<223> OTHER INFORMATION: n = A,T,C,G, or U (e.g., A or G)
<220> FEATURE:
<221> NAME/KEY: misc_feature
<222> LOCATION: (33)..(33)
<223> OTHER INFORMATION: n = A,T,C,G, or U (e.g., T,C, or U)
<220> FEATURE:
<221> NAME/KEY: misc_feature
<222> LOCATION: (34)..(34)
<223> OTHER INFORMATION: n = A,T,C,G, or U (e.g., A,T, or U)
<220> FEATURE:
<221> NAME/KEY: misc_feature
<222> LOCATION: (35)..(35)
<223> OTHER INFORMATION: n = A,T,C,G, or U (e.g., A or G)
<220> FEATURE:
<221> NAME/KEY: misc_feature
<222> LOCATION: (37)..(37)
<223> OTHER INFORMATION: n = A,T,C,G, or U (e.g., A,T, or U)
<220> FEATURE:
<221> NAME/KEY: misc_feature
<222> LOCATION: (38)..(38)
<223> OTHER INFORMATION: n = A,T,C,G, or U (e.g., T,C, or U)
<220> FEATURE:
<221> NAME/KEY: misc_feature
<222> LOCATION: (39)..(41)
<223> OTHER INFORMATION: n = A,T,C,G, or U (e.g., A or absent)
<220> FEATURE:
<221> NAME/KEY: misc_feature
<222> LOCATION: (42)..(42)
<223> OTHER INFORMATION: n = A,T,C,G, or U (e.g., T,U, or absent)
<220> FEATURE:
<221> NAME/KEY: misc_feature
<222> LOCATION: (43)..(43)
<223> OTHER INFORMATION: n = A,T,C,G, or U (e.g., C or absent)
<220> FEATURE:
<221> NAME/KEY: misc_feature
<222> LOCATION: (44)..(44)
<223> OTHER INFORMATION: n = A,T,C,G, or U (e.g., T,U, or absent)
<220> FEATURE:
<221> NAME/KEY: misc_feature
<222> LOCATION: (45)..(45)
<223> OTHER INFORMATION: n = A,T,C,G, or U (e.g., A,T, or U)
<220> FEATURE:
<221> NAME/KEY: misc_feature
<222> LOCATION: (48)..(48)
<223> OTHER INFORMATION: n = A,T,C,G, or U (e.g., A or absent)
<220> FEATURE:
<221> NAME/KEY: misc_feature
<222> LOCATION: (49)..(49)
<223> OTHER INFORMATION: n = A,T,C,G, or U (e.g., G or absent)
<220> FEATURE:
<221> NAME/KEY: misc_feature
<222> LOCATION: (50)..(50)
<223> OTHER INFORMATION: n = A,T,C,G, or U (e.g., A or G)
<220> FEATURE:
<221> NAME/KEY: misc_feature
<222> LOCATION: (53)..(53)
<223> OTHER INFORMATION: n = A,T,C,G, or U (e.g., T,C, or U)
<220> FEATURE:
<221> NAME/KEY: misc_feature
<222> LOCATION: (54)..(54)
<223> OTHER INFORMATION: may be T
<220> FEATURE:
<221> NAME/KEY: misc_feature
<222> LOCATION: (56)..(56)
```

```
<223> OTHER INFORMATION: n = A,T,C,G, or U (e.g., C or absent)
<220> FEATURE:
<221> NAME/KEY: misc_feature
<222> LOCATION: (57)..(58)
<223> OTHER INFORMATION: n = A,T,C,G, or U (e.g., A or absent)
<220> FEATURE:
<221> NAME/KEY: misc_feature
<222> LOCATION: (60)..(60)
<223> OTHER INFORMATION: n = A,T,C,G, or U (e.g., A or G)
<220> FEATURE:
<221> NAME/KEY: misc_feature
<222> LOCATION: (62)..(62)
<223> OTHER INFORMATION: may be T
<220> FEATURE:
<221> NAME/KEY: misc_feature
<222> LOCATION: (68)..(68)
<223> OTHER INFORMATION: may be T
<220> FEATURE:
<221> NAME/KEY: misc_feature
<222> LOCATION: (69)..(69)
<223> OTHER INFORMATION: n = A,T,C,G, or U (e.g., T,U, or absent)
<220> FEATURE:
<221> NAME/KEY: misc_feature
<222> LOCATION: (70)..(70)
<223> OTHER INFORMATION: n = A,T,C,G, or U (e.g., A,T,C, or U)
<220> FEATURE:
<221> NAME/KEY: misc_feature
<222> LOCATION: (71)..(71)
<223> OTHER INFORMATION: n = A,T,C,G, or U (e.g., A or G)
<220> FEATURE:
<221> NAME/KEY: misc_feature
<222> LOCATION: (72)..(72)
<223> OTHER INFORMATION: may be T
<220> FEATURE:
<221> NAME/KEY: misc_feature
<222> LOCATION: (73)..(73)
<223> OTHER INFORMATION: n = A,T,C,G, or U (e.g., G or absent)
<220> FEATURE:
<221> NAME/KEY: misc_feature
<222> LOCATION: (77)..(78)
<223> OTHER INFORMATION: n = A,T,C,G, or U (e.g., A,T, or U)
<220> FEATURE:
<221> NAME/KEY: misc_feature
<222> LOCATION: (79)..(79)
<223> OTHER INFORMATION: n = A,T,C,G, or U (e.g., A or C)
<220> FEATURE:
<221> NAME/KEY: misc_feature
<222> LOCATION: (80)..(80)
<223> OTHER INFORMATION: may be T
<220> FEATURE:
<221> NAME/KEY: misc_feature
<222> LOCATION: (85)..(85)
<223> OTHER INFORMATION: n = A,T,C,G, or U (e.g., A or absent)
<220> FEATURE:
<221> NAME/KEY: misc_feature
<222> LOCATION: (86)..(87)
<223> OTHER INFORMATION: n = A,T,C,G, or U (e.g., C or absent)
<220> FEATURE:
<221> NAME/KEY: misc_feature
<222> LOCATION: (88)..(88)
<223> OTHER INFORMATION: n = A,T,C,G, or U (e.g., T,C, or U)
<220> FEATURE:
<221> NAME/KEY: misc_feature
<222> LOCATION: (89)..(89)
<223> OTHER INFORMATION: may be T
<220> FEATURE:
<221> NAME/KEY: misc_feature
<222> LOCATION: (90)..(90)
<223> OTHER INFORMATION: n = A,T,C,G, or U (e.g., T,G, or U)
<220> FEATURE:
<221> NAME/KEY: misc_feature
<222> LOCATION: (91)..(91)
<223> OTHER INFORMATION: n = A,T,C,G, or U (e.g., A,T, or U)
<220> FEATURE:
<221> NAME/KEY: misc_feature
<222> LOCATION: (92)..(92)
<223> OTHER INFORMATION: n = A,T,C,G, or U (e.g., A or C)
<220> FEATURE:
<221> NAME/KEY: misc_feature
```

-continued

```
<222> LOCATION: (94)..(95)
<223> OTHER INFORMATION: n = A,T,C,G, or U (e.g., T,U, or absent)
<220> FEATURE:
<221> NAME/KEY: misc_feature
<222> LOCATION: (96)..(96)
<223> OTHER INFORMATION: n = A,T,C,G, or U (e.g., A,T, or U)
<220> FEATURE:
<221> NAME/KEY: misc_feature
<222> LOCATION: (97)..(97)
<223> OTHER INFORMATION: n = A,T,C,G, or U (e.g., A,T,G, or U)
<220> FEATURE:
<221> NAME/KEY: misc_feature
<222> LOCATION: (98)..(98)
<223> OTHER INFORMATION: n = A,T,C,G, or U (e.g., A or G)
<220> FEATURE:
<221> NAME/KEY: misc_feature
<222> LOCATION: (99)..(99)
<223> OTHER INFORMATION: may be T
<220> FEATURE:
<221> NAME/KEY: misc_feature
<222> LOCATION: (100)..(100)
<223> OTHER INFORMATION: n = A,T,C,G, or U (e.g., A or G)
<220> FEATURE:
<221> NAME/KEY: misc_feature
<222> LOCATION: (103)..(103)
<223> OTHER INFORMATION: n = A,T,C,G, or U (e.g., A or G)
<220> FEATURE:
<221> NAME/KEY: misc_feature
<222> LOCATION: (104)..(104)
<223> OTHER INFORMATION: n = A,T,C,G, or U (e.g., C or G)
<220> FEATURE:
<221> NAME/KEY: misc_feature
<222> LOCATION: (105)..(105)
<223> OTHER INFORMATION: n = A,T,C,G, or U (e.g., T,C,G, or U)
<220> FEATURE:
<221> NAME/KEY: misc_feature
<222> LOCATION: (107)..(107)
<223> OTHER INFORMATION: n = A,T,C,G, or U (e.g., A,T, or U)
<220> FEATURE:
<221> NAME/KEY: misc_feature
<222> LOCATION: (108)..(108)
<223> OTHER INFORMATION: n = A,T,C,G, or U (e.g., T,G, or U)
<220> FEATURE:
<221> NAME/KEY: misc_feature
<222> LOCATION: (109)..(109)
<223> OTHER INFORMATION: may be T
<220> FEATURE:
<221> NAME/KEY: misc_feature
<222> LOCATION: (110)..(110)
<223> OTHER INFORMATION: n = A,T,C,G, or U (e.g., T,C, or U)
<220> FEATURE:
<221> NAME/KEY: misc_feature
<222> LOCATION: (111)..(112)
<223> OTHER INFORMATION: n = A,T,C,G, or U (e.g., T,G, or U)
<220> FEATURE:
<221> NAME/KEY: misc_feature
<222> LOCATION: (113)..(113)
<223> OTHER INFORMATION: n = A,T,C,G, or U (e.g., T,C, or U)
<220> FEATURE:
<221> NAME/KEY: misc_feature
<222> LOCATION: (115)..(115)
<223> OTHER INFORMATION: n = A,T,C,G, or U (e.g., T,C,U, or absent)
<220> FEATURE:
<221> NAME/KEY: misc_feature
<222> LOCATION: (116)..(117)
<223> OTHER INFORMATION: may be T
<220> FEATURE:
<221> NAME/KEY: misc_feature
<222> LOCATION: (118)..(118)
<223> OTHER INFORMATION: n = A,T,C,G, or U (e.g., A,T, or U)
<220> FEATURE:
<221> NAME/KEY: misc_feature
<222> LOCATION: (119)..(121)
<223> OTHER INFORMATION: may be T

<400> SEQUENCE: 64
nnnnnnunnn nugnnannnn nnnnnuncnn annnncnnnn nnnnngcnnn agnuannnan    60
```
auaaggcunn nunccgnnnu caacnnnnun nnannnnnun gcnnngnnun nnngnuunuu    120
u    121

<210> SEQ ID NO 65
<211> LENGTH: 39
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(39)
<223> OTHER INFORMATION: n = A,T,C,G, or U
<220> FEATURE:
<221> NAME/KEY: misc_feature
<222> LOCATION: (1)..(1)
<223> OTHER INFORMATION: n = A,T,C,G, or U (e.g., T,C, or U)
<220> FEATURE:
<221> NAME/KEY: misc_feature
<222> LOCATION: (2)..(4)
<223> OTHER INFORMATION: n = A,T,C,G, or U (e.g., A or absent)
<220> FEATURE:
<221> NAME/KEY: misc_feature
<222> LOCATION: (5)..(5)
<223> OTHER INFORMATION: n = A,T,C,G, or U (e.g., T,U, or absent)
<220> FEATURE:
<221> NAME/KEY: misc_feature
<222> LOCATION: (6)..(6)
<223> OTHER INFORMATION: n = A,T,C,G, or U (e.g., C or absent)
<220> FEATURE:
<221> NAME/KEY: misc_feature
<222> LOCATION: (7)..(7)
<223> OTHER INFORMATION: n = A,T,C,G, or U (e.g., T,U, or absent)
<220> FEATURE:
<221> NAME/KEY: misc_feature
<222> LOCATION: (8)..(8)
<223> OTHER INFORMATION: n = A,T,C,G, or U (e.g., A,T, or U)
<220> FEATURE:
<221> NAME/KEY: misc_feature
<222> LOCATION: (11)..(11)
<223> OTHER INFORMATION: n = A,T,C,G, or U (e.g., A or absent)
<220> FEATURE:
<221> NAME/KEY: misc_feature
<222> LOCATION: (12)..(12)
<223> OTHER INFORMATION: n = A,T,C,G, or U (e.g., G or absent)
<220> FEATURE:
<221> NAME/KEY: misc_feature
<222> LOCATION: (13)..(13)
<223> OTHER INFORMATION: n = A,T,C,G, or U (e.g., A or G)
<220> FEATURE:
<221> NAME/KEY: misc_feature
<222> LOCATION: (16)..(16)
<223> OTHER INFORMATION: n = A,T,C,G, or U (e.g., T,C, or U)
<220> FEATURE:
<221> NAME/KEY: misc_feature
<222> LOCATION: (17)..(17)
<223> OTHER INFORMATION: may be T
<220> FEATURE:
<221> NAME/KEY: misc_feature
<222> LOCATION: (19)..(19)
<223> OTHER INFORMATION: n = A,T,C,G, or U (e.g., C or absent)
<220> FEATURE:
<221> NAME/KEY: misc_feature
<222> LOCATION: (20)..(21)
<223> OTHER INFORMATION: n = A,T,C,G, or U (e.g., A or absent)
<220> FEATURE:
<221> NAME/KEY: misc_feature
<222> LOCATION: (23)..(23)
<223> OTHER INFORMATION: n = A,T,C,G, or U (e.g., A or G)
<220> FEATURE:
<221> NAME/KEY: misc_feature
<222> LOCATION: (25)..(25)
<223> OTHER INFORMATION: may be T
<220> FEATURE:
<221> NAME/KEY: misc_feature
<222> LOCATION: (31)..(31)
<223> OTHER INFORMATION: may be T

```
<220> FEATURE:
<221> NAME/KEY: misc_feature
<222> LOCATION: (32)..(32)
<223> OTHER INFORMATION: n = A,T,C,G, or U (e.g., T,U, or absent)
<220> FEATURE:
<221> NAME/KEY: misc_feature
<222> LOCATION: (33)..(33)
<223> OTHER INFORMATION: n = A,T,C,G, or U (e.g., A,T,C, or U)
<220> FEATURE:
<221> NAME/KEY: misc_feature
<222> LOCATION: (34)..(34)
<223> OTHER INFORMATION: n = A,T,C,G, or U (e.g., A or G)
<220> FEATURE:
<221> NAME/KEY: misc_feature
<222> LOCATION: (35)..(35)
<223> OTHER INFORMATION: may be T
<220> FEATURE:
<221> NAME/KEY: misc_feature
<222> LOCATION: (36)..(36)
<223> OTHER INFORMATION: n = A,T,C,G, or U (e.g., G or absent)

<400> SEQUENCE: 65
nnnnnnnngc nnnagnuann nanauaaggc unnnunccg                       39

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70
<211> LENGTH: 12
<212> TYPE: DNA
<213> ORGANISM: Artificial Sequence
<220> FEATURE:
<223> OTHER INFORMATION: Synthetic construct

<400> SEQUENCE: 70
guuuuagagc ua                                                   12

<210> SEQ ID NO 71
<211> LENGTH: 26
<212> TYPE: DNA
<213> ORGANISM: Artificial Sequence
<220> FEATURE:
<223> OTHER INFORMATION: Synthetic construct

<400> SEQUENCE: 71
uagcaaguua aaauaaggcu aguccg                                    26

<210> SEQ ID NO 72
```

```
<400> SEQUENCE: 72

000

<210> SEQ ID NO 73
<400> SEQUENCE: 73

000

<210> SEQ ID NO 74
<400> SEQUENCE: 74

000

<210> SEQ ID NO 75
<400> SEQUENCE: 75

000

<210> SEQ ID NO 76
<400> SEQUENCE: 76

000

<210> SEQ ID NO 77
<400> SEQUENCE: 77

000

<210> SEQ ID NO 78
<400> SEQUENCE: 78

000

<210> SEQ ID NO 79
<400> SEQUENCE: 79

000

<210> SEQ ID NO 80
<211> LENGTH: 39
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: U may be T
<220> FEATURE:
<221> NAME/KEY: misc_feature
<222> LOCATION: (13)..(13)
<223> OTHER INFORMATION: L is a linker (e.g., a covalent bond, a nucleic
      acid sequence, a fragment of any one of SEQ ID NOs:40-54, 60-65,
      and 71 or any other useful linker)
<220> FEATURE:
<221> NAME/KEY: misc_feature
<222> LOCATION: (14)..(39)
<223> OTHER INFORMATION: U may be T

<400> SEQUENCE: 80
guuuuagagc uanuagcaag uuaaaauaag gcuaguccg                              39
```

<210> SEQ ID NO 81
<211> LENGTH: 80
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(38)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (39)..(39)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (40)..(80)
<223> OTHER INFORMATION: B is a second portion (e.g., any one of SEQ ID
      NOs:40-54, 60-65, and 71, or a fragment thereof)

<400> SEQUENCE: 81
nnnnnnnnnn unsunnnnnnn nnnnnnnnnn nnnnaacnn nnnnnnnnnn nnnnnnnnnn      60
annnnnnann nnnnnnnnnn                                                  80

<210> SEQ ID NO 82
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (13)..(13)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (14)..(27)
<223> OTHER INFORMATION: B is a second portion (e.g., any one of SEQ ID
      NOs:40-54, 60-65, and 71, or a fragment thereof)

<400> SEQUENCE: 82
nnnnnnnnnn unnnannnnn nnnnnnn                                          27

<210> SEQ ID NO 83
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (17)..(17)
<223> OTHER INFORMATION: L is a linker (e.g., a covalent bond, a nucleic
      acid sequence, a fragment of any one of SEQ ID NOs:40-54, 60-65,

```
               and 71, or any other useful linker or spacer described herein)
<220> FEATURE:
<221> NAME/KEY: misc_feature
<222> LOCATION: (18)..(31)
<223> OTHER INFORMATION: B is a second portion (e.g., any one of SEQ ID
      NOs:40-54, 60-65, and 71, or a fragment thereof)

<400> SEQUENCE: 83
nnnnnnnnnn ununnnnnan nnnnnnnnnn n                                        31

<210> SEQ ID NO 84
<211> LENGTH: 52
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (13)..(13)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (14)..(52)
<223> OTHER INFORMATION: B is a second portion (e.g., any one of SEQ ID
      NOs:40-54, 60-65, and 71, or a fragment thereofm wherein U may be
      T)

<400> SEQUENCE: 84
nnnnnnnnnn unnnnnnnnn ngcnnnagnu annnanauaa ggcunnnunc cg                 52

<210> SEQ ID NO 85
<211> LENGTH: 56
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (17)..(17)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (18)..(56)
<223> OTHER INFORMATION: B is a second portion (e.g., any one of SEQ ID
      NOs:40-54, 60-65, and 71, or a fragment thereof, wherein U may be
      T)

<400> SEQUENCE: 85
nnnnnnnnnn ununnnnnnn nnnnngcnnn agnuannnan auaaggcunn nunccg             56

<210> SEQ ID NO 86
<211> LENGTH: 74
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: (1)..(36)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (37)..(37)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (38)..(74)
<223> OTHER INFORMATION: B is a second portion (e.g., any one of SEQ ID
      NOs:40-54, 60-65, and 71, or a fragment thereof, wherein U may be
      T

<400> SEQUENCE: 86
guuuungnnc ununnnnnuu nnanunnnnn nanaacnnnn nnnnnnnnan unnaannnnn     60
nnagnnnnun naaa                                                      74

<210> SEQ ID NO 87
<211> LENGTH: 50
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (13)..(13)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (14)..(50)
<223> OTHER INFORMATION: B is a second portion (e.g., any one of SEQ ID
      NOs:40-54, 60-65, and 71, or a fragment thereof, wherein U may be
      T)

<400> SEQUENCE: 87
guuuungnnc unnnnnnnnn nnnnanunna annnnnnnag nnnnunnaaa               50

<210> SEQ ID NO 88
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (13)..(13)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (14)..(26)
<223> OTHER INFORMATION: B is a second portion (e.g., any one of SEQ ID
      NOs:40-54, 60-65, and 71, or a fragment thereof, wherein U may be
      T)
```

<400> SEQUENCE: 88
guuuungnnc unnnagnnnn unnaaa                                          26

<210> SEQ ID NO 89
<211> LENGTH: 52
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (13)..(13)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (14)..(52)
<223> OTHER INFORMATION: B is a second portion (e.g., any one of SEQ ID
      NOs:40-54, 60-65, and 71, or a fragment thereof, wherien U may be
      T)

<400> SEQUENCE: 89
guuuungnnc unnnnnnnnn ngcnnnagnu annnanauaa ggcunnnunc cg             52

<210> SEQ ID NO 90
<211> LENGTH: 76
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(38)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (39)..(39)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (40)..(76)
<223> OTHER INFORMATION: B is a second portion (e.g., any one of SEQ ID
      NOs:40-54, 60-65, and 71, or a fragment thereof, wherein U may be
      T)

<400> SEQUENCE: 90
nnaacanunn unuancaaau nnnnunancn nnugaaacnn nnnnnnnnn anunnaannn      60 nnnnagnnnn unnaaa                                                    76

<210> SEQ ID NO 91
<211> LENGTH: 56
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: A includes a first portion (e.g., any one of
      SEQ ID NOs:20-32 and 70, or a fragment thereof, wherein U may be

```
                                      T)
<220> FEATURE:
<221> NAME/KEY: misc_feature
<222> LOCATION: (17)..(17)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (18)..(56)
<223> OTHER INFORMATION: B is a second portion (e.g., any one of SEQ ID
      NOs:40-54, 60-65, and 71, or a fragment thereof, wherein U may be
      T)

<400> SEQUENCE: 91
nnaacanunn unuancnnnu nnnnnnnnun nnannnnnuu nnuannnnnn unnnn          56

<210> SEQ ID NO 92
<211> LENGTH: 33
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (17)..(17)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (18)..(33)
<223> OTHER INFORMATION: B is a second portion (e.g., any one of SEQ ID
      NOs:40-54, 60-65, and 71, or a fragment thereof, wherein U may be
      T)

<400> SEQUENCE: 92
nnaacanunn unuancnnnu annnnnnunn nnn                                  33

<210> SEQ ID NO 93
<211> LENGTH: 56
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: A includes a first portion (e.g., any one of
      SEQ ID NOs:20-32 and 70, or a fragment thereof, wherein U may be
      T)
<220> FEATURE:
<221> NAME/KEY: misc_feature
<222> LOCATION: (17)..(17)
<223> OTHER INFORMATION: L is a linker (e.g., a covalent bond, a nucleic
      acid sequence, a fragment of any one of SEQ ID NOs:40-54, 60-65,
      and 71, or any other useful linker or spacer described herein)
<220> FEATURE:
<221> NAME/KEY: misc_feature
<222> LOCATION: (18)..(56)
<223> OTHER INFORMATION: B is a second portion (e.g., any one of SEQ ID
      NOs:40-54, 60-65, and 71, or a fragment thereof, wherein U may be
      T)

<400> SEQUENCE: 93
nnaacanunn unuancnnnn nnnnngcnnn agnuannnan auaaggcunn nunccg         56
```

```
<210> SEQ ID NO 94
<400> SEQUENCE: 94

000

<210> SEQ ID NO 95
<400> SEQUENCE: 95

000

<210> SEQ ID NO 96
<400> SEQUENCE: 96

000

<210> SEQ ID NO 97
<400> SEQUENCE: 97

000

<210> SEQ ID NO 98
<400> SEQUENCE: 98

000

<210> SEQ ID NO 99
<400> SEQUENCE: 99

000

<210> SEQ ID NO 100
<211> LENGTH: 218
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(218)
<223> OTHER INFORMATION: where n at each of positions 1-80 can be
      present or absent such that this region can contain anywhere from
      12 to 80 nucleotides and n is a, c, t, g, u, or modified forms
      thereof; and where n at each of positions 93-192 can be present or
      absent such that this

<400> SEQUENCE: 100
nnnnnnnnnn nnnnnnnnnn nnnnnnnnnn nnnnnnnnnn nnnnnnnnnn nnnnnnnnnn      60
nnnnnnnnnn nnnnnnnnnn guuuuagagc uannnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnuagcaagu uaaaauaagg cuaguccg                             218

<210> SEQ ID NO 101
<211> LENGTH: 219
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(219)
<223> OTHER INFORMATION: where n at each of positions 1-80 can be
      present or absent such that this region can contain anywhere from
```

```
               12 to 80 nucleotides and n is a, c, t, g, u, or modified forms
               thereof; and where n at each of positions 93-192 can be present or
               absent such that this

<400> SEQUENCE: 101
nnnnnnnnnn nnnnnnnnnn nnnnnnnnnn nnnnnnnnnn nnnnnnnnnn nnnnnnnnnn      60
nnnnnnnnnn nnnnnnnnnn guuuuagagc uannnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnuagcaagu uaaaauaagg cuuuguccg                            219

<210> SEQ ID NO 102
<211> LENGTH: 163
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(163)
<223> OTHER INFORMATION: where n at each of positions 1-80 can be
      present or absent such that this region can contain anywhere from
      12 to 80 nucleotides and n is a, c, t, g, u, or modified forms
      thereof

<400> SEQUENCE: 102
nnnnnnnnnn nnnnnnnnnn nnnnnnnnnn nnnnnnnnnn nnnnnnnnnn nnnnnnnnnn      60
nnnnnnnnnn nnnnnnnnnn guuuuagagc uagaaauagc aaguuaaaau aaggcuaguc     120
cguuaucaac uugaaaaagu ggcaccgagu cggugcuuuu uuu                       163

<210> SEQ ID NO 103
<211> LENGTH: 163
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(163)
<223> OTHER INFORMATION: where n at each of positions 1-80 can be
      present or absent such that this region can contain anywhere from
      12 to 80 nucleotides and n is a, c, t, g, u, or modified forms
      thereof

<400> SEQUENCE: 103
nnnnnnnnnn nnnnnnnnnn nnnnnnnnnn nnnnnnnnnn nnnnnnnnnn nnnnnnnnnn      60
nnnnnnnnnn nnnnnnnnnn guuuuagagc uagaaauagc aaguuaaaau aaggcuaguc     120
cguuaucaac uugaaaaagu ggcaccgagu cggugcuuuu uuu                       163

<210> SEQ ID NO 104

<400> SEQUENCE: 104

000

<210> SEQ ID NO 105

<400> SEQUENCE: 105

000

<210> SEQ ID NO 106

<400> SEQUENCE: 106
```

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110
<211> LENGTH: 1368
<212> TYPE: PRT
<213> ORGANISM: Streptococcus pyogenes

<400> SEQUENCE: 110

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255
```

```
Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
```

```
              675                 680                 685
Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
995                 1000                1005

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095
```

```
Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 111
<211> LENGTH: 1368
<212> TYPE: PRT
<213> ORGANISM: Artificial Sequence
<220> FEATURE:
<223> OTHER INFORMATION: Synthetic construct

<400> SEQUENCE: 111

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
                210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
    595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
    675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
        740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp Ala Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
```

-continued

```
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
```

```
Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 112
<211> LENGTH: 1368
<212> TYPE: PRT
<213> ORGANISM: Streptococcus pyogenes

<400> SEQUENCE: 112

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Leu
                20                  25                  30

Lys Gly Leu Gly Asn Thr Asp Arg His Gly Ile Lys Lys Asn Leu Ile
            35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Val Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Thr Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
```

-continued

```
                325                 330                 335
Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Ala Lys Leu Asn Arg Glu Asp Leu Leu Arg
385                 390                 395                 400

Lys Gln Arg Thr Phe Asp Asn Gly Ser Ile Pro Tyr Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750
```

```
Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Asp Ile Leu Lys Glu Tyr Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Val Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Arg Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155
```

```
Ser Val Lys Glu Leu Leu Gly Ile Thr Ile Met Glu Arg Ser Ser
    1160                1165                1170

Phe Glu Lys Asp Pro Ile Asp Phe Leu Glu Ala Lys Gly Tyr Lys
    1175                1180                1185

Glu Val Arg Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 113
<211> LENGTH: 1629
<212> TYPE: PRT
<213> ORGANISM: Francisella tularensis

<400> SEQUENCE: 113

Met Asn Phe Lys Ile Leu Pro Ile Ala Ile Asp Leu Gly Val Lys Asn
1               5                   10                  15

Thr Gly Val Phe Ser Ala Phe Tyr Gln Lys Gly Thr Ser Leu Glu Arg
                20                  25                  30

Leu Asp Asn Lys Asn Gly Lys Val Tyr Glu Leu Ser Lys Asp Ser Tyr
            35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160
```

```
Leu Met Gln Lys Ile Leu Glu Phe Lys Leu Met Lys Leu Cys Thr Asp
                165                 170                 175
Ile Lys Asp Asp Lys Val Ser Thr Lys Thr Leu Lys Glu Ile Thr Ser
            180                 185                 190
Tyr Glu Phe Glu Leu Leu Ala Asp Tyr Leu Ala Asn Tyr Ser Glu Ser
        195                 200                 205
Leu Lys Thr Gln Lys Phe Ser Tyr Thr Asp Lys Gln Gly Asn Leu Lys
    210                 215                 220
Glu Leu Ser Tyr Tyr His His Asp Lys Tyr Asn Ile Gln Glu Phe Leu
225                 230                 235                 240
Lys Arg His Ala Thr Ile Asn Asp Arg Ile Leu Asp Thr Leu Leu Thr
                245                 250                 255
Asp Asp Leu Asp Ile Trp Asn Phe Asn Phe Glu Lys Phe Asp Phe Asp
            260                 265                 270
Lys Asn Glu Glu Lys Leu Gln Asn Gln Glu Asp Lys Asp His Ile Gln
        275                 280                 285
Ala His Leu His His Phe Val Phe Ala Val Asn Lys Ile Lys Ser Glu
    290                 295                 300
Met Ala Ser Gly Gly Arg His Arg Ser Gln Tyr Phe Gln Glu Ile Thr
305                 310                 315                 320
Asn Val Leu Asp Glu Asn Asn His Gln Glu Gly Tyr Leu Lys Asn Phe
                325                 330                 335
Cys Glu Asn Leu His Asn Lys Lys Tyr Ser Asn Leu Ser Val Lys Asn
            340                 345                 350
Leu Val Asn Leu Ile Gly Asn Leu Ser Asn Leu Glu Leu Lys Pro Leu
        355                 360                 365
Arg Lys Tyr Phe Asn Asp Lys Ile His Ala Lys Ala Asp His Trp Asp
    370                 375                 380
Glu Gln Lys Phe Thr Glu Thr Tyr Cys His Trp Ile Leu Gly Glu Trp
385                 390                 395                 400
Arg Val Gly Val Lys Asp Gln Asp Lys Lys Asp Gly Ala Lys Tyr Ser
                405                 410                 415
Tyr Lys Asp Leu Cys Asn Glu Leu Lys Gln Lys Val Thr Lys Ala Gly
            420                 425                 430
Leu Val Asp Phe Leu Leu Glu Leu Asp Pro Cys Arg Thr Ile Pro Pro
        435                 440                 445
Tyr Leu Asp Asn Asn Asn Arg Lys Pro Pro Lys Cys Gln Ser Leu Ile
    450                 455                 460
Leu Asn Pro Lys Phe Leu Asp Asn Gln Tyr Pro Asn Trp Gln Gln Tyr
465                 470                 475                 480
Leu Gln Glu Leu Lys Lys Leu Gln Ser Ile Gln Asn Tyr Leu Asp Ser
                485                 490                 495
Phe Glu Thr Asp Leu Lys Val Leu Lys Ser Ser Lys Asp Gln Pro Tyr
            500                 505                 510
Phe Val Glu Tyr Lys Ser Ser Asn Gln Gln Ile Ala Ser Gly Gln Arg
        515                 520                 525
Asp Tyr Lys Asp Leu Asp Ala Arg Ile Leu Gln Phe Ile Phe Asp Arg
    530                 535                 540
Val Lys Ala Ser Asp Glu Leu Leu Leu Asn Glu Ile Tyr Phe Gln Ala
545                 550                 555                 560
Lys Lys Leu Lys Gln Lys Ala Ser Ser Glu Leu Glu Lys Leu Glu Ser
                565                 570                 575
```

```
Ser Lys Lys Leu Asp Glu Val Ile Ala Asn Ser Gln Leu Ser Gln Ile
            580                 585                 590

Leu Lys Ser Gln His Thr Asn Gly Ile Phe Glu Gln Gly Thr Phe Leu
        595                 600                 605

His Leu Val Cys Lys Tyr Tyr Lys Gln Arg Gln Arg Ala Arg Asp Ser
    610                 615                 620

Arg Leu Tyr Ile Met Pro Glu Tyr Arg Tyr Asp Lys Lys Leu His Lys
625                 630                 635                 640

Tyr Asn Asn Thr Gly Arg Phe Asp Asp Asn Gln Leu Leu Thr Tyr
                645                 650                 655

Cys Asn His Lys Pro Arg Gln Lys Arg Tyr Gln Leu Leu Asn Asp Leu
                660                 665                 670

Ala Gly Val Leu Gln Val Ser Pro Asn Phe Leu Lys Asp Lys Ile Gly
            675                 680                 685

Ser Asp Asp Asp Leu Phe Ile Ser Lys Trp Leu Val Glu His Ile Arg
        690                 695                 700

Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
                725                 730                 735

Lys Cys Glu Lys Glu Ile Phe Asn Leu Ile Cys Lys Ile Glu Gly Ser
            740                 745                 750

Glu Asp Lys Lys Gly Asn Tyr Lys His Gly Leu Ala Tyr Glu Leu Gly
        755                 760                 765

Val Leu Leu Phe Gly Glu Pro Asn Glu Ala Ser Lys Pro Glu Phe Asp
770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
                805                 810                 815

Cys Ser Ala Asp Asn Ala His Arg Met Gln Gln Ile Lys Ile Thr Glu
            820                 825                 830

Pro Val Glu Asp Asn Lys Asp Lys Ile Ile Leu Ser Ala Lys Ala Gln
        835                 840                 845

Arg Leu Pro Ala Ile Pro Thr Arg Ile Val Asp Gly Ala Val Lys Lys
850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
            900                 905                 910

Gly Lys Ser Leu Lys Asp Arg Arg Lys Lys Ala Leu Glu Arg Ile Ser
        915                 920                 925

Pro Glu Asn Ile Phe Lys Asp Lys Asn Asn Arg Ile Lys Glu Phe Ala
930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp His Ile Ile Pro Arg Ser His Lys
                965                 970                 975

Lys Tyr Gly Thr Leu Asn Asp Glu Ala Asn Leu Ile Cys Val Thr Arg
            980                 985                 990

Gly Asp Asn Lys Asn Lys Gly Asn  Arg Ile Phe Cys Leu  Arg Asp Leu
```

-continued

```
        995                1000               1005
Ala  Asp  Asn  Tyr  Lys  Leu  Lys  Gln  Phe  Glu  Thr  Thr  Asp  Asp  Leu
        1010               1015               1020
Glu  Ile  Glu  Lys  Lys  Ile  Ala  Asp  Thr  Ile  Trp  Asp  Ala  Asn  Lys
        1025               1030               1035
Lys  Asp  Phe  Lys  Phe  Gly  Asn  Tyr  Arg  Ser  Phe  Ile  Asn  Leu  Thr
        1040               1045               1050
Pro  Gln  Glu  Gln  Lys  Ala  Phe  Arg  His  Ala  Leu  Phe  Leu  Ala  Asp
        1055               1060               1065
Glu  Asn  Pro  Ile  Lys  Gln  Ala  Val  Ile  Arg  Ala  Ile  Asn  Asn  Arg
        1070               1075               1080
Asn  Arg  Thr  Phe  Val  Asn  Gly  Thr  Gln  Arg  Tyr  Phe  Ala  Glu  Val
        1085               1090               1095
Leu  Ala  Asn  Asn  Ile  Tyr  Leu  Arg  Ala  Lys  Lys  Glu  Asn  Leu  Asn
        1100               1105               1110
Thr  Asp  Lys  Ile  Ser  Phe  Asp  Tyr  Phe  Gly  Ile  Pro  Thr  Ile  Gly
        1115               1120               1125
Asn  Gly  Arg  Gly  Ile  Ala  Glu  Ile  Arg  Gln  Leu  Tyr  Glu  Lys  Val
        1130               1135               1140
Asp  Ser  Asp  Ile  Gln  Ala  Tyr  Ala  Lys  Gly  Asp  Lys  Pro  Gln  Ala
        1145               1150               1155
Ser  Tyr  Ser  His  Leu  Ile  Asp  Ala  Met  Leu  Ala  Phe  Cys  Ile  Ala
        1160               1165               1170
Ala  Asp  Glu  His  Arg  Asn  Asp  Gly  Ser  Ile  Gly  Leu  Glu  Ile  Asp
        1175               1180               1185
Lys  Asn  Tyr  Ser  Leu  Tyr  Pro  Leu  Asp  Lys  Asn  Thr  Gly  Glu  Val
        1190               1195               1200
Phe  Thr  Lys  Asp  Ile  Phe  Ser  Gln  Ile  Lys  Ile  Thr  Asp  Asn  Glu
        1205               1210               1215
Phe  Ser  Asp  Lys  Lys  Leu  Val  Arg  Lys  Lys  Ala  Ile  Glu  Gly  Phe
        1220               1225               1230
Asn  Thr  His  Arg  Gln  Met  Thr  Arg  Asp  Gly  Ile  Tyr  Ala  Glu  Asn
        1235               1240               1245
Tyr  Leu  Pro  Ile  Leu  Ile  His  Lys  Glu  Leu  Asn  Glu  Val  Arg  Lys
        1250               1255               1260
Gly  Tyr  Thr  Trp  Lys  Asn  Ser  Glu  Glu  Ile  Lys  Ile  Phe  Lys  Gly
        1265               1270               1275
Lys  Lys  Tyr  Asp  Ile  Gln  Gln  Leu  Asn  Asn  Leu  Val  Tyr  Cys  Leu
        1280               1285               1290
Lys  Phe  Val  Asp  Lys  Pro  Ile  Ser  Ile  Asp  Ile  Gln  Ile  Ser  Thr
        1295               1300               1305
Leu  Glu  Glu  Leu  Arg  Asn  Ile  Leu  Thr  Thr  Asn  Asn  Ile  Ala  Ala
        1310               1315               1320
Thr  Ala  Glu  Tyr  Tyr  Ile  Asn  Leu  Lys  Thr  Gln  Lys  Leu  His
        1325               1330               1335
Glu  Tyr  Tyr  Ile  Glu  Asn  Tyr  Asn  Thr  Ala  Leu  Gly  Tyr  Lys  Lys
        1340               1345               1350
Tyr  Ser  Lys  Glu  Met  Glu  Phe  Leu  Arg  Ser  Leu  Ala  Tyr  Arg  Ser
        1355               1360               1365
Glu  Arg  Val  Lys  Ile  Lys  Ser  Ile  Asp  Asp  Val  Lys  Gln  Val  Leu
        1370               1375               1380
Asp  Lys  Asp  Ser  Asn  Phe  Ile  Ile  Gly  Lys  Ile  Thr  Leu  Pro  Phe
        1385               1390               1395
```

Lys Lys Glu Trp Gln Arg Leu Tyr Arg Glu Trp Gln Asn Thr Thr
1400             1405                 1410

Ile Lys Asp Asp Tyr Glu Phe Leu Lys Ser Phe Phe Asn Val Lys
1415             1420                 1425

Ser Ile Thr Lys Leu His Lys Lys Val Arg Lys Asp Phe Ser Leu
1430             1435                 1440

Pro Ile Ser Thr Asn Glu Gly Lys Phe Leu Val Lys Arg Lys Thr
1445             1450                 1455

Trp Asp Asn Asn Phe Ile Tyr Gln Ile Leu Asn Asp Ser Asp Ser
1460             1465                 1470

Arg Ala Asp Gly Thr Lys Pro Phe Ile Pro Ala Phe Asp Ile Ser
1475             1480                 1485

Lys Asn Glu Ile Val Glu Ala Ile Ile Asp Ser Phe Thr Ser Lys
1490             1495                 1500

Asn Ile Phe Trp Leu Pro Lys Asn Ile Glu Leu Gln Lys Val Asp
1505             1510                 1515

Asn Lys Asn Ile Phe Ala Ile Asp Thr Ser Lys Trp Phe Glu Val
1520             1525                 1530

Glu Thr Pro Ser Asp Leu Arg Asp Ile Gly Ile Ala Thr Ile Gln
1535             1540                 1545

Tyr Lys Ile Asp Asn Asn Ser Arg Pro Lys Val Arg Val Lys Leu
1550             1555                 1560

Asp Tyr Val Ile Asp Asp Ser Lys Ile Asn Tyr Phe Met Asn
1565             1570                 1575

His Ser Leu Leu Lys Ser Arg Tyr Pro Asp Lys Val Leu Glu Ile
1580             1585                 1590

Leu Lys Gln Ser Thr Ile Ile Glu Phe Glu Ser Ser Gly Phe Asn
1595             1600                 1605

Lys Thr Ile Lys Glu Met Leu Gly Met Lys Leu Ala Gly Ile Tyr
1610             1615                 1620

Asn Glu Thr Ser Asn Asn
1625

<210> SEQ ID NO 114
<211> LENGTH: 1409
<212> TYPE: PRT
<213> ORGANISM: Streptococcus thermophilus

<400> SEQUENCE: 114

Met Leu Phe Asn Lys Cys Ile Ile Ile Ser Ile Asn Leu Asp Phe Ser
1               5                   10                  15

Asn Lys Glu Lys Cys Met Thr Lys Pro Tyr Ser Ile Gly Leu Asp Ile
                20                  25                  30

Gly Thr Asn Ser Val Gly Trp Ala Val Ile Thr Asp Asn Tyr Lys Val
            35                  40                  45

Pro Ser Lys Lys Met Lys Val Leu Gly Asn Thr Ser Lys Tyr Ile
        50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Tyr Thr Arg Arg
                85                  90                  95

Arg Asn Arg Ile Leu Tyr Leu Gln Glu Ile Phe Ser Thr Glu Met Ala
            100                 105                 110

Thr Leu Asp Asp Ala Phe Phe Gln Arg Leu Asp Asp Ser Phe Leu Val

-continued

```
            115                 120                 125
Pro Asp Asp Lys Arg Asp Ser Lys Tyr Pro Ile Phe Gly Asn Leu Val
130                 135                 140

Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                165                 170                 175

Leu Ala Leu Ala His Met Ile Lys Tyr Arg Gly His Phe Leu Ile Glu
                180                 185                 190

Gly Glu Phe Asn Ser Lys Asn Asn Asp Ile Gln Lys Asn Phe Gln Asp
                195                 200                 205

Phe Leu Asp Thr Tyr Asn Ala Ile Phe Glu Ser Asp Leu Ser Leu Glu
210                 215                 220

Asn Ser Lys Gln Leu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
                260                 265                 270

Phe Arg Lys Cys Phe Asn Leu Asp Glu Lys Ala Ser Leu His Phe Ser
                275                 280                 285

Lys Glu Ser Tyr Asp Glu Asp Leu Glu Thr Leu Leu Gly Tyr Ile Gly
                290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
                340                 345                 350

Leu Ala Leu Leu Lys Glu Tyr Ile Arg Asn Ile Ser Leu Lys Thr Tyr
                355                 360                 365

Asn Glu Val Phe Lys Asp Asp Thr Lys Asn Gly Tyr Ala Gly Tyr Ile
370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
                420                 425                 430

Tyr Gln Ile His Leu Gln Glu Met Arg Ala Ile Leu Asp Lys Gln Ala
                435                 440                 445

Lys Phe Tyr Pro Phe Leu Ala Lys Asn Lys Glu Arg Ile Glu Lys Ile
                450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
                500                 505                 510

Ile Asn Arg Met Thr Ser Phe Asp Leu Tyr Leu Pro Glu Glu Lys Val
                515                 520                 525

Leu Pro Lys His Ser Leu Leu Tyr Glu Thr Phe Asn Val Tyr Asn Glu
530                 535                 540
```

```
Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575

Lys Arg Lys Val Thr Asp Lys Asp Ile Ile Glu Tyr Leu His Ala Ile
            580                 585                 590

Tyr Gly Tyr Asp Gly Ile Glu Leu Lys Gly Ile Glu Lys Gln Phe Asn
        595                 600                 605

Ser Ser Leu Ser Thr Tyr His Asp Leu Leu Asn Ile Ile Asn Asp Lys
    610                 615                 620

Glu Phe Leu Asp Asp Ser Ser Asn Glu Ala Ile Ile Glu Glu Ile Ile
625                 630                 635                 640

His Thr Leu Thr Ile Phe Glu Asp Arg Glu Met Ile Lys Gln Arg Leu
                645                 650                 655

Ser Lys Phe Glu Asn Ile Phe Asp Lys Ser Val Leu Lys Lys Leu Ser
                660                 665                 670

Arg Arg His Tyr Thr Gly Trp Gly Lys Leu Ser Ala Lys Leu Ile Asn
            675                 680                 685

Gly Ile Arg Asp Glu Lys Ser Gly Asn Thr Ile Leu Asp Tyr Leu Ile
690                 695                 700

Asp Asp Gly Ile Ser Asn Arg Asn Phe Met Gln Leu Ile His Asp Asp
705                 710                 715                 720

Ala Leu Ser Phe Lys Lys Lys Ile Gln Lys Ala Gln Ile Ile Gly Asp
                725                 730                 735

Glu Asp Lys Gly Asn Ile Lys Glu Val Val Lys Ser Leu Pro Gly Ser
            740                 745                 750

Pro Ala Ile Lys Lys Gly Ile Leu Gln Ser Ile Lys Ile Val Asp Glu
        755                 760                 765

Leu Val Lys Val Met Gly Gly Arg Lys Pro Glu Ser Ile Val Val Glu
    770                 775                 780

Met Ala Arg Glu Asn Gln Tyr Thr Asn Gln Gly Lys Ser Asn Ser Gln
785                 790                 795                 800

Gln Arg Leu Lys Arg Leu Glu Lys Ser Leu Lys Glu Leu Gly Ser Lys
                805                 810                 815

Ile Leu Lys Glu Asn Ile Pro Ala Lys Leu Ser Lys Ile Asp Asn Asn
                820                 825                 830

Ala Leu Gln Asn Asp Arg Leu Tyr Leu Tyr Tyr Leu Gln Asn Gly Lys
            835                 840                 845

Asp Met Tyr Thr Gly Asp Asp Leu Asp Ile Asp Arg Leu Ser Asn Tyr
        850                 855                 860

Asp Ile Asp His Ile Ile Pro Gln Ala Phe Leu Lys Asp Asn Ser Ile
865                 870                 875                 880

Asp Asn Lys Val Leu Val Ser Ser Ala Ser Asn Arg Gly Lys Ser Asp
                885                 890                 895

Asp Phe Pro Ser Leu Glu Val Val Lys Arg Lys Thr Phe Trp Tyr
                900                 905                 910

Gln Leu Leu Lys Ser Lys Leu Ile Ser Gln Arg Lys Phe Asp Asn Leu
            915                 920                 925

Thr Lys Ala Glu Arg Gly Gly Leu Leu Pro Glu Asp Lys Ala Gly Phe
        930                 935                 940

Ile Gln Arg Gln Leu Val Glu Thr Arg Gln Ile Thr Lys His Val Ala
945                 950                 955                 960
```

```
Arg Leu Leu Asp Glu Lys Phe Asn Asn Lys Lys Asp Glu Asn Asn Arg
            965                 970                 975

Ala Val Arg Thr Val Lys Ile Ile Thr Leu Lys Ser Thr Leu Val Ser
            980                 985                 990

Gln Phe Arg Lys Asp Phe Glu Leu Tyr Lys Val Arg Glu Ile Asn Asp
            995                 1000                1005

Phe His His Ala His Asp Ala Tyr Leu Asn Ala Val Ile Ala Ser
    1010            1015                1020

Ala Leu Leu Lys Lys Tyr Pro Lys Leu Glu Pro Glu Phe Val Tyr
    1025            1030                1035

Gly Asp Tyr Pro Lys Tyr Asn Ser Phe Arg Glu Arg Lys Ser Ala
    1040            1045                1050

Thr Glu Lys Val Tyr Phe Tyr Ser Asn Ile Met Asn Ile Phe Lys
    1055            1060                1065

Lys Ser Ile Ser Leu Ala Asp Gly Arg Val Ile Glu Arg Pro Leu
    1070            1075                1080

Ile Glu Val Asn Glu Glu Thr Gly Glu Ser Val Trp Asn Lys Glu
    1085            1090                1095

Ser Asp Leu Ala Thr Val Arg Arg Val Leu Ser Tyr Pro Gln Val
    1100            1105                1110

Asn Val Val Lys Lys Val Glu Glu Gln Asn His Gly Leu Asp Arg
    1115            1120                1125

Gly Lys Pro Lys Gly Leu Phe Asn Ala Asn Leu Ser Ser Lys Pro
    1130            1135                1140

Lys Pro Asn Ser Asn Glu Asn Leu Val Gly Ala Lys Glu Tyr Leu
    1145            1150                1155

Asp Pro Lys Lys Tyr Gly Gly Tyr Ala Gly Ile Ser Asn Ser Phe
    1160            1165                1170

Ala Val Leu Val Lys Gly Thr Ile Glu Lys Gly Ala Lys Lys Lys
    1175            1180                1185

Ile Thr Asn Val Leu Glu Phe Gln Gly Ile Ser Ile Leu Asp Arg
    1190            1195                1200

Ile Asn Tyr Arg Lys Asp Lys Leu Asn Phe Leu Leu Glu Lys Gly
    1205            1210                1215

Tyr Lys Asp Ile Glu Leu Ile Ile Glu Leu Pro Lys Tyr Ser Leu
    1220            1225                1230

Phe Glu Leu Ser Asp Gly Ser Arg Arg Met Leu Ala Ser Ile Leu
    1235            1240                1245

Ser Thr Asn Asn Lys Arg Gly Glu Ile His Lys Gly Asn Gln Ile
    1250            1255                1260

Phe Leu Ser Gln Lys Phe Val Lys Leu Leu Tyr His Ala Lys Arg
    1265            1270                1275

Ile Ser Asn Thr Ile Asn Glu Asn His Arg Lys Tyr Val Glu Asn
    1280            1285                1290

His Lys Lys Glu Phe Glu Glu Leu Phe Tyr Tyr Ile Leu Glu Phe
    1295            1300                1305

Asn Glu Asn Tyr Val Gly Ala Lys Lys Asn Gly Lys Leu Leu Asn
    1310            1315                1320

Ser Ala Phe Gln Ser Trp Gln Asn His Ser Ile Asp Glu Leu Cys
    1325            1330                1335

Ser Ser Phe Ile Gly Pro Thr Gly Ser Glu Arg Lys Gly Leu Phe
    1340            1345                1350

Glu Leu Thr Ser Arg Gly Ser Ala Ala Asp Phe Glu Phe Leu Gly
```

```
                  1355                1360                1365
        Val Lys Ile Pro Arg Tyr Arg Asp Tyr Thr Pro Ser Ser Leu Leu
            1370                1375                1380

Lys Asp Ala Thr Leu Ile His Gln Ser Val Thr Gly Leu Tyr Glu
            1385                1390                1395

Thr Arg Ile Asp Leu Ala Lys Leu Gly Glu Gly
            1400                1405

<210> SEQ ID NO 115
<211> LENGTH: 1388
<212> TYPE: PRT
<213> ORGANISM: Streptococcus thermophilus

<400> SEQUENCE: 115

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320
```

```
Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
            405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
    530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
    610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
    690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
```

```
                740                 745                 750
Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Gln Arg Leu Lys Arg
            770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
            835                 840                 845

Ile Pro Gln Ala Phe Leu Lys Asp Asn Ser Ile Asp Asn Lys Val Leu
            850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Ser Pro Glu Asp Lys Ala Gly Phe Ile Gln Arg Gln Leu
            915                 920                 925

Val Glu Thr Arg Gln Ile Thr Lys His Val Ala Arg Leu Leu Asp Glu
            930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Val Ala Ser Ala Leu Leu Lys Lys Tyr
            995                 1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Thr Val Leu Val Lys Gly
    1145                1150                1155
```

Thr Ile Glu Lys Gly Ala Lys Lys Ile Thr Asn Val Leu Glu
1160            1165            1170

Phe Gln Gly Ile Ser Ile Leu Asp Arg Ile Asn Tyr Arg Lys Asp
1175            1180            1185

Lys Leu Asn Phe Leu Leu Glu Lys Gly Tyr Lys Asp Ile Glu Leu
1190            1195            1200

Ile Ile Glu Leu Pro Lys Tyr Ser Leu Phe Glu Leu Ser Asp Gly
1205            1210            1215

Ser Arg Arg Met Leu Ala Ser Ile Leu Ser Thr Asn Asn Lys Arg
1220            1225            1230

Gly Glu Ile His Lys Gly Asn Gln Ile Phe Leu Ser Gln Lys Phe
1235            1240            1245

Val Lys Leu Leu Tyr His Ala Lys Arg Ile Ser Asn Thr Ile Asn
1250            1255            1260

Glu Asn His Arg Lys Tyr Val Glu Asn His Lys Lys Glu Phe Glu
1265            1270            1275

Glu Leu Phe Tyr Tyr Ile Leu Glu Phe Asn Glu Asn Tyr Val Gly
1280            1285            1290

Ala Lys Lys Asn Gly Lys Leu Leu Asn Ser Ala Phe Gln Ser Trp
1295            1300            1305

Gln Asn His Ser Ile Asp Glu Leu Cys Ser Ser Phe Ile Gly Pro
1310            1315            1320

Thr Gly Ser Glu Arg Lys Gly Leu Phe Glu Leu Thr Ser Arg Gly
1325            1330            1335

Ser Ala Ala Asp Phe Glu Phe Leu Gly Val Lys Ile Pro Arg Tyr
1340            1345            1350

Arg Asp Tyr Thr Pro Ser Ser Leu Leu Lys Asp Ala Thr Leu Ile
1355            1360            1365

His Gln Ser Val Thr Gly Leu Tyr Glu Thr Arg Ile Asp Leu Ala
1370            1375            1380

Lys Leu Gly Glu Gly
1385

<210> SEQ ID NO 116
<211> LENGTH: 1334
<212> TYPE: PRT
<213> ORGANISM: Listeria innocua

<400> SEQUENCE: 116

Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Lys Gln Ile Lys Lys Asn Phe Trp
        35                  40                  45

Gly Val Arg Leu Phe Asp Glu Gly Gln Thr Ala Ala Asp Arg Arg Met
    50                  55                  60

Ala Arg Thr Ala Arg Arg Ile Glu Arg Arg Asn Arg Ile Ser
65                  70                  75                  80

Tyr Leu Gln Gly Ile Phe Ala Glu Glu Met Ser Lys Thr Asp Ala Asn
                85                  90                  95

Phe Phe Cys Arg Leu Ser Asp Ser Phe Tyr Val Asp Asn Glu Lys Arg
            100                 105                 110

Asn Ser Arg His Pro Phe Phe Ala Thr Ile Glu Glu Glu Val Glu Tyr

```
            115                 120                 125
His Lys Asn Tyr Pro Thr Ile Tyr His Leu Arg Glu Glu Leu Val Asn
130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
                180                 185                 190

Asn Gln Val Phe Ala Ser Gly Ile Glu Asp Gly Ser Leu Lys Lys Leu
            195                 200                 205

Glu Asp Asn Lys Asp Val Ala Lys Ile Leu Val Glu Lys Val Thr Arg
210                 215                 220

Lys Glu Lys Leu Glu Arg Ile Leu Lys Leu Tyr Pro Gly Glu Lys Ser
225                 230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
                260                 265                 270

Ala Lys Asp Ser Tyr Glu Glu Asp Leu Glu Ser Leu Leu Ala Leu Ile
            275                 280                 285

Gly Asp Glu Tyr Ala Glu Leu Phe Val Ala Ala Lys Asn Ala Tyr Ser
290                 295                 300

Ala Val Val Leu Ser Ser Ile Ile Thr Val Ala Glu Thr Glu Thr Asn
305                 310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
                340                 345                 350

Tyr Glu Glu Ile Phe Ser Asn Thr Glu Lys His Gly Tyr Ala Gly Tyr
            355                 360                 365

Ile Asp Gly Lys Thr Lys Gln Ala Asp Phe Tyr Lys Tyr Met Lys Met
370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile
                405                 410                 415

Pro His Gln Leu His Leu Glu Glu Leu Glu Ala Ile Leu His Gln Gln
                420                 425                 430

Ala Lys Tyr Tyr Pro Phe Leu Lys Glu Asn Tyr Asp Lys Ile Lys Ser
            435                 440                 445

Leu Val Thr Phe Arg Ile Pro Tyr Phe Val Gly Pro Leu Ala Asn Gly
450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
                500                 505                 510

Val Leu Pro Lys His Ser Leu Cys Tyr Gln Lys Tyr Leu Val Tyr Asn
            515                 520                 525

Glu Leu Thr Lys Val Arg Tyr Ile Asn Asp Gln Gly Lys Thr Ser Tyr
530                 535                 540
```

```
Phe Ser Gly Gln Glu Lys Glu Gln Ile Phe Asn Asp Leu Phe Lys Gln
545                 550                 555                 560

Lys Arg Lys Val Lys Lys Asp Leu Glu Leu Phe Leu Arg Asn Met
            565                 570                 575

Ser His Val Glu Ser Pro Thr Ile Glu Gly Leu Glu Asp Ser Phe Asn
                580                 585                 590

Ser Ser Tyr Ser Thr Tyr His Asp Leu Leu Lys Val Gly Ile Lys Gln
            595                 600                 605

Glu Ile Leu Asp Asn Pro Val Asn Thr Glu Met Leu Glu Asn Ile Val
            610                 615                 620

Lys Ile Leu Thr Val Phe Glu Asp Lys Arg Met Ile Lys Glu Gln Leu
625                 630                 635                 640

Gln Gln Phe Ser Asp Val Leu Asp Gly Val Leu Lys Lys Leu Glu
                645                 650                 655

Arg Arg His Tyr Thr Gly Trp Gly Arg Leu Ser Ala Lys Leu Leu Met
            660                 665                 670

Gly Ile Arg Asp Lys Gln Ser His Leu Thr Ile Leu Asp Tyr Leu Met
            675                 680                 685

Asn Asp Asp Gly Leu Asn Arg Asn Leu Met Gln Leu Ile Asn Asp Ser
            690                 695                 700

Asn Leu Ser Phe Lys Ser Ile Ile Glu Lys Glu Gln Val Thr Thr Ala
705                 710                 715                 720

Asp Lys Asp Ile Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
            740                 745                 750

Ser Val Met Gly Tyr Pro Pro Gln Thr Ile Val Val Glu Met Ala Arg
            755                 760                 765

Glu Asn Gln Thr Thr Gly Lys Gly Lys Asn Asn Ser Arg Pro Arg Tyr
770                 775                 780

Lys Ser Leu Glu Lys Ala Ile Lys Glu Phe Gly Ser Gln Ile Leu Lys
785                 790                 795                 800

Glu His Pro Thr Asp Asn Gln Glu Leu Arg Asn Asn Arg Leu Tyr Leu
                805                 810                 815

Tyr Tyr Leu Gln Asn Gly Lys Asp Met Tyr Thr Gly Gln Asp Leu Asp
            820                 825                 830

Ile His Asn Leu Ser Asn Tyr Asp Ile Asp His Ile Val Pro Gln Ser
            835                 840                 845

Phe Ile Thr Asp Asn Ser Ile Asp Asn Leu Val Leu Thr Ser Ser Ala
850                 855                 860

Gly Asn Arg Glu Lys Gly Asp Asp Val Pro Pro Leu Glu Ile Val Arg
865                 870                 875                 880

Lys Arg Lys Val Phe Trp Glu Lys Leu Tyr Gln Gly Asn Leu Met Ser
                885                 890                 895

Lys Arg Lys Phe Asp Tyr Leu Thr Lys Ala Glu Arg Gly Gly Leu Thr
                900                 905                 910

Glu Ala Asp Lys Ala Arg Phe Ile His Arg Gln Leu Val Glu Thr Arg
            915                 920                 925

Gln Ile Thr Lys Asn Val Ala Asn Ile Leu His Gln Arg Phe Asn Tyr
            930                 935                 940

Glu Lys Asp Asp His Gly Asn Thr Met Lys Gln Val Arg Ile Val Thr
945                 950                 955                 960
```

```
Leu Lys Ser Ala Leu Val Ser Gln Phe Arg Lys Gln Phe Gln Leu Tyr
                965                 970                 975

Lys Val Arg Asp Val Asn Asp Tyr His His Ala His Asp Ala Tyr Leu
            980                 985                 990

Asn Gly Val Val Ala Asn Thr Leu Leu Lys Val Tyr Pro Gln Leu Glu
        995                 1000                1005

Pro Glu Phe Val Tyr Gly Asp Tyr His Gln Phe Asp Trp Phe Lys
    1010                1015                1020

Ala Asn Lys Ala Thr Ala Lys Lys Gln Phe Tyr Thr Asn Ile Met
    1025                1030                1035

Leu Phe Phe Ala Gln Lys Asp Arg Ile Ile Asp Glu Asn Gly Glu
    1040                1045                1050

Ile Leu Trp Asp Lys Lys Tyr Leu Asp Thr Val Lys Lys Val Met
    1055                1060                1065

Ser Tyr Arg Gln Met Asn Ile Val Lys Lys Thr Glu Ile Gln Lys
    1070                1075                1080

Gly Glu Phe Ser Lys Ala Thr Ile Lys Pro Lys Gly Asn Ser Ser
    1085                1090                1095

Lys Leu Ile Pro Arg Lys Thr Asn Trp Asp Pro Met Lys Tyr Gly
    1100                1105                1110

Gly Leu Asp Ser Pro Asn Met Ala Tyr Ala Val Val Ile Glu Tyr
    1115                1120                1125

Ala Lys Gly Lys Asn Lys Leu Val Phe Glu Lys Lys Ile Ile Arg
    1130                1135                1140

Val Thr Ile Met Glu Arg Lys Ala Phe Glu Lys Asp Glu Lys Ala
    1145                1150                1155

Phe Leu Glu Glu Gln Gly Tyr Arg Gln Pro Lys Val Leu Ala Lys
    1160                1165                1170

Leu Pro Lys Tyr Thr Leu Tyr Glu Cys Glu Glu Gly Arg Arg Arg
    1175                1180                1185

Met Leu Ala Ser Ala Asn Glu Ala Gln Lys Gly Asn Gln Gln Val
    1190                1195                1200

Leu Pro Asn His Leu Val Thr Leu Leu His His Ala Ala Asn Cys
    1205                1210                1215

Glu Val Ser Asp Gly Lys Ser Leu Asp Tyr Ile Glu Ser Asn Arg
    1220                1225                1230

Glu Met Phe Ala Glu Leu Leu Ala His Val Ser Glu Phe Ala Lys
    1235                1240                1245

Arg Tyr Thr Leu Ala Glu Ala Asn Leu Asn Lys Ile Asn Gln Leu
    1250                1255                1260

Phe Glu Gln Asn Lys Glu Gly Asp Ile Lys Ala Ile Ala Gln Ser
    1265                1270                1275

Phe Val Asp Leu Met Ala Phe Asn Ala Met Gly Ala Pro Ala Ser
    1280                1285                1290

Phe Lys Phe Phe Glu Thr Thr Ile Glu Arg Lys Arg Tyr Asn Asn
    1295                1300                1305

Leu Lys Glu Leu Leu Asn Ser Thr Ile Ile Tyr Gln Ser Ile Thr
    1310                1315                1320

Gly Leu Tyr Glu Ser Arg Lys Arg Leu Asp Asp
    1325                1330

<210> SEQ ID NO 117
<211> LENGTH: 1059
<212> TYPE: PRT
```

<213> ORGANISM: Wolinella succinogenes

<400> SEQUENCE: 117

```
Met Ile Glu Arg Ile Leu Gly Val Asp Leu Gly Ile Ser Ser Leu Gly
1               5                   10                  15

Trp Ala Ile Val Glu Tyr Asp Lys Asp Glu Ala Ala Asn Arg Ile
            20                  25                  30

Ile Asp Cys Gly Val Arg Leu Phe Thr Ala Ala Glu Thr Pro Lys Lys
        35                  40                  45

Lys Glu Ser Pro Asn Lys Ala Arg Arg Glu Ala Arg Gly Ile Arg Arg
    50                  55                  60

Val Leu Asn Arg Arg Val Arg Met Asn Met Ile Lys Lys Leu Phe
65                  70                  75                  80

Leu Arg Ala Gly Leu Ile Gln Asp Val Asp Leu Asp Gly Glu Gly Gly
                85                  90                  95

Met Phe Tyr Ser Lys Ala Asn Arg Ala Asp Val Trp Glu Leu Arg His
            100                 105                 110

Asp Gly Leu Tyr Arg Leu Leu Lys Gly Asp Glu Leu Ala Arg Val Leu
        115                 120                 125

Ile His Ile Ala Lys His Arg Gly Tyr Lys Phe Ile Gly Asp Asp Glu
    130                 135                 140

Ala Asp Glu Glu Ser Gly Lys Val Lys Ala Gly Val Val Leu Arg
145                 150                 155                 160

Gln Asn Phe Glu Ala Ala Gly Cys Arg Thr Val Gly Glu Trp Leu Trp
                165                 170                 175

Arg Glu Arg Gly Ala Asn Gly Lys Lys Arg Asn Lys His Gly Asp Tyr
            180                 185                 190

Glu Ile Ser Ile His Arg Asp Leu Leu Val Glu Glu Val Glu Ala Ile
        195                 200                 205

Phe Val Ala Gln Gln Glu Met Arg Ser Thr Ile Ala Thr Asp Ala Leu
    210                 215                 220

Lys Ala Ala Tyr Arg Glu Ile Ala Phe Phe Val Arg Pro Met Gln Arg
225                 230                 235                 240

Ile Glu Lys Met Val Gly His Cys Thr Tyr Phe Pro Glu Glu Arg Arg
                245                 250                 255

Ala Pro Lys Ser Ala Pro Thr Ala Glu Lys Phe Ile Ala Ile Ser Lys
            260                 265                 270

Phe Phe Ser Thr Val Ile Ile Asp Asn Glu Gly Trp Glu Gln Lys Ile
        275                 280                 285

Ile Glu Arg Lys Thr Leu Glu Glu Leu Leu Asp Phe Ala Val Ser Arg
    290                 295                 300

Glu Lys Val Glu Phe Arg His Leu Arg Lys Phe Leu Asp Leu Ser Asp
305                 310                 315                 320

Asn Glu Ile Phe Lys Gly Leu His Tyr Lys Gly Lys Pro Lys Thr Ala
                325                 330                 335

Lys Lys Arg Glu Ala Thr Leu Phe Asp Pro Asn Glu Pro Thr Glu Leu
            340                 345                 350

Glu Phe Asp Lys Val Glu Ala Glu Lys Lys Ala Trp Ile Ser Leu Arg
        355                 360                 365

Gly Ala Ala Lys Leu Arg Glu Ala Leu Gly Asn Glu Phe Tyr Gly Arg
    370                 375                 380

Phe Val Ala Leu Gly Lys His Ala Asp Glu Ala Thr Lys Ile Leu Thr
385                 390                 395                 400
```

```
Tyr Tyr Lys Asp Glu Gly Gln Lys Arg Glu Leu Thr Lys Leu Pro
            405                 410                 415

Leu Glu Ala Glu Met Val Glu Arg Leu Val Lys Ile Gly Phe Ser Asp
        420                 425                 430

Phe Leu Lys Leu Ser Leu Lys Ala Ile Arg Asp Ile Leu Pro Ala Met
            435                 440                 445

Glu Ser Gly Ala Arg Tyr Asp Glu Ala Val Leu Met Leu Gly Val Pro
        450                 455                 460

His Lys Glu Lys Ser Ala Ile Leu Pro Pro Leu Asn Lys Thr Asp Ile
465                 470                 475                 480

Asp Ile Leu Asn Pro Thr Val Ile Arg Ala Phe Ala Gln Phe Arg Lys
                485                 490                 495

Val Ala Asn Ala Leu Val Arg Lys Tyr Gly Ala Phe Asp Arg Val His
            500                 505                 510

Phe Glu Leu Ala Arg Glu Ile Asn Thr Lys Gly Glu Ile Glu Asp Ile
        515                 520                 525

Lys Glu Ser Gln Arg Lys Asn Glu Lys Glu Arg Lys Glu Ala Ala Asp
    530                 535                 540

Trp Ile Ala Glu Thr Ser Phe Gln Val Pro Leu Thr Arg Lys Asn Ile
545                 550                 555                 560

Leu Lys Lys Arg Leu Tyr Ile Gln Gln Asp Gly Arg Cys Ala Tyr Thr
                565                 570                 575

Gly Asp Val Ile Glu Leu Glu Arg Leu Phe Asp Glu Gly Tyr Cys Glu
            580                 585                 590

Ile Asp His Ile Leu Pro Arg Ser Arg Ser Ala Asp Asp Ser Phe Ala
        595                 600                 605

Asn Lys Val Leu Cys Leu Ala Arg Ala Asn Gln Gln Lys Thr Asp Arg
610                 615                 620

Thr Pro Tyr Glu Trp Phe Gly His Asp Ala Ala Arg Trp Asn Ala Phe
625                 630                 635                 640

Glu Thr Arg Thr Ser Ala Pro Ser Asn Arg Val Arg Thr Gly Lys Gly
                645                 650                 655

Lys Ile Asp Arg Leu Leu Lys Lys Asn Phe Asp Glu Asn Ser Glu Met
            660                 665                 670

Ala Phe Lys Asp Arg Asn Leu Asn Asp Thr Arg Tyr Met Ala Arg Ala
        675                 680                 685

Ile Lys Thr Tyr Cys Glu Gln Tyr Trp Val Phe Lys Asn Ser His Thr
    690                 695                 700

Lys Ala Pro Val Gln Val Arg Ser Gly Lys Leu Thr Ser Val Leu Arg
705                 710                 715                 720

Tyr Gln Trp Gly Leu Glu Ser Lys Asp Arg Glu Ser His Thr His His
                725                 730                 735

Ala Val Asp Ala Ile Ile Ile Ala Phe Ser Thr Gln Gly Met Val Gln
            740                 745                 750

Lys Leu Ser Glu Tyr Tyr Arg Phe Lys Glu Thr His Arg Glu Lys Glu
        755                 760                 765

Arg Pro Lys Leu Ala Val Pro Leu Ala Asn Phe Arg Asp Ala Val Glu
    770                 775                 780

Glu Ala Thr Arg Ile Glu Asn Thr Glu Thr Val Lys Glu Gly Val Glu
785                 790                 795                 800

Val Lys Arg Leu Leu Ile Ser Arg Pro Pro Arg Ala Arg Val Thr Gly
                805                 810                 815

Gln Ala His Glu Gln Thr Ala Lys Pro Tyr Pro Arg Ile Lys Gln Val
```

```
                820                 825                 830

Lys Asn Lys Lys Lys Trp Arg Leu Ala Pro Ile Asp Glu Glu Lys Phe
            835                 840                 845

Glu Ser Phe Lys Ala Asp Arg Val Ala Ser Ala Asn Gln Lys Asn Phe
        850                 855                 860

Tyr Glu Thr Ser Thr Ile Pro Arg Val Asp Val Tyr His Lys Lys Gly
865                 870                 875                 880

Lys Phe His Leu Val Pro Ile Tyr Leu His Glu Met Val Leu Asn Glu
            885                 890                 895

Leu Pro Asn Leu Ser Leu Gly Thr Asn Pro Glu Ala Met Asp Glu Asn
        900                 905                 910

Phe Phe Lys Phe Ser Ile Phe Lys Asp Asp Leu Ile Ser Ile Gln Thr
            915                 920                 925

Gln Gly Thr Pro Lys Lys Pro Ala Lys Ile Ile Met Gly Tyr Phe Lys
        930                 935                 940

Asn Met His Gly Ala Asn Met Val Leu Ser Ser Ile Asn Asn Ser Pro
945                 950                 955                 960

Cys Glu Gly Phe Thr Cys Thr Pro Val Ser Met Asp Lys Lys His Lys
            965                 970                 975

Asp Lys Cys Lys Leu Cys Pro Glu Glu Asn Arg Ile Ala Gly Arg Cys
        980                 985                 990

Leu Gln Gly Phe Leu Asp Tyr Trp Ser Gln Glu Gly Leu Arg Pro Pro
        995                 1000                1005

Arg Lys Glu Phe Glu Cys Asp Gln Gly Val Lys Phe Ala Leu Asp
        1010                1015                1020

Val Lys Lys Tyr Gln Ile Asp Pro Leu Gly Tyr Tyr Tyr Glu Val
        1025                1030                1035

Lys Gln Glu Lys Arg Leu Gly Thr Ile Pro Gln Met Arg Ser Ala
        1040                1045                1050

Lys Lys Leu Val Lys Lys
        1055

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121
<211> LENGTH: 7
<212> TYPE: PRT
<213> ORGANISM: Artificial Sequence
<220> FEATURE:
<223> OTHER INFORMATION: Synthetic construct

<400> SEQUENCE: 121

Ala Ser Val His Phe Pro Pro
```

```
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic construct

<400> SEQUENCE: 122

Thr Ala Thr Phe Trp Phe Gln
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic construct

<400> SEQUENCE: 123

Thr Ser Pro Val Ala Leu Leu
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic construct

<400> SEQUENCE: 124

Ile Pro Leu Lys Val His Pro
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic construct

<400> SEQUENCE: 125

Trp Pro Arg Leu Thr Asn Met
1               5

<210> SEQ ID NO 126
<211> LENGTH: 12
<212> TYPE: PRT
<213> ORGANISM: Artificial Sequence
<220> FEATURE:
<223> OTHER INFORMATION: Synthetic construct

<400> SEQUENCE: 126

Ser Phe Ser Ile Ile Leu Thr Pro Ile Leu Pro Leu
1               5                   10

<210> SEQ ID NO 127
<211> LENGTH: 15
<212> TYPE: PRT
<213> ORGANISM: Artificial Sequence
<220> FEATURE:
<223> OTHER INFORMATION: Synthetic construct

<400> SEQUENCE: 127

Ser Phe Ser Ile Ile Leu Thr Pro Ile Leu Pro Leu Gly Gly Cys
1               5                   10                  15
```

```
<210> SEQ ID NO 128
<211> LENGTH: 18
<212> TYPE: PRT
<213> ORGANISM: Artificial Sequence
<220> FEATURE:
<223> OTHER INFORMATION: Synthetic construct

<400> SEQUENCE: 128

Ser Phe Ser Ile Ile Leu Thr Pro Ile Leu Pro Leu Glu Glu Glu Gly
1               5                   10                  15

Gly Cys

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000
```

```
<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
000

<210> SEQ ID NO 148
<400> SEQUENCE: 148
000

<210> SEQ ID NO 149
```

```
<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160
```

000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

```
<210> SEQ ID NO 183
<400> SEQUENCE: 183
000

<210> SEQ ID NO 184
<400> SEQUENCE: 184
000

<210> SEQ ID NO 185
<400> SEQUENCE: 185
000

<210> SEQ ID NO 186
<400> SEQUENCE: 186
000

<210> SEQ ID NO 187
<400> SEQUENCE: 187
000

<210> SEQ ID NO 188
<400> SEQUENCE: 188
000

<210> SEQ ID NO 189
<400> SEQUENCE: 189
000

<210> SEQ ID NO 190
<400> SEQUENCE: 190
000

<210> SEQ ID NO 191
<400> SEQUENCE: 191
000

<210> SEQ ID NO 192
<400> SEQUENCE: 192
000

<210> SEQ ID NO 193
<400> SEQUENCE: 193
000

<210> SEQ ID NO 194
```

```
<400> SEQUENCE: 194
000

<210> SEQ ID NO 195
<400> SEQUENCE: 195
000

<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
000

<210> SEQ ID NO 200
<400> SEQUENCE: 200
000

<210> SEQ ID NO 201
<400> SEQUENCE: 201
000

<210> SEQ ID NO 202
<400> SEQUENCE: 202
000

<210> SEQ ID NO 203
<400> SEQUENCE: 203
000

<210> SEQ ID NO 204
<400> SEQUENCE: 204
000

<210> SEQ ID NO 205
<400> SEQUENCE: 205
```

000

<210> SEQ ID NO 206
<400> SEQUENCE: 206

000

<210> SEQ ID NO 207
<400> SEQUENCE: 207

000

<210> SEQ ID NO 208
<400> SEQUENCE: 208

000

<210> SEQ ID NO 209
<400> SEQUENCE: 209

000

<210> SEQ ID NO 210
<211> LENGTH: 12
<212> TYPE: PRT
<213> ORGANISM: Artificial Sequence
<220> FEATURE:
<223> OTHER INFORMATION: Synthetic construct

<400> SEQUENCE: 210

Arg Arg Arg Arg Arg Arg Arg Arg Arg Arg Arg Arg
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Synthetic construct

<400> SEQUENCE: 211

Arg Arg Arg Arg Arg Arg Arg Arg Arg
1               5

<210> SEQ ID NO 212
<211> LENGTH: 18
<212> TYPE: PRT
<213> ORGANISM: Artificial Sequence
<220> FEATURE:
<223> OTHER INFORMATION: Synthetic construct

<400> SEQUENCE: 212

Lys His Lys His Lys His Lys His Lys His Lys His Lys His Lys His
1               5                   10                  15

Lys His

<210> SEQ ID NO 213
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 213

Arg Lys Lys Arg Arg Gln Arg Arg
1               5

<210> SEQ ID NO 214
<211> LENGTH: 12
<212> TYPE: PRT
<213> ORGANISM: Artificial Sequence
<220> FEATURE:
<223> OTHER INFORMATION: Synthetic construct

<400> SEQUENCE: 214

Gly Arg Lys Lys Arg Arg Gln Arg Arg Arg Pro Gln
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Synthetic construct

<400> SEQUENCE: 215

Gly Arg Lys Lys Arg Arg Gln Arg Arg Arg
1               5                   10

<210> SEQ ID NO 216
<211> LENGTH: 13
<212> TYPE: PRT
<213> ORGANISM: Artificial Sequence
<220> FEATURE:
<223> OTHER INFORMATION: Synthetic construct

<400> SEQUENCE: 216

Gly Arg Lys Lys Arg Arg Gln Arg Arg Arg Pro Pro Gln
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthetic construct

<400> SEQUENCE: 217

Tyr Gly Arg Lys Lys Arg Arg Gln Arg Arg Arg
1               5                   10

<210> SEQ ID NO 218
<211> LENGTH: 18
<212> TYPE: PRT
<213> ORGANISM: Artificial Sequence
<220> FEATURE:
<223> OTHER INFORMATION: Synthetic construct

<400> SEQUENCE: 218

Arg Lys Lys Arg Arg Gln Arg Arg Arg Lys Lys Arg Arg Gln Arg
1               5                   10                  15

Arg Arg

<210> SEQ ID NO 219
<211> LENGTH: 20
<212> TYPE: PRT
<213> ORGANISM: Artificial Sequence
<220> FEATURE:
<223> OTHER INFORMATION: Synthetic construct
```

-continued

```
<220> FEATURE:
<221> NAME/KEY: MOD_RES
<222> LOCATION: (1)..(1)
<223> OTHER INFORMATION: Acetyl
<220> FEATURE:
<221> NAME/KEY: MOD_RES
<222> LOCATION: (20)..(20)
<223> OTHER INFORMATION: Cysteamide

<400> SEQUENCE: 219

Gly Leu Trp Arg Ala Leu Trp Arg Leu Leu Arg Ser Leu Trp Arg Leu
1               5                   10                  15

Leu Trp Arg Ala
            20

<210> SEQ ID NO 220
<211> LENGTH: 18
<212> TYPE: PRT
<213> ORGANISM: Artificial Sequence
<220> FEATURE:
<223> OTHER INFORMATION: Synthetic construct

<400> SEQUENCE: 220

Arg Gln Ile Lys Ile Trp Phe Gln Asn Arg Arg Met Lys Trp Lys Lys
1               5                   10                  15

Gly Gly

<210> SEQ ID NO 221
<211> LENGTH: 15
<212> TYPE: PRT
<213> ORGANISM: Artificial Sequence
<220> FEATURE:
<223> OTHER INFORMATION: Synthetic construct

<400> SEQUENCE: 221

Arg Gln Ile Arg Ile Trp Phe Gln Asn Arg Arg Met Arg Trp Arg
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Synthetic construct

<400> SEQUENCE: 222

Arg Gln Ile Lys Ile Trp Phe Gln Asn Arg Arg Met Lys Trp Lys Lys
1               5                   10                  15

<210> SEQ ID NO 223
<211> LENGTH: 17
<212> TYPE: PRT
<213> ORGANISM: Artificial Sequence
<220> FEATURE:
<223> OTHER INFORMATION: Synthetic construct

<400> SEQUENCE: 223

Cys Ser Ile Pro Pro Glu Val Lys Phe Asn Lys Pro Phe Val Tyr Leu
1               5                   10                  15

Ile

<210> SEQ ID NO 224
<211> LENGTH: 13
<212> TYPE: PRT
<213> ORGANISM: Artificial Sequence
<220> FEATURE:
```

<223> OTHER INFORMATION: Synthetic construct

<400> SEQUENCE: 224

Phe Val Gln Trp Phe Ser Lys Phe Leu Gly Arg Ile Leu
1               5                   10

<210> SEQ ID NO 225
<211> LENGTH: 18
<212> TYPE: PRT
<213> ORGANISM: Artificial Sequence
<220> FEATURE:
<223> OTHER INFORMATION: Synthetic construct

<400> SEQUENCE: 225

Lys Leu Ala Leu Lys Leu Ala Leu Lys Ala Leu Lys Ala Ala Leu Lys
1               5                   10                  15

Leu Ala

<210> SEQ ID NO 226
<211> LENGTH: 9
<212> TYPE: PRT
<213> ORGANISM: Artificial Sequence
<220> FEATURE:
<223> OTHER INFORMATION: Synthetic construct

<400> SEQUENCE: 226

Arg Arg Trp Trp Arg Arg Trp Arg Arg
1               5

<210> SEQ ID NO 227
<211> LENGTH: 18
<212> TYPE: PRT
<213> ORGANISM: Artificial Sequence
<220> FEATURE:
<223> OTHER INFORMATION: Synthetic construct

<400> SEQUENCE: 227

Leu Leu Ile Ile Leu Arg Arg Arg Ile Arg Lys Gln Ala His Ala His
1               5                   10                  15

Ser Lys

<210> SEQ ID NO 228
<211> LENGTH: 27
<212> TYPE: PRT
<213> ORGANISM: Artificial Sequence
<220> FEATURE:
<223> OTHER INFORMATION: Synthetic construct

<400> SEQUENCE: 228

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 229
<211> LENGTH: 27
<212> TYPE: PRT
<213> ORGANISM: Artificial Sequence
<220> FEATURE:
<223> OTHER INFORMATION: Synthetic construct

<400> SEQUENCE: 229

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 230
<211> LENGTH: 21
<212> TYPE: PRT
<213> ORGANISM: Artificial Sequence
<220> FEATURE:
<223> OTHER INFORMATION: Synthetic construct

<400> SEQUENCE: 230

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 231
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Acetyl
<220> FEATURE:
<221> NAME/KEY: MOD_RES
<222> LOCATION: (21)..(21)
<223> OTHER INFORMATION: Cysteamide

<400> SEQUENCE: 231

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 232
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (11)..(11)
<223> OTHER INFORMATION: Amide

<400> SEQUENCE: 232

Trp Lys Leu Phe Lys Lys Ile Leu Lys Val Leu
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Synthetic construct

<400> SEQUENCE: 233

Lys Lys Leu Phe Lys Lys Ile Leu Lys Tyr Leu
1               5                   10

<210> SEQ ID NO 234
<211> LENGTH: 11
<212> TYPE: PRT
<213> ORGANISM: Artificial Sequence
<220> FEATURE:

```
<223> OTHER INFORMATION: Synthetic construct
<220> FEATURE:
<221> NAME/KEY: MOD_RES
<222> LOCATION: (11)..(11)
<223> OTHER INFORMATION: Amide

<400> SEQUENCE: 234

Lys Lys Leu Phe Lys Lys Ile Leu Lys Tyr Leu
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (3)..(3)
<223> OTHER INFORMATION: Acm modification

<400> SEQUENCE: 235

Gly Asp Cys Leu Pro His Leu Lys Leu Cys
1               5                   10

<210> SEQ ID NO 236
<211> LENGTH: 24
<212> TYPE: PRT
<213> ORGANISM: Artificial Sequence
<220> FEATURE:
<223> OTHER INFORMATION: Synthetic construct

<400> SEQUENCE: 236

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 237
<211> LENGTH: 30
<212> TYPE: PRT
<213> ORGANISM: Artificial Sequence
<220> FEATURE:
<223> OTHER INFORMATION: Synthetic construct

<400> SEQUENCE: 237

Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30

<210> SEQ ID NO 238
<211> LENGTH: 27
<212> TYPE: PRT
<213> ORGANISM: Artificial Sequence
<220> FEATURE:
<223> OTHER INFORMATION: Synthetic construct

<400> SEQUENCE: 238

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25
```